US012780948B2

(12) United States Patent
Larson et al.

(10) Patent No.: US 12,780,948 B2
(45) Date of Patent: Nov. 3, 2026

(54) BISPECIFIC BINDING AGENTS AND USES THEREOF

(71) Applicant: MEMORIAL SLOAN KETTERING CANCER CENTER, New York, NY (US)

(72) Inventors: Steven Larson, New York, NY (US); Nai-Kong V. Cheung, New York, NY (US); Sarah Cheal, New York, NY (US); Hong Xu, New York, NY (US); Hong-Fen Guo, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 377 days.

(21) Appl. No.: 16/979,840

(22) PCT Filed: Mar. 11, 2019

(86) PCT No.: PCT/US2019/021612
§ 371 (c)(1),
(2) Date: Sep. 10, 2020

(87) PCT Pub. No.: WO2019/177970
PCT Pub. Date: Sep. 19, 2019

(65) Prior Publication Data

US 2021/0017295 A1 Jan. 21, 2021

Related U.S. Application Data

(60) Provisional application No. 62/813,592, filed on Mar. 4, 2019, provisional application No. 62/641,645, filed on Mar. 12, 2018.

(51) Int. Cl.

| | |
|---|---|
| ***C07K 16/32*** | (2006.01) |
| ***A61K 9/00*** | (2006.01) |
| ***A61K 38/17*** | (2006.01) |
| ***A61P 35/00*** | (2006.01) |
| ***C07K 16/46*** | (2006.01) |

(52) U.S. Cl.
CPC .......... *C07K 16/468* (2013.01); *A61K 9/0019* (2013.01); *A61K 38/177* (2013.01); *A61P 35/00* (2018.01); *C07K 16/32* (2013.01)

(58) Field of Classification Search
CPC ....... C07K 16/468; C07K 16/32; A61P 35/00; A61K 9/0019; A61K 38/177
See application file for complete search history.

(56) References Cited

FOREIGN PATENT DOCUMENTS

| | | | | |
|---|---|---|---|---|
| JP | 2017-527274 A | 9/2017 | | |
| WO | WO-2007131242 A2 * | 11/2007 | ......... | A61K 51/1009 |
| WO | WO-2008019366 A2 * | 2/2008 | ......... | A61K 39/0011 |
| WO | WO-2016014942 A1 * | 1/2016 | ....... | A61K 39/39558 |
| WO | WO-2016/130539 A2 | 8/2016 | | |
| WO | WO-2017120599 A1 * | 7/2017 | ............. | A61P 35/00 |

OTHER PUBLICATIONS

Keinänen et al, Pretargeting of internalizing trastuzumab and cetuximab with a 18F-tetrazine tracer in xenograft models, EJNMMI Research, 2017, 7:95, pp. 1-12 (Year: 2017).*

Green et al, Comparative Analysis of Bispecific Antibody and Streptavidin-Targeted Radioimmunotherapy for B-cell Cancers, Cancer Res, 76(22) 2016, pp. 6669-6679 (Year: 2016).*

Berguig (Intracellular Delivery of Cancer-Targeting Antibody-Drug Conjugates, University of Washington, Dept. of Bioengineering, 2013) (Year: 2013).*

Cheal S M et al: "Curative Multicycle Radioimmunotherapy Monitored by Quantitative SPECT/CT—Based Theranostics, Using Bispecific Antibody Pretargeting Strategy in Colorectal Cancer", J. Nucl. Med., vol. 58, No. 11, Nov. 1, 2017 (Nov. 1, 2017), pp. 1735-1742.

Damian J. Green et al: "Comparative Analysis of Bispecific Antibody and Streptavidin-Targeted Radioinmunotherapy for B-cell Cancers", Cancer Research, vol. 76, No. 22, Sep. 2, 2016 (Sep. 2, 2016). pp. 6669-6679.

Guozheng Liu et al: "Adding a Clearing Agent to Pretargeting Does Not Lower the Tumor Accumulation of the Effector as Predicted", Cancer Biotherapy & Radiopharmaceuticals, vol. 25 , No. 6, Dec. 1, 2010 (Dec. 1, 2010), pp. 757-762.

International Search Report and Written Opinion on PCT PCT/US2019/021612 dated May 31, 2019 (17 pages).

Outi Keinanen et al: "Pretargeting of internalizing trastuzumab and cetuximab with a F-tetrazine tracer in xenograft models", EJNMMI Research, Biomed Central LTD, London, UK, vol. 7, No. 1, Dec. 2, 2017 (Dec. 2, 2017), pp. 1-12.

Cheal et al., "Comparative efficacy and toxicity of 77Lu- vs 9-Ytheranostic anti-HER2/anti-DOTA(metal) pretargeted radioimmunotherapy (anti-HER2 DOTA-PRIT) of HER2-expressing breast cancer xenografts with curative intent." Journal of Nuclear Medicine, 2017, vol. 58, Supplement 1, Abstract No. 54, Retrieved from the Internet, <URL: https://jnm.snmjournals.org/content/58/supplement_1/54>.

Cheal et al., "Theranostic pretargeting of HER2-expressing human carcinoma xenografts in immunocompromised mice with an anti-DOTA(metal) hapten IgG-scFv bispecific antibody." Molecular Imaging and Biology, 2016, vol. 18, No. 1, SUPPL. 1, pp. S1356, Abstract No. 2233962.

Zeglis et al., "A Pretargeted PET Imaging Strategy Based on Bioorthogonal Diels-Alder Click Chemistry." J Nucl Med 2013; 54:1389-1396 001: 10.2967/jnumed.112.115840.

Boross Peter et al: "Mechanisms of action of CD20 antibodies", American Journal of Cancer Research, vol. 2, No. 6, Jan. 1, 2012, (15, pages).

* cited by examiner

*Primary Examiner* — Nelson B Moseley, II
*Assistant Examiner* — Dennis J Sullivan
(74) *Attorney, Agent, or Firm* — Foley & Lardner LLP

(57) ABSTRACT

Provided herein are compositions, methods, and uses involving (i) bispecific binding agents that specifically bind to a cancer antigen, (ii) clearing agents, and (iii) radiotherapeutic agents for treating cancer. Also provided herein are uses and methods for treating HER2-related cancers.

12 Claims, 20 Drawing Sheets

Figure 1A:
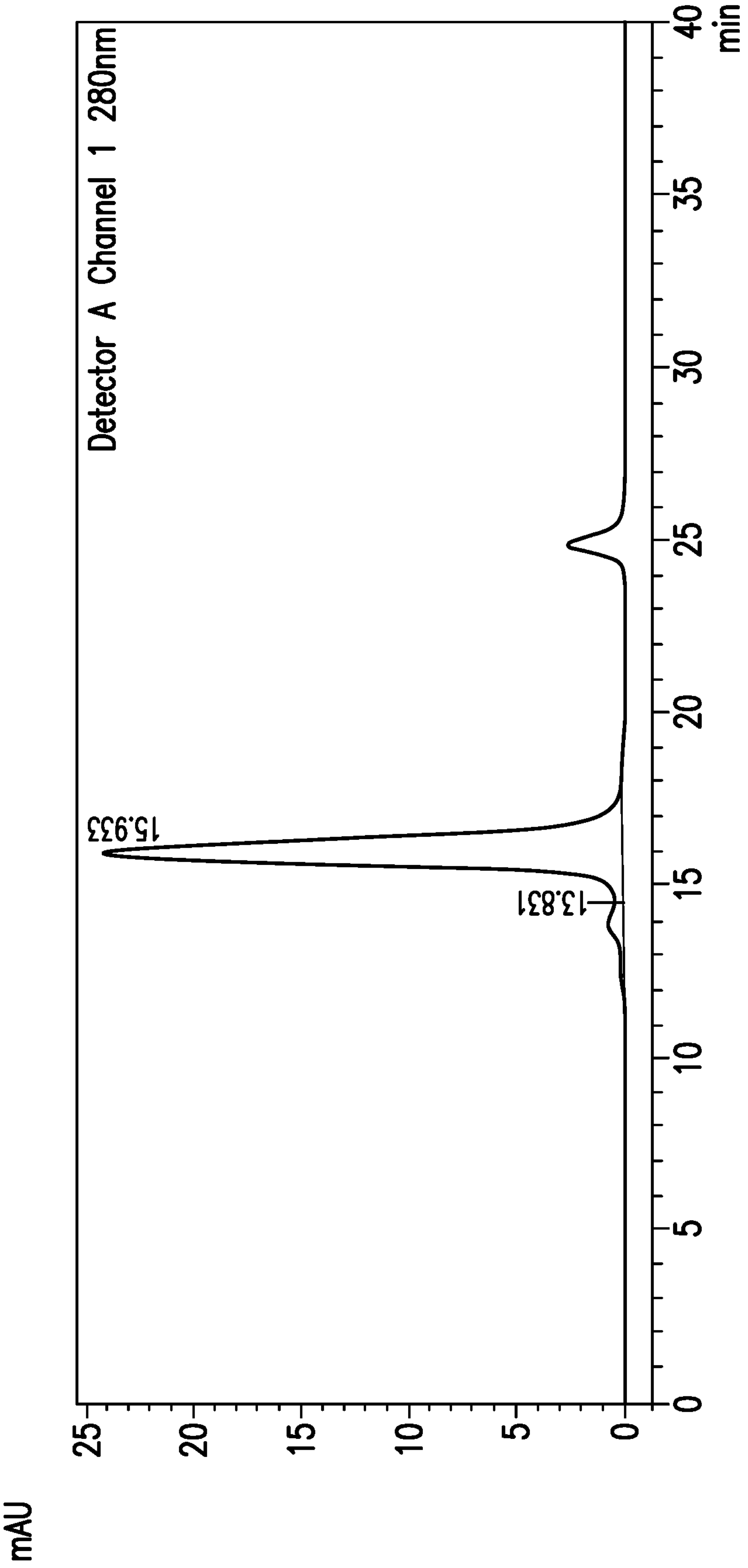

Specification includes a Sequence Listing.

BISPECIFIC BINDING AGENTS AND USES THEREOF

CROSS-REFERENCE TO RELATED APPLICATIONS

This application is a National Stage Application of PCT/US2019/021612, filed on Mar. 11, 2019, which claims the benefit of U.S. Provisional Patent Application No. 62/641,645, filed Mar. 12, 2018 and U.S. Provisional Patent Application No. 62/813,592, filed Mar. 4, 2019, each of which is incorporated by reference herein in its entirety.

SEQUENCE LISTING

This application incorporates by reference a Sequence Listing submitted with this application as text file entitled "Sequence_Listing_13542-061-228.txt" created on Mar. 7, 2019 and having a size of 144,888 bytes.

1. FIELD

Provided herein are compositions, methods, and uses involving bispecific binding agents that specifically bind to i) a first target, wherein the first target is a cancer antigen expressed by a cancer, and ii) second target, wherein the second target is not the cancer antigen. The bispecific binding agents described herein are useful in methods for treating cancer. Also provided herein are methods and uses involving (i) bispecific binding agents that specifically bind to a cancer antigen, (ii) clearing agents, and (iii) radiotherapeutic agents, for treating cancer.

2. BACKGROUND

The pharmacokinetics of full-size IgG monoclonal antibodies as carriers of therapeutic radioisotopes (i.e., radioimmunotherapy) show an unfavorable therapeutic index (e.g., the ratio of the radiation-absorbed dose to the tumor divided by the dose to a radiosensitive tissue such as blood (see, e.g., Larson et al., 2015, "Radioimmunotherapy of human tumours." Nature Reviews Cancer; 15: 347-60)), with hematological toxicity typically dose-limiting for radioimmunotherapy. Alternatively, pretargeting radioimmunotherapy ("PRIT") strategies can be employed, which separate the antibody-mediated targeting step from the administration of the cytotoxic ligand in order to reduce the residence time of the ligand in circulation (see, e.g., Kraeber-Bodere et al., 2015, "A pretargeting system for tumor PET imaging and radioimmunotherapy." Front Pharmacol. 6:54). Typical PRIT strategies involve three steps: (i) a tumor targeting step; (ii) a clearing step; and (iii) a radiotherapeutic step. First, a bispecific 4838-9683-1434.1 tumor targeting agent (e.g., a bispecific antibody) that has one specificity for a tumor antigen is administered to a subject to allow the bispecific tumor targeting agent to prelocalize to the tumor. Second, a clearing agent is administered to the subject, which removes the circulating bispecific tumor targeting agent from the blood (e.g., unbound bispecific tumor targeting agents in the blood). Third, a radiolabeled small-molecule hapten or peptide is administered to the subject, which binds to the tumor-bound bispecific tumor targeting agent and kills the tumor cell. The clearing step permits a reduction in the amount of the bispecific tumor targeting agent in the circulating blood, allowing for reduced interaction in the blood between the bispecific tumor targeting agent and the radiolabeled small-molecule hapten or peptide. In effect, the clearing step improves the therapeutic index for the PRIT method by reducing radiation exposure to non-targeted tissues, especially the blood, consequently allowing for higher doses of the radiolabeled small-molecule hapten or peptide to be administered without resulting in dose-limiting toxicity.

However, a major disadvantage of current PRIT methods includes the inability to target rapidly internalized antigens (see, e.g., Walter et al., 2010, Cancer Biotherapy and Radiopharmaceuticals, 25(2):125-142). Unlike antibody-drug conjugates that rely on cell surface receptor binding as well as internalization upon cell binding for its payload delivery, non-internalizing antibody/cell surface targets are considered optimum for PRIT (see, e.g., Boerman et al., 2003, Pretargeted Radioimmunotherapy of Cancer: Progress Step by Step*. J. Nucl. Med. 44(3):400-411; Casalini et al., 1997, Tumor Pretargeting: Role of Avidin/Streptavidin on Monoclonal Antibody Internalization. J. Nucl. Med.; 38(9):1378-1381; Walter et al., 2010, Pretargeted Radioimmunotherapy for Hematologic and Other Malignancies, Cancer Biother Radiopharm.; 25(2):125-142; Cheal et al., 2014, "Preclinical evaluation of multistep targeting of diasialoganglioside GD2 using an IgG-scFv bispecific antibody with high affinity for GD2 and DOTA metal complex." Molecular Cancer Therapeutics; 13:1802-12; Cheal et al., 2016, "Theranostic pretargeted radioimmunotherapy of colorectal cancer xenografts in mice using picomolar affinity Y-86- or Lu-177-DOTA-Bn binding scFv C825/GPA33 IgG bispecificimmunogonjugates." European Journal of Nuclear Medicine and Molecular Imaging; 43:925-37; Green et al., 2016, "Comparative Analysis of Bispecific Antibody and Streptavidin-Targeted Radioimmunotherapy for B-cell Cancers." Cancer Research; 76(22):6669-6679). Rapidly internalized antigens are nontargetable for PRIT (see Walter et al., 2010, Pretargeted Radioimmunotherapy for Hematologic and Other Malignancies, Cancer Biother Radiopharm.; 25(2):125-142; see also, Boerman et al., 2003, Pretargeted Radioimmunotherapy of Cancer: Progress Step by Step*. J. Nucl. Med. 44(3):400-411). However, many cancers are associated with antigens that internalize into the cancer cell; for example, the cancer antigen human epidermal growth factor receptor 2 ("HER2") is prone to endocytosis into cells (see, e.g., Austin et al., 2004, Molecular Biology of the Cell, 15:5268-5282). Thus, there is an unmet need for methods of treating cancers associated with antigens that internalize into cells (e.g., are internalized into cells). Moreover, due to the long time between the tumor targeting step and the clearing agent step (typically 24-120 hours (see, e.g., Knox et al., 2000, Clinical Cancer Research, 6:406-414; Bodet-Milin et al. J Nucl Med 2016, vol 57, no 10, 1505-1511; Bodet-Milin et al. Front Med (Lausanne) 2015 Nov. 27, 2:84; Schoffelen, R., Woliner-van der Weg, W., Visser, E. P. et al. Eur J Nucl Med Mol Imaging (2014) 41: 1593; Forero, et al. Blood 2004 104(1) 227-36; Weiden, et al. Cancer Biother Radiopharm 2000 15(1): 15-29)), current PRIT methods often require multiple hospital visits or an overnight stay, which may be costly and burdensome to the patient. Thus, improved, more efficient methods of PRIT are also needed.

3. SUMMARY

Provided herein is a method of treating cancer in a subject in need thereof, comprising (a) administering to the subject a therapeutically effective amount of a bispecific binding agent, wherein the bispecific binding agent comprises a first molecule covalently bound, optionally via a linker, to a second molecule, wherein the first molecule comprises a first binding site, wherein the first binding site specifically binds to a first target, wherein the first target is a cancer antigen expressed by said cancer, wherein the second molecule comprises a second binding site, wherein the second binding site specifically binds to a second target, wherein the second target is not the cancer antigen; (b) not more than 12 hours after step (a) of administering to the subject the therapeutically effective amount of the bispecific binding agent, administering to the subject a therapeutically effective amount of a clearing agent, wherein said clearing agent binds to said second binding site and functions to reduce the bispecific binding agent circulating in the blood of the subject; and (c) after step (b) of administering to the subject the therapeutically effective amount of the clearing agent, administering to the subject a therapeutically effective amount of a radiotherapeutic agent, wherein the radiotherapeutic agent comprises (i) the second target bound to a metal radionuclide, wherein the second target is a metal chelator; or (ii) the second target bound to a metal chelator, said metal chelator being bound to a metal radionuclide. In a specific embodiment, the therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg, wherein the subject is a human. In another specific embodiment, the therapeutically effective amount of the bispecific binding agent is 250 mg to 700 mg, 300 mg to 600 mg, or 400 mg to 500 mg, wherein the subject is a human. In a specific embodiment, the cancer antigen is selected from the group consisting of HER2, CA6, CD138, CD19, CD22, CD27L, CD30, CD33, CD37, CD56, CD66e, CD70, CD74, CD79b, EGFR, EGFRvIII, FRα, GCC, GPNMB, Mesothelin, MUC16, NaPi2b, Nectin 4, PSMA, STEAP1, Trop-2, 5T4, AGS-16, alpha v beta6, CA19.9, CAIX, CD174, CD180, CD227, CD326, CD79a, CEACAM5, CRIPTO, DLL3, DS6, Endothelin B receptor, FAP, GD2, Mesothelin, PMEL 17, SLC44A4, TENB2, TIM-1, CD98, Endosialin/CD248/TEM1, Fibronectin Extra-domain B, LIV-1, Mucin 1, p-cadherin, peritosin, Fyn, SLTRK6, Tenascin c, VEGFR2, PRLR, CD20, CD72, Fibronectin, GPA33, splice isoform of tenascin-C, TAG-72, B7-H3, L1CAM, Lewis Y, and polysialic acid. In a preferred embodiment, the cancer antigen is HER2. In a specific embodiment, the cancer antigen is an antigen that is internalized into a cancer cell. In a specific embodiment, the cancer antigen that is internalized into a cancer cell is selected from the group consisting of HER2, CA6, CD138, CD19, CD22, CD27L, CD30, CD33, CD37, CD56, CD66e, CD70, CD74, CD79b, EGFR, EGFRvIII, FRα, GCC, GPNMB, Mesothelin, MUC16, NaPi2b, Nectin 4, PSMA, STEAP1, Trop-2, 5T4, AGS-16, alpha v beta6, CA19.9, CAIX, CD174, CD180, CD227, CD326, CD79a, CEACAM5, CRIPTO, DLL3, DS6, Endothelin B receptor, FAP, GD2, Mesothelin, PMEL 17, SLC44A4, TENB2, TIM-1, CD98, Endosialin/CD248/TEM1, Fibronectin Extra-domain B, LIV-1, Mucin 1, p-cadherin, peritosin, Fyn, SLTRK6, Tenascin c, VEGFR2, and PRLR. In a preferred embodiment, the cancer antigen that is internalized into a cancer cell is HER2. In another embodiment, the cancer antigen is an antigen that is not internalized into a cancer cell. In a specific embodiment, the cancer antigen that is not internalized into a cancer cell is selected from the group consisting of CD20, CD72, Fibronectin, GPA33, splice isoform of tenascin-C, and TAG-72. In a preferred embodiment, the cancer antigen is HER2 and the metal chelator is DOTA or a derivative thereof.

Also provided herein is a method of treating cancer in a subject in need thereof, comprising (a) administering to the subject a first therapeutically effective amount of a bispecific binding agent, wherein the first therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg, wherein the bispecific binding agent comprises a first molecule covalently bound, optionally via a linker, to a second molecule, wherein said cancer expresses HER2, wherein the first molecule comprises an antibody or an antigen binding fragment thereof, or a single-chain variable fragment (scFv), wherein said antibody or antigen-binding fragment thereof, or scFv (i) binds to HER2 on said cancer, and (ii) comprises all three of the heavy chain complementarity determining regions (CDRs) of SEQ ID NO: 20, and all three of the light chain CDRs of SEQ ID NO: 19, wherein the second molecule comprises a second binding site, wherein the second binding site specifically binds to a second target, wherein the second target is not the cancer antigen; (b) after step (a) of administering to the subject the therapeutically effective amount of the bispecific binding agent, administering to the subject a therapeutically effective amount of a clearing agent, wherein said clearing agent binds to said second binding site and functions to reduce the bispecific binding agent circulating in the blood of the subject; and (c) after step (b) of administering to the subject the therapeutically effective amount of the clearing agent, administering to the subject a therapeutically effective amount of a radiotherapeutic agent, wherein the radiotherapeutic agent comprises (i) the second target bound to a metal radionuclide, wherein the second target is a metal chelator; or (ii) the second target bound to a metal chelator, said metal chelator being bound to a metal radionuclide, wherein the subject is a human. In a specific embodiment, the first therapeutically effective amount of the bispecific binding agent is about 450 mg.

In a specific embodiment of the bispecific binding agent, the first molecule of the bispecific binding agent comprises an antibody or an antigen-binding fragment thereof, wherein said antibody or antigen-binding fragment thereof comprises the first binding site. In a specific embodiment, the antibody is an immunoglobulin.

In a specific embodiment of the bispecific binding agent in which the first molecule comprises an immunoglobulin, said immunoglobulin comprising the first binding site, wherein the first binding site specifically binds to HER2, a heavy chain in the immunoglobulin comprises all three heavy chain CDRs of SEQ ID NO: 20, and a light chain in the immunoglobulin comprises all three light chain CDRs of SEQ ID NO: 19. In a specific embodiment, the sequence of a heavy chain variable ($V_H$) domain in a heavy chain in the immunoglobulin comprises SEQ ID NO: 20. In a specific embodiment, the sequence of a $V_H$ domain in a heavy chain in the immunoglobulin comprises a humanized form SEQ ID NO: 20. In a specific embodiment, the sequence of a light chain variable ($V_L$) domain in a light chain in the immunoglobulin comprises SEQ ID NO: 19. In a specific embodiment, the sequence of a $V_L$ domain in a light chain in the immunoglobulin comprises a humanized form SEQ ID NO: 19. In a specific embodiment, the sequence of a heavy chain in the immunoglobulin comprises any of SEQ ID NOs: 14-17. In a preferred embodiment, the sequence of a heavy chain in the immunoglobulin comprises SEQ ID NO: 15. In a more preferred embodiment, the sequence of a heavy chain in the immunoglobulin comprises SEQ ID NO: 16. In a specific embodiment, the sequence of a light chain in the immunoglobulin comprises SEQ ID NO: 11.

In a specific embodiment of the bispecific binding agent, the second molecule is an scFv comprising the second binding site. In a specific embodiment in which the second molecule is an scFv, the second target is DOTA or a derivative thereof. In a specific embodiment in which the second molecule is an scFv and the second target is DOTA or a derivative thereof, the sequence of a $V_H$ domain in the scFv comprises all three of the CDRs of SEQ ID NO: 21, and the sequence of a $V_L$ domain in the scFv comprises all three of the CDRs of SEQ ID NO: 22. In a specific embodiment, the sequence of a $V_H$ domain in the scFv is SEQ ID NO: 21. In a specific embodiment, the sequence of a $V_H$ domain in the scFv comprises a humanized form of SEQ ID NO: 21. In a specific embodiment, the sequence of a $V_H$ domain in the scFv is a humanized form of SEQ ID NO: 21. In a specific embodiment, the humanized form of SEQ ID NO: 21 is SEQ ID NO: 37. In a specific embodiment, the sequence of a $V_L$ domain in the scFv is SEQ ID NO: 22. In a specific embodiment, the sequence of a $V_L$ domain in the scFv comprises a humanized form of SEQ ID NO: 22. In a specific embodiment, the sequence of a $V_L$ domain in the scFv is a humanized form of SEQ ID NO: 22. In a specific embodiment, the humanized form of SEQ ID NO: 22 is SEQ ID NO: 38. In a specific embodiment, the sequence of the scFv comprises any of SEQ ID NOs: 31-36. In a specific embodiment, the sequence of the scFv is any of SEQ ID NOs: 31-36. In a specific embodiment, the sequence of the scFv comprises any of SEQ ID NOs: 39-44. In a specific embodiment, the sequence of the scFv is any of SEQ ID NOs: 39-44. In a preferred embodiment, the sequence of the scFv comprises SEQ ID NO: 33 (e.g., the sequence of the scFv is SEQ ID NO: 33). In a more preferred embodiment, the sequence of the scFv comprises SEQ ID NO: 44 (e.g., the sequence of the scFv is SEQ ID NO: 44).

In a specific embodiment in which the first molecule is an immunoglobulin, the immunoglobulin comprises two identical heavy chains and two identical light chains, said light chains being a first light chain and a second light chain, wherein the first light chain is fused, optionally via a first peptide linker, to the second molecule, to create a first light chain fusion polypeptide, wherein the second molecule is a first scFv that comprises the second binding site, and wherein the second light chain is fused, optionally via a second peptide linker, to a second scFv, to create a second light chain fusion polypeptide, and wherein the first and second light chain fusion polypeptides are identical. In a specific embodiment, the first light chain fusion polypeptide comprises said first peptide linker, and said second light chain fusion polypeptide comprises said second peptide linker, wherein the sequences of the first and second peptide linkers are 5-30, 5-25, 5-15, 10-30, 10-20, 10-15, 15-30, or 15-25 amino acids in length. In a specific embodiment, the peptide linkers are 7-32, 7-27, 7-17, 12-32, 12-22, 12-17, 17-32, or 17-27 amino acid residues in length. In a specific embodiment, the first light chain fusion polypeptide comprises said first peptide linker, and said second light chain fusion polypeptide comprises said second peptide linker, wherein the sequences of the first and second peptide linkers are any of SEQ ID NOs: 23 and 25-30. In a specific embodiment, the sequence of an intra-scFv peptide linker between a $V_H$ domain and a $V_L$ domain in the first scFv is 5-30, 5-25, 5-15, 10-30, 10-20, 10-15, 15-30, or 15-25 amino acids in length. In a specific embodiment, the sequence of an intra-scFv peptide linker between a $V_H$ domain and a $V_L$ domain in the first scFv is any one of SEQ ID NOs: 23 and 25-30. In a preferred embodiment, the sequence of an intra-scFv peptide linker between a $V_H$ domain and a $V_L$ domain in the first scFv is SEQ ID NO: 27. In a more preferred embodiment, the sequence of an intra-scFv peptide linker between a $V_H$ domain and a $V_L$ domain in the first scFv is SEQ ID NO: 30. In a specific embodiment, the first target is HER2. In a specific embodiment, the second target is DOTA or a derivative thereof.

In a specific embodiment of the bispecific binding agent in which the first molecule is an immunoglobulin, the immunoglobulin comprises two identical heavy chains and two identical light chains, said light chains being a first light chain and a second light chain, wherein the first light chain is fused, optionally via a first peptide linker, to the second molecule, to create a first light chain fusion polypeptide, wherein the second molecule is a first scFv that comprises the second binding site, and wherein the second light chain is fused, optionally via a second peptide linker, to a second scFv, to create a second light chain fusion polypeptide, wherein the first and second light chain fusion polypeptides are identical, wherein the first target is HER2, and wherein the second target is DOTA or a derivative thereof. In a specific embodiment, a heavy chain in the immunoglobulin comprises all three heavy chain CDRs of SEQ ID NO: 20, and a light chain in the immunoglobulin comprises all three light chain CDRs of SEQ ID NO: 19. In a specific embodiment, the sequence of a $V_H$ domain in a heavy chain in the immunoglobulin comprises SEQ ID NO: 20. In a specific embodiment, the sequence of a $V_H$ domain in a heavy chain in the immunoglobulin comprises a humanized form SEQ ID NO: 20. In a specific embodiment, the sequence of a $V_L$ domain in a light chain in the immunoglobulin comprises SEQ ID NO: 19. In a specific embodiment, the sequence of a $V_L$ domain in a light chain in the immunoglobulin comprises a humanized form SEQ ID NO: 19. In a specific embodiment, the sequence of a heavy chain in the immunoglobulin comprises any of SEQ ID NOs: 14-17. In a preferred embodiment, the sequence of a heavy chain in the immunoglobulin comprises SEQ ID NO: 15. In a more preferred embodiment, the sequence of a heavy chain in the immunoglobulin comprises SEQ ID NO: 16. In a specific embodiment, the sequence of a light chain in the immunoglobulin comprises SEQ ID NO: 11. In a specific embodiment, the sequence of a $V_H$ domain domain in the first scFv comprises all three of the CDRs of SEQ ID NO: 21, and the sequence of a $V_L$ domain in the first scFv comprises all three of the CDRs of SEQ ID NO: 22. In a specific embodiment, the sequence of a $V_H$ domain in the first scFv is SEQ ID NO: 21. In a specific embodiment, the sequence of a $V_H$ domain in the first scFv comprises a humanized form of SEQ ID NO: 21. In a specific embodiment, the sequence of a $V_H$ domain in the first scFv is a humanized form of SEQ ID NO: 21. In a specific embodiment, the humanized form of SEQ ID NO: 21 is SEQ ID NO: 37. In a specific embodiment, the sequence of a $V_L$ domain in the first scFv is SEQ ID NO: 22. In a specific embodiment, the sequence of a $V_L$ domain in the first scFv comprises a humanized form of SEQ ID NO: 22. In a specific embodiment, the sequence of a $V_L$ domain in the first scFv is a humanized form of SEQ ID NO: 22. In a specific embodiment, the humanized form of SEQ ID NO: 22 is SEQ ID NO: 38. In a specific embodiment, the sequence of the first scFv comprises any of SEQ ID NOs: 31-36. In a specific embodiment, the sequence of the first scFv is any of SEQ ID NOs: 31-36. In a specific embodiment, the sequence of the scFv comprises any of SEQ ID NOs: 39-44. In a specific embodiment, the sequence of the scFv is any of SEQ ID NOs: 39-44. In a preferred embodiment, the sequence of the first scFv comprises SEQ ID NO: 33 (e.g., the sequence of the first scFv is SEQ ID NO: 33).

In a more preferred embodiment, the sequence of the scFv comprises SEQ ID NO: 44 (e.g., the sequence of the scFv is SEQ ID NO: 44). In a specific embodiment, the sequence of the first light chain fusion polypeptide is any of SEQ ID NOs: 5-10. In a preferred embodiment, the sequence of the first light chain fusion polypeptide is SEQ ID NO: 7. In a specific embodiment, the sequence of the first light chain fusion polypeptide is any of SEQ ID NOs: 5-10, and wherein the sequence of the heavy chain is any of SEQ ID NOs: 14-17. In a preferred embodiment, the sequence of the first light chain fusion polypeptide is SEQ ID NO: 7, and wherein the sequence of the heavy chain is SEQ ID NO: 15. In a preferred embodiment, the sequence of the first light chain fusion polypeptide is SEQ ID NO: 50, and wherein the sequence of the heavy chain is SEQ ID NO: 16.

In a specific embodiment of the bispecific binding agent, the bispecific binding agent comprises an Fc domain. In a specific embodiment, the bispecific binding agent is at least 100 kDa, at least 150 kDa, at least 200 kDa, at least 250 kDa, between 100 and 300 kDa, between 150 and 300 kDa, or between 200 and 250 kDa.

In a specific embodiment of the bispecific binding agent in which the bispecific binding agent comprises an immunoglobulin, a heavy chain in the immunoglobulin has been mutated to destroy an N-linked glycosylation site. In a specific embodiment, the heavy chain has an amino acid substitution to replace an asparagine that is an N-linked glycosylation site, with an amino acid that does not function as a glycosylation site.

In a specific embodiment of the bispecific binding agent in which the bispecific binding agent comprises an immunoglobulin, a heavy chain in the immunoglobulin has been mutated to destroy a C1q binding site.

In a specific embodiment of the bispecific binding agent, the bispecific binding agent does not activate complement.

In a specific embodiment, the bispecific binding agent does not bind an Fc receptor in its soluble or cell-bound form.

In a specific embodiment in which the bispecific binding agent comprises a scFv, the scFv is disulfide stabilized.

In a specific embodiment of the methods of treating cancer described herein, the bispecific binding agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the bispecific binding agent is administered to the subject intravenously.

Also provided herein are clearing agents for use in the methods of treating cancer described herein. In a specific embodiment, the clearing agent comprises the second target (i.e., the second target of the bispecific binding agent used in the method of treating cancer) bound to a molecule that is cleared predominantly by the liver, fixed phagocytic system, spleen, or bone marrow from the circulating blood. In a specific embodiment, the clearing agent comprises a 500 kDa aminodextran conjugated to the second target. In a specific embodiment, the clearing agent comprises approximately 100-150 molecules of the second target per 500 kDa of aminodextran.

In a specific embodiment of the methods of treating cancer provided herein, the step (b) of administering to the subject the therapeutically effective amount of the clearing agent is carried out not more than 10 hours, not more than 8 hours, not more than 6 hours, not more than 4 hours, not more than 2 hours, 1-12 hours, 2-12 hours, 1-2 hours, 1-3 hours, 1-4 hours, 2-6 hours, 2-8 hours, 2-10 hours, 4-6 hours, 4-8 hours, 4-10 hours, 2 hours, or 4 hours after the step (a) of administering to the subject the therapeutically effective amount of the bispecific binding agent. In another specific embodiment, the step (b) of administering to the subject the therapeutically effective amount of the clearing agent is carried out about 2 hours, about 4 hours, about 6 hours, about 8 hours, or about 10 hours after the step (a) of administering to the subject the therapeutically effective amount of the bispecific binding agent. In another specific embodiment, the bispecific binding agent is at least 100 kDa and the step (b) of administering to the subject the therapeutically effective amount of the clearing agent is carried out not more than 4 hours after the step (a) of administering to the subject the therapeutically effective amount of the bispecific binding agent.

In a specific embodiment of the methods of treating cancer described herein, the clearing agent is administered to the subject intravenously. In a specific embodiment of the methods of treating cancer described herein, the therapeutically effective amount of the clearing agent is an amount that yields a 10:1 molar ratio of the therapeutically effective amount of bispecific binding agent administered to the subject to the therapeutically effective amount of clearing agent administered to the subject, wherein the subject is a human. In a specific embodiment of the methods of treating cancer described herein, the therapeutically effective amount of the clearing agent is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after the step (b) of administering to the subject the therapeutically effective amount of the clearing agent.

Also provided herein are radiotherapeutic agents for use in the methods of treating cancer described herein. In a specific embodiment, the radiotherapeutic agent comprises (i) the second target (i.e., the second target of the bispecific binding agent used in the method of treating cancer) bound to a metal radionuclide, wherein the second target is a metal chelator. In another specific embodiment, the radiotherapeutic agent comprises (ii) the second target (i.e., the second target of the bispecific binding agent used in the method of treating cancer) bound to a metal chelator, said metal chelator being bound to a metal radionuclide. In a specific embodiment of the radiotherapeutic agent, the metal chelator is selected from the group consisting of 1,4,7,10-traazacyclododecane-1,4,7,10-tetraacetic acid (DOTA) or a derivative thereof, DOTA-Bn or a derivative thereof, p-aminobenzyl-DOTA or a derivative thereof, diethylenetriaminepentaacetic acid (DTPA) or a derivative thereof, and DOTA-desferrioxamine. In a specific embodiment, the metal chelator is DOTA or a derivative thereof. In another specific embodiment, the metal chelator is DOTA-Bn or a derivative thereof. In a specific embodiment of the radiotherapeutic agent, the metal of said metal radionuclide is selected from the group consisting of lutetium (Lu), actinium (Ac), astatine (At), bismuth (Bi), cerium (Ce), copper (Cu), dysprosium (Dy), erbium (Er), europium (Eu), gadolinium (Gd), gallium (Ga), holmium (Ho), iodine (I), indium (In), lanthanum (La), lead (Pb), neodymium (Nd), praseodymium (Pr), promethium (Pm), rhenium (Re), samarium (Sm), scandium (Sc), terbium (Tb), thulium (Tm), ytterbium (Yb), yttrium (Y), and zirconium (Zr). In a specific embodiment of the radiotherapeutic agent, the metal of said metal radionuclide is selected from the group consisting of lutetium (Lu), actinium (Ac), astatine (At), bismuth (Bi), cerium (Ce), copper (Cu), dysprosium (Dy), erbium (Er), europium (Eu), gadolinium (Gd), gallium (Ga), holmium (Ho), iodine (I), indium (In), lanthanum (La), lead (Pb), neodymium (Nd), praseodymium (Pr), promethium (Pm), radium (Ra), rhenium (Re), samarium (Sm), scandium (Sc), terbium (Tb), thorium (Th), thulium (Tm), ytterbium (Yb), yttrium (Y), and zirconium (Zr). In a specific embodiment of the radiotherapeutic agent, the metal radionuclide is selected from the group consisting of $^{211}$At, $^{225}$AC, $^{227}$Ac, $^{212}$Bi, $^{213}$Bi, $^{64}$Cu, $^{67}$Cu, $^{67}$Ga, $^{68}$Ga, $^{157}$Gd, $^{166}$HO, $^{124}$I, $^{125}$I, $^{131}$I, $^{111}$In, $^{177}$Lu, $^{212}$Pb, $^{186}$Re, $^{188}$Re, $^{47}$Sc, $^{153}$Sm, $^{166}$Tb, $^{89}$Zr, $^{86}$Y, $^{88}$Y, and $^{90}$Y. In a specific embodiment of the radiotherapeutic agent, the metal radionuclide is selected from the group consisting of $^{211}$At, $^{225}$AC, $^{227}$Ac, $^{212}$Bi, $^{213}$Bi, $^{64}$Cu, $^{67}$Cu, $^{67}$Ga, $^{68}$Ga, $^{157}$Gd, $^{166}$Ho, $^{124}$I, $^{125}$I, $^{131}$I, $^{177}$Lu, $^{212}$Pb, $^{223}$Ra, $^{186}$Re, $^{188}$Re, $^{47}$Sc, $^{153}$Sm, $^{166}$Tb, $^{227}$Th, $^{89}$Zr, $^{86}$Y, $^{88}$Y, $^{90}$Y, and combinations of any of the foregoing. In a specific embodiment of the radiotherapeutic agent, the metal radionuclide is a combination of $^{177}$Lu and $^{227}$Ac. In a preferred embodiment, the metal radionuclide is $^{177}$Lu. In a specific embodiment in which the radiotherapeutic agent comprises (ii) the second target bound to a metal chelator, said metal chelator being bound to a metal radionuclide, the second molecule comprises streptavidin, and the second target comprises biotin. In another specific embodiment in which the radiotherapeutic agent comprises (ii) the second target bound to a metal chelator, said metal chelator being bound to a metal radionuclide, the second target comprises histamine succinyl glycine.

In a specific embodiment of the methods of treating cancer provided herein, the step (c) of administering to the subject the therapeutically effective amount of the radiotherapeutic agent is carried out 1-2 hours, 1-3 hours, 1-4 hours, 2-6 hours, 2-8 hours, 2-10 hours, 4-6 hours, 4-8 hours, 4-10 hours, not more than 1 hour, not more than 2 hours, not more than 3 hours, not more than 4 hours, not more than 5 hours, not more than 6 hours, 1 hour, 2 hours, 3 hours, 4 hours, 5 hours, or 6 hours after the step (b) of administering to the subject the therapeutically effective amount of the clearing agent. In another specific embodiment, the step (c) of administering to the subject the therapeutically effective amount of the radiotherapeutic agent is carried out about 1 hour, about 2 hours, about 3 hours, about 4 hours, about 5 hours, or about 6 hours after the step (b) of administering to the subject the therapeutically effective amount of the clearing agent. In another specific embodiment, the step (c) of administering to the subject the therapeutically effective amount of the radiotherapeutic agent is carried out about 1 hour after the step (b) of administering to the subject the therapeutically effective amount of the clearing agent. In another specific embodiment, the step (c) of administering to the subject the therapeutically effective amount of the radiotherapeutic agent is carried out not more than 16 hours after the step (a) of administering to the subject the therapeutically effective amount of the bispecific binding agent.

In a specific embodiment of the methods of treating cancer described herein, the radiotherapeutic agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the radiotherapeutic agent is administered to the subject intravenously. In a specific embodiment, the therapeutically effective amount of the radiotherapeutic agent is between 25 mCi and 250 mCi, between 50 mCi and 200 mCi, between 75 mCi and 175 mCi, or between 100 mCi and 150 mCi, wherein the subject is a human. In a specific embodiment wherein the radiotherapeutic agent is an alpha-emitting isotope, e.g. $^{225}$Ac, the therapeutically effective amount of the radiotherapeutic agent is from 0.108 mCi to 0.351 mCi, wherein the subject is a human.

The methods of treating cancer provided herein may be repeated two, three, or more times on the subject. In a specific embodiment of the methods of treating cancer, the method further comprises: (d) not more than 1 day, not more than 2 days, not more than 3 days, not more than 4 days, not more than 5 days, not more than 6 days, or not more than 1 week after step (c) of administering to the subject the therapeutically effective amount of the radiotherapeutic agent, administering to the subject a second therapeutically effective amount of the bispecific binding agent; (e) after step (d) of administering to the subject the second therapeutically effective amount of the bispecific binding agent, administering to the subject a second therapeutically effective amount of the clearing agent; and (f) after step (e) of administering to the subject the second therapeutically effective amount of the clearing agent, administering to the subject a second therapeutically effective amount of the radiotherapeutic agent. In a specific embodiment, the step (e) of administering to the subject the therapeutically effective amount of the clearing agent is carried out not more than 12 hours after step (d) of administering to the subject the second therapeutically effective amount of the bispecific binding agent. In a specific embodiment, the second therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg. In a specific embodiment, the second therapeutically effective amount of the clearing agent is an amount that yields a 10:1 molar ratio of the therapeutically effective amount of bispecific binding agent administered to the subject to the therapeutically effective amount of clearing agent administered to the subject. In a specific embodiment, the therapeutically effective amount of the clearing agent is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after the step (b) of administering to the subject the therapeutically effective amount of the clearing agent. In a specific embodiment, the second therapeutically effective amount of the radiotherapeutic agent is between 25 mCi and 250 mCi, between 50 mCi and 200 mCi, between 75 mCi and 175 mCi, or between 100 mCi and 150 mCi. In a specific embodiment, the second therapeutically effective amount of the bispecific binding agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the second therapeutically effective amount of the bispecific binding agent is administered to the subject intravenously. In a specific embodiment, the second therapeutically effective amount of the clearing agent is administered to the subject intravenously. In a specific embodiment, the second therapeutically effective amount of the radiotherapeutic agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the second therapeutically effective amount of the radiotherapeutic agent is administered to the subject intravenously.

In another specific embodiment of the methods of treating cancer, the method further comprises: (g) not more than 1 day, not more than 2 days, not more than 3 days, not more than 4 days, not more than 5 days, not more than 6 days, or not more than 1 week after step (f) of administering to the subject the second therapeutically effective amount of the radiotherapeutic agent, administering to the subject a third therapeutically effective amount of the bispecific binding agent; (h) after step (g) of administering to the subject the third therapeutically effective amount of the bispecific binding agent, administering to the subject a third therapeutically effective amount of the clearing agent; and (i) after step (h) of administering to the subject the third therapeutically effective amount of the clearing agent, administering to the subject a third therapeutically effective amount of the radiotherapeutic agent. In a specific embodiment, the step (g) of administering to the subject the therapeutically effective amount of the clearing agent is carried out not more than 12 hours after step (g) of administering to the subject the second therapeutically effective amount of the bispecific binding agent. In a specific embodiment, the third therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg. In a specific embodiment, the third therapeutically effective amount of the clearing agent is an amount that yields a 10:1 molar ratio of the therapeutically effective amount of bispecific binding agent administered to the subject to the therapeutically effective amount of clearing agent administered to the subject. In a specific embodiment, the therapeutically effective amount of the clearing agent is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after the step (b) of administering to the subject the therapeutically effective amount of the clearing agent. In a specific embodiment, the third therapeutically effective amount of the radiotherapeutic agent is between 25 mCi and 250 mCi, between 50 mCi and 200 mCi, between 75 mCi and 175 mCi, or between 100 mCi and 150 mCi. In a specific embodiment, the third therapeutically effective amount of the bispecific binding agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the third therapeutically effective amount of the bispecific binding agent is administered to the subject intravenously. In a specific embodiment, the third therapeutically effective amount of the clearing agent is administered to the subject intravenously. In a specific embodiment, the third therapeutically effective amount of the radiotherapeutic agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the third therapeutically effective amount of the radiotherapeutic agent is administered to the subject intravenously.

In a specific embodiment, the bispecific binding agent of the methods of treating cancer described herein is contained in a pharmaceutical composition, which pharmaceutical composition further comprises a pharmaceutically acceptable carrier.

In a specific embodiment in which the cancer to be treated in accordance with the methods provided herein expresses HER2, the cancer is breast cancer, gastric cancer, an osteosarcoma, desmoplastic small round cell cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, a head and neck cancer, or neuroblastoma. In a specific embodiment, the cancer is a metastatic tumor. In a specific embodiment, the metastatic tumor is a peritoneal metastasis. In a specific embodiment in which the cancer to be treated in accordance with the methods provided herein expresses HER2, the method of treating cancer further comprises administering to the subject an agent that increases cellular HER2 expression. In a specific embodiment, the agent that increases cellular HER2 expression increases HER2 half-life and availability at the cell membrane, e.g., by temporal caveolin-1 (CAV1) depletion; an example of such an agent that can be used is lovastatin. In a specific embodiment in which the cancer to be treated in accordance with the methods provided herein expresses HER2, the cancer is resistant to treatment with trastuzumab, cetuximab, lapatinib, erlotinib, or any other small molecule or antibody that targets the HER family of receptors.

4. BRIEF DESCRIPTION OF THE DRAWINGS

Figure 1B:
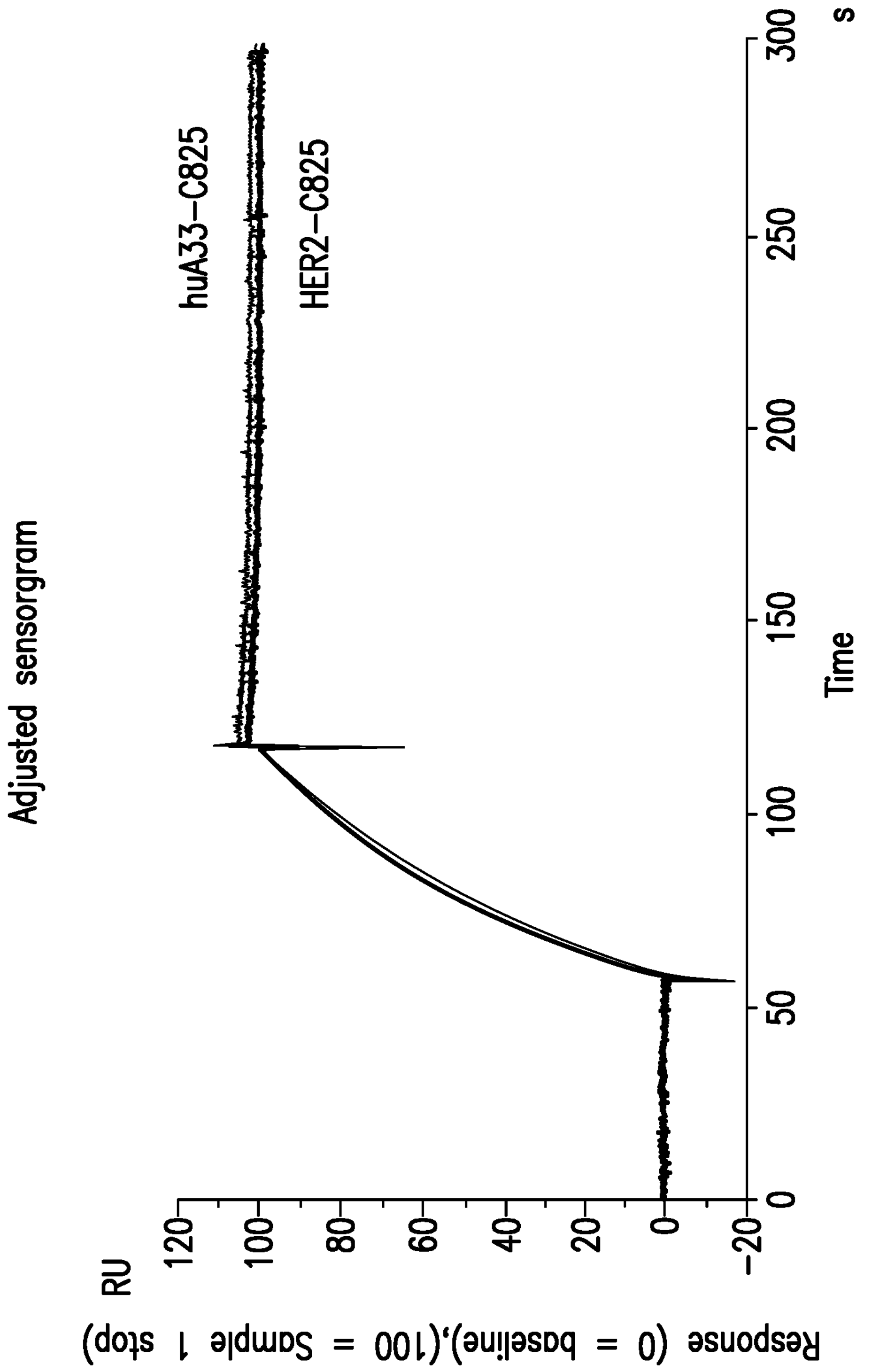
Figure 1C:
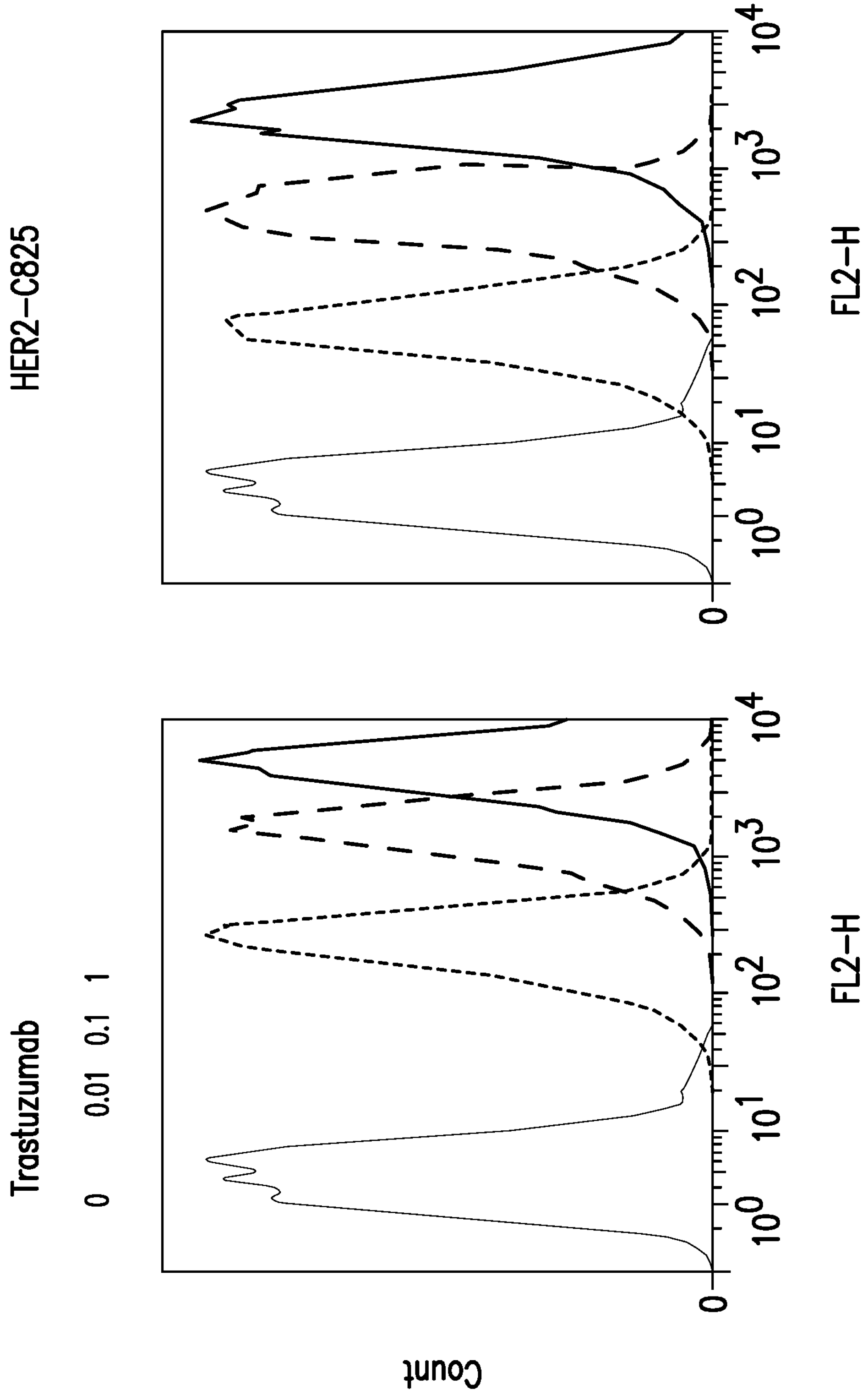

FIG. 1A-FIG. 1C. In vitro characterization of anti-HER2-C825 BsAb. FIG. 1A: Biochemical purity of HER2-C825 by SE-HPLC chromatogram (UV 280 nm). The major peak (15.933 min) is the fully-paired BsAb with an approximate molecular weight of 210 kDa (>96% integrated area under the curve). 25 min is the salt buffer peak. FIG. 1B: Biacore sensorgrams of BsAbs binding to BSA-(Y)-DOTA-Bn. FIG. 1C: FACS histograms of antibodies binding to the HER2(+) breast cancer cell line AU565. Top of the left histogram recorded the concentrations of antibodies (μg/$10^6$ cells), and Rituxan was used as negative control (MFI set at 5).

Figure 2:
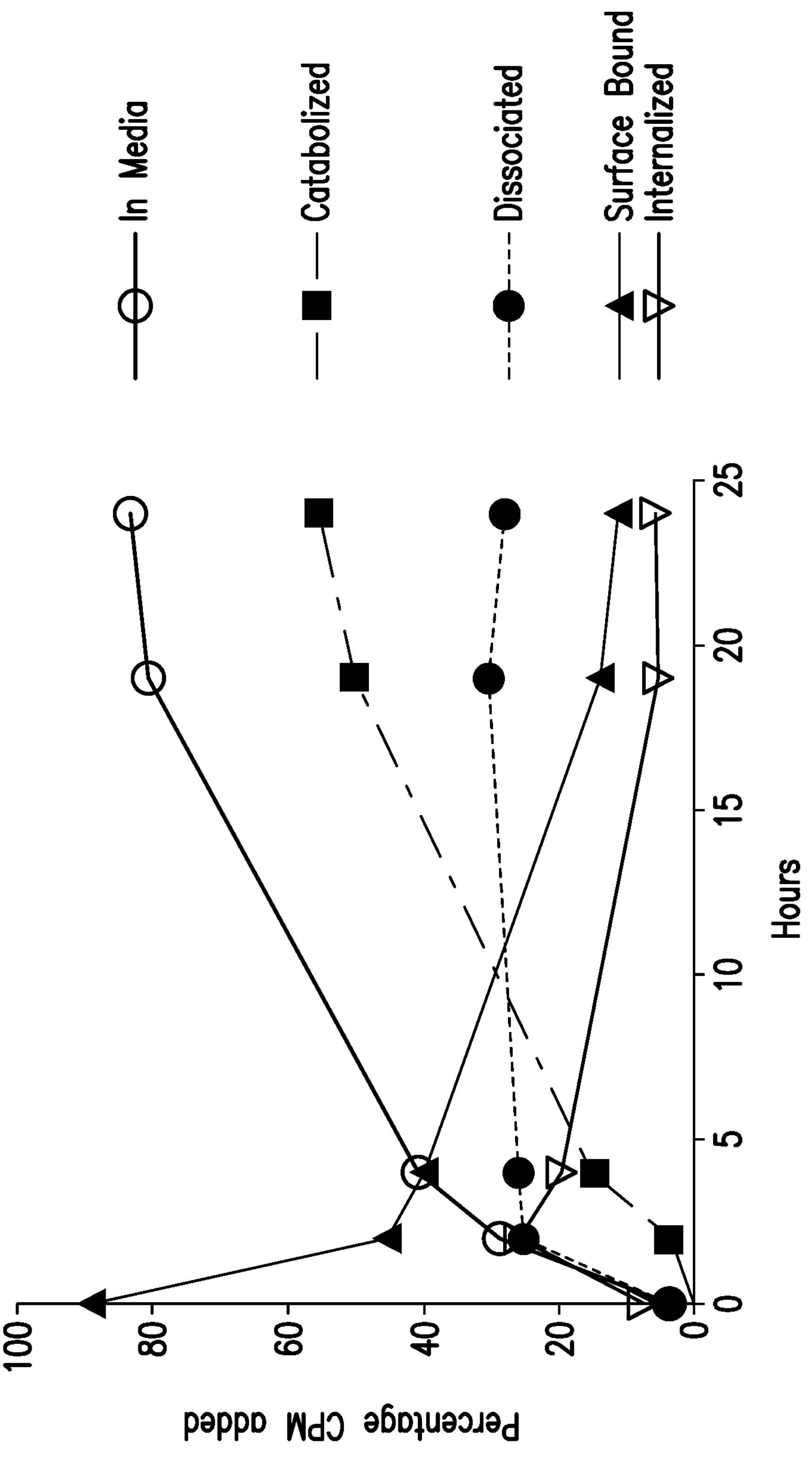

FIG. 2. HER2(+)-tumor surface-bound anti-HER2-C825 BsAb is rapidly internalized. Anti-HER2-C825 was radioiodinated and in vitro radiotracer binding studies were performed with HER2(+) BT-474 cells to determine the internalization and cellular processing at 37° C. of $^{131}$I-anti-HER2-C825. Data is presented as (n=3; mean±standard deviation (SD)).

Figure 3:
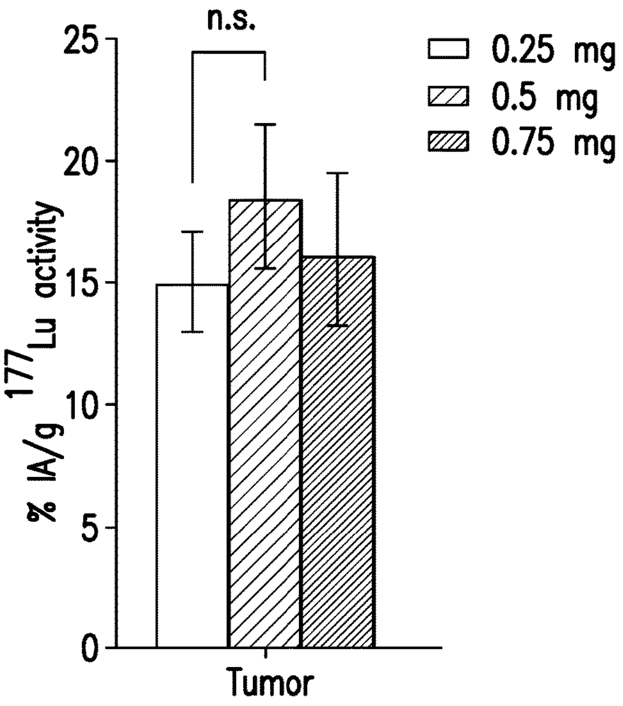

FIG. 3. Ex vivo biodistribution studies of $^{177}$Lu activity in various tissues for optimization of BsAb for anti-HER2 DOTA-PRIT with $^{177}$Lu-DOTA-Bn (5.5-5.6 MBq; ~30 pmol) in groups of nude mice bearing subcutaneous (s.c.) BT-474 tumors (n=4/group). No clearing agent step was given. $^{177}$Lu activity uptake (as percent injected activity (% IA/g); mean±SD) at 24 h p.i. in tumor following anti-HER2-DOTA-PRIT including various doses of BsAb (0.25, 0.50, or 0.75 mg BsAb/mouse; 1.19-3.57 nmol/mouse) was determined. No significant (n.s.) difference (P>0.05) was seen in tumor uptake of $^{177}$Lu activity between groups given either 0.25 mg BsAb/mouse or 0.50 mg BsAb/mouse, suggesting that 0.25 mg BsAb/mouse was optimum.

Figure 4:
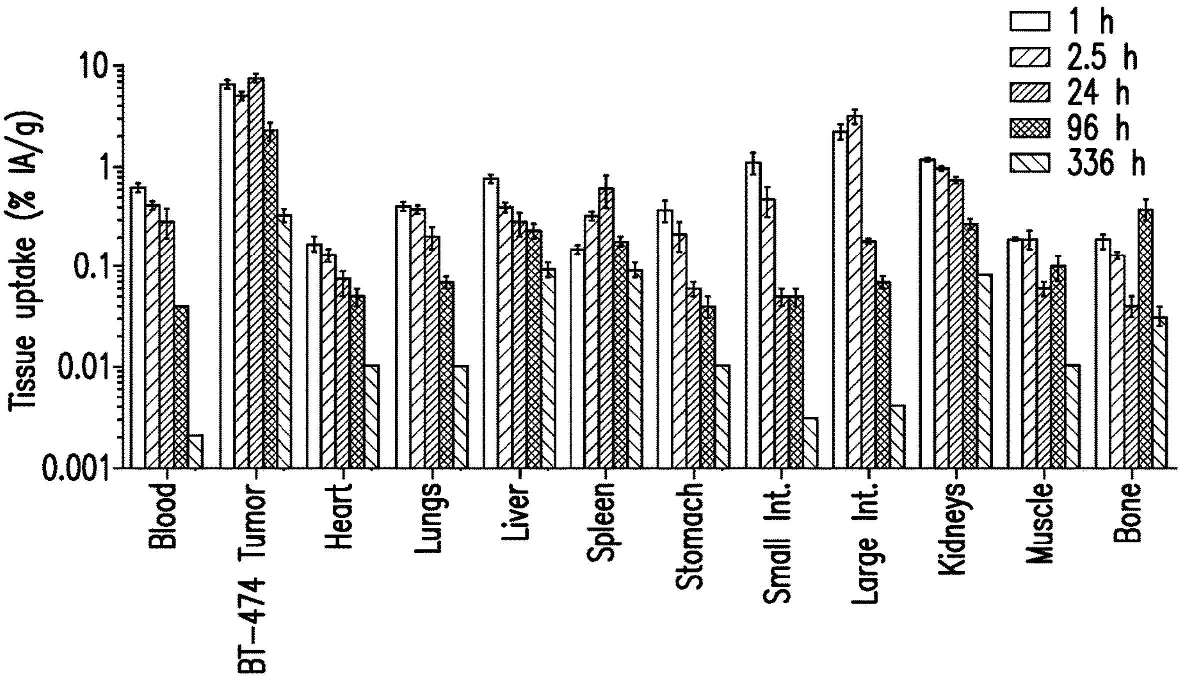

FIG. 4. Optimized anti-HER2-DOTA-PRIT shows very high tumor targeting of $^{177}$Lu activity with minimal uptake in normal tissues, including blood and kidney, as early as 1 h p.i. Serial biodistribution data from 1-336 h p.i. of pretargeted $^{177}$Lu-DOTA-Bn 5.5-6.1 MBq (~30 pmol) showing tissue uptake (as % IA/g; note: log-scale for y-axis) in s.c. BT-474 tumor and select normal tissues. Data for 24 h p.i., during which tumor uptake was maximum, is also provided in Table 10 (see below in Section 6). Data for all time points studied are provided in tabular form in Table 12 (see below in Section 6).

Figure 5A:
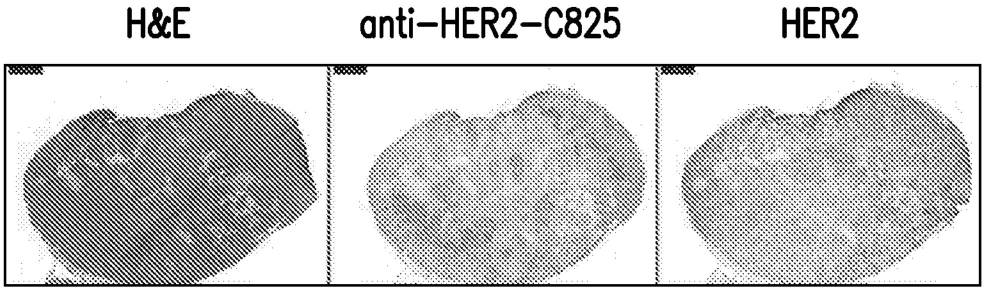
Figure 5B:
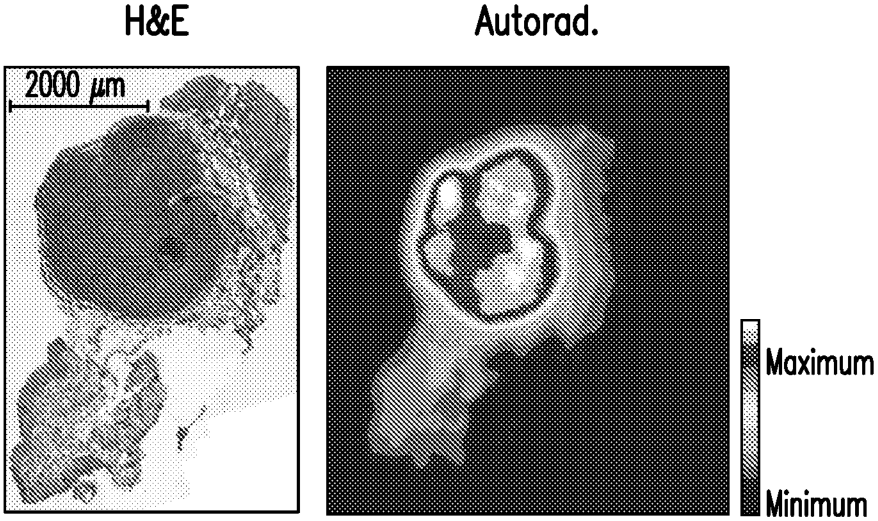

FIG. 5A and FIG. 5B. Representative histology, immunohistochemistry (IHC), and autoradiography (Autorad.) to assay the BT-474-intratumoral distribution of BsAb and pretargeted $^{177}$Lu activity. FIG. 5A: IHC at 24 h p.i. of anti-HER2-C825 BsAb (0.25 mg, 1.19 nmol). Scale bar is 1000 μm. Using image-based densitometry, the % positive area of BsAb-IHC and HER2-IHC was 51 and 61%, respectively, giving a ratio of (BsAb-IHC)/(HER2-IHC) of 0.84. FIG. 5B: H & E and autoradiography (Autorad.) of pretargeted $^{177}$Lu-DOTA-Bn (55.5 MBq, 300 pmol), 24 h p.i.. Scale bar is 2000 μm.

Figure 6A:
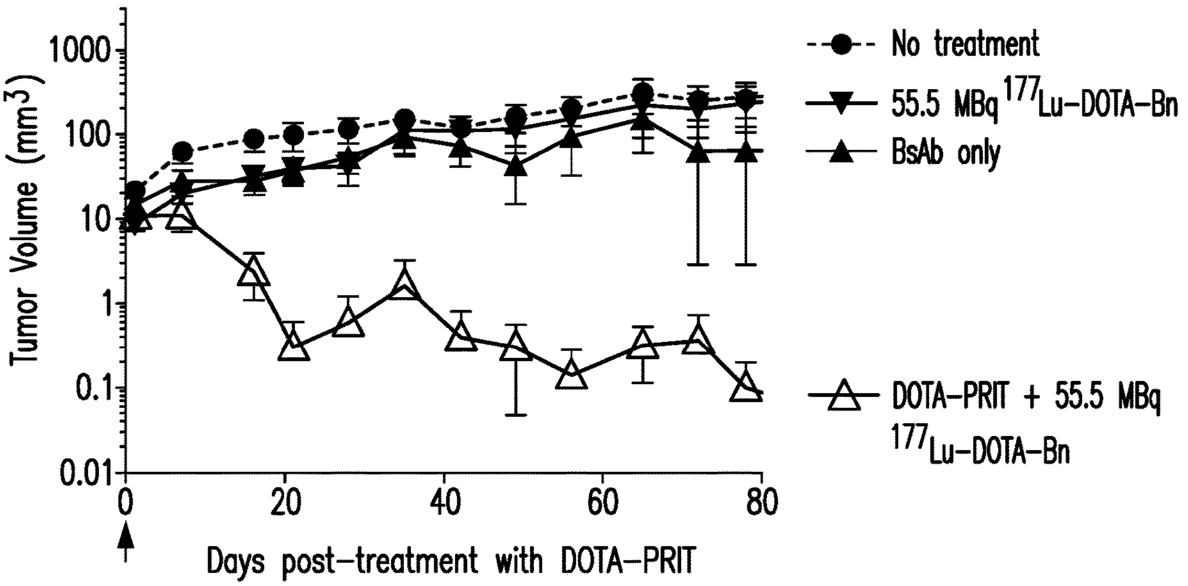
Figure 6B:
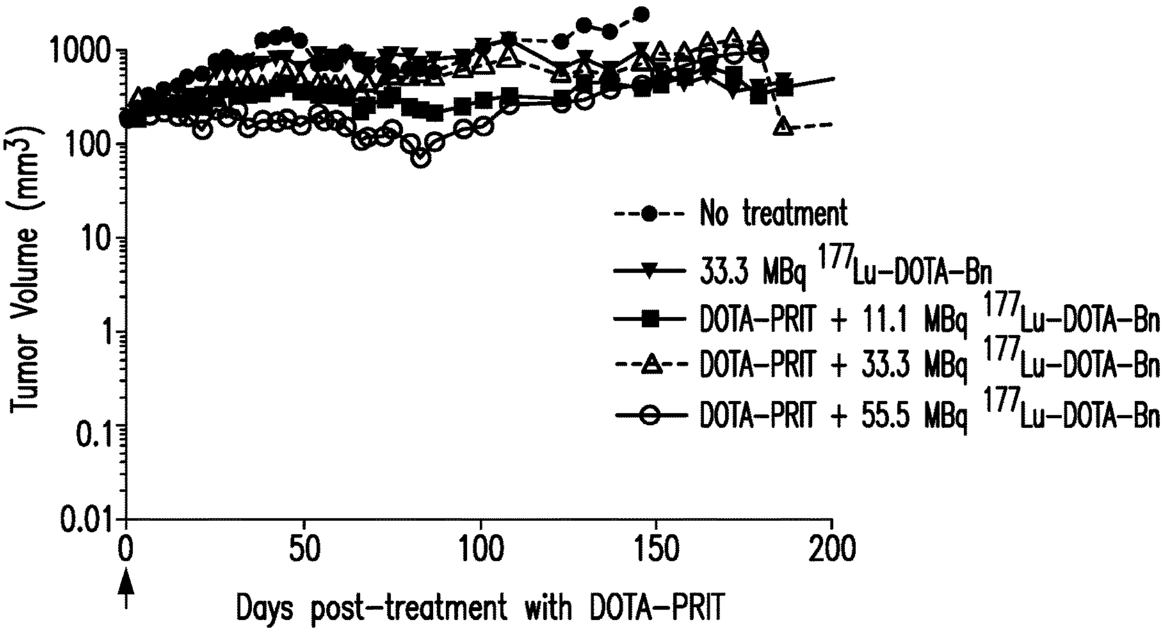

FIG. 6A and FIG. 6B. Single-cycle anti-DOTA-PRIT with IA of 55.5 MBq leads to complete responses (CRs) in mice with small-sized BT-474 tumors, but is generally ineffective in mice carrying medium-sized BT-474 tumors. Tumor volumes are presented as mean±standard error of the mean (SEM). Black arrow indicates day of injection of $^{177}$Lu-DOTA-Bn. FIG. 6A: Treatment of mice bearing small-sized tumors with single-cycle anti-HER2-DOTA-PRIT+55.5 MBq of $^{177}$Lu-DOTA-Bn versus control groups. FIG. 6B: Treatment of mice bearing medium-sized tumors with single-cycle anti-HER2-DOTA-PRIT+11.1, 33.3 or 55.5 MBq of $^{177}$Lu-DOTA-Bn versus control groups.

Figure 7:
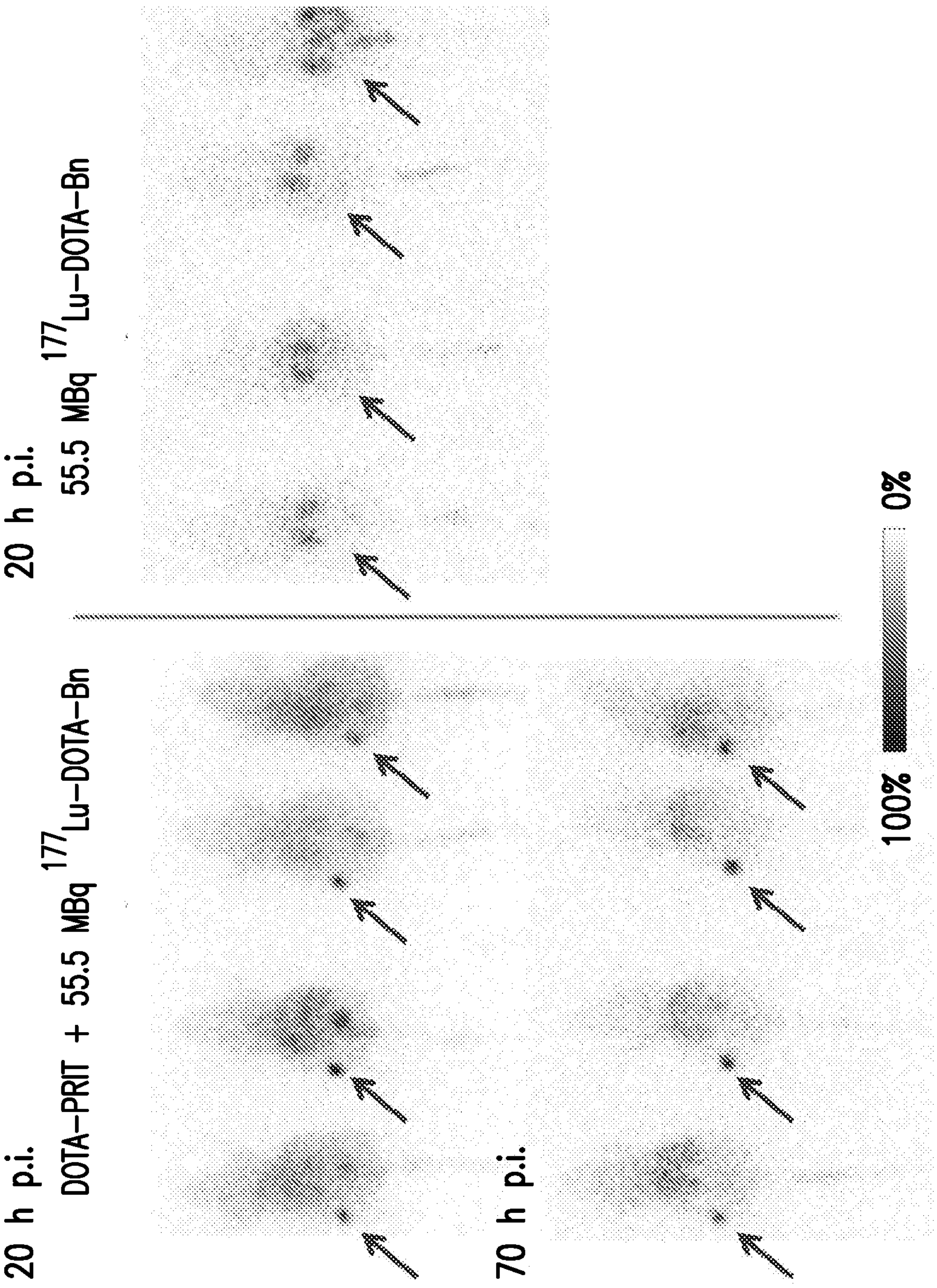

FIG. 7. Theranostic anti-HER2 DOTA-PRIT+$^{177}$Lu-DOTA-Bn. Planar scintigraphy of groups of mice bearing s.c. BT-474 xenografts (red arrows; palpable-30 mm$^3$) undergoing either anti-HER2 DOTA-PRIT+$^{177}$Lu-DOTA-Bn (left images) or treatment with non-targeted $^{177}$Lu-DOTA-Bn (right images). Pretargeting-specific tumor uptake of $^{177}$Lu activity was evident, while mice administered 55.5 MBq $^{177}$Lu-DOTA-Bn showed uptake primarily in kidney, consistent with renal clearance of $^{177}$Lu-DOTA-Bn. All images are presented on the same scale.

Figure 8:
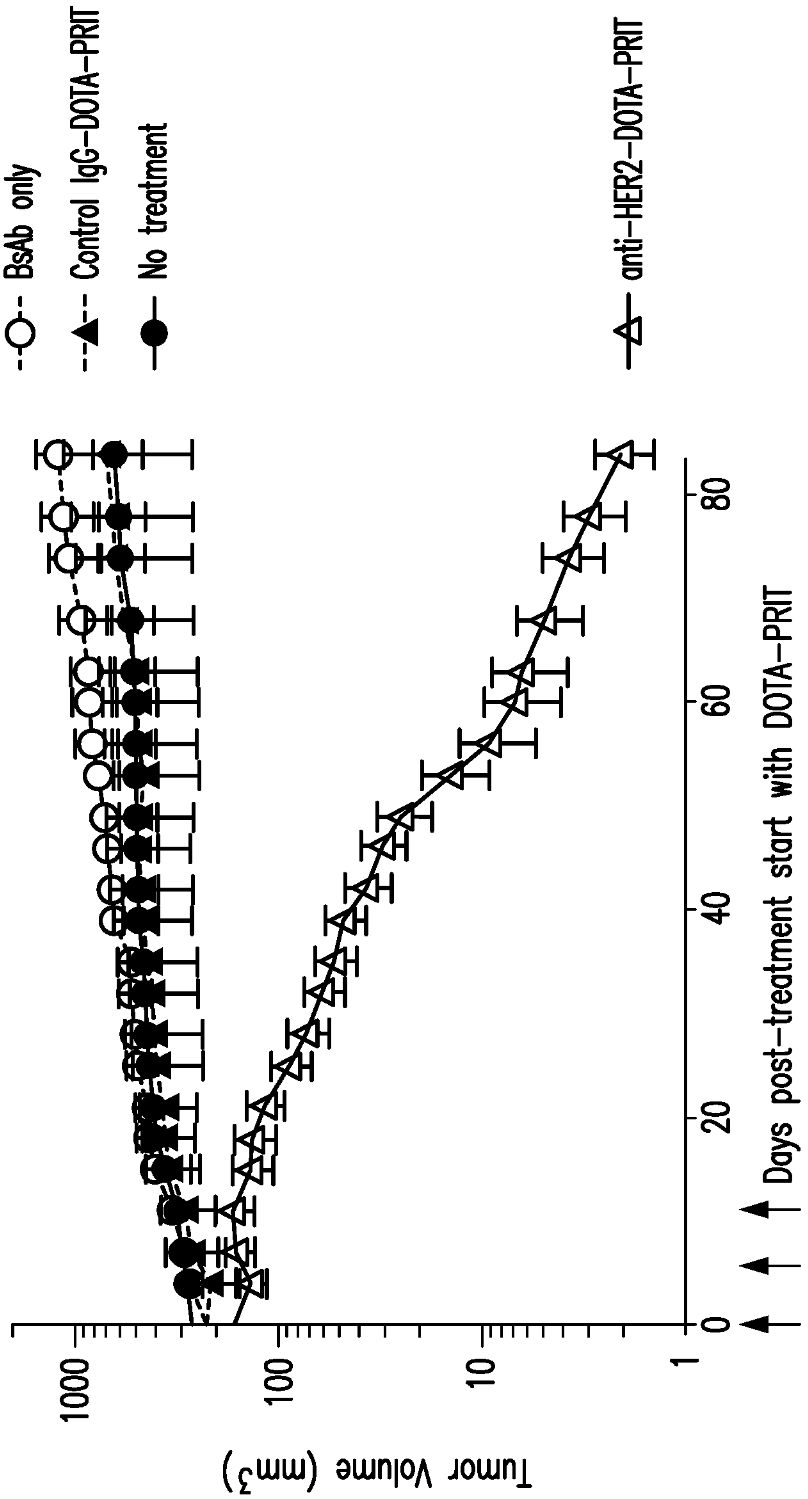

FIG. 8. Fractionated anti-DOTA-PRIT with IA of 167 MBq leads to 100% CRs in mice with medium-sized xenografts, with no recurrence at 85 d. Tumor volumes are presented as mean±SEM. Black arrow indicates day of injection of $^{177}$Lu-DOTA-Bn.

Figure 9A:
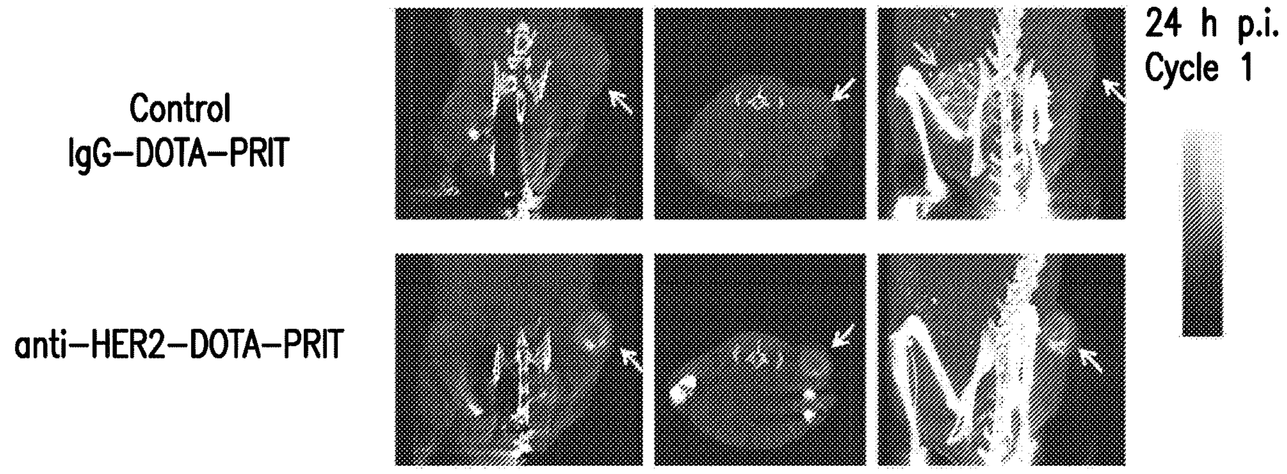
Figure 9B:
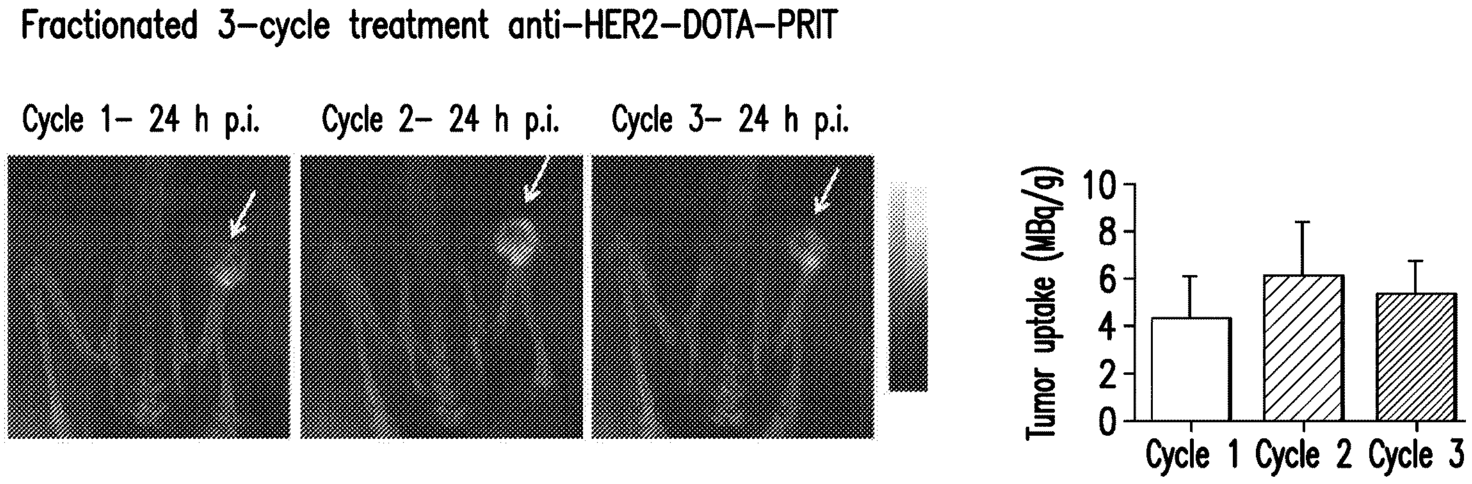

FIG. 9A and FIG. 9B. SPECT/CT monitoring of fractionated anti-HER2-DOTA-PRIT treatment. The imaging field of view was limited to the caudal half of the animal (midline to tail) to center on tumor (white arrow). Bladder is indicated when appropriate by yellow arrow. FIG. 9A: Representative SPECT/CT images of BT-474-tumor bearing animals 24 h p.i. of cycle 1 $^{177}$Lu-DOTA-Bn (55.5 MBq, 300 pmol) with pretargeted with either Control IgG-DOTA-PRIT or anti-HER2-DOTA-PRIT (from left to right: coronal and transverse slices through center of tumor, maximum intensity projection (MIP)). FIG. 9B: Representative serial SPECT/CT MIP images of a BT-474-tumor bearing animal undergoing fractionated anti-HER2-DOTA-PRIT (left), taken 24 h p.i. of each cycle radioactive injection. The image-derived region-of-interest (ROI) values for tumor uptake (mouse 1 (M1), M2 and M3) at 24 h p.i. of cycle 1, 2, or 3 $^{177}$Lu-DOTA-Bn (55.5 MBq, 300 pmol) are presented as MBq/g (mean±SD).

Figure 10:
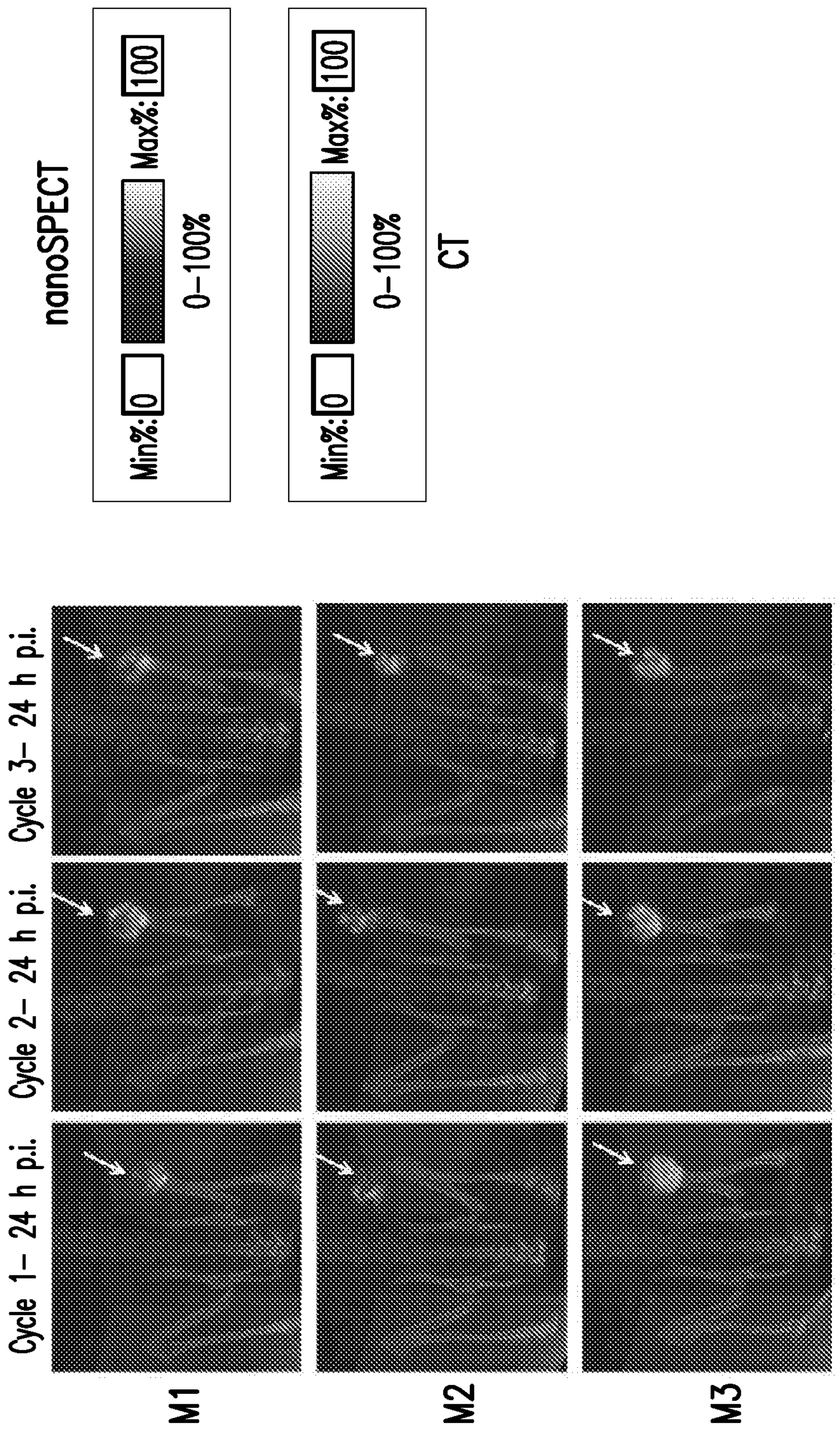

FIG. 10. Theranostic fractionated anti-HER2-DOTA-PRIT+$^{177}$Lu-DOTA-Bn. SPECT/CT images of ⅗ animals (s.c. BT-474 tumors; randomly selected animals mouse 1 (M1), M2 and M3) undergoing fractionated 3-cycle treatment with anti-HER2-DOTA-PRIT+55.5 MBq of $^{177}$Lu-DOTA-Bn. White arrows indicate tumor in lower flank.

Figure 11:
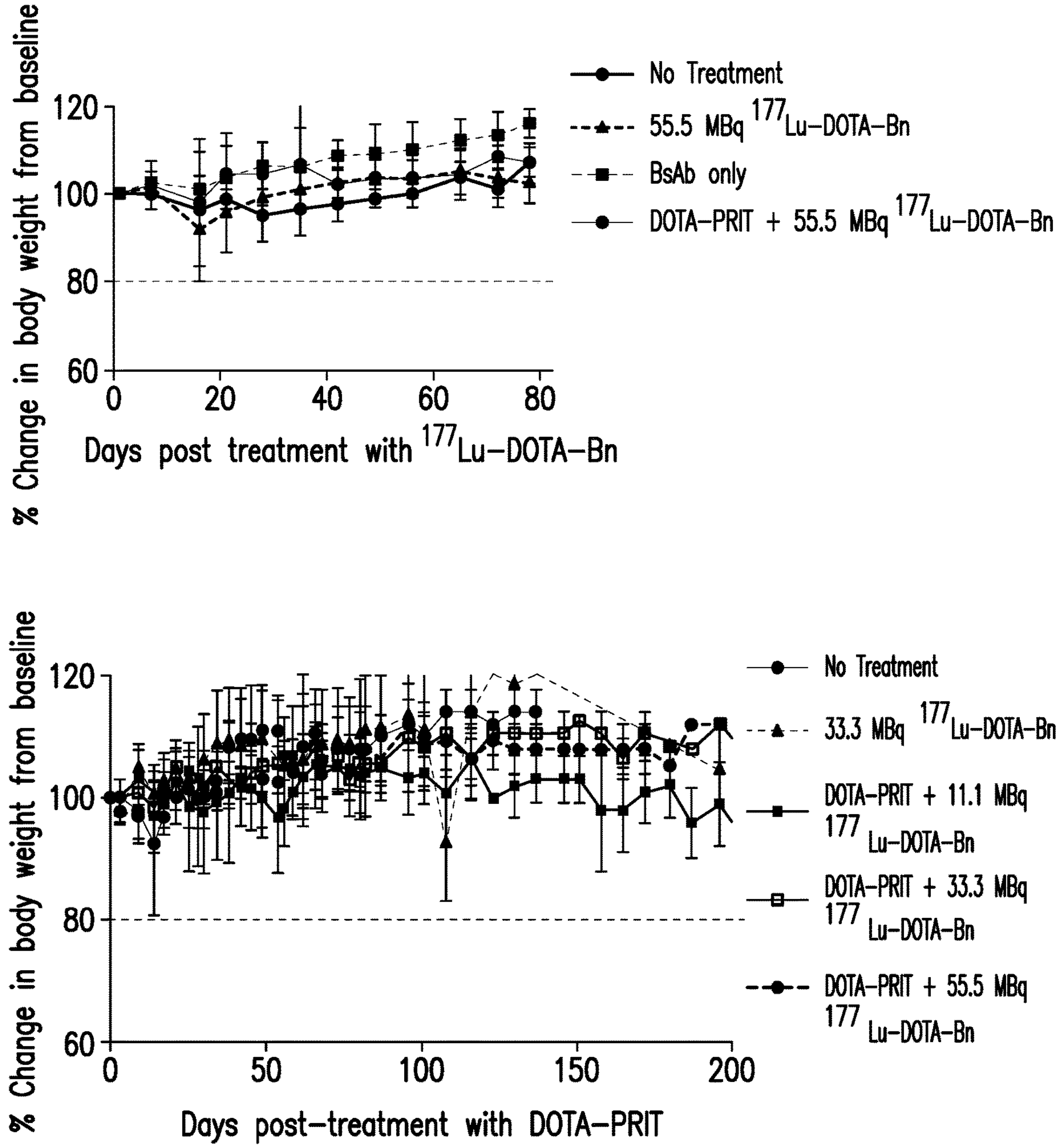
Figure 12A:
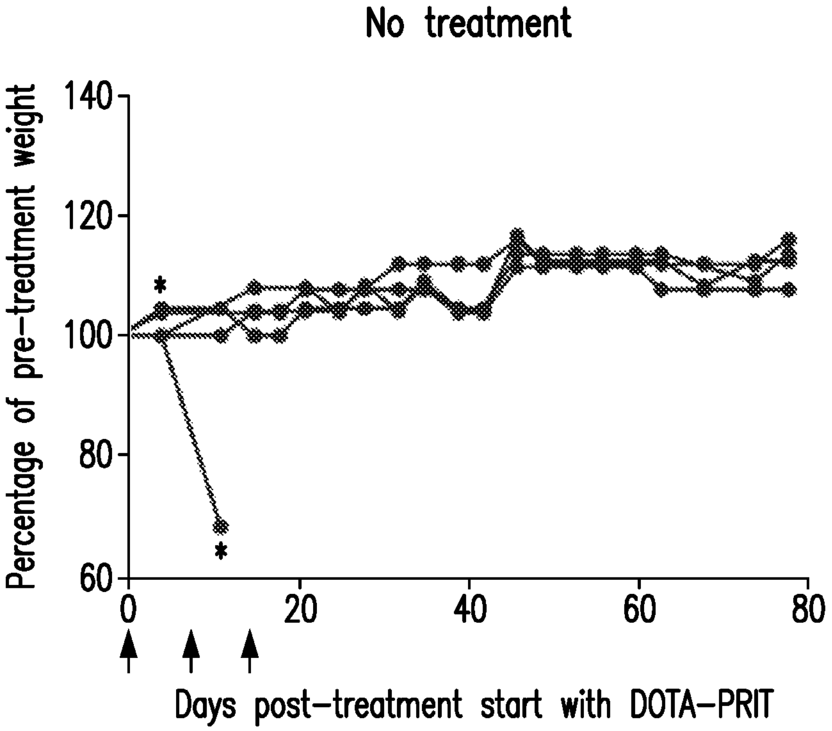
Figure 12B:
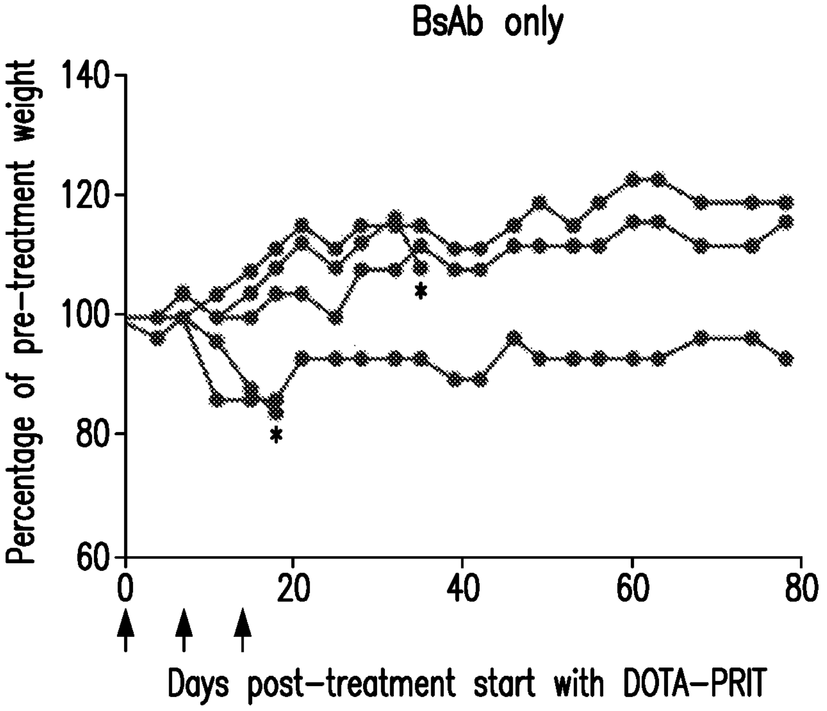
Figure 12C:
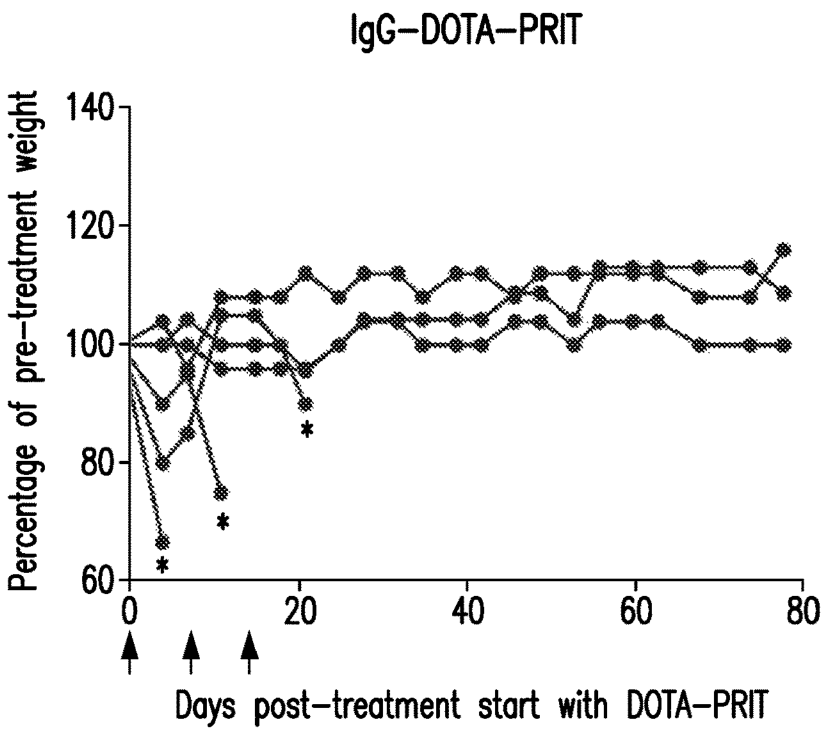
Figure 12D:
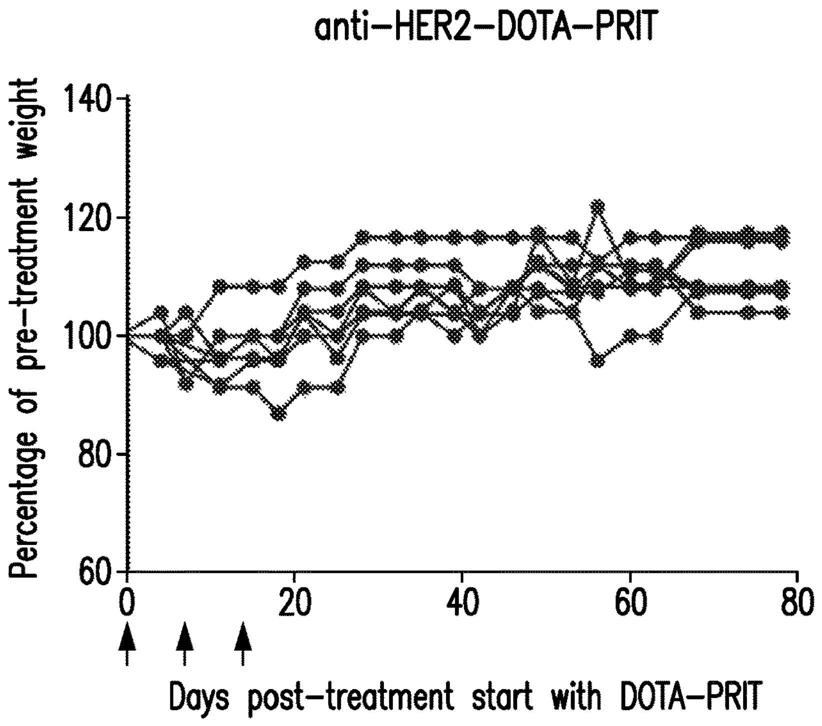

FIG. 11. Animal weights at pre-treatment (baseline, day 0) up to ~85-200 d post-treatment with single-cycle anti-HER2 DOTA-PRIT+11.1-55.5 MBq $^{177}$Lu-DOTA-Bn. Data is presented as mean±SD.

FIG. 12A-FIG. 12D. Animal weights at pre-treatment (baseline, day 0) up to 80 d post-treatment with treatment controls (FIG. 12A, FIG. 12B, and FIG. 12C) or (FIG. 12D) fractionated anti-HER2-DOTA-PRIT. Black arrows indicate days of injection of $^{177}$Lu-DOTA-Bn. An asterisk denotes day of euthanasia due to excessive weight loss (i.e. when weight drops to 80% of baseline) or day when discovered deceased.

Figure 13:
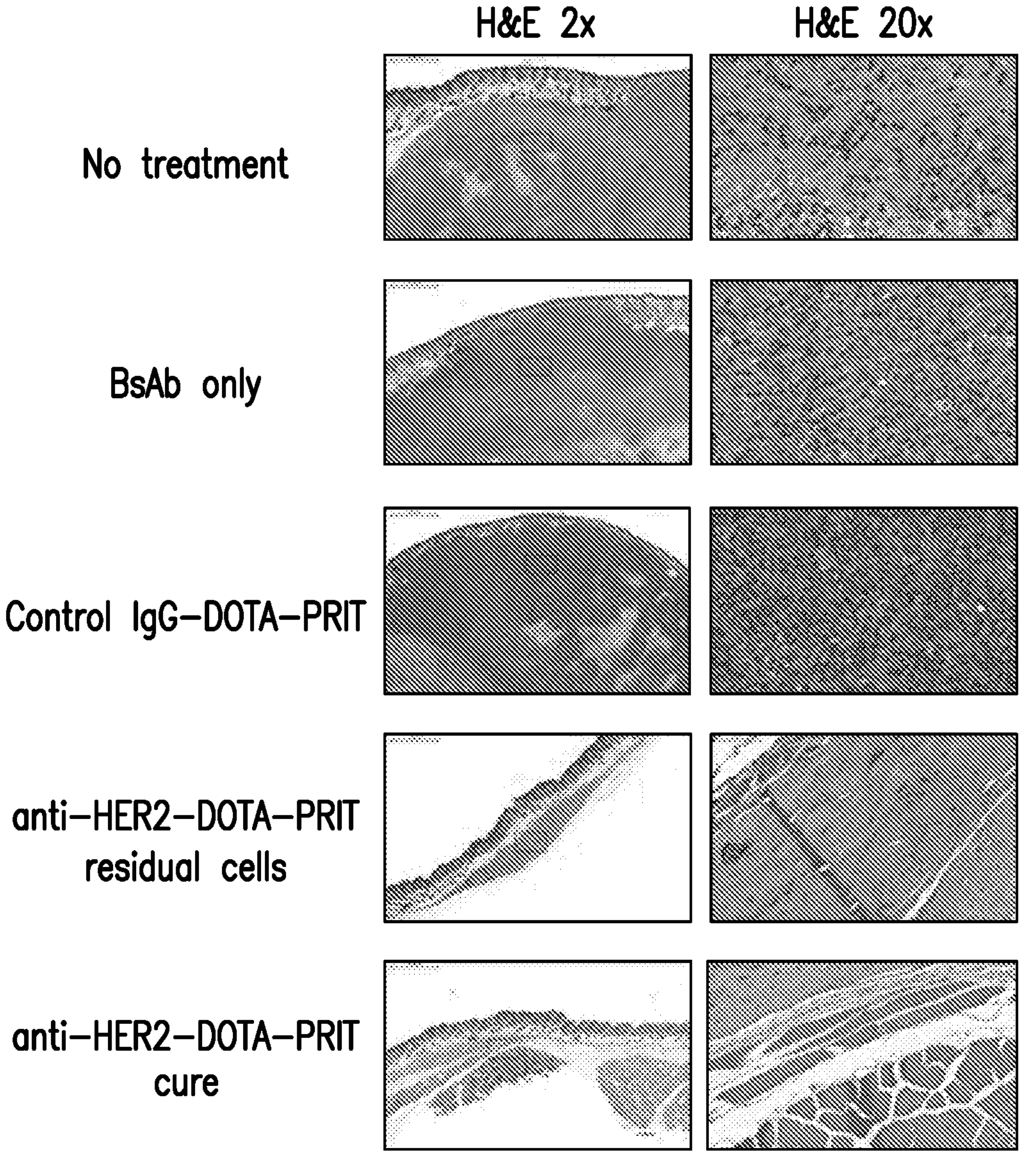
Figure 14:
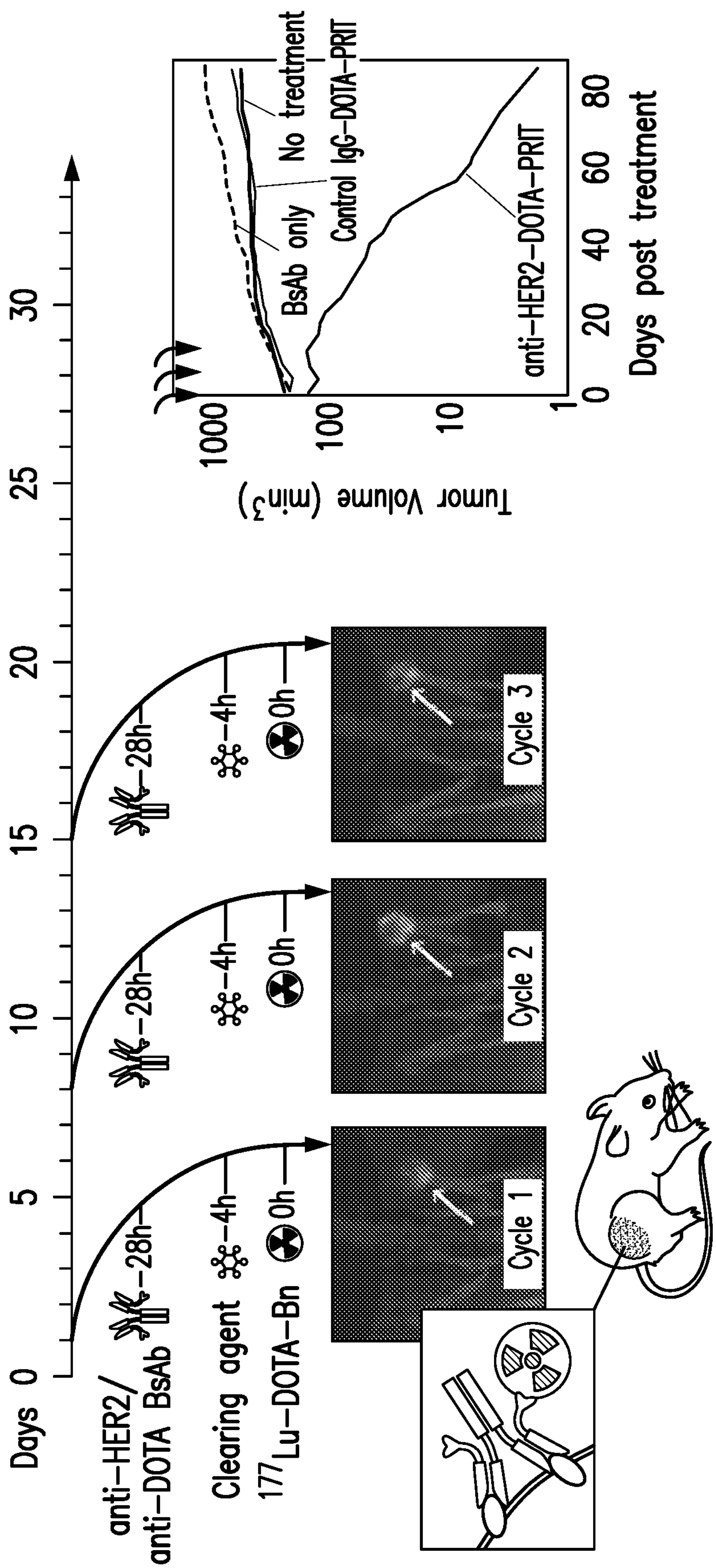

FIG. 13. Morphologic analysis of the site of BT-474 tumor-inoculation at 85 d shows that treatment with anti-HER2-DOTA-PRIT leads to cures (⅝) or microscopic residual disease (⅜), while controls (10/10) show bulk tumor present by H&E staining (see Table 24 for detailed description FIG. 14. DOTA-PRIT method.

Figure 15:
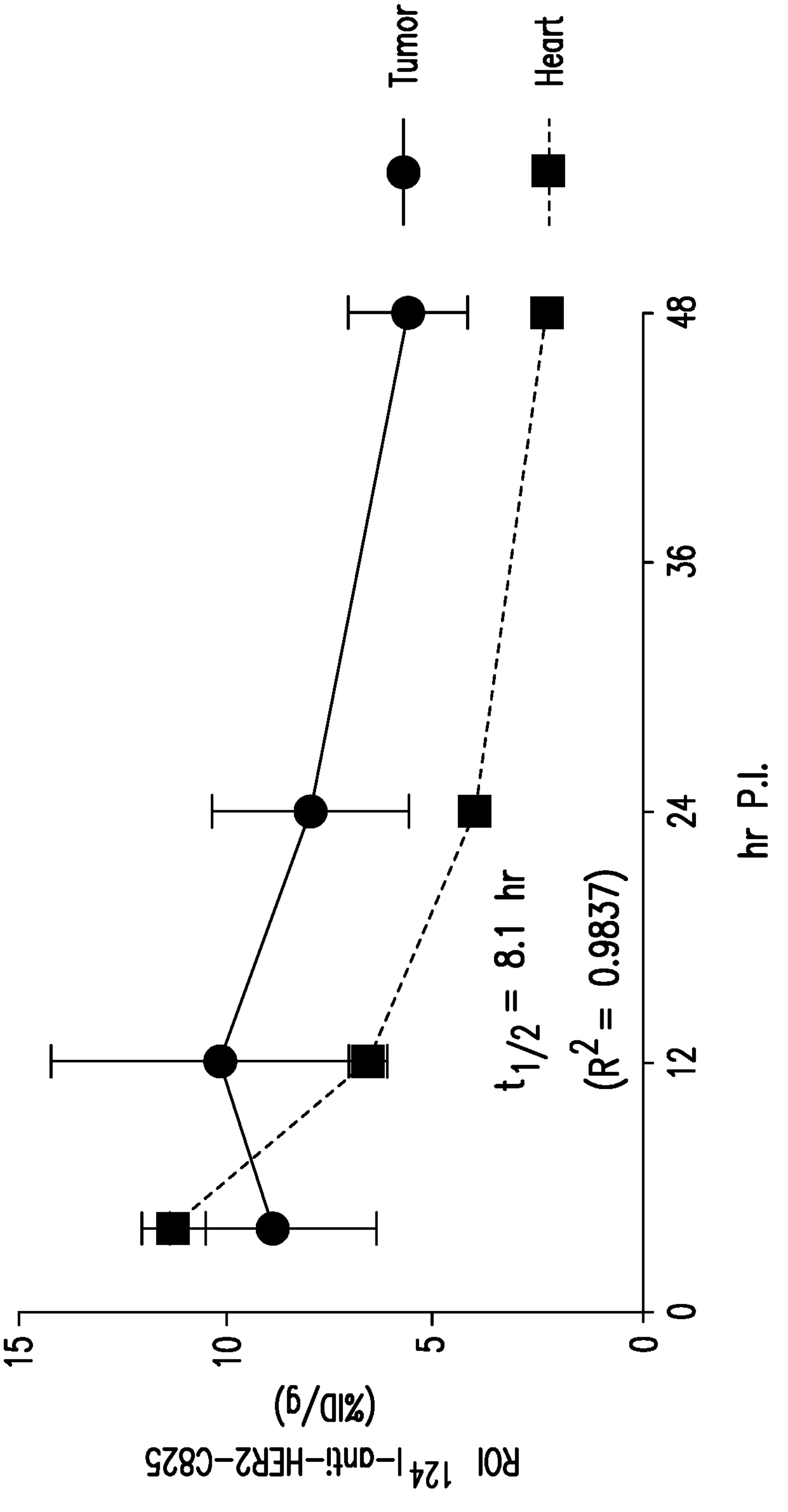

FIG. 15. Serial PET imaging of $^{124}$I-anti-HER2-C825 in nude mice bearing s.c. BT-474 tumors.

Figure 16:
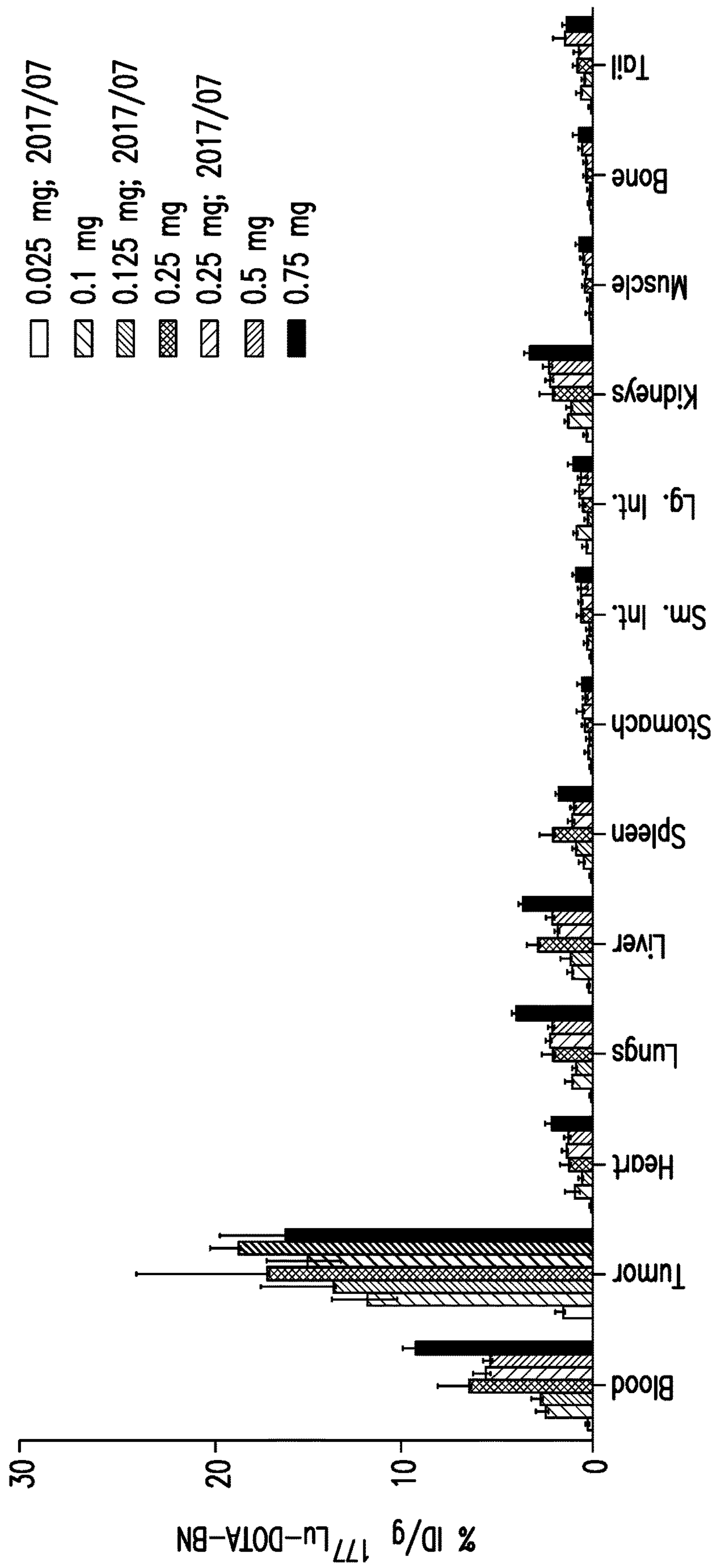

FIG. 16. BT-474 xenografts 100-200 mg weight. Uptake of $^{177}$Lu-DOTA-Bn injected at 28 h after anti-HER2-C825 BsAb antibody injection. No clearing agent was used and the dose of total antigen was varied in separate experiments, from 0.025 mg to 0.75 mg. Tumors were harvested at 24 h post-injection ("p.i.") of radioactivity or 52 h post initial antibody injection. The uptake, which depends on binding of the radiohapten to the high affinity Fv fragment attached to the antibody, was shown to be a function of dose, and increased up to a plateau at about 125-250 micrograms.

Figure 17:
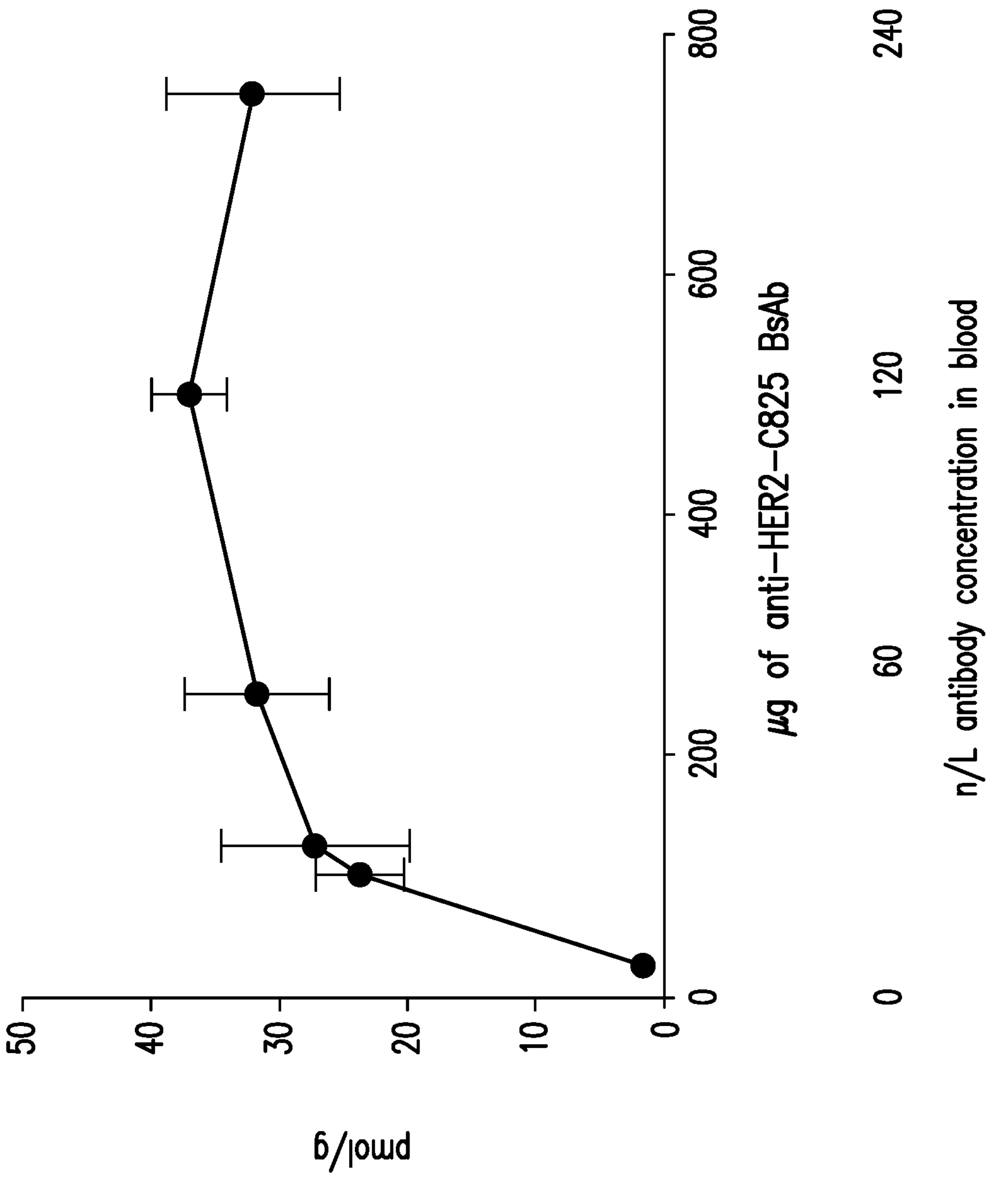

FIG. 17. Calculated retention of $^{177}$Lu-DOTA-Bn at the tumor site, as a function of dose administered, and concentration of antibody in the blood). This assumes that the uptake curve in FIG. 15 applies. Note that the uptake curve follows the usual uptake binding curve where total bound increases to a plateau due to saturation kinetics.

Figure 18:
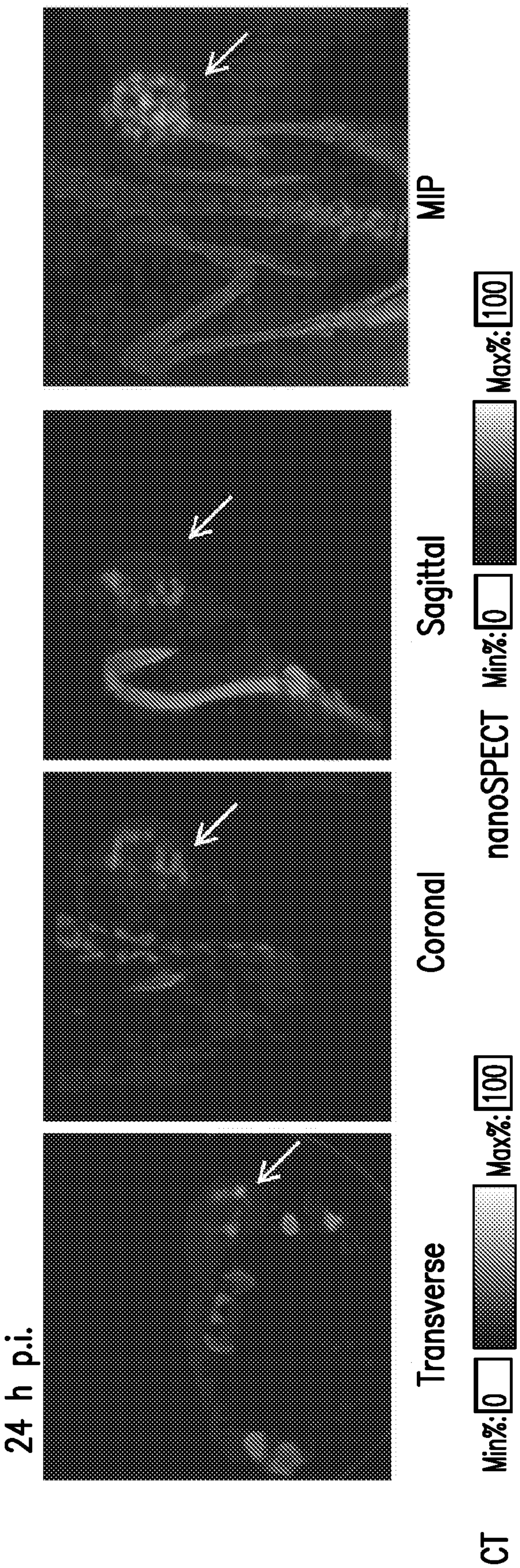

FIG. 18. Representative SPECT/CT images of a s.c. BT-474 tumor-bearing mouse (216 mm$^3$ by external caliper measurement) 24 h p.i. of anti-HER2-DOTA-PRIT pretargeted $^{177}$Lu-DOTA-Bn (55.5 MBq, ~300 pmol). The imaging field of view was limited to the caudal half of the animal (midline to tail) to center on tumor (white arrow). Immediately after imaging, the mouse was euthanized and the activity concentrations in tumor was determined by ex vivo biodistribution (as percent injected activity per gram of tissue (% IA/g), decay corrected) to be 6.06 (for n=3/5.53±0.27% IA/g). MIP=maximum intensity projection.

5. DETAILED DESCRIPTION

Provided herein are methods of treating cancer in a subject in need thereof, comprising: (a) administering to the subject a therapeutically effective amount of a bispecific binding agent, (b) not more than 12 hours after step (a) of administering to the subject the therapeutically effective amount of the bispecific binding agent, administering to the subject a therapeutically effective amount of a clearing agent, wherein said clearing agent binds to said second binding site and functions to reduce the bispecific binding agent circulating in the blood of the subject; and after step (b) of administering to the subject the therapeutically effective amount of the clearing agent, administering to the subject a therapeutically effective amount of a radiotherapeutic agent. The bispecific binding agents for use in a method of treating cancer described herein are able to specifically bind to (i) a cancer antigen expressed by the cancer being treated by the method; (ii) the clearing agent; and (iii) the radiotherapeutic agent. In a particular aspect, the bispecific binding agent for use in a method of treating cancer described herein specifically binds concurrently to (i) a cancer antigen expressed by the cancer being treated; and (ii) the radiotherapeutic agent. Without being bound by any particular theory, the bispecific binding agent forms a bridge between the cancer cell and the radiotherapeutic agent, permitting the radiotherapeutic agent to kill the cancer cell bound to the bispecific binding agent. Surprisingly, the methods of treating cancer described herein are effective even when targeting a cancer antigen that is internalized into the cancer cell (see, e.g., Section 6). Moreover, the methods of treating cancer described herein can advantageously be performed in, e.g., less than 16 hours because the step of administering the clearing agent can occur as early as one hour after administration of the bispecific binding agent (as compared to standard 24-120 hour waiting period between administration of a tumor targeting agent and a clearing agent).

Also provided herein are bispecific binding agents (see, e.g., Section 5.2), clearing agents (see, e.g., Section 5.3), and radiotherapeutic agents (see, e.g., Section 5.4) for use in the methods described herein. Also provided herein are compositions (e.g., pharmaceutical compositions) and kits (see, e.g., Section 5.5) comprising said bispecific binding agents, clearing agents, and/or radiotherapeutic agents.

5.1 Methods of Treating Cancer

In a specific embodiment, provided herein are methods for treating cancer in a subject in need thereof, comprising: (a) administering to the subject a therapeutically effective amount of a bispecific binding agent, wherein the bispecific binding agent comprises a first molecule covalently bound, optionally via a linker, to a second molecule, wherein the first molecule comprises a first binding site, wherein the first binding site specifically binds to a first target, wherein the first target is a cancer antigen expressed by said cancer, wherein the second molecule comprises a second binding site, wherein the second binding site specifically binds to a second target, wherein the second target is not the cancer antigen; (b) not more than 12 hours after step (a) of administering to the subject the therapeutically effective amount of the bispecific binding agent, administering to the subject a therapeutically effective amount of a clearing agent, wherein said clearing agent binds to said second binding site and functions to reduce the bispecific binding agent circulating in the blood of the subject; and after step (b) of administering to the subject the therapeutically effective amount of the clearing agent, administering to the subject a therapeutically effective amount of a radiotherapeutic agent, wherein the radiotherapeutic agent comprises (i) the second target bound to a metal radionuclide, wherein the second target is a metal chelator; or (ii) the second target bound, preferably covalently, to a metal chelator, said metal chelator being bound to a metal radionuclide.

Also provided herein is a method of treating cancer in a subject in need thereof, comprising: (a) administering to the subject a first therapeutically effective amount of a bispecific binding agent, wherein the first therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg, wherein the bispecific binding agent comprises a first molecule covalently bound, optionally via a linker, to a second molecule, wherein said cancer expresses HER2, wherein the first molecule comprises an antibody or an antigen binding fragment thereof, or a scFv, wherein said antibody or antigen-binding fragment thereof, or scFv (i) binds to HER2 on said cancer, and (ii) comprises all three of the heavy chain CDRs of SEQ ID NO: 20, and all three of the light chain CDRs of SEQ ID NO: 19, wherein the second molecule comprises a second binding site, wherein the second binding site specifically binds to a second target, wherein the second target is not the cancer antigen; (b) after step (a) of administering to the subject the therapeutically effective amount of the bispecific binding agent, administering to the subject a therapeutically effective amount of a clearing agent, wherein said clearing agent binds to said second binding site and functions to reduce the bispecific binding agent circulating in the blood of the subject; and (c) after step (b) of administering to the subject the therapeutically effective amount of the clearing agent, administering to the subject a therapeutically effective amount of a radiotherapeutic agent, wherein the radiotherapeutic agent comprises (i) the second target bound to a metal radionuclide, wherein the second target is a metal chelator; or (ii) the second target bound, preferably covalently, to a metal chelator, said metal chelator being bound to a metal radionuclide, wherein the subject is a human. In a specific embodiment, the therapeutically effective amount of the bispecific binding agent is about 450 mg.

Also provided herein is a method of treating cancer in a subject in need thereof, comprising (a) administering to the subject a first therapeutically effective amount of a bispecific binding agent, wherein the first therapeutically effective amount of the bispecific binding agent is 100 mg to 700 mg, 200 mg to 600 mg, 200 mg to 500 mg, 300 mg to 400 mg, about 300 mg, about 450 mg, or about 500 mg, wherein the bispecific binding agent comprises a first molecule covalently bound, optionally via a linker, to a second molecule, wherein said cancer expresses HER2, wherein the first molecule comprises an antibody or an antigen binding fragment thereof, or a scFv, wherein said antibody or antigen-binding fragment thereof, or scFv (i) binds to HER2 on said cancer, and (ii) comprises all three of the heavy chain CDRs of SEQ ID NO: 20, and all three of the light chain CDRs of SEQ ID NO: 19, wherein the second molecule comprises a second binding site, wherein the second binding site specifically binds to a second target, wherein the second target is not the cancer antigen; (b) after step (a) of administering to the subject the therapeutically effective amount of the bispecific binding agent, administering to the subject a therapeutically effective amount of a clearing agent, wherein said clearing agent binds to said second binding site and functions to reduce the bispecific binding agent circulating in the blood of the subject; and (c) after step (b) of administering to the subject the therapeutically effective amount of the clearing agent, administering to the subject a therapeutically effective amount of a radiotherapeutic agent, wherein the radiotherapeutic agent comprises (i) the second target bound to a metal radionuclide, wherein the second target is a metal chelator; or (ii) the second target bound to a metal chelator, said metal chelator being bound to a metal radionuclide, wherein the subject is a human.

In a specific embodiment, the bispecific binding agent is a bispecific binding agent described in Section 5.2. In a preferred embodiment, the first target of the bispecific binding agent is HER2 and the second target of the bispecific binding agent is DOTA. In a specific embodiment, the therapeutically effective amount of the bispecific binding agent is as described in Section 5.7. In a specific embodiment, the bispecific binding agent is administered to the subject via a route of administration described in Section 5.7.

In a specific embodiment, the clearing agent is a clearing agent described in Section 5.3 or Section 6. In a specific embodiment, the therapeutically effective amount of the clearing agent is as described in Section 5.7. In a specific embodiment, the clearing agent is administered to the subject via a route of administration described in Section 5.7. In a specific embodiment, the step (b) of administering to the subject the therapeutically effective amount of the clearing agent is carried out not more than 10 hours, not more than 8 hours, not more than 6 hours, not more than 4 hours, not more than 2 hours, 1-12 hours, 2-12 hours, 1-2 hours, 1-3 hours, 1-4 hours, 2-6 hours, 2-8 hours, 2-10 hours, 4-6 hours, 4-8 hours, 4-10 hours, 2 hours, or 4 hours after the step (a) of administering to the subject the therapeutically effective amount of the bispecific binding agent. In another specific embodiment, the step (b) of administering to the subject the therapeutically effective amount of the clearing agent is carried out about 2 hours, about 4 hours, about 6 hours, about 8 hours, or about 10 hours after the step (a) of administering to the subject the therapeutically effective amount of the bispecific binding agent. In a specific embodiment, the bispecific binding agent is at least 100 kDa and the step (b) of administering to the subject the therapeutically effective amount of the clearing agent is carried out not more than 4 hours after the step (a) of administering to the subject the therapeutically effective amount of the bispecific binding agent. In a specific embodiment, the step (b) of administering to the subject the therapeutically effective amount of the clearing agent is carried out at a time that is at most 10% greater than or at most 10% less than a time described herein after the step (a) of administering to the subject the therapeutically effective amount of the bispecific binding agent.

In a specific embodiment, the radiotherapeutic agent is a radiotherapeutic agent described in Section 5.4 or Section 6. In a preferred embodiment, the radiotherapeutic agent comprises DOTA or a derivative thereof bound to a metal radionuclide. In a preferred embodiment in which the radiotherapeutic agent comprises DOTA or a derivative thereof bound to a metal radionuclide, the metal radionuclide is $^{177}$Lu. In a specific embodiment, the therapeutically effective amount of the radiotherapeutic agent is as described in Section 5.7. In a specific embodiment, the radiotherapeutic agent is administered to the subject via a route of administration described in Section 5.7. In a specific embodiment, the step (c) of administering to the subject the therapeutically effective amount of the radiotherapeutic agent is carried out 1-2 hours, 1-3 hours, 1-4 hours, 2-6 hours, 2-8 hours, 2-10 hours, 4-6 hours, 4-8 hours, 4-10 hours, not more than 1 hour, not more than 2 hours, not more than 3 hours, not more than 4 hours, not more than 5 hours, not more than 6 hours, 1 hour, 2 hours, 3 hours, 4 hours, 5 hours, or 6 hours after the step (b) of administering to the subject the therapeutically effective amount of the clearing agent. In a specific embodiment, the step (c) of administering to the subject the therapeutically effective amount of the radiotherapeutic agent is carried out about 1 hour, about 2 hours, about 3 hours, about 4 hours, about 5 hours, or about 6 hours after the step (b) of administering to the subject the therapeutically effective amount of the clearing agent. In a specific embodiment, the step (c) of administering to the subject the therapeutically effective amount of the radiotherapeutic agent is carried out about 1 hour after the step (b) of administering to the subject the therapeutically effective amount of the clearing agent. In a specific embodiment, the step (c) of administering to the subject the therapeutically effective amount of the radiotherapeutic agent is carried out not more than 16 hours after the step (a) of administering to the subject the therapeutically effective amount of the bispecific binding agent. In a specific embodiment, the step (c) of administering to the subject the therapeutically effective amount of the radiotherapeutic agent is carried out at a time that is at most 10% greater than or at most 10% less than a time described herein after the step (b) of administering to the subject the therapeutically effective amount of the clearing agent. In a specific embodiment, the step (c) of administering to the subject the therapeutically effective amount of the radiotherapeutic agent is carried out at a time that is at most 10% greater than or at most 10% less than a time described herein after the step (a) of administering to the subject the therapeutically effective amount of the bispecific binding agent.

The cancer to be treated in accordance with a method described herein may be any cancer known to the skilled artisan. In a specific embodiment, the cancer is a cancer described in Section 5.6 or Section 6. In a specific embodiment, the cancer is a cancer described in Table 1, below. One skilled in the art will understand that the cancer to be treated according to a method described herein dictates the identity of the first target of the bispecific binding agent (see, e.g., Section 5.2 and Section 6) utilized in the methods described herein. For example, for use of a bispecific binding agent having a first target of HER2 in a method of treating cancer described herein, the cancer to be treated is a cancer(s) that expresses HER2 (e.g., breast cancer). In a specific embodiment, the cancer is a cancer that expresses HER2, including but not limited to, breast cancer, gastric cancer, an osteosarcoma, desmoplastic small round cell cancer, squamous cell carcinoma of head and neck cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, neuroblastoma, or any other neoplastic tissue that expresses the HER2 receptor. In a specific embodiment, the cancer that expresses HER2 is resistant to treatment with trastuzumab, cetuximab, lapatinib, erlotinib, or any other small molecule or antibody that targets the HER family of receptors. In a specific embodiment, the tumor that is resistant to treatment with trastuzumab, cetuximab, lapatinib, erlotinib, or any other small molecule or antibody that targets the HER family of receptors is responsive to treatment with a bispecific binding agent of the invention. In a specific embodiment, the cancer that expresses HER2 is resistant to treatment with necitumumab, pantitumumab, pertuzumab, or ado-trastuzumab emtansine. In a specific embodiment, the cancer that expresses HER2 is resistant to treatment with necitumumab, pantitumumab, pertuzumab, or ado-trastuzumab emtansine is responsive to treatment with a bispecific binding agent of the invention. In a specific embodiment, a cancer is considered resistant to a therapy (e.g., trastuzumab, cetuximab, necitumumab, panitumumab, pertuzumab, ado-trastuzumab emtansine, lapatinib, erlotinib, or any small molecule that targets the HER family of receptors) if it has no response, or has an incomplete response (a response that is less than a complete remission), or progresses, or relapses after the therapy.

In a specific embodiment, the methods of treating cancer described herein is performed as part of a multicycle regimen as described in Section 5.7.

In a specific embodiment, the subject is a subject described in Section 5.6.

In specific embodiments, treatment can be to achieve beneficial or desired clinical results including, but not limited to, alleviation of a symptom, diminishment of extent of a disease, stabilizing (i.e., not worsening) of state of a disease, delay or slowing of disease progression, amelioration or palliation of the disease state, and remission (whether partial or total). In a specific embodiment, "treatment" can also be to prolong survival as compared to expected survival if not receiving treatment.

5.2 Bispecific Binding Agents

Provided herein are bispecific binding agents for use in the methods of treating cancer described herein (see, e.g., Section 5.1 and Section 6). The bispecific binding agents described herein comprise a first molecule covalently bound, optionally via a linker, to a second molecule, wherein the first molecule comprises a first binding site, wherein the first binding site specifically binds to a first target, wherein the first target is a cancer antigen expressed by said cancer, wherein the second molecule comprises a second binding site, wherein the second binding site specifically binds to a second target, wherein the second target is not the cancer antigen. In a specific embodiment, the bispecific binding agent is a bispecific binding agent described in Section 6.

The first molecule of the bispecific binding agent mediates binding of the bispecific binding agent to a cancer cell. In particular, the first molecule of the bispecific binding agent comprises the first binding site, which specifically binds to the first target, said first target being a cancer antigen expressed by the cancer to be treated with the bispecific binding agent according to the methods provided herein (see, e.g., Section 5.1 and Section 6).

In a specific embodiment, the first molecule comprises an antibody or an antigen-binding fragment thereof, wherein said antibody or antigen-binding fragment thereof comprises the first binding site. In a specific embodiment, the antibody of the first molecule of the bispecific binding agent is an immunoglobulin. The antibody in the bispecific binding agents of the invention can be, as non-limiting examples, a monoclonal antibody, a naked antibody, a chimeric antibody, a humanized antibody, or a human antibody. As used herein, the term "immunoglobulin" is used consistent with its well-known meaning in the art, and comprises two heavy chains and two light chains. Methods for making antibodies are described hereinbelow.

In a specific embodiment where the first molecule comprises an antibody or an antigen-binding fragment thereof, wherein said antibody or antigen-binding fragment thereof comprises the first binding site, the antibody is a human antibody. Methods of producing human antibodies are known to one skilled in the art, such as, for example, phage display methods using antibody libraries derived from human immunoglobulin sequences, using transgenic mice, immunizing mice transplanted with human peripheral blood leukocytes, splenocytes or bone marrows (e.g., Trioma techniques of XTL), using in vitro activated B cells, and using a technique referred to as "guided selection". See, e.g., U.S. Pat. Nos. 4,444,887, 4,716,111, 5,567,610, and 5,229,275; and PCT publications WO 98/46645, WO 98/60433, WO 98/24893, WO 98/16664, WO 96/34096, WO 96/33735, WO 91/10741, Cole et al., Monoclonal Antibodies and Cancer Therapy, Alan R. Riss, (1985); and Boerner et al., J. Immunol., 147(1):86-95, (1991).

A chimeric antibody is a recombinant protein that contains the variable domains including the complementarity-determining regions (CDRs) of an antibody derived from one species, preferably a rodent antibody, while the constant domains of the antibody molecule is derived from those of a different species, e.g., a human antibody where human applications are contemplated. For veterinary applications, the constant domains of the chimeric antibody may be derived from that of other species, such as, for example, horse, monkey, cow, pig, cat, or dog. For example, for use of a bispecific binding agent in a method of treating cancer in a dog, the constant domains of the chimeric antibody forming part of the bispecific binding agent may be derived from the constant domains of dog antibodies.

A humanized antibody is an antibody produced by recombinant DNA technology, in which some or all of the amino acids of a human immunoglobulin light or heavy chain that are not required for antigen specificity (e.g., the constant regions and the framework regions of the variable domains) are used to substitute for the corresponding amino acids from the light or heavy chain of the cognate, nonhuman antibody. By way of example, a humanized version of a non-human (e.g., murine) antibody to a given antigen has on both of its heavy and light chains (1) constant regions of a human antibody; (2) framework regions from the variable domains of a human antibody; and (3) CDRs from the non-human antibody. When necessary, one or more residues in the human framework regions can be changed to residues at the corresponding positions in the murine antibody so as to preserve or improve the binding affinity of the humanized antibody to the antigen. This change is sometimes called "back mutation." Similarly, forward mutations may be made to revert back to murine sequence for a desired reason, e.g., stability or affinity to antigen. Without being bound by any theory, humanized antibodies generally are less likely to elicit an immune response in humans as compared to chimeric human antibodies because the former contain considerably fewer non-human components. Methods for making humanized antibodies are known to one skilled in the art. See, e.g., EP 0 239 400; Jones et al., Nature 321:522-525 (1986); Riechmann et al., Nature 332:323-327 (1988); Verhoeyen et al., Science 239: 1534-1536 (1988); Queen et al., Proc. Nat. Acad. ScL USA 86:10029 (1989); U.S. Pat. No. 6,180,370; and Orlandi et al., Proc. Natl. Acad. Sd. USA 86:3833 (1989).

Antigen binding fragments can be Fab fragments, F(ab')2 fragments, or a portion of an antibody described herein which comprises the amino acid residues that confer on the antibody its specificity for the antigen (e.g., the complementarity determining regions (CDR)). The antibody can be derived from any animal species, such as rodents (e.g., mouse, rat or hamster) and humans. Methods for making antigen binding fragments of antibodies are known in the art. For example, antigen binding fragments can be produced by enzymatic cleavage, synthetic or recombinant techniques, as known in the art and/or as described herein.

As used herein, the terms "variable region" or "variable domain" of an antibody are used interchangeably and are commonly known in the art. Generally, the spatial orientation of CDRs and FRs in a variable domain are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction and specificity of the antibody with antigen. In certain embodiments, the variable region is a rodent (e.g., mouse or rat) variable region. In certain embodiments, the variable region is a human variable region. In certain embodiments, the variable region comprises rodent (e.g., mouse or rat) CDRs and human FRs. In particular embodiments, the variable region is a primate (e.g., non-human primate) variable region. In certain embodiments, the variable region comprises rodent or murine CDRs and primate (e.g., non-human primate) FRs.

CDRs are defined in various ways in the art, including the Kabat, Chothia, and IMGT, and Exemplary definitions. The Kabat definition is based on sequence variability (Kabat, Elvin A. et al., Sequences of Proteins of Immunological Interest. Bethesda: National Institutes of Health, 1983). With respect to the Kabat numbering system, (i) the $V_H$ CDR1 is typically present at amino acid positions 31 to 35 of the heavy chain, which can optionally include one or two additional amino acids following amino acid position 35 (referred to in the Kabat numbering scheme as 35A and 35B); (ii) the $V_H$ CDR2 is typically present at amino acid positions 50 to 65 of the heavy chain; and (iii) the $V_H$ CDR2 is typically present at amino acid positions 95 to 102 of the heavy chain (Kabat, Elvin A. et al., Sequences of Proteins of Immunological Interest. Bethesda: National Institutes of Health, 1983). With respect to the Kabat numbering system, (i) the $V_L$ CDR1 is typically present at amino acid positions 24 to 34 of the light chain; (ii) the $V_L$ CDR2 is typically present at amino acid positions 50 to 56 of the light chain; and (iii) the $V_L$ CDR3 is typically present at amino acid positions 89 to 97 of the light chain (Kabat, Elvin A. et al., Sequences of Proteins of Immunological Interest. Bethesda: National Institutes of Health, 1983). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

The Chothia definition is based on the location of the structural loop regions (Chothia et al., (1987) J Mol Biol 196: 901-917; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which will be referred to herein as the "Chothia CDRs" (see also, e.g., U.S. Pat. No. 7,709,226 and Martin, A., "Protein Sequence and Structure Analysis of Antibody Variable Domains," in Antibody Engineering, Kontermann and Dübel, eds., Chapter 31, pp. 422-439, Springer-Verlag, Berlin (2001)). With respect to the Chothia numbering system, using the Kabat numbering system of numbering amino acid residues in the $V_H$ region, (i) the $V_H$ CDR1 is typically present at amino acid positions 26 to 32 of the heavy chain; (ii) the $V_H$ CDR2 is typically present at amino acid positions 53 to 55 of the heavy chain; and (iii) the $V_H$ CDR3 is typically present at amino acid positions 96 to 101 of the heavy chain. In a specific embodiment, with respect to the Chothia numbering system, using the Kabat numbering system of numbering amino acid residues in the $V_H$ region, (i) the $V_H$ CDR1 is typically present at amino acid positions 26 to 32 or 34 of the heavy chain; (ii) the $V_H$ CDR2 is typically present at amino acid positions 52 to 56 (in one embodiment, CDR2 is at positions 52A-56, wherein 52A follows position 52) of the heavy chain; and (iii) the $V_H$ CDR3 is typically present at amino acid positions 95 to 102 of the heavy chain (in one embodiment, there is no amino acid at positions numbered 96-100). With respect to the Chothia numbering system, using the Kabat numbering system of numbering amino acid residues in the $V_L$ region, (i) the $V_L$ CDR1 is typically present at amino acid positions 26 to 33 of the light chain; (ii) the $V_L$ CDR2 is typically present at amino acid positions 50 to 52 of the light chain; and (iii) the $V_L$ CDR3 is typically present at amino acid positions 91 to 96 of the light chain. In a specific embodiment, with respect to the Chothia numbering system, using the Kabat numbering system of numbering amino acid residues in the $V_L$ region, (i) the $V_L$ CDR1 is typically present at amino acid positions 24 to 34 of the light chain; (ii) the $V_L$ CDR2 is typically present at amino acid positions 50 to 56 of the light chain; and (iii) the $V_L$ CDR3 is typically present at amino acid positions 89 to 97 of the light chain (in one embodiment, there is no amino acid at positions numbered 96-100). These Chothia CDR positions may vary depending on the antibody, and may be determined according to methods known in the art.

The IMGT definition is from the IMGT ("IMGT®, the international ImMunoGeneTics information System® website imgt.org, founder and director: Marie-Paule Lefranc, Montpellier, France; see, e.g., Lefranc, M.-P., 1999, The Immunologist, 7:132-136 and Lefranc, M.-P. et al., 1999, Nucleic Acids Res., 27:209-212, both of which are incorporated herein by reference in their entirety). With respect to the IMGT numbering system, (i) the $V_H$ CDR1 is typically present at amino acid positions 25 to 35 of the heavy chain; (ii) the $V_H$ CDR2 is typically present at amino acid positions 51 to 57 of the heavy chain; and (iii) the $V_H$ CDR2 is typically present at amino acid positions 93 to 102 of the heavy chain. With respect to the IMGT numbering system, (i) the $V_L$ CDR1 is typically present at amino acid positions 27 to 32 of the light chain; (ii) the $V_L$ CDR2 is typically present at amino acid positions 50 to 52 of the light chain; and (iii) the $V_L$ CDR3 is typically present at amino acid positions 89 to 97 of the light chain.

The cancer antigen that is the first target of a bispecific binding agent described herein may be any cancer antigen known in the art. Nonlimiting examples of cancer antigens and nonlimiting examples of cancers expressing said antigens are provided in Table 1, below. In a preferred embodiment, the cancer antigen is HER2.

TABLE 1

| Cancer Antigen | Exemplary Cancer(s) |
|---|---|
| HER2 | Breast cancer, colon, esophageal cancer, gastric cancer, an osteosarcoma, desmoplastic small round cell cancer, squamous cell carcinoma of head and neck cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, thyroid, leukemia, melanoma, Ewing's sarcoma, rhabdomyosarcoma, neuroblastoma |
| CA6 | Ovarian cancer, breast cancer, cervical cancer, and pancreatic cancer |

TABLE 1-continued

| Cancer Antigen | Exemplary Cancer(s) |
|---|---|
| CD138 | Leukemias and lymphomas |
| CD19 | Leukemias and lymphomas |
| CD22 | Leukemias and lymphomas |
| CD27L | Leukemias and lymphomas |
| CD30 | Leukemias and lymphomas |
| CD33 | Leukemias and lymphomas |
| CD37 | Leukemias and lymphomas |
| CD56 | Myeloma, myeloid leukemia, neuroendocrine tumors, Wilm's tumor, adult neuroblastoma, NK/T cell lymphomas, pancreatic acinar-cell carcinoma, pheochromocytoma, small-cell lung carcinoma, and some mesodermally-derived tumors (e.g., myosarcoma) |
| CD66e | Colon cancer |
| CD70 | Leukemias and lymphomas |
| CD74 | Glioma, thyroid cancer, lymphoma, lung cancer, liver cancer, pancreatic cancer, stomach cancer, colorectal cancer, head & neck cancer, renal cancer, urothelial cancer, prostate cancer, endometrial cancer, breast cancer, cervical cancer, ovarian cancer, skin cancer, melanoma |
| CD79b | Leukemias and lymphomas |
| EGFR | Lung, Colon, Head and Neck |
| EGFRvIII | Glioma |
| FRα | Breast and Head and Neck |
| GCC | hepatocellular Carcinoma |
| GPNMB | Melanoma |
| Mesothelin | Mesothelioma |
| MUC16 | Ovarian Cancer |
| NaPi2b | Ovarian Cancer, MX35 |
| Nectin 4 | Breast, Lung, Ovarian cancer |
| PSMA | Prostate Cancer; Brain Cancer, a variety of cancer associated vasculature |
| STEAP1 | Prostate Cancer |
| Trop-2 | Clon, ovarian, endometrial |
| 5T4 (also known as TPBG) | colon, ovarian, endometrial, cancer stem cells, esophageal, breast, cervical, non-small-cell-lung, prostate, renal, gastric, and bladder cancers |
| AGS-16 | tumors associated with Papilloma virus, head and neck, cervical cancers |
| alpha v beta6 | multiple cancers, including Gliomas, melanomas |
| CA19.9 | Colon Cancer |
| CAIX | Clear cell Renal Cancer |
| CD174 | Colon cancer, gastric cancer |
| CD180 | Colon cancer, lymphomas |
| CD227 (also known as MUC-1) | Breast, bladder |
| CD326 (also known as Epcam) | Colon cancer |
| 17 1A | Colon cancer |
| CD79a | Lymphoma, non-small-cell lung cancer, myeloma |
| CEACAM5 | Colorectal cancer |
| CRIPTO | breast, pancreatic, ovarian, and colon carcinomas |
| DLL3 | Neuroendocrine tumors |
| DS6 | Gynecologic Malignancies |
| Endothelin B receptor | Prostate Cancer |
| FAP alpha | stroma of most neoplasms, especially colorectal, pancreatic etc |
| GD2 | Neuroblastoma, Small cell lung cancer, sarcomas, Gliomas |
| Mesothelin | Mesothelioma |
| PMEL 17 | melanoma |
| SLC44A4 | Breast, Prostate |
| TENB2 | Prostate Cancer |
| TIM-1 | Ovarian, Lung, Renal |
| CD98 | Triple negative Breast Cancer |
| Endosialin (also known as CD248 and Tem1) | Sarcoma, Neuroblastoma |
| Fibronectin Extra-domain B (also known as ED-B) | wide variety of cancers as a marker of tumor associated angiogenesis |
| LIV-1 (also known as ZIP6) | breast, cancer, hepatocellular |
| Mucin 1 | many human epithelial cancers |
| p-cadherin | gastric cancer, bladder cancer |
| Fyn | colon and breast cancer |
| SLTRK6 | Urothelial Cancers |
| Tenascin c | Glioblastoma multiforme |
| VEGFR2 (also known as CD309) | tumor associated vasculature, numerous tumors |
| PRLR | Breast Cancer |
| CD20 | Lymphoma Leukemia |
| CD72 | Lymphoma Leukemia |

TABLE 1-continued

| Cancer Antigen | Exemplary Cancer(s) |
|---|---|
| Fibronectin | tumor associated vasculature |
| GPA33 | colon, gastric pancreatic |
| splice isoform of tenascin-C | Glioblastoma |
| TAG-72 | Colon, Breast, Lung |
| B7-H3 | Prostate, Gliomas |
| L1CAM | Ovarian, Glioma, Colon, endometrial, other cancer stem cells and invasive epithelial tumors |
| Lewis Y | epithelial tumors: breast, GI tract; prostate |
| polysialic acid | Small cell lung cancer, Wilms tumors |

Traditionally, pretargeting radioimmunotherapy ("PRIT") strategies have been performed with antigens that are expressed on the cell surface and are not prone to endocytosis (see, e.g., Casalini et al., Journal of Nuclear Medicine, 1997; 38:1378-1381; Liu, et al., Cancer Biother Radiopharm, 2007; 22(1):33-39; Knight, et al., Molecular Pharmaceutics, 2017; 14(7): 2307-2313; edited by Baum, Richard P. Therapeutic Nuclear Medicine 2014, Springer-Verlag Berlin Heidelberg, pg 612; edited by Oldham, Robert K. and Dillman, Robert O. Principles of Cancer Biotherapy 2009, Springer, ph 486). Without being bound by any particular theory, the finding that internalization of a binding agent (e.g., an antibody) bound to the cancer antigen does not yield optimal presentation of the tumor targeting agent (e.g., a bispecific antibody) on the surface of the cancer cell for interaction with a radiotherapeutic agent (see, e.g., Boerman et al., 2003, Pretargeted Radioimmunotherapy of Cancer: Progress Step by Step*. J. Nucl. Med. 44(3):400-411; Casalini et al., 1997, Tumor Pretargeting: Role of Avidin/Streptavidin on Monoclonal Antibody Internalization. J. Nucl. Med.; 38(9):1378-1381; Walter et al., 2010, Pretargeted Radioimmunotherapy for Hematologic and Other Malignancies, Cancer Biother Radiopharm.; 25(2):125-142). However, the working examples described herein (see Section 6) surprisingly reveal that high therapeutic indices for a bispecific binding agent described herein targeting HER2, which is prone to endocytosis (see, e.g., Austin et al., 2004, Molecular Biology of the Cell, 15:5268-5282), can be achieved when used in accordance with the methods of treating cancer described here (see, e.g., Section 5.1 and Section 6). Thus, in a specific embodiment, the cancer antigen is an antigen that is internalized into a cancer cell. Nonlimiting examples of cancer antigens that are internalized into a cancer cell include: HER2, CA6, CD138, CD19, CD22, CD27L, CD30, CD33, CD37, CD56, CD66e, CD70, CD74, CD79b, EGFR, EGFRvIII, FRα, GCC, GPNMB, Mesothelin, MUC16, NaPi2b, Nectin 4, PSMA, STEAP1, Trop-2, 5T4, AGS-16, alpha v beta6, CA19.9, CAIX, CD174, CD180, CD227, CD326, CD79a, CEACAM5, CRIPTO, DLL3, DS6, Endothelin B receptor, FAP, GD2, Mesothelin, PMEL 17, SLC44A4, TENB2, TIM-1, CD98, Endosialin/CD248/TEM1, Fibronectin Extra-domain B LIV-1, Mucin 1, p-cadherin, peritosin, Fyn, SLTRK6, Tenascin c, VEGFR2, and PRLR. See, e.g., Table 1 for a list of exemplary cancers expressing the foregoing cancer antigens.

In another specific embodiment, the cancer antigen is an antigen that is not internalized into a cancer cell. Nonlimiting examples of cancer antigens that are not internalized into a cancer cell include: CD20, CD72, Fibronectin, GPA33, splice isoform of tenascin-C, and TAG-72. See, e.g., Table 1 for a list of exemplary cancers expressing the foregoing cancer antigens. In a specific embodiment in which the cancer antigen is an ovarian cancer antigen, the first molecule is the antibody MX35. In a specific embodiment in which the cancer antigen is Fyn3, the first molecule is the antibody SC-16. In a specific embodiment in which the cancer antigen is B7-H3, the first molecule is the antibody 8H9.

In a preferred embodiment, the cancer antigen is HER2. HER2 is a member of the epidermal growth factor receptor (EGFR) family of receptor tyrosine kinases. In a specific embodiment, HER2 is human HER2. GenBank™ accession number NM 004448.3 (SEQ ID NO: 1) provides an exemplary human HER2 nucleic acid sequence. GenBank™ accession number NP 004439.2 (SEQ ID NO: 2) provides an exemplary human HER2 amino acid sequence. In another specific embodiment, HER2 is canine HER2. GenBank™ accession number NM 001003217.1 (SEQ ID NO: 3) provides an exemplary canine HER2 nucleic acid sequence. GenBank™ accession number NP 001003217.1 (SEQ ID NO: 4) provides an exemplary canine HER2 amino acid sequence.

In a specific embodiment of the bispecific binding agents of the invention, the first molecule is an antibody or antigen-binding fragment thereof that specifically binds to HER2. In a preferred embodiment, the antibody is an immunoglobulin that specifically binds to HER2. In a specific embodiment, the antibody or antigen-binding fragment thereof comprises the heavy chain and/or the light chain of a HER2-specific antibody known in the art, such as, for example, trastuzumab (see, for example, Baselga et al. 1998, Cancer Res 58(13): 2825-2831), M-111 (see, for example, Higgins et al., 2011, J Clin Oncol, 29(Suppl): Abstract TPS119), pertuzumab (see, for example, Franklin et al., 2004, Cancer Cell, 5: 317-328), ertumaxomab (see, for example, Kiewe and Thiel, 2008, Expert Opin Investig Drugs, 17(10): 1553-1558), MDXH210 (see, for example, Schwaab et al., 2001, Journal of Immunotherapy, 24(1): 79-87), 2B1 (see, for example, Borghaei et al., 2007, J Immunother, 30: 455-467), and MM-302 (see, for example, Wickham and Futch, 2012, Cancer Research, 72(24): Supplement 3), each of which is incorporated by reference herein in its entirety.

In a specific embodiment where the first molecule is an antibody or antigen-binding fragment thereof that binds to HER2, a heavy chain in the antibody or antigen-binding fragment thereof that specifically binds to HER2 comprises all three heavy chain complementarity determining regions (CDRs) of the heavy chain variable ($V_H$) domain of trastuzumab, and a light chain in the antibody or antigen-binding fragment thereof that specifically binds to HER2 comprises all three light chain CDRs of the light chain variable ($V_L$) domain of trastuzumab. In a specific embodiment, a heavy chain in the antibody or antigen-binding fragment thereof that specifically binds to HER2 comprises all three heavy chain CDRs of SEQ ID NO: 14, and a light chain in the antibody or antigen-binding fragment thereof that specifically binds to HER2 comprises all three light chain CDRs of SEQ ID NO: 11. In a specific embodiment, a $V_H$ domain in a heavy chain in the antibody or antigen-binding fragment thereof that specifically binds to HER2 comprises the $V_H$ domain of trastuzumab. In a specific embodiment, the sequence of a $V_H$ domain in a heavy chain in the antibody or antigen-binding fragment thereof that specifically binds to HER2 comprises SEQ ID NO: 20 (see Table 4). In a specific embodiment, the antibody or antigen-binding fragment thereof that specifically binds to HER2 comprises a variant of the $V_H$ domain of trastuzumab that has no more than 5 amino acid mutations relative to the native sequence of the $V_H$ domain of trastuzumab. In a specific embodiment, a light chain $V_L$ domain in a light chain in the antibody or antigen-binding fragment thereof that specifically binds to HER2 comprises the $V_L$ domain of trastuzumab. In a specific embodiment, the sequence of a $V_L$ domain in a light chain in the antibody or antigen-binding fragment thereof that specifically binds to HER2 comprises SEQ ID NO: 19 (see Table 4). In a specific embodiment, the antibody or antigen-binding fragment thereof that specifically binds to HER2 comprises a variant of the $V_L$ domain of trastuzumab that has no more than 5 amino acid mutations relative to the native sequence of the $V_L$ domain of trastuzumab. In a specific embodiment, one or more of the amino acid mutation(s) in the $V_H$ domain and/or $V_L$ domain of the antibody or antigen-binding fragment thereof relative to the native sequence of the $V_H$ domain and/or $V_L$ domain, respectively, of trastuzumab is a conservative amino acid substitution with respect to the native sequence of the $V_H$ domain and/or $V_L$ domain, respectively, of trastuzumab. In a preferred embodiment, the antibody that specifically binds to HER2 is an immunoglobulin.

Conservative amino acid substitutions are amino acid substitutions that occur within a family of amino acids, wherein the amino acids are related in their side chains. Generally, genetically encoded amino acids are divided into families: (1) acidic, comprising aspartate and glutamate; (2) basic, comprising arginine, lysine, and histidine; (3) non-polar, comprising isoleucine, alanine, valine, proline, methionine, leucine, phenylalanine, tryptophan; and (4) uncharged polar, comprising cysteine, threonine, glutamine, glycine, asparagine, serine, and tyrosine. In addition, an aliphatic-hydroxy family comprises serine and threonine. In addition, an amide-containing family comprises asparagine and glutamine. In addition, an aliphatic family comprises alanine, valine, leucine and isoleucine. In addition, an aromatic family comprises phenylalanine, tryptophan, and tyrosine. Finally, a sulfur-containing side chain family comprises cysteine and methionine. As an example, one skilled in the art would reasonably expect an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Preferred conservative amino acid substitution groups include: lysine-arginine, alanine-valine, phenylalanine-tyrosine, glutamic acid-aspartic acid, valine-leucine-isoleucine, cysteine-methionine, and asparagine-glutamine.

In a specific embodiment where the first molecule is an antibody or antigen-binding fragment thereof that binds to HER2, the antibody or antigen-binding fragment thereof comprises the heavy chain of trastuzumab. In a specific embodiment, the sequence of a heavy chain comprises the sequence of any one of SEQ ID NOs: 14-17 (see Table 2). In a specific embodiment, the antibody or antigen-binding fragment thereof comprises a variant of the heavy chain of trastuzumab (see, e.g., SEQ ID NOs: 14-17 (see Table 2)). In a preferred embodiment, the sequence of a heavy chain in the antibody or antigen-binding fragment thereof comprises SEQ ID NO: 15. In a more preferred embodiment, the sequence of a heavy chain in the antibody or antigen-binding fragment thereof comprises SEQ ID NO: 16. In a specific embodiment, the antibody or antigen-binding fragment thereof that comprises a variant of the heavy chain of trastuzumab that has no more than 5 amino acid mutations relative to the native sequence of the heavy chain of trastuzumab. In a specific embodiment, the antibody or antigen-binding fragment thereof comprises the light chain of trastuzumab. In a specific embodiment, the sequence of a light chain in the antibody or antigen-binding fragment thereof comprises SEQ ID NO: 11. In a specific embodiment, the antibody or antigen-binding fragment thereof comprises a variant of the light chain of trastuzumab. In a specific embodiment, the antibody or antigen-binding fragment thereof comprises a variant of the light chain of trastuzumab that has no more than 5 amino acid mutations relative to the native sequence of the light chain of trastuzumab. In a specific embodiment, one or more of the amino acid mutation(s) in the heavy and/or light chain of the antibody or antigen-binding fragment thereof relative to the native sequence of the heavy and/or light chain, respectively, of trastuzumab is a conservative amino acid substitution with respect to the native sequence of the heavy and/or light chain, respectively, of trastuzumab.

TABLE 2

Heavy Chain Sequences.

| DESCRIPTION | SEQUENCE (SEQ ID NO:) |
|---|---|
| Trastuzumab $V_H$ domain with human IgG1 constant region | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRWGGDGFYAMDYWGQGTLVTVSS*ASTKGPSVFPL APSSKSTSGGTAALGCLVKDYFPEPVTVSWNSGALTSGVHTFPAVLQS SGLYSLSSVVTVPSSSLGTQTYICNYNHKPSNTKVDKRVEPKSCDKTHT CPPCPAPELLGGPSVFLFPPKPKDTIMISRTPEVTCVVVDVSHEDPEV KFNWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDKS RWQQGNVFSCSVMHEALHNHYTQKSLSLSPGK* (SEQ ID NO: 14) |

TABLE 2 -continued

Heavy Chain Sequences.

| DESCRIPTION | SEQUENCE (SEQ ID NO:) |
|---|---|
| Trastuzumab $V_H$ domain with human IgG1 constant region and N297A | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSS*ASTKGPSVFPLAPSS*<br>*KSTSGGTAALGCLVKDYFPEPVTVSWNSGALTSGVHTFPAVLQSSGLYS*<br>*LSSVVTVPSSSLGTQTYICNVNHKPSNTKVDKRVEPKSCDKTHTCPPC*<br>*PAPELLGGPSVFLFPPKPKDTLMISRTPEVTCVVVDVSHEDPEVKFN*<br>*WYVDGVEVHNAKTKPREEQY***A***STYRVVSVLTVLHQDWLNGKEYKCK*<br>*VSNKALPAPIEKTISKAKGQPREPQVYTLPPSRDELTKNQVSLTCLVKG*<br>*FYPSDIAVEWESNGQPENNYKTTPPVLDSDGSFFLYSKLTVDKSRWQ*<br>*QGNVFSCSVMHEALHNHYTQKSLSLSPGK* (SEQ ID NO: 15) |
| Trastuzumab $V_H$ domain with human IgG1 constant region, N297A, and K3 22A | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYSRWGGDGFYAMDYWGQGTLVTVSS*ASTKGPSVFPL*<br>*APSSKSTSGGTAALGCLVKDYFPEPVTVSWNSGALTSGVHTFPAVLQS*<br>*SGLYSLSSVVTVPSSSLGTQTYICNVNHKPSNTKVDKRVEPKSCDKTHT*<br>*CPPCPAPELLGGPSVFLFPPKPKDTLMISRTPEVTCVVVDVSHEDPEV*<br>*KFNWYVDGVEVHNAKTKPREEQY***A***STYRVVSVLTVLHQDWLNGKEY*<br>*KC***A***VSNKALPAPIEKTISKAKGQPREPQVYTLPPSRDELTKNQVSLTC*<br>*LVKGFYPSDIAVEWESNGQPENNYKTTPPVLDSDGSFFLYSKLTVDKS*<br>*RWQQGNVFSCSMHEALHNHYTQKSLSLSPGK* (SEQ ID NO: 16) |
| Trastuzumab $V_H$ domain with human IgG1 constant region; K322A | EVQLVESGGGLVQPGGSLRLSCAASGFNIKDTYIEWVRQAPGKG<br>LEWVARTYPTNGYTRYADSVKGRFTISADTSKNTAYLQMNSLRA<br>EDTAVYYCSRWGGDGFYAMDYWGQGTLVTVSS*ASTKGPSVFPL*<br>*APSSKSTSGGTAALGCLVKDYFPEPVTVSWNSGALTSGVHTFPAVLQS*<br>*SGLYSLSSVVTVPSSSLGTQTYICNYNHKPSNTKVDKRVEPKSCDKTHT*<br>*CPPCPAPELLGGPSVFLFPPKPKDTLMISRTPEVTCVVVDVSHEDPEV*<br>*KFNWYVDGVEVHNAKTKPREEQYNSTYRVVSVLTVLHQDWLNGKEY*<br>*KC***A***VSNKALPAPIEKTISKAKGQPREPQVYTLPPSRDELTKNQVSLTC*<br>*LVKGFYPSDIAVEWESNGQPENNYKTTPPVLDSDGSFFLYSKLTVDKS*<br>*RWQQGNVFSCSMHEALHNHYTQKSLSLSPGK* (SEQ ID NO: 17) |

The non-italicized, non-underlined sequence represents the $V_H$ domain.
The italicized sequence represents the constant region.
The underlined, italicized, and bold sequences represent the mutations described in the "DESCRIPTION" column.

TABLE 3

Light Chain Sequence.

| DESCRIPTION | SEQUENCE (SEQ ID NO:) |
|---|---|
| Trastuzumab light chain | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQHYTTPPTFGQGTKVEIKR*TVAAPS*<br>*VFIFPPSDEQLKSGTASVVCLLNNFYPREAKVQWKVDN*<br>*ALQSGNSQESVTEQDSKDSTYSLSSTLTLSKADYEKHK*<br>*VYACEVTHQGLSSPVTKSFNRGEC*<br>(SEQ ID NO: 11) |

The non-italicized sequence represents the $V_L$ domain.
The italicized sequence represents the constant region.

TABLE 4

Trastuzumab $V_L$ and $V_H$ Domain Sequences.

| DESCRIPTION | SEQUENCE (SEQ ID NO:) |
|---|---|
| Trastuzumab $V_L$ domain | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQHYTTPPTFGQGTKVEIKR<br>(SEQ ID NO: 19) |
| Trastuzumab $V_H$ domain | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSS (SEQ ID NO: 20) |

In a specific embodiment where the first molecule is an antibody or antigen-binding fragment thereof that binds to HER2, the antibody or antigen-binding fragment thereof binds to the same epitope as a HER2-specific antibody known in the art. In a specific embodiment, the antibody or antigen-binding fragment thereof binds to the same epitope as trastuzumab. Binding to the same epitope can be determined by assays known to one skilled in the art, such as, for example, mutational analyses or crystallographic studies. In a specific embodiment, the antibody or antigen-binding fragment thereof competes for binding to HER2 with an antibody known in the art. In a specific embodiment, the antibody or antigen-binding fragment thereof competes for binding to HER2 with trastuzumab. Competition for binding to HER2 can be determined by assays known to one skilled in the art, such as, for example, flow cytometry. In a specific embodiment, the antibody or antigen-binding fragment thereof comprises a $V_H$ domain with at least 85%, 90%, 95%, 98%, or at least 99% similarity to the $V_H$ domain of a HER2-specific antibody known in the art. In a specific embodiment, the antibody or antigen-binding fragment thereof comprises the $V_H$ domain of a HER2-specific antibody known in the art, comprising between 1 and 5 conservative amino acid substitutions relative to the $V_H$ domain of the HER2-specific antibody known in the art. In a specific embodiment, the antibody or antigen-binding fragment thereof comprises a $V_L$ domain with at least 85%, 90%, 95%, 98%, or at least 99% similarity to the $V_L$ domain of a HER2-specific antibody known in the art. In a specific embodiment, the antibody or antigen-binding fragment thereof comprises the $V_L$ domain of a HER2-specific antibody known in the art, comprising between 1 and 5 conservative amino acid substitutions relative to the $V_L$ domain of the HER2-specific antibody known in the art. In a specific embodiment, the antibody or antigen-binding fragment thereof comprises a $V_H$ domain of a heavy chain described in Table 2 above (e.g., the $V_H$ domain of any one of SEQ ID NOs: 14-17). In a specific embodiment, the antibody or antigen-binding fragment thereof comprises the $V_L$ domain of the light chain described in Table 3 above (i.e., the $V_L$ domain of SEQ ID NO: 11).

The sequences of the variable regions of an anti-HER2 antibody described herein may be modified by insertions, substitutions and deletions to the extent that the resulting antibody maintains the ability to specifically bind to HER2, as determined by, for example, ELISA, flow cytometry, and BiaCore™. The ordinarily skilled artisan can ascertain the maintenance of this activity by performing the functional assays as described hereinbelow, such as, for example, binding analyses and cytotoxicity analyses.

In a specific embodiment where the first molecule is an immunoglobulin that binds to HER2, the immunoglobulin is an IgG1 immunoglobulin.

In a specific embodiment, the first molecule of the bispecific binding agent is covalently bound via a linker to the second molecule of the bispecific binding agent. In a specific embodiment, the linker that covalently binds the first molecule to the second molecule is a peptide linker. In a specific embodiment, the peptide linker is between 5-30, 5-25, 5-15, 10-30, 10-20, 10-15, 15-30, or 15-25 amino acid residues in length. In a specific embodiment, the peptide linker is between 7-32, 7-27, 7-17, 12-32, 12-22, 12-17, 17-32, or 17-27 amino acid residues in length. In a specific embodiment, the peptide linker displays one or more characteristics suitable for a peptide linker known to one of ordinary skill in the art. In a specific embodiment, the peptide linker comprises amino acids that allow for peptide linker solubility, such as, for example, serine and threonine. In a specific embodiment, the peptide linker comprises amino acids that allow for peptide linker flexibility, such as, for example, glycine. In a specific embodiment, the peptide linker connects the N-terminus of the first molecule to the C-terminus of the second molecule. In a preferred embodiment, the peptide linker connects the C-terminus of the first molecule to the N-terminus of the second molecule. In a specific embodiment, the peptide linker is a linker as described in Table 5 below (e.g., any one of SEQ ID NOs: 23 and 25-30). In another specific embodiment, the peptide linker is a linker as described in Table 5 below (e.g., any one of SEQ ID NOs: 51-56). In a specific embodiment, the peptide linker is SEQ ID NO: 23. In a preferred embodiment, the peptide linker is SEQ ID NO:

TABLE 5

Peptide Linker Sequences

| DESCRIPTION | SEQUENCE (SEQ ID NO:) |
|---|---|
| $(G_4S)_2$AS Linker | GGGGSGGGGSAS (SEQ ID NO: 23) |
| $G_4S$ Linker | GGGGS (SEQ ID NO: 25) |
| $(G_4S)_2$ Linker | GGGGSGGGGS (SEQ ID NO: 26) |
| $(G_4S)_3$ Linker | GGGGSGGGGSGGGGS (SEQ ID NO: 27) |
| $(G_4S)_4$ Linker | GGGGSGGGGSGGGGSGGGGS (SEQ ID NO: 28) |
| $(G_4S)_5$ Linker | GGGGSGGGGSGGGGSGGGGSGGGGS (SEQ ID NO: 29) |
| $(G_4S)_6$ Linker | GGGGSGGGGSGGGGSGGGGSGGGGSGGGGS (SEQ ID NO: 30) |
| $TSG_4S$ Linker | TSGGGGS (SEQ ID NO: 51) |
| $TS(G_4S)_2$ Linker | TSGGGGSGGGGS (SEQ ID NO: 52) |
| $TS(G_4S)_3$ Linker | TSGGGGSGGGGSGGGGS (SEQ ID NO: 53) |
| $TS(G_4S)_4$ Linker | TSGGGGSGGGGSGGGGSGGGGS (SEQ ID NO: 54) |
| $TS(G_4S)_5$ Linker | TSGGGGSGGGGSGGGGSGGGGSGGGGS (SEQ ID NO: 55) |
| $TS(G_4S)_6$ Linker | TSGGGGSGGGGSGGGGSGGGGSGGGGSGGGGS (SEQ ID NO: 56) |

In another specific embodiment, the first molecule of the bispecific binding agent is directly covalently bound to the second molecule of the bispecific binding agent (i.e., there is no linker between the first molecule and the second molecule of the bispecific binding agent).

The second molecule of the bispecific binding agent mediates interaction between the bispecific binding agent and the radiotherapeutic agent, wherein said radiotherapeutic agent comprises (i) the second target (of the bispecific binding agent) bound to a metal radionuclide, wherein the second target is a metal chelator; or (ii) the second target (of the bispecific binding agent) bound, preferably covalently, to a metal chelator, said metal chelator being bound to a metal radionuclide. In particular, the second molecule of the bispecific binding agent comprises the second binding site, which specifically binds to the second target. In a specific embodiment, the second target is the metal chelator that forms part of the radiotherapeutic agent. In another specific embodiment, the second target is a molecule that is bound, preferably covalently, to a metal chelator, said metal chelator forming part of the radiotherapeutic agent.

In a specific embodiment, the second molecule comprises an antibody or an antigen-binding fragment thereof, wherein said antibody or antigen-binding fragment thereof comprises the second binding site. In a preferred embodiment, the second molecule comprises a single chain variable fragment (scFv), wherein said scFv comprises the second binding site. A scFv is an art-recognized term. An scFv is a fusion protein of the $V_H$ domain and $V_L$ domain of an immunoglobulin, wherein the fusion protein retains the same antigen specificity as the whole immunoglobulin. The $V_H$ domain is fused to the $V_L$ domain via a peptide linker (such a peptide linker is sometimes referred to herein as an "intra-scFv peptide linker").

In a specific embodiment of the invention in which the second molecule is an scFv, the scFv has an intra-scFv peptide linker that is between 5-30, 5-25, 5-15, 10-30, 10-20, 10-15, 15-30, or 15-25 amino acid residues in length. In a specific embodiment, the intra-scFv peptide linker displays one or more characteristics suitable for a peptide linker known to one of ordinary skill in the art. In a specific embodiment, the intra-scFv peptide linker comprises amino acids that allow for intra-scFv peptide linker solubility, such as, for example, serine and threonine. In a specific embodiment, the intra-scFv peptide linker comprises amino acids that allow for intra-scFv peptide linker flexibility, such as, for example, glycine. In a specific embodiment, the intra-scFv peptide linker connects the N-terminus of the $V_H$ domain to the C-terminus of the $V_L$ domain. In a specific embodiment, the intra-scFv peptide linker connects the C-terminus of the $V_H$ domain to the N-terminus of the $V_L$ domain. In a specific embodiment, the intra-scFv peptide linker is a linker as described in Table 5 above (e.g., any one of SEQ ID NOs: 23 and 25-30). In a specific embodiment, the intra-scFv peptide linker is SEQ ID NO: 27. In a specific embodiment, the intra-scFv peptide linker is SEQ ID NO: 30.

In a specific embodiment, the second target of the bispecific binding agent is a metal chelator. In such an embodiment, the second target of the bispecific binding agent is the metal chelator of the radiotherapeutic agent (see, e.g., Section 5.4) used in combination with the bispecific binding agent in a method of treating cancer described herein (see, e.g., Section 5.1 and Section 6). The metal chelator may be any metal chelator known in the art. Nonlimiting examples of metal chelators include 1,4,7,10-traazacyclododecane-1, 4,7,10-tetraacetic acid (DOTA) and metal-chelating derivatives thereof (e.g., p-aminobenzyl-DOTA (benzyl-1,4,7,10-tetraazacyclododecane-N,N',N",N'"-tetraacetic acid with an amino group in the para position ("p") of the benzene ring), DOTA-Bn (benzyl-1,4,7,10-tetraazacyclododecane-N,N', N",N'"-tetraacetic acid), and DOTA-desferrioxamine) and diethylenetriaminepentaacetic acid (DTPA) and metal-chelating derivatives thereof. In a specific embodiment in which the second target is a metal chelator, the metal chelator is DOTA or a metal-chelating derivative thereof (e.g., DOTA-Bn or DOTA-desferrioxamine) or DTPA or a metal-chelating derivative thereof. Nonlimiting examples of derivatives of DOTA are described in Leon-Rodriquez & Kovacs, 2008, The Synthesis and Chelation Chemistry of DOTA-Peptide Conjugates, Bioconjugate Chemistry; 19(2): 391-402, which is incorporated by reference herein in its entirety. In a preferred embodiment, the second target is DOTA-Bn.

In a specific embodiment in which the second molecule is an antibody or antigen-binding fragment thereof or scFv that binds to a metal chelator, binding of the bispecific binding agent (via its second molecule) to the metal chelator does not significantly impede the chelation ability of the metal chelator. For example, in a specific embodiment, binding of the bispecific binding agent (via its second molecule) to the metal chelator does not reduce the chelation ability of the metal chelator by more than 3%, 5%, 10%, 15%, 20%, 30%, or 40% as compared to the chelation ability of the metal chelator prior to interaction with the second molecule. Methods for determining the chelation ability of the metal chelator in the presence and absence of a bispecific binding agent described herein are known in the art, such as, e.g., Antczak, et al., Bioconjugate Chem. 2006, 17, 1551-1560 for metal chelatation methods.

In a specific embodiment in which the second molecule is an antibody or antigen-binding fragment thereof or scFv that binds to a metal chelator, the second molecule specifically binds to DOTA or a metal-chelating derivative thereof (e.g., DOTA-Bn). In a preferred embodiment, the second molecule is a scFv that specifically binds to DOTA or a metal-chelating derivative thereof (e.g., DOTA-Bn). In another preferred embodiment, the second molecule is a scFv that specifically binds to DOTA-Bn. In a specific embodiment, the second molecule comprises the $V_H$ domain and the $V_L$ domain of an anti-DOTA (or a metal-chelating derivative thereof (e.g., DOTA-Bn)) antibody or antigen-binding fragment thereof or scFv known in the art, such as, for example, 2D12.5 (see, for example, Orcutt et al., "Engineering an antibody with picomolar affinity to DOTA chelates of multiple radionuclides for pretargeted radioimmunotherapy and imaging." Nucl Med Biol 2011; 38:223-33), C825, which is a murine scFv with high affinity for benzyl-1,4,7,10-tetraazacyclododecane-N,N',N",N'"-tetraacetic acid (DOTA-Bn) (see, for example, Orcutt et al., 2011, Nucl. Med. Biol. 38:223-233 and U.S. Pat. No. 8,648,176), or any of the anti-DOTA (or metal-chelating derivative thereof) antibodies described in U.S. Pat. No. 8,648,176 and Orcutt, et al. Mol Imaging Biol. 2011, 13(2) 215-21, each of which is incorporated by reference herein in its entirety.

In a specific embodiment where the second molecule is an antibody or antigen-binding fragment thereof or scFv that binds to DOTA or a metal-chelating derivative thereof, the second molecule binds to the same epitope as an antibody or antigen-binding fragment thereof or scFv that specifically binds to DOTA or a metal-chelating derivative thereof (e.g., DOTA-Bn) known in the art. In a specific embodiment, the second molecule binds to the same epitope as C825. Binding to the same epitope can be determined by assays known to one skilled in the art, such as, for example, mutational analyses or crystallographic studies. In a specific embodiment, the second molecule competes for binding to DOTA or a metal-chelating derivative thereof (e.g., DOTA-Bn) with an antibody or antigen-binding fragment thereof or scFv that specifically binds to DOTA or a metal-chelating derivative thereof (e.g., DOTA-Bn) known in the art. In a specific embodiment, the second molecule that specifically binds to DOTA or a metal-chelating derivative thereof (e.g., DOTA-Bn) competes for binding to DOTA-Bn with C825. Competition for binding to DOTA or a metal-chelating derivative thereof (e.g., DOTA-Bn) can be determined by assays known to one skilled in the art, such as, for example, flow cytometry. In a specific embodiment, the second molecule comprises a $V_H$ domain with at least 85%, 90%, 95%, 98%, or at least 99% similarity to the $V_H$ domain of an antibody or antigen-binding fragment thereof or scFv that specifically binds to DOTA or a metal-chelating derivative thereof (e.g., DOTA-Bn) known in the art. In a specific embodiment, the second molecule comprises the $V_H$ domain of an antibody or antigen-binding fragment thereof or scFv that specifically binds to DOTA or a metal-chelating derivative thereof (e.g., DOTA-Bn) known in the art, comprising between 1 and 5 conservative amino acid substitutions relative to the antibody or antigen-binding fragment thereof or scFv that specifically binds to DOTA or a derivative thereof (e.g., DOTA-Bn). In a specific embodiment, the second molecule comprises a $V_L$ domain with at least 85%, 90%, 95%, 98%, or at least 99% similarity to the $V_L$ domain of an antibody or antigen-binding fragment thereof or scFv that specifically binds to DOTA or a metal-chelating derivative thereof (e.g., DOTA-Bn) known in the art. In a specific embodiment, the second molecule comprises the $V_L$ domain of an antibody or antigen-binding fragment thereof or scFv that specifically binds to DOTA or a metal-chelating derivative thereof (e.g., DOTA-Bn) known in the art, comprising between 1 and 5 conservative amino acid substitutions relative to the antibody or antigen-binding fragment thereof or scFv that specifically binds to DOTA or a metal-chelating derivative thereof (e.g., DOTA-Bn).

In a specific embodiment where the second molecule is an antibody or antigen-binding fragment thereof or a scFv that specifically binds to DOTA-Bn, a $V_H$ domain in the second molecule comprises all three CDRs of the $V_H$ domain of C825, and a $V_L$ domain in the second molecule comprises all three CDRs of the $V_L$ domain of C825. In a specific embodiment, a $V_H$ domain in the second molecule comprises all three CDRs of SEQ ID NO: 21, and a $V_L$ domain in the second molecule comprises all three CDRs of SEQ ID NO: 22.

In a preferred embodiment where the second molecule is an antibody or antigen-binding fragment thereof or scFv that specifically binds DOTA or a metal-chelating derivative thereof (e.g., DOTA-Bn), the second molecule is derived from murine C825, and thus contains the $V_H$ domain and $V_L$ domain of murine C825 (SEQ ID NOS: 21 and 22, respectively, (see Table 6 below)). In a specific embodiment, the second molecule is a scFv. In a specific embodiment, the scFv is derived from murine C825 and has no more than 5 amino acid mutations relative to native murine C825 $V_H$ domain and/or $V_L$ domain sequences. In a specific embodiment, the sequence of the $V_H$ domain of the scFv is SEQ ID NO: 21. In a specific embodiment, the sequence of the $V_L$ domain of the scFv is SEQ ID NO: 22. In a specific embodiment, the sequence of the scFv comprises any one of the murine sequences set forth in Table 7, below (e.g., any one of SEQ ID NOs: 31-36). In a preferred embodiment, the sequence of the scFv comprises SEQ ID NO: 33. In a specific embodiment, the scFv comprises a variant of the $V_H$ domain of murine C825 that has no more than 5 amino acid mutations relative to the native sequence of the $V_H$ domain of murine C825. In a specific embodiment, the scFv comprises a variant of the $V_L$ domain of murine C825 that has no more than 5 amino acid mutations relative to the native sequence of the $V_L$ domain of murine C825. In a specific embodiment, the scFv comprises a $V_H$ domain that is a variant of the $V_H$ domain of murine C825 that has no more than 5 amino acid mutations relative to the native sequence of the $V_H$ domain of murine C825. In a specific embodiment, the scFv comprises a $V_L$ domain that is a variant of the $V_L$ domain of murine C825 that has no more than 5 amino acid mutations relative to the native sequence of the $V_L$ domain of murine C825. In a specific embodiment, the scFv comprises a $V_H$ domain that is a variant of the $V_H$ domain of murine C825 that has no more than 5 amino acid mutations relative to the native sequence of the $V_H$ domain of murine C825, and the scFv comprises a $V_L$ domain that is a variant of the $V_L$ domain of murine C825 that has no more than 5 amino acid mutations relative to the native sequence of the $V_L$ domain of murine C825.

TABLE 6

Murine and humanized C825 $V_H$ Domain and $V_L$ Domain Sequences

| DESCRIPTION | SEQUENCE (SEQ ID NO:) |
|---|---|
| Murine C825 $V_H$ domain | HVKLQESGPGLVQPSQSLSLTCTVSGFSLTDYGVH<br>WVRQSPGKGLEWLGVIWSGGGTAYNTALISRLNIY<br>RDNSKNQVFLEMNSLQAEDTAMYYCARRGSYPYNY<br>FDAWGCGTTVTVSS (SEQ ID NO: 21) |
| Murine C825 $V_L$ domain | QAVVIQESALTTPPGETVTLTCGSSTGAVTASNYA<br>NWVQEKPDHCFTGLIGGHNNRPPGVPARFSGSLIG<br>DKAALTIAGTQTEDEAIYFCALWYSDHWVIGGGTR<br>LTVLG (SEQ ID NO: 22) |
| Humanized C825 $V_H$ domain[1] | HVQLVESGGGLVQPGGSLRLSCAASGFSLTDYGVH<br>WVRQAPGKGLEWLGVIWSGGGTAYNTALISRFTIS<br>RDNSKNTLYLQMNSLRAEDTAVYYCARRGSYPYNY<br>FDAWGCGTLVTVSS (SEQ ID NO: 37) |
| Humanized C825 $V_L$ domain[1] | QAVVTQEPSLTVSPGGTVTLTCGSSTGAVTASNYA<br>NWVQQKPGQCPRGLIGGHNNRPPGVPARFSGSLLG<br>GKAALTLLGAQPEDEAEYYCALWYSDHWVIGGGTK<br>LTVLG (SEQ ID NO: 38) |

[1]The amino acid sequences of the humanized C825 $V_H$ domain and the humanized C825 $V_L$ domain shown here and also in Table 7 were obtained from International publication no. WO 2016/130539 (see SEQ ID NO: 3 and SEQ ID NO: 4 of WO 2016/130539), which is incorporated by reference herein in its entirety.

TABLE 7

Exemplary murine and humanized anti-DOTA scFv Sequences.

| DESCRIPTION | SEQUENCE (SEQ ID NO:) |
|---|---|
| Murine C825 $V_H$-($G_4S$) intra-scFv linker-murine C825 $V_L$ | *HVKLQESGPGLVQPSQSLSLTCTVSGFSLTDYGVHWVRQSPGKGLEW*<br>*LGVIWSGGGTAYNTALISRLNIYRDNSKNQVFLEMNSLQAEDTAMYYC*<br>*ARRGSYPYNYFDAWGCGTTVTVSS*ggggsQAVVIQESALTTPPGETVTL<br>TCGSSTGAVTASNYANWVQEKPDHCFTGLIGGHNNRPPGVPARFS<br>GSLIGDKAALTIAGTQTEDEAIYFCALWYSDHWVIGGGTRLTVLG<br>(SEQ ID NO: 31) |
| Murine C825 $V_H$-$(G_4S)_2$ intra-scFv linker-murine C825 $V_L$ | *HVKLQESGPGLVQPSQSLSLTCTVSGFSLTDYGVHWVRQSPGKGLEW*<br>*LGVIWSGGGTAYNTALISRLNIYRDNSKNQVFLEMNSLQAEDTAMYYC*<br>*ARRGSYPYNYFDAWGCGTTVTVSS*ggggsggggsQAVVIQESALTTPPGE<br>TVTLTCGSSTGAVTASNYANWVQEKPDHCFTGLIGGHNNRPPGVP<br>ARFSGSLIGDKAALTIAGTQTEDEAIYFCALWYSDHWVIGGGTRLT<br>VLG (SEQ ID NO: 32) |
| Murine C825 $V_H$-$(G_4S)_3$ intra-scFv linker-murine C825 $V_L$ | *HVKLQESGPGLVQPSQSLSLTCTVSGFSLTDYGVHWVRQSPGKGLEW*<br>*LGVIWSGGGTAYNTALISRLNIYRDNSKNQVFLEMNSLQAEDTAMYYC*<br>*ARRGSYPYNYFDAWGCGTTVTVSS*ggggsggggsggggsQAVVIQESALTT<br>PPGETVTLTCGSSTGAVTASNYANWVQEKPDHCFTGLIGGHNNRP<br>PGVPARFSGSLIGDKAALTIAGTQTEDEAIYFCALWYSDHWVIGG<br>GTRLTVLG (SEQ ID NO: 33) |
| Murine C825 $V_H$-$(G_4S)_4$ intra-scFv linker-murine C825 $V_L$ | *HVKLQESGPGLVQPSQSLSLTCTVSGFSLTDYGVHWVRQSPGKGLEW*<br>*LGVIWSGGGTAYNTALISRLNIYRDNSKNQVFLEMNSLQAEDTAMYYC*<br>*ARRGSYPYNYFDAWGCGTTVTVSS*ggggsggggsggggsggggsQAVVIQES<br>ALTTPPGETVTLTCGSSTGAVTASNYANWVQEKPDHCFTGLIGGH<br>NNRPPGVPARFSGSLIGDKAALTIAGTQTEDEAIYFCALWYSDHW<br>VIGGGTRLTVLG (SEQ ID NO: 34) |

TABLE 7 -continued

Exemplary murine and humanized anti-DOTA scFv Sequences.

| DESCRIPTION | SEQUENCE (SEQ ID NO:) |
|---|---|
| Murine C825 $V_H$-$(G_4S)_5$ intra-scFv linker-murine C825 $V_L$ | *HVKLQESGPGLVQPSQSLSLTCTVSGFSLTDYGVHWVRQSPGKGLEW*<br>*LGVIWSGGGTAYNTALISRLNIYRDNSKNQVFLEMNSLQAEDTAMYYC*<br>*ARRGSYPYNYFDAWGCGTTVTVSS*ggggsggggsggggsggggsggggsQAVV<br>IQESALTTPPGETVTLTCGSSTGAVTASNYANWVQEKPDHCFTGLI<br>GGHNNRPPGVPARFSGSLIGDKAALTIAGTQTEDEAIYFCALWYSD<br>HWVIGGGTRLTVLG (SEQ ID NO: 35) |
| Murine C825 $V_H$-$(G_4S)_6$ intra-scFv linker-murine C825 $V_L$ | *HVKLQESGPGLVQPSQSLSLTCTVSGFSLTDYGVHWVRQSPGKGLEW*<br>*LGVIWSGGGTAYNTALISRLNIYRDNSKNQVFLEMNSLQAEDTAMYYC*<br>*ARRGSYPYNYFDAWGCGTTVTVSS*ggggsggggsggggsggggsggggsggggsQ<br>AVVIQESALTTPPGETVTLTCGSSTGAVTASNYANWVQEKPDHCF<br>TGLIGGHNNRPPGVPARFSGSLIGDKAALTIAGTQTEDEAIYFCAL<br>WYSDHWVIGGGTRLTVLG (SEQ ID NO: 36) |
| Humanized C825 $V_H$-$(G_4S)$ intra-scFv linker-humanized C825 $V_L$ | *HVQLVESGGGLVQPGGSLRLSCAASGFSLTDYGVHWVRQAPGKGLE*<br>*WLGVIWSGGGTAYNTALISRFTISRDNSKNTLYLQMNSLRAEDTAVYYC*<br>*ARRGSYPYNYFDAWGCGTLVTVSS*ggggsQAVVTQEPSLTVSPGGTVT<br>LTCGSSTGAVTASNYANWVQQKPGQCPRGLIGGHNNRPPGVPAR<br>FSGSLLGGKAALTLLGAQPEDEAEYYCALWYSDHWVIGGGTKLT<br>VLG (SEQ ID NO: 39) |
| Humanized C825 $V_H$-$(G_4S)_2$ intra-scFv linker-humanized C825 $V_L$ | *HVQLVESGGGLVQPGGSLRLSCAASGFSLTDYGVHWVRQAPGKGLE*<br>*WLGVIWSGGGTAYNTALISRFTISRDNSKNTLYLQMNSLRAEDTAVYYC*<br>*ARRGSYPYNYFDAWGCGTLVTVSS*ggggsggggsQAVVTQEPSLTVSPG<br>GTVTLTCGSSTGAVTASNYANWVQQKPGQCPRGLIGGHNNRPPG<br>VPARFSGSLLGGKAALTLLGAQPEDEAEYYCALWYSDHWVIGGG<br>TKLTVLG (SEQ ID NO: 40) |
| Humanized C825 $V_H$-$(G_4S)_3$ intra-scFv linker-humanized C825 $V_L$ | *HVQLVESGGGLVQPGGSLRLSCAASGFSLTDYGVHWVRQAPGKGLE*<br>*WLGVIWSGGGTAYNTALISRFTISRDNSKNTLYLQMNSLRAEDTAVYYC*<br>*ARRGSYPYNYFDAWGCGTLVTVSS*ggggsggggsggggsQAVVTQEPSLTV<br>SPGGTVTLTCGSSTGAVTASNYANWVQQKPGQCPRGLIGGHNNR<br>PPGVPARFSGSLLGGKAALTLLGAQPEDEAEYYCALWYSDHWVI<br>GGGTKLTVLG (SEQ ID NO: 41) |
| Humanized C825 $V_H$-$(G_4S)_4$ intra-scFv linker-humanized C825 $V_L$ | *HVQLVESGGGLVQPGGSLRLSCAASGFSLTDYGVHWVRQAPGKGLE*<br>*WLGVIWSGGGTAYNTALISRFTISRDNSKNTLYLQMNSLRAEDTAVYYC*<br>*ARRGSYPYNYFDAWGCGTLVTVSS*ggggsggggsggggsggggsQAVVTQEP<br>SLTVSPGGTVTLTCGSSTGAVTASNYANWVQQKPGQCPRGLIGGH<br>NNRPPGVPARFSGSLLGGKAALTLLGAQPEDEAEYYCALWYSDH<br>WVIGGGTKLTVLG (SEQ ID NO: 42) |
| Humanized C825 $V_H$-$(G_4S)_5$ intra-scFv linker-humanized C825 $V_L$ | *HVQLVESGGGLVQPGGSLRLSCAASGFSLTDYGVHWVRQAPGKGLE*<br>*WLGVIWSGGGTAYNTALISRFTISRDNSKNTLYLQMNSLRAEDTAVYYC*<br>*ARRGSYPYNYFDAWGCGTLVTVSS*ggggsggggsggggsggggsggggsQAVV<br>TQEPSLTVSPGGTVTLTCGSSTGAVTASNYANWVQQKPGQCPRGL<br>IGGHNNRPPGVPARFSGSLLGGKAALTLLGAQPEDEAEYYCALWY<br>SDHWVIGGGTKLTVLG (SEQ ID NO: 43) |
| Humanized C825 $V_H$-$(G_4S)_6$ intra-scFv linker-humanized C825 $V_L$ | *HVQLVESGGGLVQPGGSLRLSCAASGFSLTDYGVHWVRQAPGKGLE*<br>*WLGVIWSGGGTAYNTALISRFTISRDNSKNTLYLQMNSLRAEDTAVYYC*<br>*ARRGSYPYNYFDAWGCGTLVTVSS*ggggsggggsggggsggggsggggsggggsQ<br>AVVTQEPSLTVSPGGTVTLTCGSSTGAVTASNYANWVQQKPGQC<br>PRGLIGGHNNRPPGVPARFSGSLLGGKAALTLLGAQPEDEAEYYC<br>ALWYSDHWVIGGGTKLTVLG (SEQ ID NO: 44) |

The italicized sequence represents the VH domain.
The lowercase sequence represents the intra-scFv linker.
The underlined sequence represents the VL domain.

In a specific embodiment where the second molecule is an antibody or antigen-binding fragment thereof or scFv that specifically binds to DOTA or a metal-chelating derivative thereof, the sequence of a $V_H$ domain in the second molecule comprises a humanized form of SEQ ID NO: 21. In a specific embodiment where the second molecule is an antibody or antigen-binding fragment thereof or scFv that specifically binds to DOTA or a metal-chelating derivative thereof, the sequence of a $V_H$ domain in the second molecule is a humanized form of SEQ ID NO: 21. In a preferred embodiment, the humanized form of SEQ ID NO: 21 is SEQ ID NO: 37. In a specific embodiment, the sequence of a $V_L$ domain in the second molecule comprises a humanized form of SEQ ID NO: 22. In a specific embodiment, the sequence of a $V_L$ domain in the second molecule is a humanized form of SEQ ID NO: 22. In a preferred embodiment, the humanized form of SEQ ID NO: 22 is SEQ ID NO: 38. In a preferred embodiment, the second molecule is a scFv. In a specific embodiment, the sequence of the scFv comprises any one of the humanized sequences set forth in Table 7, above (e.g., any one of SEQ ID NOs: 39-44). In a specific embodiment, the sequence of the scFv is any one of the humanized sequences set forth in Table 7, above (e.g., any one of SEQ ID NOs: 39-44). In a preferred embodiment, the sequence of the scFv comprises SEQ ID NO: 44 (e.g., the sequence of the scFv is SEQ ID NO: 44). In a specific embodiment, the scFv comprises a $V_H$ domain that is a variant of the $V_H$ domain of a humanized form of C825 that has no more than 5 amino acid mutations relative to the sequence of the $V_H$ domain of the humanized form. In a specific embodiment, the scFv comprises a $V_L$ domain that is a variant of the $V_L$ domain of a humanized form of C825 that has no more than 5 amino acid mutations relative to the sequence of the $V_L$ domain of the humanized form. Methods for making humanized antibodies are known to the skilled artisan and are described above.

The sequences of the variable regions of the second molecule that specifically binds to DOTA or a metal-chelating derivative thereof (e.g., DOTA-Bn) may be modified by insertions, substitutions and deletions to the extent that the resulting scFv maintains the ability to bind to DOTA or the metal-chelating derivative thereof, as determined by, for example, ELISA, flow cytometry, and BiaCore™. The ordinarily skilled artisan can ascertain the maintenance of this activity by performing the functional assays as described herein below, such as, for example, binding analyses and cytotoxicity analyses.

In a preferred embodiment of the bispecific binding agents of the invention, the first molecule is an immunoglobulin and the second molecule is a scFv. In a specific embodiment, the immunoglobulin of the first molecule comprises two identical heavy chains and two identical light chains, said light chains being a first light chain and a second light chain, wherein the first light chain is fused, optionally via a first peptide linker, to the second molecule, to create a first light chain fusion polypeptide, wherein the second molecule is a first scFv that comprises the second binding site, and wherein the second light chain is fused, optionally via a second peptide linker, to a second scFv, to create a second light chain fusion polypeptide, and wherein the first and second light chain fusion polypeptides are identical. Since the first and second light chain fusion polypeptides are identical, the first and second peptide linkers of the bispecific binding agent are identical, and the first and second scFvs of the bispecific binding agent are identical. In a specific embodiment, the first light chain fusion polypeptide comprises said first peptide linker, and said second light chain fusion polypeptide comprises said second peptide linker, wherein the sequences of the first and second peptide linkers are 5-30, 5-25, 5-15, 10-30, 10-20, 10-15, 15-30, or 15-25 amino acids in length. In a specific embodiment, the first light chain fusion polypeptide comprises said first peptide linker, and said second light chain fusion polypeptide comprises said second peptide linker, wherein the sequences of the first and second peptide linkers are 7-32, 7-27, 7-17, 12-32, 12-22, 12-17, 17-32, or 17-27 amino acids in length. In a specific embodiment, the first light chain fusion polypeptide comprises said first peptide linker, and said second light chain fusion polypeptide comprises said second peptide linker, wherein the sequences of the first and second peptide linkers are selected from the group consisting of SEQ ID NOs: 23 and 25-30. In a specific embodiment, the sequence of the first and second peptide linkers is SEQ ID NO: 23. In a specific embodiment, the first scFv comprises an intra-scFv peptide linker between a $V_H$ domain and a $V_L$ domain in the first scFv. In a specific embodiment, the sequence of the intra-scFv peptide linker is 5-30, 5-25, 5-15, 10-30, 10-20, 10-15, 15-30, or 15-25 amino acids in length. In a specific embodiment, the sequences of the intra-peptide linker is selected from the group consisting of any one of SEQ ID NOs: 23 and 25-30. In a specific embodiment, the sequence of the intra-scFv peptide linker is SEQ ID NO: 27. In a specific embodiment, the sequence of the intra-scFv peptide linker is SEQ ID NO: 30.

In a specific embodiment of the bispecific binding agents of the invention, the first molecule is an immunoglobulin that specifically binds to HER2 and the second molecule is a scFv that specifically binds to DOTA-Bn. In a specific embodiment, the immunoglobulin of the first molecule comprises two identical heavy chains and two identical light chains, said light chains being a first light chain and a second light chain, wherein the first light chain is fused, optionally via a first peptide linker, to the second molecule, to create a first light chain fusion polypeptide, wherein the second molecule is a first scFv that comprises the second binding site, and wherein the second light chain is fused, optionally via a second peptide linker, to a second scFv, to create a second light chain fusion polypeptide, and wherein the first and second light chain fusion polypeptides are identical. In a specific embodiment, the first light chain fusion polypeptide comprises said first peptide linker, and said second light chain fusion polypeptide comprises said second peptide linker, wherein the sequences of the first and second peptide linkers are 5-30, 5-25, 5-15, 10-30, 10-20, 10-15, 15-30, or 15-25 amino acids in length. In a specific embodiment, the first light chain fusion polypeptide comprises said first peptide linker, and said second light chain fusion polypeptide comprises said second peptide linker, wherein the sequences of the first and second peptide linkers are 7-32, 7-27, 7-17, 12-32, 12-22, 12-17, 17-32, or 17-27 amino acids in length. In a specific embodiment, the first light chain fusion polypeptide comprises said first peptide linker, and said second light chain fusion polypeptide comprises said second peptide linker, wherein the sequences of the first and second peptide linkers are selected from the group consisting of SEQ ID NOs: 23 and 25-30 (see Table 8). In a specific embodiment, the first light chain fusion polypeptide comprises said first peptide linker, and said second light chain fusion polypeptide comprises said second peptide linker, wherein the sequences of the first and second peptide linkers are selected from the group consisting of SEQ ID NOs: 51-56 (see Table 8). In a specific embodiment, the sequence of the first and second peptide linkers is SEQ ID NO: 23. In a specific embodiment, the sequence of the first and second peptide linkers is SEQ ID NO: 53. In a specific embodiment, a heavy chain in the immunoglobulin is a heavy chain described herein. In a specific embodiment, a light chain in the immunoglobulin is a light chain described herein. In a specific embodiment, a heavy chain in the immunoglobulin comprises all three heavy chain CDRs of SEQ ID NO: 20, and a light chain in the immunoglobulin comprises all three light chain CDRs of SEQ ID NO: 19. In a specific embodiment, the sequence of a $V_H$ domain in a heavy chain in the immunoglobulin comprises SEQ ID NO: 20. In a preferred embodiment, the sequence of a $V_L$ domain in a light chain in the immunoglobulin comprises SEQ ID NO: 19. In a specific embodiment, the sequence of a heavy chain in the immunoglobulin comprises any of SEQ ID NOs: 14-17. In a preferred embodiment, the sequence of a heavy chain in the immunoglobulin comprises SEQ ID NO: 15. In another preferred embodiment, the sequence of a heavy chain in the immunoglobulin comprises SEQ ID NO: 16. In a preferred embodiment, the sequence of a light chain in the immunoglobulin comprises SEQ ID NO: 11. In a specific embodiment, the sequence of a $V_H$ domain in a heavy chain in the immunoglobulin comprises a humanized form SEQ ID NO: 20. In a specific embodiment, the sequence of a $V_L$ domain in a light chain in the immunoglobulin comprises a humanized form SEQ ID NO: 19. In a specific embodiment, the first scFv comprises an intra-scFv peptide linker between a $V_H$ domain and a $V_L$ domain in the first scFv. In a specific embodiment, the sequence of the intra-scFv peptide linker is 5-30, 5-25, 5-15, 10-30, 10-20, 10-15, 15-30, or 15-25 amino acids in length. In a specific embodiment, the sequences of the intra-peptide linker is selected from the group consisting of any one of SEQ ID NOs: 23 and 25-30. In a preferred embodiment, the sequence of the intra-scFv peptide linker is SEQ ID NO: 27. In a preferred embodiment, the sequence of the intra-scFv peptide linker is SEQ ID NO: 30. In a specific embodiment, the sequence of a $V_H$ domain in the first scFv comprises all three of the CDRs of SEQ ID NO: 21, and wherein the sequence of a $V_L$ domain in the first scFv comprises all three of the CDRs of SEQ ID NO: 22. In a specific embodiment, the sequence of a $V_H$ domain in the first scFv is SEQ ID NO: 21. In a specific embodiment, the sequence of a $V_L$ domain in the first scFv is SEQ ID NO: 22. In a specific embodiment, the sequence of a $V_H$ domain in the first scFv comprises a humanized form of SEQ ID NO: 21. In a specific embodiment, the humanized form of SEQ ID NO: 21 is SEQ ID NO: 37. In a specific embodiment, the sequence of a $V_L$ domain in the first scFv comprises a humanized form of SEQ ID NO: 22. In a specific embodiment, the humanized form of SEQ ID NO: 22 is SEQ ID NO: 38. In a specific embodiment, the first scFv is an scFv described herein. In a specific embodiment, the first scFv comprises the sequence of any of SEQ ID NOs: 31-36. In a preferred embodiment, the scFv comprises the sequence of SEQ ID NO: 33. In a specific embodiment, the first scFv comprises the sequence of any of SEQ ID NOs: 39-44. In a preferred embodiment, the scFv comprises the sequence of SEQ ID NO: 44. In a specific embodiment, the sequence of the first light chain fusion polypeptide is any of SEQ ID NOs: 5-10. In a preferred embodiment, the sequence of the first light chain fusion polypeptide is SEQ ID NO: 7. In a specific embodiment, the sequence of the first light chain fusion polypeptide is any of SEQ ID NOs: 45-50. In a preferred embodiment, the sequence of the first light chain fusion polypeptide is SEQ ID NO: 50. In a specific embodiment, the sequence of the first light chain fusion polypeptide is any of SEQ ID NOs: 5-10, and wherein the sequence of the heavy chain is any of SEQ ID NOs: 14-17. In a preferred embodiment, the sequence of the first light chain fusion polypeptide is SEQ ID NO: 7, and wherein the sequence of the heavy chain is SEQ ID NO: 15. In a specific embodiment, the sequence of the first light chain fusion polypeptide is any of SEQ ID NOs: 45-50, and the sequence of the heavy chain is any of SEQ ID NOs: 14-17. In a preferred embodiment, the sequence of the first light chain fusion polypeptide is SEQ ID NO: 50, and the sequence of the heavy chain is SEQ ID NO: 16.

TABLE 8

Light Chain Fusion Polypeptide Sequence.

| DESCRIPTION | SEQUENCE (SEQ ID NO:) |
|---|---|
| Trastuzumab LC-(G$_4$S)$_2$AS linker-murine C825 $V_H$-G$_4$S linker-murine C825 $V_L$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*ggggsggggsasHVKLQESGPGLVQPSQSLSLTCTVSGFSLTDYGVHWVRQSPGKGLEWLGVIWSGGGTAYNTALISRLNIYRDNSKNQVFLEMNSLQAEDTAMYYCARRGSYPYNYFDAWGCGTTVTVSS**ggggsQAVVIQESALTTPPGETVTLTCGSSTGAVTASNYANWVQEKPDHCFTGLIGGHNNRPPGVPARFSGSLIGDKAALTIAGTQTEDEAIYFCALWYSDHWVIGGGTRLTVLG** (SEQ ID NO: 5) |
| Trastuzumab LC-(G$_4$S)$_2$AS linker-murine C825 $V_H$-(G$_4$S)$_2$ linker-murine C825 $V_L$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*ggggsggggsasHVKLQESGPGLVQPSQSLSLTCTVSGFSLTDYGVHWVRQSPGKGLEWLGVIWSGGGTAYNTALISRLNIYRDNSKNQVFLEMNSLQAEDTAMYYCARRGSYPYNYFDAWGCGTTVTVSS**ggggsggggsQAVVIQESALTTPPGETVTLTCGSSTGAVTASNYANWVQEKPDHCFTGLIGGHNNRPPGVPARFSGSLIGDKAALTIAGTQTEDEAIYFCALWYSDHWVIGGGTRLTVLG** (SEQ ID NO: 6) |
| Trastuzumab LC-(G$_4$S)$_2$AS linker-murine C825 $V_H$-(G$_4$S)$_3$ linker-murine C825 $V_L$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*ggggsggggsasHVKLQESGPGLVQPSQSLSLTCTVSGFSLTDYGVHWVRQSPGKGLEWLGVIWSGGGTAYNTALISRLNIYRDNSKNQVFLEMNSLQAEDTAMYYCARRGSYPYNYFDAWGCGTTVTVSS**ggggsggggsggggsQAVVIQESALTTPPGETVTLTCGSSTGAVTASNYANWVQEKPDHCFTGLIGGHNNRPPGVPARFSGSLIGDKAALTIAGTQTEDEAIYFCALWYSDHWVIGGGTRLTVLG** (SEQ ID NO: 7) |
| Trastuzumab LC-(G$_4$S)$_2$AS linker-murine C825 $V_H$-(G$_4$S)$_4$ linker-murine C825 $V_L$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*ggggsggggsasHVKLQESGPGLVQPSQSLSLTCTVSGFSLTDYGVHWVRQSPGKGLEWLGVIWSGGGTAYNTALISRLNIYRDNSKNQVFLEMNSLQAEDTAMYYCARR |

TABLE 8 -continued

| Light Chain Fusion Polypeptide Sequence. | |
|---|---|
| DESCRIPTION | SEQUENCE (SEQ ID NO:) |
| | GSYPYNYFDAWGCGTTVTVSS**ggggsggggsggggsggggsQAVVIQES**<br>**ALTTPPGETVTLTCGSSTGAVTASNYANWVQEKPDHCFTGLI**<br>**GGHNNRPPGVPARFSGSLIGDKAALTIAGTQTEDEAIYFCALW**<br>**YSDHWVIGGGTRLTVLG** (SEQ ID NO: 8) |
| Trastuzumab LC-<br>$(G_4S)_2$AS linker-<br>murine C825 $V_H$-<br>$(G_4S)_5$ linker-<br>murine C825 $V_L$ | DIQMTQSPSSLSASVGDRVTITCRASQDVNTAVAWYQQKPGKAP<br>KLLIYSASFLYSGVPSRFSGSRSGTDFTLTISSLQPEDFATYYCQQH<br>YTTPPTFGQGTKVEIKR*TVAAPSVFIFPPSDEQLKSGTASVVCLLNNF*<br>*YPREAKVQWKVDNALQSGNSQESVTEQDSKDSTYSLSSTLTLSKADYE*<br>*KHKVYACEVTHQGLSSPVTKSFNRGEC*ggggsggggsasHVKLQESGPG<br>LVQPSQSLSLTCTVSGFSLTDYGVHWVRQSPGKGLEWLGVIWSG<br>GGTAYNTALISRLNIYRDNSKNQVFLEMNSLQAEDTAMYYCARR<br>GSYPYNYFDAWGCGTTVTVSS**ggggsggggsggggsggggsggggsQAVVI**<br>**QESALTTPPGETVTLTCGSSTGAVTASNYANWVQEKPDHCFT**<br>**GLIGGHNNRPPGVPARFSGSLIGDKAALTIAGTQTEDEAIYFC**<br>**ALWYSDHWVIGGGTRLTVLG** (SEQ ID NO: 9) |
| Trastuzumab LC-<br>$(G_4S)_2$AS linker-<br>murine C825 $V_H$-<br>$(G_4S)_6$ linker-<br>murine C825 $V_L$ | DIQMTQSPSSLSASVGDRVTITCRASQDVNTAVAWYQQKPGKAP<br>KLLIYSASFLYSGVPSRFSGSRSGTDFTLTISSLQPEDFATYYCQQH<br>YTTPPTFGQGTKVEIKR*TVAAPSVFIFPPSDEQLKSGTASVVCLLNNF*<br>*YPREAKVQWKVDNALQSGNSQESVTEQDSKDSTYSLSSTLTLSKADYE*<br>*KHKVYACEVTHQGLSSPVTKSFNRGEC*ggggsggggsasHVKLQESGPG<br>LVQPSQSLSLTCTVSGFSLTDYGVHWVRQSPGKGLEWLGVIWSG<br>GGTAYNTALISRLNIYRDNSKNQVFLEMNSLQAEDTAMYYCARR<br>GSYPYNYFDAWGCGTTVTVSS**ggggsggggsggggsggggsggggsggggsQ**<br>**AVVIQESALTTPPGETVTLTCGSSTGAVTASNYANWVQEKPD**<br>**HCFTGLIGGHNNRPPGVPARFSGSLIGDKAALTIAGTQTEDEA**<br>**IYFCALWYSDHWVIGGGTRLTVLG** (SEQ ID NO: 10) |
| Trastuzumab LC-<br>TS$(G_4S)_3$ linker-<br>humanized C825<br>$V_H$-$G_4S$ linker-<br>humanized C825 $V_L$ | DIQMTQSPSSLSASVGDRVTITCRASQDVNTAVAWYQQKPGKAP<br>KLLIYSASFLYSGVPSRFSGSRSGTDFTLTISSLQPEDFATYYCQQH<br>YTTPPTFGQGTKVEIKR*TVAAPSVFIFPPSDEQLKSGTASVVCLLN*<br>*NFYPREAKVQWKVDNALQSGNSQESVTEQDSKDSTYSLSSTLTL*<br>*SKADYEKHKVYACEVTHQGLSSPVTKSFNRGEC*tsggggsggggsgggg<br>sHVQLVESGGGLVQPGGSLRLSCAASGFSLTDYGVHWVRQAPGK<br>GLEWLGVIWSGGGTAYNTALISRFTISRDNSKNTLYLQMNSLRAE<br>DTAVYYCARRGSYPYNYFDAWGCGTLVTVSS**ggggsQAVVTQEP**<br>**SLTVSPGGTVTLTCGSSTGAVTASNYANWVQQKPGQCPRGLI**<br>**GGHNNRPPGVPARFSGSLLGGKAALTLLGAQPEDEAEYYCAL**<br>**WYSDHWVIGGGTKLTVLG** (SEQ ID NO: 45) |
| Trastuzumab LC-<br>TS$(G_4S)_3$ linker-<br>humanized C825<br>$V_H$-$(G_4S)_2$ linker-<br>humanized C825 $V_L$ | DIQMTQSPSSLSASVGDRVTITCRASQDVNTAVAWYQQKPGKAP<br>KLLIYSASFLYSGVPSRFSGSRSGTDFTLTISSLQPEDFATYYCQQH<br>YTTPPTFGQGTKVEIKR*TVAAPSVFIFPPSDEQLKSGTASVVCLLNNF*<br>*YPREAKVQWKVDNALQSGNSQESVTEQDSKDSTYSTSSTLTLSKADYE*<br>*KHKVYACEVTHQGLSSPVTKSFAIRGEC*tsggggsggggsggggsHVQLVES<br>GGGLVQPGGSLRLSCAASGFSLTDYGVHWVRQAPGKGLEWLGV<br>IWSGGGTAYNTALISRFTISRDNSKNTLYLQMNSLRAEDTAVYYC<br>ARRGSYPYNYFDAWGCGTLVTVSS**ggggsggggsQAVVTQEPSLTV**<br>**SPGGTVTLTCGSSTGAVTASNYANWVQQKPGQCPRGLIGGH**<br>**NNRPPGVPARFSGSLLGGKAALTLLGAQPEDEAEYYCALWYS**<br>**DHWVIGGGTKLTVLG** (SEQ ID NO: 46) |
| Trastuzumab LC-<br>TS$(G_4S)_3$ linker-<br>humanized C825<br>VH-$(G_4S)_3$ linker-<br>humanized C825 $V_L$ | DIQMTQSPSSLSASVGDRVTITCRASQDVNTAVAWYQQKPGKAP<br>KLLIYSASFLYSGVPSRFSGSRSGTDFTLTISSLQPEDFATYYCQQH<br>YTTPPTFGQGTKVEIKR*TVAAPSVFIFPPSDEQLKSGTASVVCLLNNF*<br>*YPREAKVQWKVDNALQSGNSQESVTEQDSKDSTYSTSSTLTLSKADYE*<br>*KHKVYACEVTHQGLSSPVTKSFAIRGEC*tsggggsggggsggggsHVQLVES<br>GGGLVQPGGSLRLSCAASGFSLTDYGVHWVRQAPGKGLEWLGV<br>IWSGGGTAYNTALISRFTISRDNSKNTLYLQMNSLRAEDTAVYYC<br>ARRGSYPYNYFDAWGCGTLVTVSS**ggggsggggsggggsQAVVTQEP**<br>**SLTVSPGGTVTLTCGSSTGAVTASNYANWVQQKPGQCPRGLI**<br>**GGHNNRPPGVPARFSGSLLGGKAALTLLGAQPEDEAEYYCAL**<br>**WYSDHWVIGGGTKLTVLG** (SEQ ID NO: 47) |
| Trastuzumab LC-<br>TS$(G_4S)_3$ linker-<br>humanized C825<br>VH-$(G_4S)_4$ linker-<br>humanized C825 $V_L$ | DIQMTQSPSSLSASVGDRVTITCRASQDVNTAVAWYQQKPGKAP<br>KLLIYSASFLYSGVPSRFSGSRSGTDFTLTISSLQPEDFATYYCQQH<br>YTTPPTFGQGTKVEIKR*TVAAPSVFIFPPSDEQLKSGTASVVCLLNNF*<br>*YPREAKVQWKVDNALQSGNSQESVTEQDSKDSTYSLSSTLTLSKADYE*<br>*KHKVYACEVTHQGLSSPVTKSENRGEC*tsggggsggggsggggsHVQLVES<br>GGGLVQPGGSLRLSCAASGFSLTDYGVHWVRQAPGKGLEWLGV<br>IWSGGGTAYNTALISRFTISRDNSKNTLYLQMNSLRAEDTAVYYC<br>ARRGSYPYNYFDAWGCGTLVTVSS**ggggsggggsggggsggggsQAVVT**<br>**QEPSLTVSPGGTVTLTCGSSTGAVTASNYANWVQQKPGQCPR**<br>**GLIGGHNNRPPGVPARFSGSLLGGKAALTLLGAQPEDEAEYY**<br>**CALWYSDHWVIGGGTKLTVLG** (SEQ ID NO: 48) |

TABLE 8 -continued

Light Chain Fusion Polypeptide Sequence.

| DESCRIPTION | SEQUENCE (SEQ ID NO:) |
|---|---|
| Trastuzumab LC-TS$(G_4S)_3$ linker-humanized C825 VH-$(G_4S)_5$ linker-humanized C825 $V_L$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC*tsggggsggggsggggsHVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS**ggggsggggsggggsggggsggggsQAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG** (SEQ ID NO: 49) |
| Trastuzumab LC-TS$(G_4S)_3$ linker-humanized C825 $V_H$-$(G_4S)_6$ linker-humanized C825 $V_L$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC*tsggggsggggsggggsHVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS**ggggsggggsggggsggggsggggsggggsQAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG** (SEQ ID NO: 50) |

The uppercase, non-italicized, non-bold, non-underlined sequence represents the $V_L$ domain of the trastuzumab light chain.
The uppercase, italicized sequence represents the constant region of the trastuzumab light chain.
The lowercase, non-italicized, non-bold, non-underlined sequence represents the linker conjugating the light chain to the scFv.
The uppercase, underlined sequence represents the $V_H$ domain of the scFv.
The uppercase, bold sequence represents the $V_L$ domain of the scFv.
The uppercase, underlined, italicized, and bold sequences represent the mutations described in the "DESCRIPTION" column.
The lowercase bold sequences represent the intra-scFv linker.

In a preferred embodiment of the bispecific binding agents of the invention, the bispecific binding agent comprises a first molecule covalently bound via a linker to a second molecule, wherein the first molecule comprises a first binding site, wherein the first binding site specifically binds to a first target, wherein the first target is a cancer antigen expressed by said cancer, wherein the cancer antigen is HER2, wherein the second molecule comprises a second binding site, wherein the second binding site specifically binds to a second target, wherein the second target is DOTA-Bn, wherein the first molecule comprises an immunoglobulin, wherein said immunoglobulin comprises the first binding site, wherein the immunoglobulin comprises two identical heavy chains and two identical light chains, said light chains being a first light chain and a second light chain, wherein the first light chain is fused, optionally via a first peptide linker, to the second molecule, to create a first light chain fusion polypeptide, wherein the second molecule is a first scFv that comprises the second binding site, and wherein the second light chain is fused via a second peptide linker to a second scFv, to create a second light chain fusion polypeptide, and wherein the first and second light chain fusion polypeptides are identical, wherein the sequence of the first light chain fusion polypeptide is SEQ ID NO: 7 and the sequence of the heavy chain is SEQ ID NO: 15.

In a more preferred embodiment of the bispecific binding agents of the invention, the bispecific binding agent comprises a first molecule covalently bound via a linker to a second molecule, wherein the first molecule comprises a first binding site, wherein the first binding site specifically binds to a first target, wherein the first target is a cancer antigen expressed by said cancer, wherein the cancer antigen is HER2, wherein the second molecule comprises a second binding site, wherein the second binding site specifically binds to a second target, wherein the second target is DOTA-Bn, wherein the first molecule comprises an immunoglobulin, wherein said immunoglobulin comprises the first binding site, wherein the immunoglobulin comprises two identical heavy chains and two identical light chains, said light chains being a first light chain and a second light chain, wherein the first light chain is fused, optionally via a first peptide linker, to the second molecule, to create a first light chain fusion polypeptide, wherein the second molecule is a first scFv that comprises the second binding site, and wherein the second light chain is fused via a second peptide linker to a second scFv, to create a second light chain fusion polypeptide, and wherein the first and second light chain fusion polypeptides are identical, wherein the sequence of the first light chain fusion polypeptide is SEQ ID NO: 50 and the sequence of the heavy chain is SEQ ID NO: 16.

In another specific embodiment, the second target is a molecule that is bound to the metal chelator of a radiotherapeutic agent described herein. In such an embodiment, the second molecule and second target (to which the second molecule binds) can be the members of any well-known binding pairs (e.g., ligand-receptors), but must be selected such that interaction between the second molecule of the bispecific binding agent and the second target bound to the metal chelator of the radiotherapeutic agent does not significantly impede chelation of the metal radionuclide of the radiotherapeutic agent. In a specific embodiment, the second target comprises biotin and the second molecule comprises streptavidin or avidin. In a specific embodiment, the second target comprises histamine succinyl glycine and the second molecule comprises an antibody or an antigen-binding fragment thereof or an scFv that binds to histamine succinyl glycine.

For use of a bispecific binding agent described herein in a method of treating cancer described herein in a subject of a particular species, a bispecific binding agent is used that binds to the first target of that particular species. For example, to treat a human, the first target of the bispecific binding agent binds to the human homolog of the first target. For example, if the first target of the bispecific binding agent is HER2 and a cancer that expresses HER2 is to be treated in a human, then the bispecific binding agent comprises a first binding site that specifically binds to human HER2. In another example, to treat a canine, the first target of the bispecific binding agent binds to the canine homolog of the first target. For example, if the first target of the bispecific binding agent is HER2 and a cancer that expresses HER2 is to be treated in a canine, then the bispecific binding agent comprises a first binding site that specifically binds to canine HER2. Bispecific binding agents that are cross-reactive with the first target of various species can be used to treat subjects in those species. For example, the anti-HER2 antibody trastuzumab is expected to bind both human and canine HER2 due to the relative conservation of the epitope in HER2 recognized by trastuzumab. See, also, for example, Singer et al., 2012, Mol Immunol, 50: 200-209.

In addition, for use of a bispecific binding agent described herein in a method of treating cancer described herein in a subject of a particular species, the bispecific binding agent, preferably, the constant region of an immunoglobulin portion of the bispecific binding agent, is derived from that particular species. For example, to treat a human, the bispecific binding agent can comprise an antibody that is an immunoglobulin, wherein the immunoglobulin comprises a human constant region. In another example, to treat a canine, the bispecific binding agent can comprise an antibody that is an immunoglobulin, wherein the immunoglobulin comprises a canine constant region. In a specific embodiment, when treating a human, the immunoglobulin is humanized. In another specific embodiment, when treating a human, the immunoglobulin is human.

In a specific embodiment, the bispecific binding agent comprises a variant Fc region, wherein said variant Fc region comprises at least one amino acid modification relative to a wild-type Fc region, such that said molecule does not bind or has reduced binding to an Fc receptor (FcR), in soluble form or cell-bound form (including on immune-effector cells, such as, for example, NK cells, monocytes, and neutrophils). These FcRs include, but are not limited to, FcR1 (CD64), FcRII (CD32), and FcRIII (CD16). The affinity to FcR(n), the neonatal Fc receptor, is not affected, and thus maintained in the bispecific binding agent. For example, if the immunoglobulin is an IgG, preferably, the IgG has reduced or no affinity for an Fc gamma receptor. In a specific embodiment, one or more positions within the Fc region that makes a direct contact with Fc gamma receptor, such as, for example, amino acids 234-239 (hinge region), amino acids 265-269 (B/C loop), amino acids 297-299 (C'/E loop), and amino acids 327-332 (F/G) loop, are mutated such that the bispecific binding agent has a decreased or no affinity for an Fc gamma receptor. See, for example, Sondermann et al., 2000, Nature, 406: 267-273, which is incorporated herein by reference in its entirety. Preferably, for an IgG, the mutation N297A is made to destroy Fc receptor binding. In a specific embodiment, affinity of the bispecific binding agent or fragment thereof for an Fc gamma receptor is determined by, for example, BiaCore™ assay, as described, for example, in Okazaki et al., 2004. J Mol Biol, 336(5):1239-49. In a specific embodiment, the bispecific binding agent comprising such a variant Fc region binds an Fc receptor on a FcR-bearing immune-effector cell with less than 25%, 20%, 15%, 10%, or 5% binding as compared to a reference Fc region. Without being bound by any particular theory, a bispecific binding agent comprising such a variant Fc region will have a decreased ability to induce a cytokine storm. In preferred embodiments, the bispecific binding agent comprising such a variant Fc region does not bind an Fc receptor in soluble form or as a cell-bound form.

In a specific embodiment, the bispecific binding agent comprises a variant Fc region, such as, for example, an Fc region with additions, deletions, and/or substitutions to one or more amino acids in the Fc region of an antibody provided herein in order to alter effector function, or enhance or diminish affinity of antibody to FcR. In a preferred embodiment, the affinity of the antibody to FcR is diminished. Reduction or elimination of effector function is desirable in certain cases, such as, for example, in the case of antibodies whose mechanism of action involves blocking or antagonism but not killing of the cells bearing a target antigen. In a specific embodiment, the Fc variants provided herein may be combined with other Fc modifications, including but not limited to modifications that alter effector function. In a specific embodiment, such modifications provide additive, synergistic, or novel properties in antibodies or Fc fusions. Preferably, the Fc variants provided herein enhance the phenotype of the modification with which they are combined.

In a specific embodiment, the bispecific binding agent of the invention is aglycosylated or has reduced glycosylation content compared to a wild-type immunoglobulin. In another specific embodiment where the bispecific binding agent comprises an immunoglobulin, a heavy chain in the immunoglobulin is aglycosylated or has reduced glycosylation content as compared to a wild-type heavy chain. Preferably, this is achieved by mutating an antibody or antigen-binding fragment thereof of the first molecule portion of the bispecific binding agent in its Fc receptor to destroy one or more glycosylation sites (e.g., N-linked glycosylation sites). In another specific embodiment, an antibody or antigen binding fragment thereof of a bispecific binding agent is mutated to destroy one or more N-linked glycosylation sites. In certain preferred embodiments, an antibody or antigen binding fragment thereof of a bispecific binding agent has been mutated to destroy an N-linked glycosylation site. In a specific embodiment, a heavy chain of an antibody or antigen-binding fragment thereof of in the bispecific binding agent comprises an amino acid substitution to replace an asparagine that is an N-linked glycosylation site with an amino acid that does not function as a glycosylation site. In a preferred embodiment, the reduced glycosylation content of the bispecific binding agent is achieved by deleting a glycosylation site of the Fc region of a bispecific binding agent, by modifying position 297 from asparagine to alanine (N297A). For example, in a specific embodiment, the bispecific binding agent comprises a heavy chain with the sequence of SEQ ID NO: 15 or 16. As used herein, "glycosylation site" includes any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. Methods for modifying the glycosylation content of antibodies are well known in the art, see, for example, U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In another embodiment, aglycosylation of the bispecific binding agents of the invention can be achieved by recombinantly producing the bispecific binding agent in a cell or expression system incapable of glycosylation, such as, for example, bacteria. In another embodiment, aglycosylation or reduction of the glycosylation content of the bispecific binding agents of the invention can be achieved by enzymatically removing the carbohydrate moieties of the glycosylation site.

In a specific embodiment, the bispecific binding agent of the invention does not bind or has reduced binding affinity (relative to a reference or wild type immunoglobulin) to the complement component C1q. Preferably, this is achieved by mutating an antibody or antigen-binding fragment thereof of the bispecific binding agent to destroy a C1q binding site. In certain preferred embodiments, the method encompasses deleting the C1q binding site of an Fc region of the bispecific binding agent, by modifying position 322 from lysine to alanine (K322A) (see, e.g., Idusogie et al., 2000. J Immunol. 164(8):4178-84 for a description of the K322A modification). For example, in a specific embodiment, the bispecific binding agent comprises a heavy chain with the sequence of SEQ ID NO: 16 or 17. In a specific embodiment, affinity of the bispecific binding agent or fragment thereof for the complement component C1q is determined by, for example, BiaCore™ assay, as described, for example, in Okazaki et al., 2004. J Mol Biol, 336(5):1239-49. In a specific embodiment, the bispecific binding comprising a destroyed C1q binding site binds the complement component C1q with less than 25%, 20%, 15%, 10%, or 5% binding compared to a reference or wild type immunoglobulin. In a specific embodiment, the bispecific binding agent does not activate complement.

In a specific embodiment, the bispecific binding agent of the invention comprises an immunoglobulin, wherein the immunoglobulin (i) comprises at least one amino acid modification relative to a wild-type Fc region, such that said molecule does not bind or has reduced binding to an Fc receptor in soluble form or as cell-bound form; (ii) comprises one or more mutations in the Fc region to destroy an N-linked glycosylation site; and (iii) does not or has reduced binding to the complement component C1q. For example, in a specific embodiment, the bispecific binding agent comprises an IgG comprising a first mutation, N297A, in the Fc region to (i) abolish or reduce binding to an Fc receptor in soluble form or as cell-bound form; and (ii) destroy an N-linked glycosylation site in the Fc region; and a second mutation, K322A, in the Fc region to (iii) abolish or reduce binding to the complement component C1q. See, for example, SEQ ID NO: 16.

In a specific embodiment, the bispecific binding agent comprises an Fc domain. In a preferred embodiment, the first molecule of the bispecific binding agent comprises an Fc domain.

In a specific embodiment, the bispecific binding agent is at least 100 kDa, at least 150 kDa, at least 200 kDa, at least 250 kDa, between 100 and 300 kDa, between 150 and 300 kDa, or between 200 and 250 kDa. In a specific embodiment, the bispecific binding agent is at least 100 kDa.

The bispecific binding agents provided herein can bind the first and second target with a wide range of affinities. The affinity or avidity of an antibody for an antigen can be determined experimentally using any suitable method. See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein. The measured affinity of a particular antibody-antigen interaction can vary if measured under different conditions (e.g., salt concentration, pH). Thus, measurements of affinity and other antigen-binding parameters are preferably made with standardized solutions of antibody and antigen, and a standardized buffer. The affinity, $K_D$ is a ratio of $k_{off}/k_{on}$. Generally, a $K_D$ in the micromolar range is considered low affinity. Generally, a $K_D$ in the picomolar range is considered high affinity.

In a specific embodiment in which the first target of the bispecific binding agent is HER2, the bispecific binding agent preferably has been shown to bind to one or more HER2-positive carcinoma cell lines such as, e.g., MDA-MB-361, MDA-MB-468, AU565, SKBR3, HTB27, HTB26, HCC1954, MCF7, OVCAR3, SKOV3, NCI-N87, KATO III, AGS, SNU-16, HT144, SKMEL28, M14, HTB63, RG160, RG164, CRL1427, U205, SKEAW, SKES-1, HTB82, NMB7, SKNBE(2)C, IMR32, SKNBE(2)S, SKNBE(1)N, NBS, 15B, 93-VU-147T, PCI-30, UD-SCC2, PCI-15B, SCC90, UMSCC47, NCI-H524, NCI-H69, NCI-H345, as determined by assays known to one skilled in the art, such as, for example, ELISA, BiaCore™ flow cytometry, and cell based assays. In a specific embodiment, the bispecific binding agent binds to the HER2-positive carcinoma cell line with an EC50 in the nanomolar range.

In a specific embodiment, use of the bispecific binding agent in a method described herein (see, e.g., Section 5.1 and Section 6) reduces tumor progression, metastasis, and/or tumor size. See, for example, Section 6.

5.2.1 Bispecific Binding Agent Production

Also provided herein are methods for producing bispecific binding agents described in Section 5.1 and Section 6. In a specific embodiment, provided herein are methods for producing a bispecific binding agent comprising a first molecule covalently bound, optionally via a linker, to a second molecule, wherein the first molecule comprises a first binding site, wherein the first binding site specifically binds to a first target, wherein the first target is a cancer antigen expressed by said cancer, wherein the second molecule comprises a second binding site, wherein the second binding site specifically binds to a second target, wherein the second target is not the cancer antigen. In a specific embodiment, provided herein are methods for producing a bispecific binding agent comprising a first molecule covalently bound, optionally via a linker, to a second molecule, wherein said cancer expresses HER2, wherein the first molecule comprises an antibody or an antigen binding fragment thereof, or a scFv, wherein said antibody or antigen-binding fragment thereof, or scFv (i) binds to HER2 on said cancer, and (ii) comprises all three of the heavy chain CDRs of SEQ ID NO: 20, and all three of the light chain CDRs of SEQ ID NO: 19, wherein the second molecule comprises a second binding site, wherein the second binding site specifically binds to a second target, wherein the second target is not the cancer antigen.

Methods that can be used to produce bispecific binding agents described herein are known to one of ordinary skill in the art, for example, by chemical synthesis, by purification from biological sources, or by recombinant expression techniques, including, for example, from mammalian cell or transgenic preparations. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, for example, Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

A variety of methods exist in the art that can be used for the production of bispecific binding agents. For example, the bispecific binding agent may be made by recombinant DNA methods, such as those described in U.S. Pat. No. 4,816,567. The one or more DNAs encoding a bispecific binding agent provided herein can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA may be placed into expression vectors, which are then transformed into host cells such as NS0 cells, Simian COS cells, Chinese hamster ovary (CHO) cells, yeast cells, algae cells, eggs, or myeloma cells that do not otherwise produce immunoglobulin protein, to obtain the synthesis of the bispecific binding agents in the recombinant host cells. The DNA also may be modified, for example, by substituting the coding sequence for human heavy and light chain constant domains of a desired species in place of the homologous human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of a bispecific binding agent provided herein. In a specific embodiment, the DNA is as described in Section 5.2.1.1.

Bispecific binding agents provided herein also can be prepared using transgenic animals such as mammals, such as goats, cows, horses, sheep, and the like, that contain and express transgene(s) encoding at least one bispecific binding agent that is a protein such as an antibody, e.g., to produce such antibodies in their milk. Such animals can be provided using known methods. See, for example, but not limited to, U.S. Pat. Nos. 5,827,690; 5,849,992; 4,873,316; 5,849,992; 5,994,616, 5,565,362; 5,304,489, and the like, each of which is entirely incorporated herein by reference.

Bispecific binding agents provided herein also can be prepared using transgenic plants and cultured plant cells (for example, but not limited to tobacco and maize) that contain and express transgene(s) encoding at least one bispecific binding agent, e.g., to produce such bispecific binding agents in the plant parts or in cells cultured therefrom Bispecific binding agents provided herein also can be prepared using bacteria that are transformed to contain and express plasmids encoding at least one bispecific binding agent, e.g., to produce such bispecific binding agents in the bacteria.

In a specific embodiment, the bispecific binding agents can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, and high performance liquid chromatography. See, for example, Colligan, Current Protocols in Immunology, or Current Protocols in Protein Science, John Wiley & Sons, NY, N.Y., (1997-2001), e.g., chapters 1, 4, 6, 8, 9, and 10.

In a specific embodiment, the bispecific binding agents provided herein include, for example, products of chemical synthetic procedures, and products produced by recombinant techniques from a eukaryotic host, including, for example, yeast, higher plant, insect and mammalian cells. In a specific embodiment, the bispecific binding agent is generated in a host such that the bispecific binding agent is aglycosylated. In a specific embodiment, the bispecific binding agent is generated in a bacterial cell such that the bispecific binding agent is aglycosylated. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14.

Purified antibodies can be characterized by, for example, ELISA, ELISPOT, flow cytometry, immunocytology, Biacore™ analysis, Sapidyne KinExA™ kinetic exclusion assay, SDS-PAGE and Western blot, or by HPLC analysis.

See, also, Section 6 for a detailed example for the design and production of a bispecific binding agent described herein.

5.2.1.1 Polynucleotides

In a specific embodiment, provided herein are polynucleotides comprising a nucleotide sequence encoding a bispecific binding agent described herein or a fragment thereof (e.g., a heavy chain and/or a light chain fusion polypeptide) that specifically binds to a first target (e.g., HER2) and a second target (e.g., DOTA or a derivative thereof), as described in Section 5.2 and Section 6. Also provided herein are vectors comprising such polynucleotides. The polynucleotides and vectors can be used for recombinant production of the bispecific binding agents or fragments thereof.

The term "purified" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a bispecific binding agent described herein is isolated or purified.

Nucleic acid molecules can be in the form of RNA, such as mRNA, hnRNA, or in the form of DNA, including, but not limited to, cDNA and genomic DNA obtained by cloning or produced synthetically, or any combinations thereof.

In a specific embodiment, the polynucleotide used for recombinant production comprises nucleotide sequences encoding a bispecific binding agent or fragment thereof (e.g., a heavy chain or light chain fusion polypeptide) as described in Section 5.2 and Section 6, wherein the bispecific binding agent comprises a first molecule covalently bound, optionally via a linker, to a second molecule, wherein the first molecule comprises a first binding site, wherein the first binding site specifically binds to a first target, wherein the first target is a cancer antigen expressed by said cancer, wherein the second molecule comprises a second binding site, wherein the second binding site specifically binds to a second target, wherein the second target is not the cancer antigen. In a specific embodiment where the polynucleotide comprises nucleotide sequences encoding a fragment of a bispecific binding agent, the polynucleotide can be combined, e.g., ex vivo, to produce the bispecific binding agent. For example, the translation product of a polynucleotide comprising nucleotide sequences encoding a heavy chain of a bispecific binding agent and the translation product of a polynucleotide comprising nucleotide sequences encoding a light chain fusion polypeptide of the bispecific binding agent may be combined, e.g., ex vivo, to produce a bispecific binding agent.

In another specific embodiment, the polynucleotide used for recombinant production comprises nucleotide sequences encoding a bispecific binding agent or fragment thereof as described in Section 5.2 and Section 6, wherein the bispecific binding agent comprises a first molecule covalently bound, optionally via a linker, to a second molecule, wherein said cancer expresses HER2, wherein the first molecule comprises an antibody or an antigen binding fragment thereof, or a scFv, wherein said antibody or antigen-binding fragment thereof, or scFv (i) binds to HER2 on said cancer, and (ii) comprises all three of the heavy chain CDRs of SEQ ID NO: 20, and all three of the light chain CDRs of SEQ ID NO: 19, wherein the second molecule comprises a second binding site, wherein the second binding site specifically binds to a second target, wherein the second target is not the cancer antigen.

In a particular embodiment, the polynucleotide used for recombinant production comprises nucleotide sequences encoding a bispecific binding agent, or fragment thereof, which bispecific binding agent or fragment (i) specifically binds to HER2 and DOTA or a derivative thereof, and (ii) comprises an amino acid sequence as described herein.

In a specific embodiment, one or more portions of a bispecific binding agent described herein is produced by expression from a nucleotide sequence set forth in Table 9. In a preferred embodiment for producing the bispecific binding agent, the sequence of the light chain is SEQ ID NO: 11, and the nucleotide sequence encoding the light chain that is expressed to produce the light chain is SEQ ID NO: 13. In a preferred embodiment for producing the bispecific binding agent, the sequence of the scFv is SEQ ID NO: 33, and the nucleotide sequence encoding the scFv that is expressed to produce the scFv is SEQ ID NO: 38. In a preferred embodiment for producing the bispecific binding agent, the sequence of the light chain is SEQ ID NO: 11 and the sequence of the scFv is SEQ ID NO: 33, and the nucleotide sequence encoding the light chain that is expressed to produce the light chain is SEQ ID NO: 13 and the nucleotide sequence encoding the scFv that is expressed to produce the scFv is SEQ ID NO: 38. In a preferred embodiment for producing the bispecific binding agent, the sequence of the light chain fusion polypeptide is SEQ ID NO: 7 and the nucleotide sequence encoding the light chain fusion polypeptide that is expressed to produce the light chain fusion polypeptide is SEQ ID NO: 18. In a preferred embodiment for producing the bispecific binding agent, the sequence of the heavy chain is SEQ ID NO: 15, and the nucleotide sequence encoding the heavy chain that is expressed to produce the heavy chain is SEQ ID NO: 12.

TABLE 9

Exemplary nucleic acid sequences.

| DESCRIPTION | SEQUENCE (SEQ ID NO:) |
|---|---|
| Nucleic acid encoding HER2-C825 Light Chain a SEQ ID NO: 11 | gatattcagatgactcagtctccctcttccctgtccgcttcagtcggcgatcgggtcactattacttgtcggctt<br>cacaggatgtcaacacagccgtggcttggtaccagcagaagcccgggaaagcacctaagctgctgatctactc<br>tgccagtttcctgtattctggcgtcccaagtaggttttcaggctcccggagcggaactgacttcaccctgacaat<br>ttccagcctgcagcccgaggattttgctacctactattgccagcagcattatactacccccccaacattcggcca<br>gggcacaaaagtcgaaatcaagcggaccgtggccgcccctccgtgttcatcttccccccctccgacgagc<br>agctgaagtccggcaccgcctccgtggtgtgcctgctgaacaacttctacccccgggaggccaaggtgcagt<br>ggaaggtggacaacgccctgcagtccggcaactcccaggagtccgtgaccgagcaggactccaaggactc<br>cacctactccctgtcctccaccctgaccctgtccaaggccgactacgagaagcacaaggtgtacgcctgcga<br><br>ggtgacccaccagggcctgtcctcccccgtgaccaagtccttcaaccggggcgagtgc (SEQ ID NO: 13) |
| Nucleic acid encoding scFy of SEQ ID NO: 33 | catgtgaaactgcaggaaagcggcccaggtctggtccagccatcccagtctctgagcctgacatgcactgtg<br>agcggattctctctgacagactatggggtgcactgggtcagacagagtccaggaaaggggctggagtggct<br>gggcgtcatctggtcaggcggagggactgcttataacaccgcactgatcagcagactgaatatctaccgcga<br>caactctaaaaatcaggtgttcctggagatgaacagtctgcaggccgaagataccgctatgtactattgcgcca<br>ggcggggcagctacccttataattactttgacgcttggggttgtggcaccacagtgacagtctccagcggtgg<br>aggagggagtggtggaggagggtcaggtggaggagggtcccaggcagtggtcattcaggagtctgccctg<br>actacccccctggagaaaccgtgacactgacttgcggatctagtacaggggcagtgactgcctccaactat<br>gcaaattgggtccaggaaaagcctgatcactgtttcactggcctgatcggtggccataacaatcgaccacccg<br>gagtgccagctaggttttcaggttccctgatcggcgacaaagccgctctgaccattgctggcacccagacaga<br>ggatgaagcaatctacttttgtgccctgtggtattccgatcactgggtcattgggggggggacacgtctgactgt<br>gctgggg (SEQ ID NO: 24) |
| Nucleic acid encoding HER2-C825 Light Chain Fusion Polypep tide of SEQ ID NO: 7 | gatattcagatgactcagtctccctcttccctgtccgcttcagtcggcgatcgggtcactattacttgtcggctt<br>cacaggatgtcaacacagccgtggcttggtaccagcagaagcccgggaaagcacctaagctgctgatctactc<br>tgccagtttectgtattctggcgteccaagtaggifitcaggctcccggageggaactgacttcaccctgacaat<br>ttccagcctgcagcccgaggattttgctacctactattgccagcagcattatactacccccccaacattcggcca<br>gggcacaaaagtcgaaatcaagcggaccgtggccgcccctccgtgttcatcttccccccctccgacgagc<br>agctgaagtccggcaccgcctccgtggtgtgcctgctgaacaacttctacccccgggaggccaaggtgcagt<br>ggaaggtggacaacgccctgcagtccggcaactcccaggagtccgtgaccgagcaggactccaaggactc<br>cacctactccctgtcctccaccctgaccctgtccaaggccgactacgagaagcacaaggtgtacgcctgcga<br>ggtgacccaccagggcctgtcctcccccgtgaccaagtccttcaaccggggcgagtgcggtggtggtggta<br>gcggcggcggtggaagcgcatcccatgtgaaactgcaggaaagcggcccaggtctggtccagccatccca<br>gtctctgagcctgacatgcactgtgagcggattctctctgacagactatggggtgcactgggtcagacagagt<br>ccaggaaaggggctggagtggctgggcgtcatctggtcaggcggagggactgcttataacaccgcactgat |

TABLE 9 -continued

Exemplary nucleic acid sequences.

| DESCRIPTION | SEQUENCE (SEQ ID NO:) |
|---|---|
| | cagcagactgaatatctaccgcgacaactctaaaaatcaggtgttectggagatgaacagtctgcaggccgaa gataccgctatgtactattgcgccaggcggggcagctacccttataattactttgacgcttggggttgtggcacc acagtgacagtctccagcggtggaggagggagtggtggaggagggtcaggtggaggagggtcccaggca gtggtcattcaggagtctgccctgactaccccccctggagaaaccgtgacactgacttgcggatctagtacag gggcagtgactgcctccaactatgcaaattgggtccaggaaaagcctgatcactgtttcactggcctgatcggt ggccataacaatcgaccacccggagtgccagctaggttttcaggttccctgatcggcgacaaagccgctctg accattgctggcacccagacagaggatgaagcaatctacttttgtgccctgtggtattccgatcactgggtcatt gggggggggacacgtctgactgtgctgggg (SEQ ID NO: 18) |
| Nucleic acid encoding HER2-C825 Heavy Chain of SEQ ID NO: 15 | gaagtgcagctggtcgagagcggaggaggtctggtgcagcccggaggttccctgagactgtcctgtgccgc atctgggtttaatatcaaggacacatacatccactgggtgagacaggcacccggcaaaggactggagtgggt cgccaggatctaccctaccaacgggtacacaagatatgctgactctgtgaagggccggttcaccatctccgcc gatactagcaaaaacaccgcttacctgcagatgaattccctgagggcagaagataccgctgtctactactgttc aagatgggggggggatggifittacgctatggattattggggccagggcaccctggtgaccgtgtectccgcc tccaccaagggcccatcggtcttccccctggcaccctcctccaagagcacctctgggggcacagcggccct gggctgcctggtcaaggactacttccccgaaccggtgacggtgtcgtggaactcaggcgccctgaccagcg gcgtgcacaccttcccggccgtcctacagtcctcaggactctactccctcagcagcgtggtgaccgtgccctc cagcagcttgggcacccagacctacatctgcaacgtgaatcacaagcccagcaacaccaaggtggacaag agagttgagcccaaatcttgtgacaaaactcacacatgcccaccgtgcccagcacctgaactcctgggggga ccgtcagtcttcctcttccccccaaaacccaaggacaccctcatgatctcccggacccctgaggtcacatgcgt ggtggtggacgtgagccacgaagaccctgaggtcaagttcaactggtacgtggacggcgtggaggtgcata atgccaagacaaagccgcgggaggagcagtacgccagcacgtaccgtgtggtcagcgtcctcaccgtcct gcaccaggactggctgaatggcaaggagtacaagtgcaaggtctccaacaaagccctcccagcccccatcg agaaaaccatctccaaagccaaagggcagccccgagaaccacaggtgtacaccctgcccccatcccggga tgagctgaccaagaaccaggtcagcctgacctgcctggtcaaaggcttctatcccagcgacatcgccgtgga gtgggagagcaatgggcagccggagaacaactacaagaccacgcctcccgtgctggactccgacggctcc ttcttcctctacagcaagctcaccgtggacaagagcaggtggcagcaggggaacgtcttctcatgctccgtga tgcatgaggctctgcacaaccactacacgcagaagagcctctccctgtctccgggtaaa (SEQ ID NO: 12) |

The polynucleotides for use as provided herein can be obtained by any method known in the art. For example, if the nucleotide sequence encoding a bispecific binding agent or fragment thereof described herein is known, a polynucleotide encoding the bispecific binding agent or fragment thereof can be may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding a bispecific binding agent or fragment thereof for use as provided herein may be generated from nucleic acid from a suitable source. If a clone containing a nucleic acid encoding a particular bispecific binding agent or fragment thereof is not available, but the sequence of the bispecific binding agent or fragment thereof is known, a nucleic acid encoding the bispecific binding agent or fragment thereof may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody provided herein) by PCR amplification using synthetic primers that hybridize to the 3' and 5' ends of the sequence or by cloning using an oligonucleotide probe specific for the particular gene sequence to identify, for example, a cDNA clone from a cDNA library that encodes the antibody. Amplified nucleic acids generated by PCR may then be cloned into replicable cloning vectors using any method well known in the art. See, for example, Section 5.2.1.2.

In a specific embodiment, the amino acid sequence of the antibody of the bispecific binding agent is known in the art. In such embodiments, a polynucleotide encoding such an antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate bispecific binding agents having a different amino acid sequence, for example, to create amino acid substitutions, deletions, and/or insertions. For example, such manipulations can be performed to render the encoded amino acid aglycosylated, or to destroy the antibody's ability to bind to C1q, Fc receptor, or to activate the complement system.

Isolated nucleic acid molecules provided herein can include nucleic acid molecules comprising an open reading frame (ORF), optionally with one or more introns, for example, but not limited to, at least one specified portion of at least one CDR, as CDR1, CDR2 and/or CDR3 of at least one heavy chain or light chain; nucleic acid molecules comprising the coding sequence for an anti-HER2 antibody or variable region, an anti-DOTA (or derivative thereof) scFv, or a single chain fusion polypeptide; and nucleic acid molecules which comprise a nucleotide sequence substantially different from those described above but which, due to the degeneracy of the genetic code, still encode at least one bispecific binding agent as described herein and/or as known in the art.

The nucleic acids for use as provided herein can conveniently comprise sequences in addition to a polynucleotide provided herein. For example, a multi-cloning site comprising one or more endonuclease restriction sites can be inserted into the nucleic acid to aid in isolation of the polynucleotide. In addition, translatable sequences can be inserted to aid in the isolation of the translated polynucleotide provided herein. For example, a hexa-histidine marker sequence provides a convenient means to purify the polypeptides provided herein. The nucleic acid provided herein—excluding the coding sequence—is optionally a vector, adapter, or linker for cloning and/or expression of a polynucleotide provided herein.

Additional sequences can also be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

In a specific embodiment, using routine recombinant DNA techniques, one or more of the CDRs of an antibody described herein may be inserted within framework regions for humanization of the antibody. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds HER2. One or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are provided herein and within the skill of the art.

In a specific embodiment, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, for example, Gateway™. (Invitrogen)). See, also, U.S. Pat. No. 5,314,995.

In a specific embodiment, a polynucleotide provided herein is in the form of a vector (e.g., expression vector) as described in Section 5.2.1.2.

5.2.1.2 Cells and Vectors

In a specific embodiment, provided herein are cells (e.g., ex vivo cells) expressing (e.g., recombinantly) bispecific binding agents described herein for use in producing the bispecific binding agents described herein. Also provided herein are vectors (e.g., expression vectors) comprising nucleotide sequences (see, for example, Section 5.2.1.1) encoding a bispecific binding agent or fragment thereof described herein for recombinant expression in host cells, preferably in mammalian cells, for use in producing the bispecific binding agents described herein. Also provided herein are cells (e.g., ex vivo cells) comprising such vectors or nucleotide sequences for recombinantly expressing a bispecific binding agent described herein. Also provided herein are methods for producing a bispecific binding agent described herein, comprising expressing such bispecific binding agent from a cell (e.g., ex vivo cell). In a preferred embodiment, the cell is an ex vivo cell.

In a specific embodiment, provided herein is a vector comprising one or more polynucleotide as described in Section 5.2.1.1, wherein said vector is for use in producing a bispecific binding agent described herein.

In a specific embodiment, a polynucleotide as described in Section 5.2.1.1 can be cloned into a suitable vector and can be used to transform or transfect any suitable host for recombinant production of bispecific binding agents, using methods well known in the art.

In a specific embodiment, the vector is a mammalian vector, used for recombinant expression of the bispecific binding agent in a mammalian host or host cell. Non-limiting examples of mammalian expression vectors include, vectors such as pIRESlneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Non-limiting example of mammalian host cells that can be used in combination with such mammalian vectors include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

In a specific embodiment, the vector is a viral vector, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. In a specific embodiment, the viral vector is manipulated to render the virus replication deficient. In a specific embodiment, the viral vector is manipulated to eliminate toxicity to the host.

In a specific embodiment, a vector or polynucleotide described herein is be transferred to a cell (e.g., an ex vivo cell) by conventional techniques and the resulting cell can be cultured by conventional techniques to produce a bispecific binding agent described herein. In a preferred embodiment, the cell is a CHO cell. In an especially preferred embodiment, the cell is a CHO-S cell.

In a specific embodiment, a polynucleotide described herein can be expressed in a stable cell line that comprises the polynucleotide integrated into a chromosome by introducing the polynucleotide into the cell.

5.3 Clearing Agents

Provided herein are clearing agents for use in the methods of treating cancer described herein (see, e.g., Section 5.1). As described above, when used in a method of treating cancer described herein, the clearing agent is administered to the subject after (e.g., not more than 12 hours after) step (a) of administering to the subject the therapeutically effective amount of the bispecific binding agent. The clearing agents described herein function to reduce the amount of bispecific binding agent circulating in the blood of the subject prior to administering to the subject a therapeutically effective amount of the radiotherapeutic agent. In a specific embodiment, the clearing agent comprises a molecule that is cleared predominantly by the liver, fixed phagocytic system, spleen, or bone marrow from the circulating blood. Without being bound by any particular theory, administration of the clearing agent to the subject (i) after administration of the bispecific binding agent to the subject, but (ii) before administration of the radiotherapeutic agent to the subject, clears or reduces the bispecific binding agent circulating in the blood of the subject, resulting in reduced exposure of non-targeted, normal tissue (e.g., tissue not expressing the cancer antigen) in the subject to the subsequent administration of the radiotherapeutic agent. Thus, without being bound by any theory, administration of the clearing agent allows for improved therapeutic indices by limiting radiation from the radiotherapeutic agent in non-targeted, normal tissue (i.e., tissue not expressing the cancer antigen) allowing for higher doses of the radiotherapeutic agent to be administered to the subject without resulting in dose-limiting radiation toxicity.

For use in a method of treating cancer described herein, the clearing agent binds the bispecific binding agent used in the method of treating cancer. Thus, for use of a clearing agent in a method of treating cancer described herein, a clearing agent should be selected that binds to the bispecific binding agent used in the method. Accordingly, one skilled in the art will understand that the clearing agent is selected based on the structure and specificity of the bispecific binding agent used in the method. In a specific embodiment, the clearing agent comprises the second target (of the bispecific binding agent) or a derivative of the second target, which derivative retains the ability to bind the second molecule (preferably at the second binding site), bound to a molecule that is cleared from the circulating blood. The derivatives of the second target, as described herein, retain the ability to bind the second molecule (preferably at the second binding site). In a specific embodiment, the clearing agent comprises the second target (of the bispecific binding agent) or a derivative thereof bound to a molecule that is cleared predominantly by the liver, fixed phagocytic system, spleen, or bone marrow from the circulating blood. For example, if the second target of the bispecific binding agent is DOTA, a clearing agent for use in combination with the bispecific binding agent can comprise DOTA bound to a molecule that is cleared predominantly by the liver, fixed phagocytic system, spleen, or bone marrow from the circulating blood. In another example, if the second target of the bispecific binding agent is DOTA, a clearing agent for use in combination with the bispecific binding agent can comprise a derivative of DOTA (e.g., isothiocyanate-benzyl-DOTA) bound to a molecule that is cleared predominantly by the liver, fixed phagocytic system, spleen, or bone marrow from the circulating blood. For use of a derivative of the second target (of the bispecific binding agent) in a clearing agent, the derivative of the second target must retain its ability to bind to the bispecific binding agent (specifically, to the second binding site of the second molecule of the bispecific binding agent).

Molecules that are cleared predominantly by the liver, fixed phagocytic system, spleen, or bone marrow from the circulating blood are known to the skilled artisan. Nonlimiting examples of molecules that are cleared predominantly by the liver, fixed phagocytic system, spleen, or bone marrow from the circulating blood include: aminodextran, galactosylated albumin, galactose, galactosamine, mannose, lactose, muramyl tripeptide, RGD peptide, and glycyrrhizin (see, e.g., Mishra et al., 2013, Efficient Hepatic Delivery of Drugs: Novel Strategies and Their Significance, BioMed Research International, vol. 2013, Article ID 32184, 20 pages). The skilled artisan will understand that molecules that are cleared predominantly by the liver, fixed phagocytic system, spleen, or bone marrow from the circulating blood include molecules that bind to, e.g., a surface receptor protein on a liver cell, a spleen cell, or bone marrow cell that is internalized into the cell. For example, for a clearing agent to be cleared predominantly by the liver from the circulating blood, the clearing agent should comprise a molecule that interacts with a liver cell (e.g., a hepatocyte). For example, for clearance by the liver, the clearing agent may comprise a molecule that interacts with a receptor on a hepatocyte, for example, the asialoglycoprotein receptor. In this example, the clearing agent may comprise galactosylated albumin bound to the second target (of the bispecific binding agent), such that the second target in the clearing agent binds the bispecific binding agent in the circulating blood, the galactosylated albumin interacts with the asialoglycoprotein receptor on hepatocytes (see, e.g., Stockert, Physiol Rev. 1995; 75:591-609), and the bispecific binding agent bound to the clearing agent is internalized by the hepatocyte and cleared from the subject by the liver.

In a specific embodiment, the clearing agent comprises a 500 kDa aminodextran conjugated to the second target. In a specific embodiment, the second target is DOTA. In a specific embodiment, the clearing agent comprises 500 kDa aminodextran conjugated to DOTA. In a specific embodiment, the clearing agent comprises a 500 kDa aminodextran conjugated to a derivative of the second target. In a specific embodiment, the second target is DOTA. In a specific embodiment in which the second target is DOTA, the derivative of the second target is isothiocyanate-benzyl-DOTA. In a specific embodiment, the clearing agent comprises 500 kDa aminodextran conjugated to isothiocyanate-benzyl-DOTA.

In a specific embodiment, the clearing agent comprises approximately 100-150 molecules of the second target per 500 kDa of aminodextran. In a specific embodiment, the second target is DOTA. In a specific embodiment, the clearing agent comprises approximately 100-150 molecules of DOTA per 500 kDa of aminodextran. In a specific embodiment, the clearing agent comprises approximately 100-150 molecules of a derivative of the second target per 500 kDa of aminodextran. In a specific embodiment, the second target is DOTA. In a specific embodiment in which the second target is DOTA, the derivative of the second target is isothiocyanate-benzyl-DOTA. In a specific embodiment, the clearing agent comprises approximately 100-150 molecules of isothiocyanate-benzyl-DOTA per 500 kDa of aminodextran. In a specific embodiment in which the second target is DOTA, the clearing agent further comprises non-radioactive lutetium or yttrium molecule.

One skilled in the art will appreciate that a suitable clearing agent for use in a method of treating cancer described herein is one that preferably is easily manufactured, easily characterized, and has a consistent composition. For example, suitable clearing agents include those agents that have a single chemical composition, such as, e.g., a fully synthetic dedrimer-conjugate.

Clearing agents and methods of producing clearing agents are known in the art (see, e.g., Orcutt et al. Mol Cancer Ther 2012, 11(6) 1365-72, U.S. Pat. Nos. 6,075,010, 6,416,738, and International Patent Application Publication No. WO 2012/085789 A1. For example, to produce a clearing agent comprising 100-150 molecules of isothiocyanate-benzyl-DOTA per 500 kDa of aminodextran, aminodextran is reacted in large excess of the isothiocyanate-benzyl-DOTA to achieve a quantitative reaction. See, e.g., Orcutt et al., 2012, Effect of small-molecule-binding affinity on tumor uptake in vivo: a systematic study using a pretargeted bispecific antibody. Mol Cancer Ther; 11: 1365-72 for a description of how to produce a clearing agent described herein.

In a specific embodiment in which the clearing agent comprises a second target that is a metal chelator, the clearing agent further comprises a non-radioactive metal capable of interacting with the metal chelator. For example, if the clearing agent comprises DOTA or a derivative thereof, the non-radioactive metal used to generate the non-radioactive clearing agent may be $^{175}Lu$ or $^{89}Y$. In a specific embodiment, the clearing agent comprises 100-150 molecules of isothiocyanate-benzyl-DOTA per 500 kDa of aminodextran, wherein the isothiocyanate-benzyl-DOTA is in complex with $^{175}$Lu.

For use in a method of treating cancer described herein, it is preferable to utilize a clearing agent that clears unbound bispecific binding agent from the circulating blood (sometimes referred to herein as "clearance") within hours. In a specific embodiment, the clearing agent clears the unbound bispecific binding agent from the circulating blood in less than 24 hours, less than 23 hours, less than 22 hours, less than 21 hours, less than 20 hours, less than 19 hours, less than 18 hours, less than 17 hours, 16 hours, less than 15 hours, less than 14 hours, less than 13 hours, less than 12 hours, less than 11 hours, less than 10 hours, less than 9 hours, less than 8 hours, less than 7 hours, 6 hours, less than 5 hours, less than 4 hours, less than 3 hours, less than 2 hours, or less than 1 hour. In a specific embodiment, the clearing agent clears the unbound bispecific binding agent from the circulating blood in 1-2 hours, 1-3 hours, 1-4 hours, 2-6 hours, 2-8 hours, 2-10 hours, 4-6 hours, 4-8 hours, 4-10 hours, not more than 1 hour, not more than 2 hours, not more than 3 hours, not more than 4 hours, not more than 5 hours, not more than 6 hours, 1 hour, 2 hours, 3 hours, 4 hours, 5 hours, or 6 hours.

In a specific embodiment, the bispecific binding agent is considered to be cleared from the circulating blood if at least 80%, at least 85%, at least 90%, at least 91%, at least 92%, at least 93%, at least 94%, at least 95%, at least 96%, at least 97%, at least 98%, or at least 99% of bispecific binding agent is cleared from the circulating blood within 1 hour, 2 hours, 3 hours, or 4 hours of administering the clearing agent to the subject. Methods for determining the percent of bispecific binding agent cleared from the circulating blood are known to the skilled artisan, see, e.g., Breitz, et al., J Nucl Med 2000 41(1) 131-40 and the assays described in Section 6.

5.4 Radiotherapeutic Agents

Also provided herein are radiotherapeutic agents for use in the methods of treating cancer described herein (see, e.g., Section 5.1 and Section 6). As described above, when used in a method of treating cancer described herein, the radiotherapeutic agent is administered to the subject after step (b) of administering to the subject the therapeutically effective amount of the clearing agent. Without being bound by any particular theory, for use in a method of treating cancer described herein, the radiotherapeutic agent binds to the bispecific binding agent and mediates killing of cancer cells to which the bispecific binding agent is bound, along with other cells by cross-fire effects, radiation-induced by standard effect, and abscopal effects. The first molecule of a bispecific binding agent described herein (see, e.g., Section 5.2 and Section 6) specifically binds to a cancer antigen (i.e., the first target of the bispecific binding agent) on a cancer cell in the subject, and the second molecule of the bispecific binding agent specifically binds to the second target, said second target forming part of the radiotherapeutic agent. Thus, without being bound by any particular theory, the bispecific binding agent forms a bridge between the cancer cell and the radiotherapeutic agent, permitting the radiotherapeutic agent to kill the bispecific binding agent-bound cancer cell. Accordingly, for use of a radiotherapeutic agent in combination with a bispecific binding agent in a method of treating cancer described herein, a radiotherapeutic agent should be selected that comprises the second target of the bispecific binding agent. The radiotherapeutic agent comprises (i) the second target bound to a metal radionuclide, wherein the second target is a metal chelator; or (ii) the second target bound to a metal chelator, said metal chelator being bound to a metal radionuclide. Thus, one skilled in the art will understand that the radiotherapeutic agent for use in a method of treating cancer described herein is selected based on the structure and specificity of the bispecific binding agent used in the method. In a preferred embodiment, the radiotherapeutic agent comprises DOTA or a derivative thereof bound to a metal radionuclide. In a preferred embodiment in which the radiotherapeutic agent comprises DOTA or a derivative thereof bound to a metal radionuclide, the metal radionuclide is $^{177}$Lu.

In a specific embodiment, the radiotherapeutic agent comprises (i) the second target (of the bispecific binding agent) bound to a metal radionuclide, wherein the second target is a metal chelator. For example, if the first molecule of the bispecific binding agent is an immunoglobulin that binds (via its first binding site) to the cancer antigen HER2 (i.e., the first target) on a cancer cell, and the second molecule of the bispecific binding agent is a single chain variable fragment (scFv) that binds (via its second binding site) to the metal chelator DOTA (i.e., the second target) or a derivative thereof, then the radiotherapeutic agent may comprise the metal chelator DOTA or the derivative thereof bound to a metal radionuclide. In a specific embodiment in which the radiotherapeutic agent comprises DOTA or a derivative thereof, the metal radionuclide is $^{177}$Lu.

In another specific embodiment, the radiotherapeutic agent comprises (ii) the second target (of the bispecific binding agent used in the method of treating cancer) bound, preferably covalently, to a metal chelator, said metal chelator being bound to a metal radionuclide. For example, if the first molecule of the bispecific binding agent is an immunoglobulin that binds (via its first binding site) to the cancer antigen HER2 (i.e., the first target) on a cancer cell, and the second molecule of the bispecific binding agent is streptavidin, which binds (via its second binding site) to biotin (i.e., the second target), then the radiotherapeutic agent may comprise biotin bound a metal chelator, said metal chelator bound to a metal radionuclide. In a specific embodiment, the second target is covalently bound to the metal chelator.

Metal chelators that may form part of a radiotherapeutic agent described herein are known in the art. Nonlimiting examples of metal chelators include DOTA or a derivative thereof (e.g., DOTA-Bn and DOTA-desferrioxamine) and DTPA or a derivative thereof. In a specific embodiment, the metal chelator is DOTA or a derivative thereof. In a specific embodiment, the metal chelator is DOTA-Bn.

Metals that may form part of a radiotherapeutic agent described herein are known in the art. Nonlimiting examples of metals include lutetium (Lu), actinium (Ac), astatine (At), bismuth (Bi), cerium (Ce), copper (Cu), dysprosium (Dy), erbium (Er), europium (Eu), gadolinium (Gd), gallium (Ga), holmium (Ho), iodine (I), indium (In), lanthanum (La), lead (Pb), neodymium (Nd), praseodymium (Pr), promethium (Pm), rhenium (Re), samarium (Sm), scandium (Sc), terbium (Tb), thulium (Tm), ytterbium (Yb), yttrium (Y), and zirconium (Zr). In a specific embodiment, the metal is yttrium (Y). In a preferred embodiment, the metal is lutetium (Lu). Nonlimiting examples of metal radionuclides include $^{211}At$, $^{225}Ac$, $^{227}Ac$, $^{212}Bi$, $^{213}Bi$, $^{64}Cu$, $^{67}Cu$, $^{67}Ga$, $^{68}Ga$, $^{157}Gd$, $^{166}Ho$, $^{124}I$, $^{125}I$, $^{131}I$, $^{111}In$, $^{177}Lu$, $^{212}Pb$, $^{186}Re$, $^{188}$ e, $^{47}Sc$, $^{153}Sm$, $^{166}Tb$, $^{89}Zr$, $^{86}Y$, $^{88}Y$, and $^{90}Y$. The skilled artisan will understand that the metal radionuclide of the radiotherapeutic agent is selected based on its ability to bind the metal chelator of the radiotherapeutic agent. For example, if the metal chelator of the radiotherapeutic agent is DOTA, then a metal radionuclide capable of binding DOTA, such as, e.g., Lu or Y, is used. In a specific embodiment, the metal radionuclide has picomolar affinity for the metal chelator. Additionally, the metal radionuclide of the radiotherapeutic agent must be selected such that the radiotherapeutic agent comprising the metal chelator bound to the radionuclide retains its ability to be bound by the bispecific binding agent (i.e., via the second binding site of the bispecific binding agent). In a specific embodiment in which the metal chelator of the radionuclide is DOTA or a derivative thereof, the metal radionuclide is $^{86}Y$, $^{90}Y$, $^{88}Y$, or $^{177}Lu$. In a preferred embodiment in which the metal chelator of the radionuclide is DOTA or a derivative thereof, the metal radionuclide is $^{177}Lu$.

In another specific embodiment, the metal chelator of a radiotherapeutic agent described herein comprises a compound of Formula I or a pharmaceutically acceptable salt thereof, wherein $M^1$ is $^{175}Lu^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{135}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$ or $^{160}Gd^{3+}$; $X^1$, $X^2$, $X^3$, and $X^4$ are each independently a lone pair of electrons (i.e. providing an oxygen anion) or H; $X^5$, $X^6$, and $X^7$ are each independently a lone pair of electrons (i.e. providing an oxygen anion) or H; and n is 1, 2, 3, 4, 5, 6, 7, 8, 9, 10, 11, 12, 13, 14, 15, 16, 17, 18, 19, 20, 21, or 22. In certain embodiments, n is 3.

In another In a specific embodiment of the compound of Formula I, at least two of $X^1$, $X^2$, $X^3$, and $X^4$ are each independently a lone pair of electrons. In a specific embodiment of the compound of Formula I, three of $X^1$, $X^2$, $X^3$, and $X^4$ are each independently a lone pair of electrons and the remaining $X^1$, $X^2$, $X^3$, or $X^4$ is H.

In a specific embodiment in which the metal chelator of a radiotherapeutic agent described herein comprises a compound of Formula I, the radiotherapeutic agent further comprises a radionuclide cation. In a specific embodiment, the compound of Formula I can bind a radionuclide cation with a $K_d$ of about 1 pM-1 nM (e.g., about 1-10 pM; 1-100 pM; 5-50 pM; 100-500 pM; or 500 pM-1 nM). In a specific embodiment, the $K_d$ is in the range of about 1 nM to about 1 pM, for example, no more than about 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 150 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2.5 pM, 2 pM, or 1 pM. In a specific embodiment in which the metal chelator of a radiotherapeutic agent described herein comprises a compound of Formula I, the metal chelator comprises Formula II

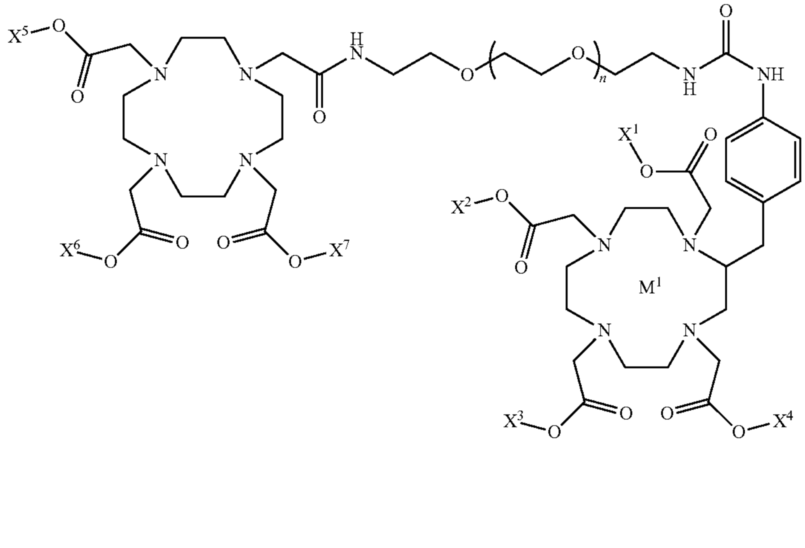

(I)

(II)

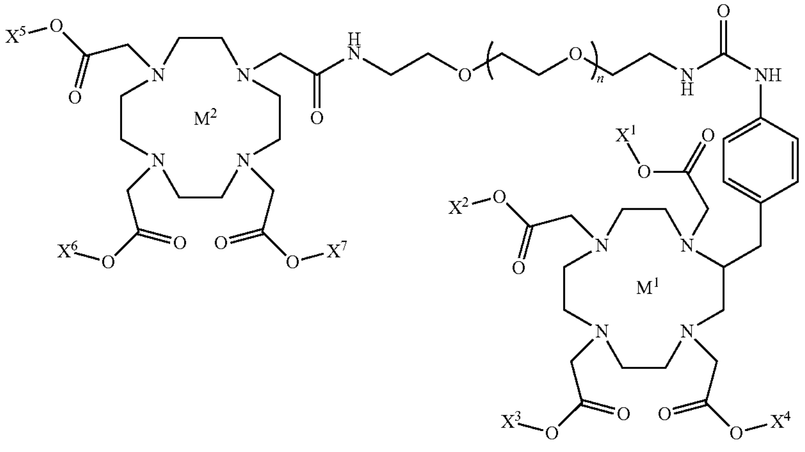

or a pharmaceutically acceptable salt thereof, wherein $M^1$ is $^{175}Ln^{3+}$, $^{45}Sc^{3+}$, $^{69}Ga^{3+}$, $^{71}Ga^{3+}$, $^{89}Y^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, or $^{160}Gd^{3+}$; $M^2$ is the radionuclide cation; $X^1$, $X^2$, $X^3$, and $X^4$ are each independently a lone pair of electrons (i.e. providing an oxygen anion) or H; $X^5$, $X^6$, and $X^7$ are each independently a lone pair of electrons (i.e. providing an oxygen anion) or H; and n is 1, 2, 3, 4, 5, 6, 7, 8, 9, 10, 11, 12, 13, 14, 15, 16, 17, 18, 19, 20, 21, or 22. In certain embodiments, n is 3.

In a specific embodiment of the metal chelator of Formula I or II, at least two of $X^5$, $X^6$, and $X^7$ are each independently a lone pair of electrons. Additionally or alternatively, in some embodiments of the bischelate, the radionuclide cation is a divalent cation or a trivalent cation. The radionuclide cation may be an alpha particle-emitting isotope, a beta particle-emitting isotope, an Auger-emitter, or a combination of any two or more thereof. Examples of alpha particle-emitting isotopes include, but are not limited to, $^{213}Bi$, $^{211}At$, $^{225}Ac$, $^{152}Dy$, $^{212}Bi$, $^{223}Ra$, $^{219}Rn$, $^{215}Po$, $^{211}Bi$, $^{221}Fr$, $^{217}At$, and $^{255}Fm$. Examples of beta particle-emitting isotopes include, but are not limited to, $^{86}Y$, $^{90}Y$, $^{89}Sr$, $^{165}Dy$, $^{186}Re$, $^{188}Re$, $^{177}Lu$, and $^{67}Cu$. Examples of Auger-emitters include $^{111}In$, $^{67}Ga$, $^{51}Cr$, $^{58}Co$, $^{99m}Tc$, $^{103m}Rh$, $^{195m}Pt$, $^{119}Sb$, $^{161}Ho$, $^{189m}Os$, $^{192}Ir$, $^{201}Tl$, and $^{203}Pb$. In some embodiments of the metal chelator of Formula I or II, the radionuclide cation is $^{68}Ga$, $^{227}Th$, or $^{64}Cu$.

In some embodiments of the metal chelator of Formula I or II, the radionuclide cation has a decay energy in the range of 20 to 6,000 keV. Decay energies can be within the range of 60 to 200 keV for an Auger emitter, 100-2,500 keV for a beta emitter, and 4,000-6,000 keV for an alpha emitter. Maximum decay energies of useful beta-particle-emitting nuclides can range from 20-5,000 keV, 100-4,000 keV, or 500-2,500 keV. Decay energies of useful Auger-emitters can be <1,000 keV, <100 keV, or <70 keV. Decay energies of useful alpha-particle-emitting radionuclides can range from 2,000-10,000 keV, 3,000-8,000 keV, or 4,000-7,000 keV.

In a specific embodiment, the metal radionuclide of the radiotherapeutic agent is a theranostic isotope. As used herein, a theranostic isotope is a metal radionuclide that may be simultaneously utilized for therapeutic (e.g., treating cancer) and imaging (e.g., in vivo) purposes. Thus, a radiotherapeutic agent comprising a theranostic isotope allows the radiotherapeutic agent to (i) kill the targeted cancer cells and (ii) be imaged in vivo to monitor the, e.g., presence, location, and amount of the radiotherapeutic agent in the subject, thus permitting monitoring of the treatment of the cancer. In a specific embodiment, a theranostic isotope is an emitter of both β-particles and γ-radiation. Without being bound by any particular theory, emission of the β-particles provides the therapeutic purpose (i.e., kills the cancer cell) and emission of the γ-radiation allows for γ-scintigraphy for imaging purposes. Further, the γ-emissions allow for high-resolution single-photon emission computed tomography/computed tomography (SPECT/CT) imaging for, e.g., pre-therapy dosimetry of the bispecific binding agent and treatment monitoring (see, e.g., Ljungberg et al., 2016, MIRD Pamphlet No. 26: Joint EANM/MIRD Guidelines for Quantitative $^{177}Lu$ SPECT Applied for Dosimetry of Radiopharmaceutical Therapy." Journal of Nuclear Medicine, 57:151-62; Delker et al., 2016, Dosimetry for (177)Lu-DKFZ-PSMA-617: a new radiopharmaceutical for the treatment of metastatic prostate cancer. European Journal of Nuclear Medicine and Molecular Imagine, 43:42-51). Nonlimiting examples of theranostic isotopes include $^{177}Lu$, $^{155}Tb$, $^{90}Y$, $^{131}I$, $^{166}Ho$, $^{152}Sm$, and $^{111}In$. Nonlimiting examples of isotope pairs that may be used for imaging and therapy include $^{111}In/^{90}Y$, $^{111}In/^{225}Ac$, $^{124}I/^{131}I$, $^{68}Ga/^{177}Lu$, $^{68}Ga/^{90}Y$, $^{86}Y/^{90}Y$, $^{64}Cu/^{67}Cu$. Such isotope pairs are selected such that the therapeutic isotope and the diagnostic isotope have similar binding properties to the metal chelator. Accordingly, also provided herein is a method of diagnosing or prognosing a cancer, comprising carrying out a method of treating cancer of the invention using a radiotherapeutic agent comprising a theranostic isotope, and detecting an image in the subject of the theranostic radionuclide in the subject.

As will be clear to one skilled in the art, the metal radionuclide of the radiotherapeutic agent, when bound to a metal chelator, is preferably noncovalently bound (i.e., by chelation) to the metal chelator.

See, e.g., Cheal et al., 2014, Preclinical evaluation of multistep targeting of diasialoganglioside GD2 using an IgG-scFv bispecific antibody with high affinity for GD2 and DOTA metal complex, Molecular Cancer Therapeutics; 13:1803-12 for methods of producing radiotherapeutic agents.

5.5 Pharmaceutical Compositions and Kits

In a specific embodiment, provided herein are compositions (e.g., pharmaceutical compositions) comprising a therapeutically effective amount of a bispecific binding agent described herein (see, e.g., Section 5.2 or Section 6). In a specific embodiment, provided herein are compositions (e.g., pharmaceutical compositions) comprising a therapeutically effective amount of a clearing agent described herein (see, e.g., Section 5.3 and Section 6). In a specific embodiment, provided herein are compositions (e.g., pharmaceutical compositions) comprising a therapeutically effective amount of a radiotherapeutic agent described herein (see, e.g., Section 5.4 and Section 6). Also provided herein are kits comprising one or more compositions (e.g., pharmaceutical compositions) comprising a therapeutically effective amount of a bispecific binding agent described herein (see, e.g., Section 5.2 or Section 6), one or more compositions (e.g., pharmaceutical compositions) comprising a therapeutically effective amount of a clearing agent described herein (see, e.g., Section 5.3 and Section 6), and/or one or more compositions (e.g., pharmaceutical compositions) comprising a therapeutically effective amount of a radiotherapeutic agent described herein (see, e.g., Section 5.4 and Section 6). Compositions may be used in the preparation of individual, single unit dosage forms. Compositions comprising a bispecific binding agent provided herein or a radiotherapeutic agent provided herein can be formulated for intravenous, subcutaneous, intramuscular, parenteral, transdermal, transmucosal, intraperitoneal, or intrathoracic administration, or administration into other body compartment, such as intrathecal, intrathecal, intraventricular, or intraparenchymal administration. Compositions comprising a clearing agent provided herein can be formulated for intravenous administration. In a specific embodiment of a composition comprising a bispecific binding agent, the composition is formulated for intraperitoneal administration to treat peritoneal metastases. In a specific embodiment of a composition comprising a bispecific binding agent, the composition is formulated for intrathecal administration. In a specific embodiment of a composition comprising a bispecific binding agent, the composition is formulated for intrathecal administration to treat brain metastases. See, for example, Kramer et al., 2010, 97: 409-418. In a specific embodiment of a composition comprising a bispecific binding, the composition is formulated for intraventricular administration in the brain. In a specific embodiment of a composition comprising a bispecific binding, the composition is formulated for intraventricular administration to treat brain metastases. See, for example, Kramer et al., 2010, 97: 409-418. In a specific embodiment of a composition comprising a bispecific binding, the composition is formulated for intraparenchymal administration in the brain. In a specific embodiment of a composition comprising a bispecific binding, the composition is formulated for intraparenchymal administration to treat a brain tumor or brain tumor metastases. See, for example, Luther et al., 2014, Neuro Oncol, 16: 800-806, and Clinical Trial ID NO NCT01502917. In a preferred embodiment of a composition comprising a bispecific binding agent, the composition is formulated for intravenous administration. In a preferred embodiment of a composition comprising a clearing agent, the composition is formulated for intravenous administration. In a preferred embodiment of a composition comprising a radiotherapeutic agent, the composition is formulated for intravenous administration.

In a specific embodiment, compositions provided herein comprise at least one of any suitable auxiliary, such as, but not limited to, diluent, binder, stabilizer, buffers, salts, lipophilic solvents, preservative (e.g., ascorbic acid), adjuvant, detergent, or other incipient to stabilize and prevent aggregation, or the like. In a specific embodiment, pharmaceutically acceptable auxiliaries are preferred. Non-limiting examples of, and methods of preparing such sterile solutions are well known in the art, such as, but not limited to, Gennaro, Ed., Remington's Pharmaceutical Sciences, 18$^{th}$ Edition, Mack Publishing Co. (Easton, Pa.) 1990. Pharmaceutically acceptable carriers can be routinely selected that are suitable for the mode of administration, solubility and/or stability of the bispecific binding agent, clearing agent, or radiotherapeutic agent as described herein.

In a specific embodiment, a pharmaceutical composition described herein is to be used in accordance with the methods provided herein (see, e.g., Section 5.1 and Section 6).

5.5.1 Kits

Provided herein are kits comprising one or more bispecific binding agent, clearing agent, and/or radiotherapeutic agent as described herein, or one or more composition as described herein. In a specific embodiment, the kit comprises (i) packaging material and (ii) at least one vial comprising a composition comprising a bispecific binding agent or composition thereof described herein, at least one vial comprising a clearing agent or composition thereof described herein, and/or at least one vial comprising a composition comprising a radiotherapeutic agent or composition thereof described herein. In a specific embodiment, the vial comprises a solution of at least one bispecific binding agent, clearing agent, or radiotherapeutic agent or composition thereof as described herein with the prescribed buffers and/or preservatives, optionally in an aqueous diluents. In a specific embodiment, the compositions provided herein can be provided to a subject as solutions or as dual vials comprising a vial of lyophilized bispecific binding agent, clearing agent, or radiotherapeutic agent or composition(s) thereof that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of subject treatment and thus can provide a more convenient treatment regimen than currently available.

In a specific embodiment, a kit comprising a bispecific binding agent, clearing agent, and/or radiotherapeutic agent or composition(s) thereof described herein is useful for administration over a period of immediately to twenty-four hours or greater. In a specific embodiment, a kit comprising a bispecific binding agent, clearing agent, and/or radiotherapeutic agent or composition(s) thereof described herein can optionally be safely stored at temperatures of from about 2° C. to about 40° C. and retain the biologically activity of the agent for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The kits can be provided indirectly to a subject, such as a subject as described in Section 5.6, by providing to pharmacies, clinics, or other such institutions and facilities, solutions or multi-vials comprising a vial(s) of lyophilized bispecific binding agent, clearing agent, or radiotherapeutic agent or composition(s) thereof that is reconstituted with a second vial(s) containing the aqueous diluent. The solution in this case can be up to one liter or even larger in size, providing a large reservoir from which smaller portions of the at least one bispecific binding agent, clearing agent, or radiotherapeutic agent solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, e.g., as made or developed by Becton Dickensen (Franklin Lakes, N.J.,), Disetronic (Burgdorf, Switzerland; Bioject, Portland, Oreg.; National Medical Products, Weston Medical (Peterborough, UK), Medi-Ject Corp (Minneapolis, Minn.). Recognized devices comprising a dual vial system include those pen-injector systems for reconstituting a lyophilized drug in a cartridge for delivery of the reconstituted solution such as the HumatroPen®.

In a specific embodiment, the kits comprise packaging material. In a specific embodiment, the packaging material provides, in addition to the information required by a regulatory agencies, the conditions under which the product can be used. In a specific embodiment, the packaging material provides instructions to the subject to reconstitute the at least one bispecific binding agent, clearing agent, and/or radiotherapeutic agent in the aqueous diluent(s) to form a solution(s) and to use the solution(s) over a period of 2-24 hours or greater for the multi-vial, wet/dry, product. For the single vial, solution product, the label indicates that such solution can be used over a period of 2-24 hours or greater. In a preferred embodiment, the kit is useful for human pharmaceutical product use. In a specific embodiment, the kit is useful for veterinarian pharmaceutical use. In a preferred embodiment, the kit is useful for canine pharmaceutical product use. In a preferred embodiment, the kit is useful for intravenous administration. In another preferred embodiment, the kit is useful for subcutaneous, intramuscular, parenteral, transdermal, transmucosal, intraperitoneal, intrathoracic, intrathecal, intraventricular, or intraparenchymal administration.

5.6 Patient Population

A subject treated in accordance with the methods provided herein can be any mammal, such as a rodent, a cat, a canine, a horse, a cow, a pig, a monkey, a primate, or a human, etc. In a specific embodiment, the subject is a canine. In a preferred embodiment, the subject is a human.

In a specific embodiment, a subject treated in accordance with the methods provided herein has been diagnosed with a cancer. Nonlimiting examples of cancers include bladder cancer, brain cancer, a breast cancer (e.g. triple negative Breast Cancer), a cervical cancer, clear cell Renal Cancer, a colon cancer, a colon carcinoma, colorectal cancer, desmoplastic small round cell cancer, endometrial cancer, an epithelial tumor (e.g., breast, GI tract), esophageal cancer, Ewing's sarcoma, gastric cancer, gastric junction adenocarcinoma, gastroesophageal junction adenocarcinoma, a glioblastoma (e.g., glioblastoma multiforme), a glioma, a gynecologic malignancy, a head and neck cancer, hepatocellular carcinoma, a leukemia, lung cancer, a lymphoma, a melanoma, mesothelioma, myeloma, neuroblastoma, a neuroendocrine tumor, non-small-cell lung cancer, an osteosarcoma, ovarian cancer, pancreatic cancer, prostate cancer, renal cancer, rhabdomyosarcoma, salivary gland cancer, a sarcoma, small cell lung cancer, soft tissue sarcoma, squamous cell carcinoma of head and neck cancer, a cancer of the stroma of most neoplasms (e.g., especially colorectal, pancreatic), a tumor associated with vasculature, a tumor associated with Papilloma virus, a urothelial cancer, a wide variety of cancers as a marker of tumor associated angiogenesis, Wilms tumors, other cancer stem cells and invasive epithelial tumors, and cancer associated with vasculature (see, e.g., Table 1). In a specific embodiment, the cancer is a metastatic cancer. In a specific embodiment, the metastatic cancer comprises a peritoneal metastasis.

The skilled artisan will understand that the cancer to be treated with a bispecific binding agent described herein in accordance with the methods provided herein dictates the first target of the bispecific binding agent used in the method of treating cancer. For instance, if the cancer to be treated is a cancer that expresses HER2, then the bispecific binding agent used in the method of treating the cancer that expresses HER2 comprises a first binding site, wherein the first binding site specifically binds to HER2 (i.e., the first target of said bispecific binding agent). In other words, the cancer that is treated in accordance with a method provided herein expresses the cancer antigen that is the first target of the bispecific binding agent.

In a preferred embodiment, the first target of the bispecific binding agent is HER2 and subject to be treated in accordance with the methods described herein has been diagnosed with a cancer that expresses HER2 (e.g., breast cancer, gastric cancer, an osteosarcoma, desmoplastic small round cell cancer, squamous cell carcinoma of head and neck cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, neuroblastoma, or any other neoplastic tissue that expresses the HER2 receptor). In a specific embodiment of treating a HER2-expressing cancer, the subject is resistant to treatment with trastuzumab, cetuximab, lapatinib, erlotinib, or any other small molecule or antibody that targets the HER family of receptors. In a specific embodiment, the cancer that is resistant to treatment with trastuzumab, cetuximab, lapatinib, erlotinib, or any other small molecule or antibody that targets the HER family of receptors is responsive to a method of treating cancer of the invention (see, e.g., Section 5.1 and Section 6).

In a specific embodiment, the subject treated in accordance with the methods provided herein has previously received one or more chemotherapy regimens for metastatic disease, e.g., brain or peritoneal metastases. In a specific embodiment, the subject has not previously received treatment for metastatic disease.

5.7 Doses, Routes of Administration, and Regimens

In a specific embodiment, the therapeutically effective amount of a bispecific binding agent administered to a subject according to the methods provided herein (see, e.g., Section 5.1) is a dose determined by the needs of the subject. In a specific embodiment, the dose is determined by a physician according to the needs of the subject.

In a specific embodiment, the therapeutically effective amount of the bispecific binding agent administered to a subject according to a method of treating cancer described herein is determined based on the concentration of cancer antigen (i.e., the cancer antigen that is the first target of the bispecific binding agent) on a cancer cell of the subject and/or the degree of uptake of the bispecific binding agent by said cancer cell. In a specific embodiment, the degree of uptake will be confirmed by a theranostic approach for both laboratory and clinical situations, and confirmed by biopsy or ex vivo tissue counting. In a specific embodiment, the therapeutically effective amount of the bispecific binding agent is determined using the law of mass action (see, e.g., O'Donoghue et al., 2011, $^{124}$I-huA33 antibody uptake is driven by A33 antigen concentration in tissues from colorectal cancer patients imaged by immune-PET. J. Nucl. Med.; 52(12):1878-85 and Section 6.3), based on results in animal model studies as described in Section 6.3. Without being bound by any particular theory, the therapeutically effective amount of the bispecific agent preferably is an amount that provides sufficient bispecific binding agent to come near to saturation (e.g., in the range of 50-90% saturation) of the binding capacity of the target cancer antigen (i.e., the first target of the bispecific binding agent) on a cancer cell because near saturation of the cancer antigen should allow for the greatest amount of radiotherapeutic agent binding to the bispecific binding agent bound to the cancer cells in the subject, thus providing therapeutic efficacy and/or to allow in vivo imaging results. In a specific embodiment, the therapeutically effective amount of the bispecific binding agent is an amount that is estimated to achieve at least 60%, at least 65%, at least 70%, at least 75%, at least 80%, at least 85%, at least 90%, at least 95%, at least 98%, or at least 99% saturation of the cancer antigen by the bispecific binding agent on the cancer cell according to the law of mass action. In a specific embodiment, the therapeutically effective amount of the bispecific binding agent is an amount that is estimated to achieve between 60% and 100%, between 70% and 99%, between 70% and 95%, between 70% and 90%, between 75% and 85%, between 80% and 90% saturation of the cancer antigen by the bispecific binding agent on the cancer cell according to the law of mass action. In a specific embodiment, the therapeutically effective amount of the bispecific binding agent is an amount that is estimated to achieve approximately 80% saturation of the cancer antigen by the bispecific binding agent on the cancer cell according to the law of mass action.

In a specific embodiment in which the first target of the bispecific binding agent is HER2, the dose of the bispecific binding agent is less than the US Food & Drug Administration-("FDA") approved dose of trastuzumab for the cancer of the subject. See, for example, Trastuzumab [Highlights of Prescribing Information], South San Francisco, Calif.: Genentech, Inc.; 2014. In a specific embodiment, the therapeutically effective amount of the bispecific binding agent is approximately 50%, approximately 60%, approximately 70%, approximately 80%, approximately 90%, or approximately 95% less than an FDA-approved dose of trastuzumab. In a specific embodiment, the therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg, wherein the subject is a human. When used in connection with a therapeutically effective amount, "about" refers to an amount within 1%, 3%, 5%, or 10% of the amount recited. In a specific embodiment, the therapeutically effective amount of the bispecific binding agent is 250 mg to 700 mg, 300 mg to 600 mg, or 400 mg to 500 mg, wherein the subject is a human. In a specific embodiment, the therapeutically effective amount of the bispecific binding agent is between 1.0 mg/kg and 8.0 mg/kg, between 2.0 mg/kg and 7.0 mg/kg, between 3.0 mg/kg and 6.5 mg/kg, between 4.0 mg/kg and 6.5 mg/kg, between or 5.0 mg/kg and 6.5 mg/kg.

In a specific embodiment, the therapeutically effective amount of the bispecific binding agent is administered via intravenous infusion over 30 minutes. In a specific embodiment, the therapeutically effective amount of the bispecific binding agent is administered via intravenous infusion over 30 to 90 minutes. In a specific embodiment, the bispecific binding agent is administered to the subject intravenously, subcutaneously, intramuscularly, parenterally, transdermally, transmucosally, intraperitoneally, intra thoracic, or into some other body compartment, such as intrathecally, intraventricularly, or intraparenchymally. In a preferred embodiment, binding agent is administered to the subject intravenously.

In a specific embodiment, the therapeutically effective amount of the clearing agent administered to a subject according to the methods provided herein is an amount determined by the needs of the subject. One skilled in the art will understand that the therapeutically effective amount of the clearing agent will depend on the structure of the clearing agent, the structure of the bispecific binding agent, and/or the therapeutically effective amount of the bispecific binding agent administered to the subject. In a specific embodiment, the therapeutically effective amount of the clearing agent is in proportion to the therapeutically effective amount of the bispecific binding agent administered to the subject. In a specific embodiment in which the clearing agent comprises approximately 100-150 molecules of (Y or Lu)DOTA-Bn per 500 kDa of aminodextran, the therapeutically effective amount of the clearing agent is an amount that is a 10:1 molar ratio of the therapeutically effective amount of the bispecific binding agent administered to the subject to the therapeutically effective amount of the clearing agent administered to the subject. In other words, in a specific embodiment, the therapeutically effective amount of bispecific binding agent administered to the subject is an amount that is a 10-fold molar excess of the therapeutically effective amount of the clearing agent administered to the subject. For example, for every 100 mg of a 210 kDa bispecific binding agent having a molecular weight of 0.476 micromoles administered to a subject, 25 mg of a 500 kDa clearing agent having a molecular weight of 0.05 micromoles is administered to the subject. In a specific embodiment in which the bispecific binding agent comprises the heavy chain of SEQ ID NO: 15 and the light chain fusion polypeptide of SEQ ID NO: 7 and the clearing agent comprises approximately 100-150 molecules of (Y or Lu)DOTA-Bn per 500 kDa of aminodextran, between 15 mg and 35 mg, between 20 mg and 35 mg, or between 20 mg and 30 mg of the clearing agent is administered to the subject for every 100 mg of bispecific binding agent that is administered to the subject.

In a specific embodiment, the therapeutically effective amount of the clearing agent is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after the step (b) of administering to the subject the therapeutically effective amount of the clearing agent. Methods known to the skilled artisan for determining the percent reduction in serum concentration of bispecific binding agent are known in the art, e.g., ELISA of serum samples prior to and after administration of the clearing agent.

In a preferred embodiment, the clearing agent is administered to the subject intravenously.

In a specific embodiment, the therapeutically effective amount of the radiotherapeutic agent administered to a subject according to the methods provided herein is an amount determined by the needs of the subject. One skilled in the art will understand that the therapeutically effective amount of the radiotherapeutic agent will depend on the identity of the metal radionuclide radiotherapeutic agent. For example, in a specific embodiment in which the metal radionuclide of the radiotherapeutic agent is $^{177}$Lu or an equivalent β-emitter, the therapeutically effective amount of the radiotherapeutic agent is between 25 mCi and 250 mCi, between 50 mCi and 200 mCi, between 75 mCi and 175 mCi, or between 100 mCi and 150 mCi. In another specific embodiment in which the metal radionuclide of the radiotherapeutic agent is $^{177}$Lu or an equivalent β-emitter, the therapeutically effective amount of the radiotherapeutic agent is between 50 mCi and 200 mCi.

In a specific embodiment, the therapeutically effective amount of the radiotherapeutic agent is administered to the subject intravenously, subcutaneously, intramuscularly, parenterally, transdermally, transmucosally, intraperitoneally, intra thoracic, or into other body compartment, such as intrathecally, intrathecally, intraventricularly, or intraparenchymally. In a preferred embodiment, the radiotherapeutic agent is administered to the subject intravenously.

The methods of treating cancer described herein may also form part of a multi-cycle treatment regimen. For example, a method of treating cancer described herein may be repeated two, three, or more times on the same subject. In a specific embodiment, a method of treating cancer described herein is repeated two times on the same subject. For example, in a specific embodiment, a method of treating cancer described in Section 5.1 further comprises: (d) not more than 1 day, not more than 2 days, not more than 3 days, not more than 4 days, not more than 5 days, not more than 6 days, or not more than 1 week after step (c) of administering to the subject the therapeutically effective amount of the radiotherapeutic agent, administering to the subject a second therapeutically effective amount of the bispecific binding agent; (e) after step (d) of administering to the subject the second therapeutically effective amount of the bispecific binding agent, administering to the subject a second therapeutically effective amount of the clearing agent; and (f) after step (e) of administering to the subject the second therapeutically effective amount of the clearing agent, administering to the subject a second therapeutically effective amount of the radiotherapeutic agent. In a specific embodiment, the step (e) of administering to the subject the therapeutically effective amount of the clearing agent is carried out not more than 12 hours after step (d) of administering to the subject the second therapeutically effective amount of the bispecific binding agent. In a specific embodiment, a method of treating cancer described herein is repeated three times on the same subject. For example, in a specific embodiment, a method of treating cancer described in Section 5.1 further comprises: (d) not more than 1 day, not more than 2 days, not more than 3 days, not more than 4 days, not more than 5 days, not more than 6 days, or not more than 1 week after step (c) of administering to the subject the therapeutically effective amount of the radiotherapeutic agent, administering to the subject a second therapeutically effective amount of the bispecific binding agent; (e) after step (d) of administering to the subject the second therapeutically effective amount of the bispecific binding agent, administering to the subject a second therapeutically effective amount of the clearing agent; (f) after step (e) of administering to the subject the second therapeutically effective amount of the clearing agent, administering to the subject a second therapeutically effective amount of the radiotherapeutic agent; (g) not more than 1 day, not more than 2 days, not more than 3 days, not more than 4 days, not more than 5 days, not more than 6 days, or not more than 1 week after step (f) of administering to the subject the second therapeutically effective amount of the radiotherapeutic agent, administering to the subject a third therapeutically effective amount of the bispecific binding agent; (h) after step (g) of administering to the subject the third therapeutically effective amount of the bispecific binding agent, administering to the subject a third therapeutically effective amount of the clearing agent; and (i) after step (h) of administering to the subject the third therapeutically effective amount of the clearing agent, administering to the subject a third therapeutically effective amount of the radiotherapeutic agent. In a specific embodiment, the step (e) of administering to the subject the therapeutically effective amount of the clearing agent is carried out not more than 12 hours after step (d) of administering to the subject the second therapeutically effective amount of the bispecific binding agent. In a specific embodiment, the step (g) of administering to the subject the therapeutically effective amount of the clearing agent is carried out not more than 12 hours after step (g) of administering to the subject the second therapeutically effective amount of the bispecific binding agent.

The second and/or third therapeutically effective amounts of the bispecific binding agent in a multi-cycle method of treating cancer described herein may be the same or different therapeutically effective amounts as compared to the therapeutically effective amount of the bispecific binding agent administered to the subject in step (a). In a specific embodiment, the second therapeutically effective amount of the bispecific binding agent is the same as the therapeutically effective amount of the bispecific binding agent administered to the subject in step (a). In a specific embodiment, the second therapeutically effective amount of the bispecific binding agent is less than the therapeutically effective amount of the bispecific binding agent administered to the subject in step (a). In a specific embodiment, the second therapeutically effective amount of the bispecific binding agent is more than the therapeutically effective amount of the bispecific binding agent administered to the subject in step (a). In a specific embodiment, the third therapeutically effective amount of the bispecific binding agent is the same as the therapeutically effective amount of the bispecific binding agent administered to the subject in step (a). In a specific embodiment, the third therapeutically effective amount of the bispecific binding agent is less than the therapeutically effective amount of the bispecific binding agent administered to the subject in step (a). In a specific embodiment, the third therapeutically effective amount of the bispecific binding agent is more than the therapeutically effective amount of the bispecific binding agent administered to the subject in step (a). In a specific embodiment, the second therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg. In a specific embodiment, the third therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg. In a specific embodiment, the second therapeutically effective amount of the bispecific binding agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the second therapeutically effective amount of the bispecific binding agent is administered to the subject intravenously. In a specific embodiment, the third therapeutically effective amount of the bispecific binding agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the third therapeutically effective amount of the bispecific binding agent is administered to the subject intravenously.

The second and/or third therapeutically effective amounts of the clearing agent in a multi-cycle method of treating cancer described herein may be the same or different therapeutically effective amounts as compared to the therapeutically effective amount of the clearing agent administered to the subject in step (b). In a specific embodiment, the second therapeutically effective amount of the clearing agent is the same as the therapeutically effective amount of the clearing agent administered to the subject in step (b). In a specific embodiment, the second therapeutically effective amount of the clearing agent is less than the therapeutically effective amount of the clearing agent administered to the subject in step (b). In a specific embodiment, the second therapeutically effective amount of the clearing agent is more than the therapeutically effective amount of the clearing agent administered to the subject in step (b). In a specific embodiment, the third therapeutically effective amount of the clearing agent is the same as the therapeutically effective amount of the clearing agent administered to the subject in step (b). In a specific embodiment, the third therapeutically effective amount of the clearing agent is less than the therapeutically effective amount of the clearing agent administered to the subject in step (b). In a specific embodiment, the third therapeutically effective amount of the clearing agent is more than the therapeutically effective amount of the clearing agent administered to the subject in step (b). In a specific embodiment, the second therapeutically effective amount of the clearing agent is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after the step (b) of administering to the subject the therapeutically effective amount of the clearing agent. In a specific embodiment in which the clearing agent comprises approximately 100-150 molecules of (Y)DOTA-Bn per 500 kDa of aminodextran, the second therapeutically effective amount of the clearing agent is an amount that yields a 10:1 molar ratio of the therapeutically effective amount of bispecific binding agent administered to the subject to the therapeutically effective amount of clearing agent administered to the subject. In a specific embodiment, the third therapeutically effective amount of the clearing agent is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after the step (b) of administering to the subject the therapeutically effective amount of the clearing agent. In a specific embodiment in which the clearing agent comprises approximately 100-150 molecules of (Y)DOTA-Bn per 500 kDa of aminodextran, the third therapeutically effective amount of the clearing agent is an amount that yields a 10:1 molar ratio of the therapeutically effective amount of bispecific binding agent administered to the subject to the therapeutically effective amount of clearing agent administered to the subject. In a preferred embodiment, the second therapeutically effective amount of the clearing agent is administered to the subject intravenously. In a preferred embodiment, the third therapeutically effective amount of the clearing agent is administered to the subject intravenously.

The second and/or third therapeutically effective amounts of the radiotherapeutic agent in a multi-cycle method of treating cancer described herein may be the same or different therapeutically effective amounts as compared to the therapeutically effective amount of the radiotherapeutic agent administered to the subject in step (c). In a specific embodiment, the second therapeutically effective amount of the radiotherapeutic agent is the same as the therapeutically effective amount of the radiotherapeutic agent administered to the subject in step (c). In a specific embodiment, the second therapeutically effective amount of the radiotherapeutic agent is less than the therapeutically effective amount of the radiotherapeutic agent administered to the subject in step (c). In a specific embodiment, the second therapeutically effective amount of the radiotherapeutic agent is more than the therapeutically effective amount of the radiotherapeutic agent administered to the subject in step (c). In a specific embodiment, the third therapeutically effective amount of the radiotherapeutic agent is the same as the therapeutically effective amount of the radiotherapeutic agent administered to the subject in step (c). In a specific embodiment, the third therapeutically effective amount of the radiotherapeutic agent is less than the therapeutically effective amount of the radiotherapeutic agent administered to the subject in step (c). In a specific embodiment, the third therapeutically effective amount of the radiotherapeutic agent is more than the therapeutically effective amount of the radiotherapeutic agent administered to the subject in step (c). In a specific embodiment, the second therapeutically effective amount of the radiotherapeutic agent is between 25 mCi and 250 mCi, between 50 mCi and 200 mCi, between 75 mCi and 175 mCi, or between 100 mCi and 150 mCi. In a specific embodiment, the third therapeutically effective amount of the radiotherapeutic agent is between 25 mCi and 250 mCi, between 50 mCi and 200 mCi, between 75 mCi and 175 mCi, or between 100 mCi and 150 mCi. In a specific embodiment, the second therapeutically effective amount of the radiotherapeutic agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the second therapeutically effective amount of the radiotherapeutic agent is administered to the subject intravenously. In a specific embodiment, the third therapeutically effective amount of the radiotherapeutic agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally. In a preferred embodiment, the third therapeutically effective amount of the radiotherapeutic agent is administered to the subject intravenously.

5.8 Combination Therapy

In a specific embodiment, a bispecific binding agent provided herein may be administered in combination with one or more additional pharmaceutically active agents, e.g., a cancer chemotherapeutic agent. In a specific embodiment, such combination therapy may be achieved by way of simultaneous, sequential, or separate dosing of the individual components of the treatment. In a specific embodiment, the bispecific binding agent and one or more additional pharmaceutically active agents may be synergistic, such that the dose of either or of both of the components may be reduced as compared to the dose of either component that would be given as a monotherapy. Alternatively, in a specific embodiment, the bispecific binding agent and the one or more additional pharmaceutically active agents may be additive, such that the dose of the bispecific binding agent and of the one or more additional pharmaceutically active agents is similar or the same as the dose of either component that would be given as a monotherapy.

In a specific embodiment, a bispecific binding agent provided herein is administered on the same day as one or more additional pharmaceutically active agents. In a specific embodiment, the bispecific binding agent is administered 1, 2, 3, 4, 5, 6, 7, 8, 9, 10, 11, or 12 hours before the one or more additional pharmaceutically active agents. In a specific embodiment, the bispecific binding agent is administered 1, 2, 3, 4, 5, 6, 7, 8, 9, 10, 11, or 12 hours after the one or more additional pharmaceutically active agents. In a specific embodiment, the bispecific binding agent is administered 1, 2, 3, or more days before the one or more additional pharmaceutically active agents. In a specific embodiment, the bispecific binding agent is administered 1, 2, 3 or more days after the one or more additional pharmaceutically active agents. In a specific embodiment, the bispecific binding agent is administered 1, 2, 3, 4, 5, or 6 weeks before the one or more additional pharmaceutically active agents. In a specific embodiment, the bispecific binding agent is administered 1, 2, 3, 4, 5, or 6 weeks after the one or more additional pharmaceutically active agents.

In a specific embodiment in which the cancer is breast cancer, the additional pharmaceutically active agent is doxorubicin. In a specific embodiment in which the cancer is breast cancer, the additional pharmaceutically active agent is cyclophosphamide. In a specific embodiment in which the cancer is breast cancer, the additional pharmaceutically active agent is paclitaxel. In a specific embodiment in which the cancer is breast cancer, the additional pharmaceutically active agent is docetaxel. In a specific embodiment in which the cancer is breast cancer, the one or more additional pharmaceutically active agents is carboplatin.

In a specific embodiment, the additional pharmaceutically active agent is an agent that increases cell death, apoptosis, autophagy, or necrosis of tumor cells.

In a specific embodiment, a bispecific binding agent provided herein is administered in combination with two additional pharmaceutically active agents, e.g., for a cancer that expresses HER2, two additional pharmaceutically active agents used in combination with trastuzumab (see, Trastuzumab [Highlights of Prescribing Information]. South San Francisco, Calif.: Genentech, Inc.; 2014). In a specific embodiment in which the cancer is a cancer that expresses HER2, the two additional pharmaceutically active agents are doxorubicin and paclitaxel. In a specific embodiment in which the cancer is a cancer that expresses HER2, the two additional pharmaceutically active agents are doxorubicin and docetaxel. In a specific embodiment in which the cancer is a cancer that expresses HER2, the two additional pharmaceutically active agents are cyclophosphamide and paclitaxel. In a specific embodiment in which the cancer is a cancer that expresses HER2, the two additional pharmaceutically active agents are cyclophosphamide and docetaxel. In a specific embodiment in which the cancer is a cancer that expresses HER2, the two additional pharmaceutically active agents are docetaxel and carboplatin. In a specific embodiment in which the cancer is a cancer that expresses HER2, the two additional pharmaceutically active agents are cisplatin and capecitabine. In a specific embodiment in which the cancer is a cancer that expresses HER2, the two additional pharmaceutically active agents are cisplatin and 5-fluorouracil.

In a specific embodiment, a bispecific binding agent provided herein is administered following multi-modality anthracycline based therapy.

In a specific embodiment, a bispecific binding agent provided herein is administered after one or more chemotherapy regimens for metastatic disease, e.g., brain or peritoneal metastases. In specific embodiments, a bispecific binding agent provided herein is administered in combination with cytoreductive chemotherapy. In a specific embodiment, the administering is performed after treating the subject with cytoreductive chemotherapy.

In a specific embodiment in which the cancer is a cancer that expresses HER2, the additional pharmaceutically active agent is an agent that increases cellular HER2 expression, such as, for example, external beam or radioimmunotherapy. See, for example, Wattenberg et al., 2014, British Journal of Cancer, 110: 1472. In a specific embodiment, the additional pharmaceutically active agent is an agent that directly controls the HER2 signaling pathway, e.g., lapatinib. See, for example, Scaltiri et al., 2012, 28(6): 803-814.

6. EXAMPLES

6.1 Example 1: A Preclinical Model of Theranostic Anti-Dota Hapten Bispecific Antibody Pretargeted Radioimmunotherapy of Internalizing Solid Tumor-Antigens: Curative Treatment of HER2-Positive Breast Carcinoma References cited in this Example are identified by numbers in brackets. The corresponding citation is provided in Section 6.1.5.

6.1.1 Introduction

The pharmacokinetics of the full-size IgG monoclonal antibodies as carriers of therapeutic radioisotopes (i.e., radioimmunotherapy, RIT) show an unfavorable therapeutic index ("TI"; defined herein as the ratio of the radiation-absorbed dose to the tumor divided by the dose to a radiosensitive tissue such as blood [1]), with hematological toxicity typically dose-limiting for radioimmunotherapy ("RIT"). Alternatively, pretargeting MT ("PRIT") strategies can be employed, which separate the antibody-mediated targeting step from the administration of the cytotoxic ligand in order to reduce the residence time of the ligand in circulation [2].

Using a pretargeting "DOTA-PRIT" platform, high TI targeting has been demonstrated with cures in preclinical animal models of human carcinoma xenografts for carbohydrate targets (diasialogangioside GD2 [3] on human neuroblastoma xenografts) or glycoprotein targets (GPA33 [4] on human colon cancer xenografts) with negligible toxicity following treatment with ~30-111MBq/mouse total injected activity ("IA") of $^{177}$Lu-DOTA-Bn. Also with DOTA-PRIT, high TI targeting with cures was recently demonstrated preclinically for CD20(+) human lymphoma xenografts with 26-37 MBq total IA of $^{90}$Y-DOTA-biotin C825-hapten [5].

In DOTA-PRIT, a non-radioactive bispecific binding agent (e.g., a bispecific antibody ("BsAb")) with one specificity for a tumor antigen and a second specificity for a hapten such as a low molecular-weight radiometal complex of S-2-(4-aminobenzyl)-1,4,7,10-tetraazacyclododecane tetraacetic acid chelate ("[M]-DOTA-Bn" [6], e.g., as the β-emitter $^{177}$Lu-DOTA-Bn). After sufficient tumor uptake and clearance of unbound BsAb (accelerated with a clearing agent ("CA")), $^{177}$Lu-DOTA-Bn is administered, which is captured by tumor-localized BsAb or otherwise rapidly renally cleared from the body. In this example, a variation of the DOTA-PRIT platform was tested using HER2, an antigen with expression on a much wider spectrum of human cancers, but prone to endocytosis, a property uniquely different from other commonly studied PRIT targets. Unlike antibody-drug conjugates that rely on cell surface receptor binding as well as internalization upon cell binding for its payload delivery, non-internalizing antibody/cell surface targets are considered optimum for PRIT. Specifically during DOTA-PRIT, an intravenously ("i.v.") administered non-radioactive BsAb accumulates at the tumor and serves as a receptor for subsequently administered radiolabeled-hapten (e.g., radiolabeled DOTA-Bn). Without being bound to any particular theory, it was previously hypothesized that if extensive internalization of the BsAb occurs on the tumor-surface, it can have a significant impact on the efficiency of the hapten-targeting step.

The anti-HER2 monoclonal antibody is an example of an internalizing antibody [7]. HER2 (transmembrane tyrosine kinase receptor HER2/neu or c-erbB-2; molecular weight (MW) 185 kD) is a member of the HER/erbB family of cell surface receptors, and high HER2 expression is prognostic for survival in several cancer types, including breast [8], gastric [9], and gynecologic malignancies [10]. Trastuzumab can prolong survival in breast or ovarian cancer patients with HER2-positive ("HER2(+)") disease [11, 12]. Unfortunately, despite initial response to trastuzumab, resistance is common [13]. To enhance the efficacy of trastuzumab, antibody-based delivery of a cytotoxin [14] or therapeutic radionuclide [15] have been tested. Several preclinical RIT studies with trastuzumab-radioisotope conjugates have also been described (e.g., with α-emitter [16-23] or with β-emitters [24-28]); however, without being bound by any particular theory, it is hypothesized that the TI could potentially be improved with a PRIT approach.

In this example, a theranostic isotope to permit simultaneous therapy and imaging was implemented for anti HER2-DOTA-PRIT. $^{177}$Lu has a physical half-life of 6.73 days ("d"), and is an emitter of both β-particles and γ-radiation (β-maximum energy: 0.5 MeV; β-particle range in tissue Rmax: 2 mm; γ: 208 keV, 11% abundance), allowing for therapy and γ-scintigraphy, respectively. $^{177}$Lu was the focus of the efforts in this example for DOTA-PRIT treatment of solid tumors, since the long biological retention kinetics of pretargeted $^{177}$Lu-DOTA-Bn in tumor for GD2 and GPA33 is a good match with the long physical half-life of $^{177}$Lu, and its relatively short β-particle range is theoretically well-suited for treatment of smaller tumor volumes (optimal tumor diameter for cure probability of 0.9=2.0 mm [29]) while minimizing collateral radiation damage to normal tissues. Finally, the $^{177}$Lu γ-emissions allow for high-resolution single-photon emission computed tomography/computed tomography (SPECT/CT) imaging for pre-therapy dosimetry as well as treatment monitoring, which is emerging as a quantitative clinical imaging modality for targeted therapies with $^{177}$Lu-radiopharmaceuticals [30, 31].

In the present example, the aims were to (1) produce an anti-HER2-C825 BsAb to enable proof-of-concept studies with anti-HER2-DOTA-PRIT, (2) characterize the HER2(+) tumor cell-surface internalization kinetics of the anti-HER2-C825 BsAb/HER2 antigen complex, (3) demonstrate highly specific tumor targeting of $^{177}$Lu-DOTA-Bn with anti-HER2-DOTA-PRIT and (4) to test if TI was sufficient for safe and effective theranostic application of anti-HER2-DOTA-PRIT in mice bearing established subcutaneous ("s.c.") human HER2(+) breast carcinoma xenografts.

6.1.2 Materials and Methods

6.1.2.1 Cloning and Expression of Anti-HER2-C825 Bsab

The bispecific binding agent "HER2-C825 BsAb" was prepared as an IgG-scFv[36] format using the sequences for trastuzumab[37] and murine C825[38]. The heavy chain of the HER2-C825 BsAb (sometimes also referred to herein as "anti-HER2-C825") comprises the amino acid of SEQ ID No. 15 and the light chain fusion polypeptide of the HER2-C825 BsAb comprises the amino acid sequence of SEQ ID NO: 7. The BsAb (molecular weight~210 kDa) was produced in CHO cells and purified by protein A affinity chromatography as previously described[3]. The control BsAb huA33-C825 was made using the same platform as previously described [4]. Biochemical purity analysis of the BsAb was performed using SE-HPLC (column: TSKgel G3000SWx1; running buffer: 400 mM sodium perchlorate pH 6.0; flow rate 0.5 mL/min), with eluted BsAb detected by UV absorbance at 280 nm.

6.1.2.2 Surface Plasmon Resonance Studies

Biacore T100 Biosensor, CM5 sensor chip, and related reagents were purchased from GE Healthcare. A BSA-(Y)-DOTA-Bn conjugate was prepared as previously described [3]. The antigen was immobilized using the Amine Coupling Kit (GE Healthcare). Purified BsAbs were analyzed, and data were fit to a bivalent analyte model using the Biacore T100 evaluation software as previously described[3].

6.1.2.3 Cell Lines

BT-474 is ductal carcinoma with epithelial morphology, luminal B subtype, estrogen receptor α-positive ("ER(+)"), progesterone positive/negative ("PR(+/−)") and HER2(+), while MDA-MB-231 is an adenocarcinoma cell line with epithelial morphology, claudin-low subtype, and has a triple-negative immunoprofile (ER(−), PR(−), and HER2(−)) [39]. Cell lines were obtained from American Type Culture Collection (Manassas, Va.) and periodically tested for *mycoplasma* negativity using a commercial kit (Lonza). All cell lines were maintained in a humidified incubator at 37° C. containing 5% $CO_2$, limited to less than 10 passages, and cultured in Dulbecco's modified Eagle-high-glucose/F-12 (DME-HG/F-12) medium supplemented with non-essential amino acids (0.1 mM), 10% heat-inactivated fetal calf serum (FCS), 100 units/mL of penicillin, and 100 μg/mL streptomycin.

6.1.2.4 Internalization and Cellular Processing of Anti-HER2-C825

Trastuzumab is known to internalize upon binding to surface HER2 antigen[7]. The internalization kinetics of anti-HER2-C825 following binding to BT-474 cell surface HER2 antigen at 37° C. were assessed using the radiotracer $^{131}$I-anti-HER2-C825 based on previously described assays [7, 40]. In brief, cells were plated at a density of $5.0\times10^5$ cells/mL in 12-well plates and allowed to adhere overnight. Cells were pre-incubated on ice with $^{131}$I-anti-HER2-C825 (prepared using the IODOGEN method [41] to a specific activity of 132 MBq/mg and purified using SEC to radiochemical purity>98%; diluted into complete media; 160 ng/mL; 0.8 nM) for 1 h. Next, the cells were extensively washed with complete media chilled on ice and the plates were transferred to the 37° C. incubator. At various time-points up to 24 h, the radioactive distribution in the outside media, cell-surface, as well as the fraction of activity internalized by the cells was determined (n=3-6 per time-point) by quantification in the gamma counter. An acid-wash protocol was used to strip cell-surface antibody, consisting of treating the cells on ice three times for 5 minutes (min) with 2 M urea, 50 mM glycine, 150 mM NaCl, pH 2.4, and pooling the supernatants. The outside media was assayed further using trichloroacetic acid (TCA) precipitation (~1 mL of collected media was mixed with 0.9 mL of 20% w/v TCA) to determine if the $^{131}$I-activity was antibody-bound (suggesting passive dissociation or "shedding" [40]), or in the form of low-molecular weight metabolites, suggesting intracellular metabolism followed by exocytosis. Controls consisted either of incubation at 4° C. or wells consisting of the $^{131}$I-anti-HER2-C825 diluted into media only. These control wells were also subjected to TCA precipitation in order to inhibit internalization and determine the basal catabolism (via degradation) rate of the tracer, respectively. For kinetic analysis, data was curve fitted using a nonlinear model, with one-phase association using Prism software package, Graphpad Software Inc., San Diego, Calif.

6.1.2.5 Xenograft Models

All animal experiments were approved by the Institutional Animal Care and Use Committee of Memorial Sloan Kettering Cancer Center (New York, N.Y.), and institutional guidelines for the proper and humane use of animals in research were followed. Female athymic nude mice (6-8 weeks old) were obtained from Harlan/Envigo. Mice were allowed to acclimate for a minimum of 1 week. For the BT-474 tumor model, mice were implanted with estrogen (17β-estradiol; 0.72 mg/pellet 60-d release; Innovative Research of America) by trochar injection 3 days (d) before inoculation with cells. No estrogen supplementation was required for the MDA-MB-231 xenograft model. For establishment of all tumor xenografts, mice were inoculated with $5.0\times10^6$ cells in a 200 μL cell suspension of a 1:1 mixture of media with reconstituted basement membrane (BD Matrigel™, Collaborative Biomedical Products Inc., Bedford, Mass.) on lower flank via s.c. injection, and used within 3-4 weeks. Tumor volumes were estimated using the formula for the volume (V) of an ellipsoid: V=4/3π(length/2×width/2×height/2), with dimensions in millimeters (mm).

6.1.2.6 Anti-HER2 Dota-Prit Reagents and Dosing Protocol

The three anti-HER2 DOTA-PRIT reagents were: anti-HER2-C825 BsAb, clearing agent, and the radiotherapeutic agent $^{177}$Lu-DOTA-Bn. All reagents were administered intravenously ("i.v.") via a lateral tail vein and given at the following times relative to $^{177}$Lu-DOTA-Bn injection: [t=−28 hours (h)] for anti-HER2-C825, followed by CA at [t=−4 h] and $^{177}$Lu-DOTA-Bn at [t=0 h]. The CA (a 500 kDa dextran-(Y)-DOTA-Bn conjugate; 61 moles of (Y)-DOTA-Bn per mole of dextran) was prepared according to previously described methods [42] and formulated in saline for injection. $^{177}$Lu-DOTA-Bn was also prepared according to previously described methods [4]. Radioactivity in samples was measured using a CRC-15R dose calibrator (Capintec, Ramsey, N.J.) using the appropriate settings for each isotope.

6.1.2.7 Biodistribution Studies to Optimize In Vivo Anti-HER2 Dota-Prit

Prior to therapy studies, BsAb and CA dose-titration experiments were carried out in groups of BT-474-tumor bearing mice with tracer administered activities of $^{177}$Lu-DOTA-Bn/mouse (5.6 MBq (~30 pmol)) to optimize DOTA-PRIT reagent doses for efficient in vivo tumor targeting. For this purpose, specific TI benchmarks of at least 20:1 for blood and 10:1 for kidney at 24 h p.i. of $^{177}$Lu-DOTA-Bn were set, while maximizing radioactivity uptake in tumor. Groups were sacrificed at 24 h post-injection ("p.i.") of $^{177}$Lu-DOTA-Bn for biodistribution assay of $^{177}$Lu activity in select tissues. For biodistribution analysis, mice were euthanized by $CO_2$(g) asphyxiation, and tumor and selected organs were harvested, rinsed with water and allowed to air-dry, weighed, and radioassayed by gamma scintillation counting (Perkin Elmer Wallac Wizard 3"). Count rates were background- and decay-corrected, converted to activities using a system calibration factor specific for the isotope, normalized to the administered activity, and expressed as % IA/g (mean±SEM).

6.1.2.8 Dosimetry Calculations

For dosimetry calculations, a serial biodistribution study was carried out in BT-474 tumor-bearing mice (n=24) with the optimized DOTA-PRIT protocol+5.5-6.1 MBq (~30 pmol) of $^{177}$Lu-DOTA-Bn. Groups of HER2(+) BT-474 tumor-bearing mice (n=4-5) were given PRIT+5.5-6.1 MBq (~30 pmol) of $^{177}$Lu-DOTA-Bn and sacrificed at 1.0 (n=5), 2.5 (n=5), 24 (n=5), 96 (n=5), and 336 h p.i. (n=4) for biodistribution analysis of $^{177}$Lu activity in tumor and select normal tissues (Table 15). For each tissue, the non-decay-corrected time-activity concentration data were fit using Excel to a 1-component, 2-component, or more complex exponential function as appropriate, and analytically integrated to yield the cumulated activity concentration per unit administered activity (MBq-h/g per MBq). The $^{177}$Lu equilibrium dose constant for non-penetrating radiations (8.49 g-cGy/MBq-h) was used to estimate the tumor-to-tumor and select organ-to-organ self-absorbed doses, assuming complete local absorption of the $^{177}$Lu beta rays only, and ignoring the gamma ray and non-self dose contributions.

6.1.2.9 Immunohistochemistry ("IHC") and Autoradiography Experiments

For IHC of HER2-expressing tumors, groups of BT-474-tumor bearing nude mice were administered i.v. 0.25 mg (1.19 nmol) of anti-HER2-C825. Twenty-four hours p.i., the animals were sacrificed and tumors were frozen in OCT. The IHC detection of HER2 was performed at the Molecular Cytology Core Facility of Memorial Sloan Kettering Cancer Center using Discovery XT processor (Ventana Medical Systems, Roche, Tucson-AZ). The tissue sections were blocked for 30 minutes (min) in 10% normal goat serum, 2% BSA in PBS. Next, the sections were incubated with a rabbit polyclonal HER2 antibody (Enzo, cat # alx-810-227) at 5.0 ug/ml concentrations for 5 h, followed by 1 h incubation with biotinylated goat anti-rabbit IgG (Vector labs, cat #:PK6101) at 5.75 ug/mL. The detection was performed with Blocker D, Streptavidin-HRP and DAB detection kit (Ventana Medical Systems). All reagents were used according to the manufacturer instructions. For IHC to determine anti-HER2-C825 antibody distribution, the same procedure was followed except the primary antibody step was excluded and biotinylated goat anti-human IgG (Vector, Cat # BA3000) antibody was used.

For ex vivo autoradiography, tumors were excised, snap-frozen and embedded in OCT at 24 h p.i. of $^{177}$Lu-DOTA-Bn. Series of sequential 10 μm thick cryosections were cut immediately and exposed to a phosphor plate overnight at −20° C. for determination of $^{177}$Lu activity distribution. Digital autoradiographic images at 25 μm pixel size were obtained as follows. Tumor sections were exposed to a phosphor-imaging plate (Fujifilm BAS-MS2325, Fuji Photo Film, Japan) overnight at −20° C. Upon the completion of an exposure, the imaging plates were removed from the cassette and placed in a Typhoon FLA 7000 (GE healthcare, USA) to readout the image. The image reader creates 16-bit grayscale digital images with pixel size of 25 μm. These images are then converted to tiff image format files for subsequent analysis. Finally, H&E staining was performed to visualize tumor morphology in consecutive sections, and images were acquired in a similar manner. Images were manually registered using Photoshop CS6 software (Adobe Systems).

6.1.2.10 Theranostic Anti-HER2-Dota-Prit Therapy

To evaluate the toxicity and efficacy of anti-HER2-DOTA-PRIT therapy in an animal model of human breast cancer, therapy studies were carried out in BT-474 tumor-bearing mice with either "small" or "medium-sized" s.c. xenografts. Tumors with volumes ranging from palpable-30 $mm^3$ were classified as "small", and tumor volumes ranging from 100-400 $mm^3$ were classified as "medium-sized". Treatment groups were monitored for 85-200 d and survivors were submitted for histopathology studies (see below).

Initially, single-cycle treatment with anti-HER2 DOTA-PRIT+55.5 MBq of $^{177}$Lu-DOTA-Bn (300 pmol) was evaluated in groups of mice bearing small s.c. xenografts and compared with treatment controls (estimated dose to tumor: 22 Gy). These groups were monitored for 85 d post-treatment. During this study, planar scintigraphy (using previously described methods[3]) was used up to 70 h p.i. of $^{177}$Lu-DOTA-Bn to verify tumor targeting of $^{177}$Lu activity.

Next, groups of mice bearing medium-sized s.c. xenografts were treated in a single-cycle anti-HER2 PRIT dose escalation trial with 11.1, 33.3, or 55.5 MBq of $^{177}$Lu-DOTA-Bn (60-300 pmol)/mouse and compared with control groups (estimated absorbed radiation doses to tumor: 4.4-22 Gy). These groups were monitored for ~200d post-treatment in order to study tumor recurrence and chronic toxicity of anti-HER2-DOTA-PRIT.

In a third therapeutic study, a three-cycle fractionated DOTA-PRIT regimen with 55.5 MBq $^{177}$Lu-DOTA-Bn (300 pmol)/mouse/cycle was evaluated in groups of mice bearing medium-sized s.c. xenografts (estimated absorbed radiation doses to tumor: 70 Gy). To achieve this, the total IA of 167 MBq $^{177}$Lu-DOTA-Bn/mouse was given in three equal weekly administrations, with each of the three DOTA-PRIT reagents given during each cycle (designated as "anti-HER2-DOTA-PRIT"). A control treatment arm was included that replaced anti-HER2-C825 with the anti-GPA33 targeting BsAb huA33-C825 [4] (designated as "Control IgG-DOTA-PRIT") in order to verify that efficacy was dependent on anti-HER2-C825 tumor-specific targeting. These groups were monitored for ~85 d post-treatment. Three mice undergoing treatment with anti-HER2-DOTA-PRIT, as well as a single mouse undergoing Control IgG-DOTA-PRIT, were randomly selected for SPECT/CT imaging to assay tumor targeting and to quantify tumor uptake of $^{177}$Lu activity.

6.1.2.11 Response to Therapy and Toxicity Assessment

Mice were monitored daily and weighed at least twice weekly for evidence of treatment induced toxicity. Animals were observed until they were sacrificed due to excessive tumor burden>2500 $mm^3$ or less if tumor caused mobility concerns. Animals showing a weight loss greater than 15% of their initial (pre-treatment) body weight in 1 or 2 d, or 20% or more of their pre-treatment weight, were removed from the group at that time and sacrificed. To further evaluate toxicity, randomly selected animals undergoing treatment were submitted for histopathologic evaluation of the xenotransplant, kidney, bone marrow (sternum, vertebrae, femur, and tibia), liver, and spleen (unless otherwise noted) by a board-certified veterinary pathologist at the Memorial Sloan Kettering Cancer Center Laboratory of Comparative Pathology. Hematology and clinical chemistry panels were also collected. A CR is defined as tumor regression to unmeasurable (<10 $mm^3$). A cure is defined as no histopathologic evidence of neoplasia at site of tumor inoculation at necropsy. The breast cancer xenografts developed distant metastasis in 33.3% (2/6) of treated survivors at 200 d, but in no animals evaluated at 85 d (see Table 21, Table 24, and Table 27).

6.1.2.12 Statistics

All statistics were determined using Prism software package, Graphpad Software Inc., San Diego, Calif. Statistical comparisons between two individual groups were analyzed by Student's unpaired t test when appropriate, with the level of statistical significance set at $P<0.05$.

6.1.2.13 Abbreviations

BsAb: bispecific antibody; TI: therapeutic index; CR: complete responses; d: days; RIT: radioimmunotherapy; PRIT: pretargeted radioimmunotherapy; IA: injected activity; [M]-DOTA-Bn: radiometal complex of S-2-(4-aminobenzyl)-1,4,7,10-tetraazacyclododecane tetraacetic acid chelate; CA: clearing agent; MW: molecular weight; SPECT/CT: single-photon emission computed tomography computed tomography; s.c.: subcutaneous; h: hours; p.i.: post-injection; % IA/g: percent injected activity per gram; SEM: standard error of the mean; IHC: immunohistochemistry; ROI: region-of-interest; RBC: red blood cells; HGB: hemoglobin; PLT: platelets; i.v.: intraveneous; V: volume; min: minutes.

6.1.3 Results

6.1.3.1 In Vitro Characterization of Anti-HER2-C825 BsAb

Biochemical purity analysis of anti-HER2-C825 by size-exclusion-high pressure liquid chromatography ("SE-HPLC") is shown in FIG. 1A. SE-HPLC showed a major peak (96.5% by ultraviolet ("UV") analysis) with an approximate molecular weight ("MW") of 210 Kilo Dalton ("kD"), as well as some minor peaks assumed to be aggregates removable by gel filtration. The BsAb remained stable by SE-HPLC after multiple freeze and thaw cycles (data not shown).

The binding affinity to antigen Bovine serum albumin (BSA)-(Y)-DOTA-Bn was measured by Biacore T100. Anti-HER2-C825 had a $k_{on}$ of $2.10\times10^4 M^{-1}s^{-1}$, a $k_{off}$ of $1.25\times10^{-4}$ $s^{-1}$, and overall $K_D$ of 6.0 nM—comparable to control BsAb huA33-C825 ($k_{on}$ of $1.90\times10^4 M^{-1}s^{-1}$, $k_{off}$ of $2.20\times10^{-4}$ $s^{-1}$, and overall $K_D$ of 11.6 nM; FIG. 1B). The binding to tumor targets was measured by flow cytometry. Anti-HER2-C825 was equally efficient as parental trastuzumab in binding to the HER2(+) breast cancer cell line AU565 (FIG. 1C). In summary, anti-HER2-C825 retained high binding capability to both targets HER2 and DOTA.

6.1.3.2 Internalization Kinetics and Cellular Processing of Anti-HER2-C825

To characterize the internalization kinetics and cellular processing of anti-HER2-C825 by HER2-expressing (HER2 (+)) cells, anti-HER2-C825 was radioiodinated with iodine-131 ($^{131}I$) and in vitro cell-binding studies were conducted with HER2(+) BT-474 cells up to 24 hours ("h") at 37° C. Cell-surface $^{131}$I-anti-HER2-C825 was rapidly internalized by BT-474 cells following incubation at 37° C., with 25.6±1.16% of the added radioactivity showing peak internalization at 2 h, respectively (FIG. 2).

In addition, internalized radioactivity at 4° C. was on average~15 fold less than that at 37° C. when assayed at 4 h (n=6; data not shown). At 37° C. from 2 to 24 h, the internalized radioactivity was observed to decrease to 5.6±0.21%, suggesting that exocytosis was occurring. This was also apparent by the rate of increase in the percentage catabolized radioactivity observed in the extracellular media (i.e., accumulation of low-molecular weight catabolites), which showed a K=0.054 and a half-time of 12.82 h ($R^2$=0.995). For the surface-bound activity fraction, ~50% of the activity was lost in the first 2 h of incubation at 37° C., while the remaining activity decayed with a half-life of 8.5 h ($R^2$=0.992). After incubation for 24 h (the time interval between BsAb and CA injections during DOTA-PRIT), 11.1±0.48% of initially bound anti-HER2-C825 remained on the cell surface.

Control experiments to assay the in vitro stability of $^{131}$I-anti-HER2-C825 in media at 37° C. from 0 to 24 h showed that the percent change in antibody-associated radioactivity between those two time points was −2.1%, suggesting that the observed catabolized activity in the extracellular media fraction was primarily due to internalization and exocytosis of $^{131}$I-anti-HER2-C825.

6.1.3.3 Optimization of Anti-HER2 Dota-Prit In Vivo

The optimized doses of BsAb and CA for in vivo anti-HER2 DOTA-PRIT were determined to be 0.25 mg (1.19 nmol) and 62.5 μg (0.125 nmol of dextran; 7.63 nmol of (Y)-DOTA-Bn), respectively, using groups of BT-474 tumor bearing mice. A summary of select biodistribution data from these optimization efforts is provided in Table 10, while remaining data is presented in FIG. 3 and Table 11. This targeting regimen led to tumor uptake (as percent injected activity per gram % IA/g; mean±standard error of the mean (SEM)) at 24 h post-injection ("p.i.") of 7.58±0.78, with kidney as the tissue with the highest normal uptake of 0.73±0.05. Notably, without administration of the CA-step (i.e., with anti-HER2-C825 given at [time ("t")=−28 h] followed by $^{177}$Lu-DOTA-Bn [t=0 h]), both the tumor and blood uptakes of $^{177}$Lu activity at 24 h p.i. were much higher, 19.94±3.54% IA/g and 4.95±1.17% IA/g, respectively, consequently leading to unfavorable tumor-to-blood ratios (4.0±1.2) (Table 10). With optimized CA dose, the average tumor and blood uptakes were reduced by ~60% (from ~20 to 7.6% IA/g) or ~95% (from ~5 to 0.3% IA/g) compared with no CA control, respectively, significantly improving the tumor-to-blood ratio (26.7±9.0), but at the expense of lower tumor uptake.

TABLE 10

Select biodistribution data 24 h p.i. of $^{177}$Lu-DOTA-Bn (~5.6 MBq, 30 pmol, unless otherwise noted) from individual experiments designed to identify the optimum anti-HER2-DOTA-PRIT protocol and demonstrate HER2(+)-tumor specific targeting in mice bearing either s.c. HER2(+) (BT-474) or s.c. HER2-negative ("HER2(−)") (MDA-MB-468) tumors. All tumors ranged from 100-200 mg ex vivo. n.d. = not determined. Int. = intestine. Data is presented as % IA/g (mean ± SEM).

| | Tumor type | | | | |
|---|---|---|---|---|---|
| Tissues | BT-474 PRIT + CA[a] ~30 pmol (n = 5) | BT-474 PRIT + CA[b] ~300 pmol (n = 3) | BT-474 PRIT + no CA (n = 4) | MDA-MB-468 PRIT + no CA (n = 5) | BT-474 no PRIT, only $^{177}$Lu-DOTA-Bn[c] (n = 2) |
| Blood | 0.28 ± 0.09 | 0.29 ± 0.05 | 4.95 ± 0.58 | 6.59 ± 1.31 | 0.002 ± 0.00 |
| Heart | 0.07 ± 0.02 | 0.11 ± 0.02 | 1.14 ± 0.14 | 1.78 ± 0.29 | n.d. |
| Lungs | 0.20 ± 0.05 | 0.20 ± 0.02 | 2.11 ± 0.23 | 2.44 ± 0.42 | n.d. |
| Liver | 0.27 ± 0.07 | 0.33 ± 0.04 | 1.85 ± 0.15 | 2.69 ± 0.35 | 0.04 ± 0.01 |
| Spleen | 0.60 ± 0.21 | 0.22 ± 0.07 | 1.00 ± 0.11 | 1.06 ± 0.16 | 0.02 ± 0.00 |
| Stomach | 0.06 ± 0.01 | 0.04 ± 0.01 | 0.34 ± 0.04 | 0.27 ± 0.04 | n.d. |
| Small Int. | 0.05 ± 0.01 | 0.05 ± 0.01 | 0.58 ± 0.06 | 0.61 ± 0.11 | n.d. |
| Large Int. | 0.18 ± 0.01 | 0.20 ± 0.11 | 0.58 ± 0.06 | 0.35 ± 0.06 | n.d. |
| Kidneys | 0.73 ± 0.05 | 0.56 ± 0.08 | 2.31 ± 0.26 | 2.39 ± 0.54 | 0.38 ± 0.01 |

TABLE 10-continued

Select biodistribution data 24 h p.i. of $^{177}$Lu-DOTA-Bn (~5.6 MBq, 30 pmol, unless otherwise noted) from individual experiments designed to identify the optimum anti-HER2-DOTA-PRIT protocol and demonstrate HER2(+)-tumor specific targeting in mice bearing either s.c. HER2(+) (BT-474) or s.c. HER2-negative ("HER2(−)") (MDA-MB-468) tumors. All tumors ranged from 100-200 mg ex vivo. n.d. = not determined. Int. = intestine. Data is presented as % IA/g (mean ± SEM).

| | Tumor type | | | | |
|---|---|---|---|---|---|
| Tissues | BT-474 PRIT + CA[a] ~30 pmol (n = 5) | BT-474 PRIT + CA[b] ~300 pmol (n = 3) | BT-474 PRIT + no CA (n = 4) | MDA-MB-468 PRIT + no CA (n = 5) | BT-474 no PRIT, only $^{177}$Lu-DOTA-Bn[c] (n = 2) |
| Muscle | 0.06 ± 0.01 | 0.04 ± 0.01 | 0.38 ± 0.04 | 0.50 ± 0.14 | n.d. |
| Bone | 0.04 ± 0.01 | 0.04 ± 0.01 | 0.39 ± 0.08 | 0.62 ± 0.17 | n.d. |
| Tumor | 7.58 ± 0.78 | 5.53 ± 0.27 | 19.94 ± 1.77 | 2.75 ± 0.17 | 0.07 ± 0.01 |

[a]0.25 mg of anti-HER2-C825, 62.5 μg (25% (w/w)) CA, and ~5.6 MBq of $^{177}$Lu-DOTA-Bn
[b]0.25 mg of anti-HER2-C825, 62.5 μg (25% (w/w)) CA, and 55.5 MBq of $^{177}$Lu-DOTA-Bn
[c]no BsAb or CA injected, only ~16.8 MBq of $^{177}$Lu-DOTA-Bn (90 pmol)

TABLE 11

Ex vivo biodistribution studies of $^{177}$Lu activity in various tissues for optimization of CA for anti-HER2 DOTA-PRIT with $^{177}$Lu-DOTA-Bn in nude mice bearing s.c. BT-474 tumors. Groups of HER2(+)-tumor bearing mice (n = 4/group) were injected with 0.25 mg (1.19 nmol) of anti-HER2-C825 [t = −28 h], followed with CA (0-28% (w/w)/mouse with respect to administered anti-HER2-C825 BsAb mass of 0.25 mg/mouse; 0-70 μg/mouse; 0-0.14 nmol of dextran; 0-8.5 nmol of (Y)-DOTA-Bn) [t = −4 h], and 5.5-5.6 MBq (~30 pmol) of $^{177}$Lu-DOTA-Bn [t = 0 h], and sacrificed at 24 h p.i. for biodistribution in tumor and normal tissue. $^{177}$Lu activity concentration data is presented as % IA/g (mean ± standard deviation ("SD")). Tumor sizes are presented as gram (g) (mean ± SD).

| Tissues | 0% (saline) (n = 4) | 7.5% w/w 18.75 μg (n = 4) | 14% w/w 37.5 μg (n = 4) | 28% w/w 70 μg (n = 4) |
|---|---|---|---|---|
| Blood | 4.95 ± 1.17 | 1.03 ± 0.58 | 0.52 ± 0.08 | 0.27 ± 0.08 |
| Heart | 1.14 ± 0.29 | 0.45 ± 0.27 | 0.15 ± 0.03 | 0.11 ± 0.04 |
| Lungs | 2.11 ± 0.45 | 0.46 ± 0.23 | 0.35 ± 0.05 | 0.25 ± 0.05 |
| Liver | 1.85 ± 0.30 | 0.49 ± 0.25 | 0.46 ± 0.04 | 0.33 ± 0.02 |
| Spleen | 1.00 ± 0.21 | 0.58 ± 0.14 | 0.69 ± 0.20 | 0.73 ± 0.18 |
| Stomach | 0.34 ± 0.09 | 0.12 ± 0.03 | 0.14 ± 0.03 | 0.05 ± 0.02 |
| Small Int. | 0.58 ± 0.12 | 0.22 ± 0.12 | 0.17 ± 0.07 | 0.07 ± 0.01 |
| Large Int. | 0.58 ± 0.12 | 0.24 ± 0.08 | 0.36 ± 0.16 | 0.19 ± 0.04 |
| Kidneys | 2.31 ± 0.52 | 0.75 ± 0.46 | 0.78 ± 0.09 | 0.75 ± 0.08 |
| Muscle | 0.38 ± 0.09 | 0.11 ± 0.03 | 0.08 ± 0.02 | 0.08 ± 0.02 |
| Bone | 0.39 ± 0.16 | 0.09 ± 0.07 | 0.04 ± 0.01 | 0.11 ± 0.16 |
| Tumor | 19.94 ± 3.54 | 7.26 ± 0.55 | 6.76 ± 2.39 | 6.98 ± 3.15 |
| Tumor size (g) | 0.082 ± 0.021 | 0.122 ± 0.020 | 0.082 ± 0.023 | 0.095 ± 0.035 |
| | Tumor-to-tissue ratios | | | |
| Blood | 4.0 ± 1.2 | 7.1 ± 4.1 | 13.1 ± 5.1 | 25.6 ± 13.9 |
| Heart | 17.5 ± 5.4 | 16.0 ± 9.6 | 45.1 ± 18.9 | 63.5 ± 35.2 |
| Lungs | 9.5 ± 2.6 | 15.8 ± 7.9 | 19.6 ± 7.4 | 28.5 ± 14.3 |
| Liver | 10.8 ± 2.6 | 15.0 ± 7.8 | 14.6 ± 5.3 | 21.2 ± 9.7 |
| Spleen | 19.9 ± 5.5 | 12.6 ± 3.3 | 9.8 ± 4.4 | 9.6 ± 4.9 |
| Stomach | 59.1 ± 18.8 | 59.2 ± 17.0 | 50.1 ± 20.7 | 133.0 ± 76.7 |
| Small Int. | 34.5 ± 9.3 | 33.7 ± 19.2 | 39.8 ± 21.2 | 99.7 ± 47.9 |
| Large Int. | 34.4 ± 9.3 | 29.9 ± 10.7 | 18.9 ± 10.9 | 37.7 ± 18.5 |
| Kidneys | 8.6 ± 2.5 | 9.7 ± 6.0 | 8.7 ± 3.2 | 9.4 ± 4.3 |
| Muscle | 52.1 ± 15.2 | 67.5 ± 20.1 | 84.5 ± 37.6 | 84.6 ± 45.2 |
| Bone | 50.8 ± 22.7 | 80.6 ± 61.9 | 159.0 ± 66.7 | 63.5 ± 97.0 |

To demonstrate HER2-specific targeting, biodistribution studies were performed in mice bearing s.c. HER2(−) MDA-MB-468. Tumor uptake of pretargeted $^{177}$Lu activity at 24 h p.i. in HER2(−) tumors was ~7-fold lower (2.75±0.17% IA/g) than in HER2(+) BT-474 tumors (19.94±1.7% IA/g) (Table 10). In addition, injection of BT-474 tumor bearing animals with $^{177}$Lu-DOTA-Bn alone (i.e., no PRIT control) showed negligible uptake in tumor at 24 h p.i. (0.07±0.01% IA/g), as well as minimal uptake in blood (0.002±0.00% IA/g) and kidney (0.38±0.01% IA/g), demonstrating that $^{177}$Lu-DOTA-Bn has minimal whole-body retention due to rapid renal clearance (Table 10).

Using the optimized anti-HER2 DOTA-PRIT regimen, serial biodistribution studies were performed at various times from 1-336 h p.i. in BT-474 tumor bearing mice to determine the time of peak tumor uptake and perform dosimetry calculations for subsequent therapy studies. As shown in FIG. 4 (see also Table 10 and Table 12), peak tumor uptake of pretargeted $^{177}$Lu activity (~5.6 MBq/~30 pmol) was observed at 24 h p.i. to be 7.58±0.78, with corresponding activities of 0.28±0.09 for blood (tumor-to-blood ratio: 26.7±9.0) and 0.73±0.05 for kidney (tumor-to-kidney ratio: 10.4±1.3). Also, $^{177}$Lu activity in tumor remained relatively constant from 1-24 h p.i., ranging from ~5-8% IA/g, suggesting that tumor targeting was very rapid, and that the biologic clearance of activity from tumor was relatively slow. The tumor activity dropped to 2.29±0.41% IA/g and 0.32±0.06% IA/g at 96 and 336 h p.i., respectively, leading to an approximate tumor clearance half-life of 38.6 h ($R^2$=0.894).

TABLE 12

$^{177}$Lu activity data determined using ex vivo biodistribution from groups of nude mice bearing s.c. BT-474-tumors at each time indicated p.i. (from 1-336 h) is presented as % IA/g (mean ± standard error of mean ("SEM")). These data are also shown in FIG. 4 and were used for dosimetry calculations (Table 13).

| Tissues | 1.0 h (n = 5) | 2.5 h (n = 5) | 24 h (n = 5) | 96 h (n = 5) | 336 h (n = 4) |
|---|---|---|---|---|---|
| Blood | 0.62 ± 0.06 | 0.41 ± 0.04 | 0.28 ± 0.09 | 0.04 ± 0.00 | 0.002 ± 0.00 |
| Heart | 0.17 ± 0.03 | 0.13 ± 0.02 | 0.07 ± 0.02 | 0.05 ± 0.01 | 0.01 ± 0.00 |
| Lungs | 0.40 ± 0.05 | 0.37 ± 0.03 | 0.20 ± 0.05 | 0.07 ± 0.01 | 0.01 ± 0.00 |
| Liver | 0.76 ± 0.06 | 0.39 ± 0.04 | 0.27 ± 0.07 | 0.23 ± 0.04 | 0.09 ± 0.02 |
| Spleen | 0.15 ± 0.02 | 0.33 ± 0.03 | 0.60 ± 0.21 | 0.18 ± 0.02 | 0.09 ± 0.02 |
| Stomach | 0.37 ± 0.09 | 0.21 ± 0.07 | 0.06 ± 0.01 | 0.04 ± 0.01 | 0.01 ± 0.00 |
| Small Int. | 1.11 ± 0.27 | 0.47 ± 0.16 | 0.05 ± 0.01 | 0.05 ± 0.01 | 0.003 ± 0.00 |
| Large Int. | 2.22 ± 0.37 | 3.18 ± 0.52 | 0.18 ± 0.01 | 0.07 ± 0.01 | 0.004 ± 0.00 |
| Kidneys | 1.17 ± 0.02 | 0.95 ± 0.05 | 0.73 ± 0.05 | 0.27 ± 0.03 | 0.08 ± 0.01 |
| Muscle | 0.19 ± 0.01 | 0.19 ± 0.04 | 0.06 ± 0.01 | 0.10 ± 0.03 | 0.01 ± 0.00 |
| Bone | 0.18 ± 0.03 | 0.13 ± 0.01 | 0.04 ± 0.01 | 0.38 ± 0.09 | 0.03 ± 0.01 |
| Tumor | 6.65 ± 0.46 | 4.95 ± 0.34 | 7.58 ± 0.78 | 2.29 ± 0.41 | 0.32 ± 0.06 |
| Tumor size (g) | 0.112 ± 0.062 | 0.135 ± 0.040 | 0.182 ± 0.094 | 0.151 ± 0.104 | 0.183 ± 0.078 |
| | | | Tumor-to-tissue ratios | | |
| Blood | 10.7 ± 1.3 | 12.1 ± 1.5 | 26.7 ± 9.0 | 63.6 ± 12.2 | 160.8 ± 30.3 |
| Heart | 38.7 ± 6.7 | 37.5 ± 5.2 | 105.3 ± 27.7 | 42.4 ± 10.3 | 37.8 ± 7.7 |
| Lungs | 16.6 ± 2.3 | 13.5 ± 1.6 | 38.7 ± 10.0 | 34.7 ± 8.8 | 29.2 ± 8.2 |
| Liver | 8.7 ± 0.9 | 12.6 ± 1.6 | 28.3 ± 8.3 | 10.1 ± 2.6 | 3.7 ± 1.0 |
| Spleen | 44.9 ± 6.3 | 14.9 ± 1.8 | 12.6 ± 4.5 | 12.9 ± 2.9 | 3.5 ± 0.9 |
| Stomach | 17.8 ± 4.6 | 23.6 ± 7.7 | 122.3 ± 17.1 | 57.3 ± 13.7 | 51.4 ± 12.4 |
| Small Int. | 6.0 ± 1.5 | 10.6 ± 3.7 | 140.4 ± 22.8 | 44.0 ± 12.6 | 116.9 ± 30.0 |
| Large Int. | 3.0 ± 0.5 | 1.6 ± 0.3 | 41.7 ± 5.4 | 31.8 ± 8.6 | 75.6 ± 26.4 |
| Kidneys | 5.7 ± 0.5 | 5.2 ± 0.5 | 10.4 ± 1.3 | 8.4 ± 1.7 | 3.8 ± 0.9 |
| Muscle | 35.7 ± 3.6 | 25.8 ± 5.1 | 118.5 ± 26.8 | 22.5 ± 8.7 | 64.3 ± 18.4 |
| Bone | 37.3 ± 6.0 | 37.5 ± 4.3 | 189.6 ± 46.7 | 6.0 ± 1.7 | 10.0 ± 3.6 |

Absorbed dose estimates were obtained for tumor and tissues assayed by biodistribution in order to guide therapy studies and predict the dose-limiting tissue. As shown in Table 13, the estimated absorbed doses of $^{177}$Lu-DOTA-Bn (as cGy/MBq) for blood, tumor, liver, spleen, and kidney were 1.4, 39.9, 3.3, 0.3, and 5.6, respectively. The estimated dose to kidney was highest among normal tissues, leading to a TI of 7. Based on estimated maximum tolerated doses of 250 and 2000 cGy for blood (bone marrow) and kidney, respectively [32], the estimated maximum tolerated activity is −180 MBq, with blood (bone marrow) as the dose-limiting tissue (TI for blood: 28).

TABLE 13

Estimated absorbed doses for optimized anti-HER2-DOTA-PRIT with $^{177}$Lu-DOTA-Bn in nude mice carrying s.c. HER2(+) BT-474 tumors, based on serial biodistribution data from 1.0-336 h p.i. of $^{177}$Lu-DOTA-Bn.

| Tissues | $^{177}$Lu-DOTA-Bn cGy/MBq | $^{177}$Lu-therapy Therapeutic Index |
|---|---|---|
| Blood | 1.4 | 28 |
| Tumor | 39.9 | |
| Heart | 0.4 | 100 |
| Lung | 1.3 | 31 |
| Liver | 3.3 | 12 |
| Spleen | 0.3 | 133 |
| Stomach | 0.3 | 133 |
| Small Intestine | 0.4 | 100 |
| Large Intestine | 0.8 | 50 |
| Kidneys | 5.6 | 7 |
| Muscle | 0.9 | 44 |
| Bone | 0.7 | 57 |

Prior to therapy studies, a pilot SPECT/CT imaging study was conducted with a group of BT-474 tumored mice given optimized anti-HER2 DOTA-PRIT in conjunction with a therapeutic amount of IA of $^{177}$Lu-DOTA-Bn (~56 MBq, 300 pmol). The images clearly revealed tumor delineation in the lower flank at 24 h p.i. of $^{177}$Lu-DOTA-Bn (FIG. 3), suggesting high absolute tumor uptake, as well as high tumor-to-blood ratio. Biodistribution was done immediately following imaging, showing tumor, blood, and kidney uptakes of 5.53±0.27, 0.29±0.05, and 0.56±0.08, respectively (Table 10), suggesting that high TIs would be maintained for critical tissues during therapy.

The intratumoral BsAb-targeting and its relationship with HER2-expression, as well as the tumor microdistribution of pretargeted $^{177}$Lu activity was investigated using immunohistochemistry ("IHC") and autoradiography with excised BT-474 tumors at 24 h p.i. of BsAb or pretargeted $^{177}$Lu-DOTA-Bn, respectively. These studies revealed homogeneous uptake of BsAb at HER2-positive tumor regions and very uniform and homogeneous tumor distribution of pretargeted $^{177}$Lu activity (FIG. 5).

6.1.3.4 Therapy Studies

Therapy studies were carried out to determine the effect of estimated tumor dose on response for a wide range of starting tumor sizes, as well as to determine if it was feasible to achieve a high probability of cures, particularly with dosimetry-based treatment planning with estimated absorbed tumor doses of ~70 Gy. A summary of the three anti-HER2 DOTA-PRIT therapy studies is provided in Table 14.

TABLE 14

Summary of anti-HER2 DOTA-PRIT efficacy and toxicity studies.

| DOTA-PRIT treatment (number of mice/group) | Control groups (number of mice/group) | Tumor sizes (range, $mm^3$) | Tumor dose (Gy) | Blood dose (Gy) | Kidney dose (Gy) | Therapeutic Outcome/Study Endpoint |
|---|---|---|---|---|---|---|
| Single-cycle treatment with 55.5 MBq (5) | No treatment (5); BsAb only (5); 55.5 MBq of $^{177}$Lu-DOTA-Bn alone (5) | Small; palpable-30 | 22 | 0.8 | 0.3 | 5/5 CR and 3/4 cures/85 d[a] |
| Single-cycle treatment with 11.1, 33.3, or 55.5 MBq (5) | No treatment (5); 33.3 MBq of $^{177}$Lu-DOTA-Bn alone (5) | Medium; ~100-400 | 4.4, 13, or 22 | 0.2, 0.5, or 0.8 | 0.6, 1.9, 3.1 | 4/15 CR and 2/6 cures[b]/200 d |
| Triple-cycle fractionated treatment with 55.5 MBq (total IA: 167 MBq) (8) | No treatment (6); BsAb only (5)[d]; IgG-DOTA-PRIT (6)[d] | Medium; ~100-400 | 66 | 2.3 | 9.3 | 8/8 CR, 5/8 cures/85 d |

[a]a single mouse in BsAb only treatment group also showed a CR and cure at 85 d

[b]one each in 11.1 and 55.5 MBq DOTA-PRIT treated groups

[d]total BsAb mass administered per mouse 0.75 mg (3.57 nmol)

Shown in FIG. 6A, single-cycle anti-HER2-DOTA-PRIT with 55.5 MBq $^{177}$Lu-DOTA-Bn (estimated delivered absorbed tumor dose: 22 Gy) was effective in treating small s.c. xenografts, resulting in a high frequency of complete responses ("CRs") (5/5, 100%) with no recurrence observed in any animals at 85 d when survivors (4/5, 80%) were submitted for necropsy. Planar scintigraphy of groups of mice undergoing either anti-HER2-DOTA-PRIT or treatment with only 55.5 MBq $^{177}$Lu-DOTA-Bn clearly showed pretargeting-specific tumor uptake at 20 h p.i., which persisted at tumor at least 70 h p.i. (FIG. 7). Tumor response in control groups was generally not seen and tumors showed progression with no CRs, with the exception of a single mouse in the BsAb only group, which showed tumor shrinkage to CR at ~40 d post-treatment with no subsequent recurrence (1/5, 20%). On day 40 post-treatment, there was no statistical significance between tumor volumes for control groups (data not shown). In addition, at 85 d, tumor sizes for control groups progressed on average to 380-3130% of pre-treatment volumes, with animals treated with BsAb only showing the least average progression.

Treatment of mice bearing medium-sized s.c. xenografts with single-cycle anti-HER2-DOTA-PRIT with 11.1-55.5 MBq of $^{177}$Lu-DOTA-Bn did not produce generally remarkable tumor responses compared to controls, suggesting that estimated absorbed tumor doses of 4.4-22 Gy were insufficient for producing a high probability of tumor CRs (FIG. 6B). On day 40 post-treatment there was no statistical significance between tumor volumes for control or treatment groups (data not shown). A small proportion of anti-HER2-DOTA-PRIT treated animals irrespective of IA (4/15, 26.7%) showed CR by ~75-100 d post-treatment (2/5 from 11.1 MBq, and 1/5 from the 33.3 MBq or 55.5 MBq groups), most likely the effect of the trastuzumab-like action of the BsAb.

Although single-cycle treatment was ineffective in treating medium-sized tumor, fractionated delivery of a greater tumor absorbed radiation dose showed to be highly effective. Treatment of groups of mice bearing medium-sized s.c. xenografts with 3 cycles of anti-HER2-DOTA-PRIT plus $^{177}$Lu-DOTA-Bn (55.5 MBq/cycle, estimated delivered absorbed tumor dose 66 Gy) led to 100% CRs (8/8), whereas tumor progression with no CRs were observed in the treatment controls (FIG. 8). Tumor volumes at 85 d for control non-treated, BsAb treated, or Control IgG-DOTA-PRIT groups were 134±89%, 396±252%, or 114±155% of pre-treatment volume, respectively.

SPECT/CT was conducted on select mice undergoing fractionated treatment to verify and quantify tumor uptake. As shown in FIG. 9A, imaging of randomly-selected mice at 24 h p.i. of cycle 1 $^{177}$Lu-DOTA-Bn pretargeted with either Control IgG-DOTA-PRIT or anti-HER2-DOTA-PRIT showed anti-HER2-C825 tumor-specific targeting of radioactivity, with negligible tumor uptake during Control IgG-DOTA-PRIT. Also, three randomly-selected mice undergoing fractioned anti-HER2-DOTA-PRIT were serially imaged by SPECT/CT imaging. Representative images for one of the animals at 24 h p.i. of cycles 1, 2, and 3 of $^{177}$Lu-DOTA-Bn, are provided in FIG. 9B, while the data for two mice are provided in FIG. 10. Image-derived region-of-interest (ROI) analysis of the tumor region was also conducted, and a graph displaying the tumor $^{177}$Lu activities (expressed as MBq per gram of tumor; MBq/g) during each cycle of treatment as a function of time (h) post-cycle 1 treatment start, is also provided in FIG. 9B, showing that the average tumor uptake ranged from ~4.3-6.1 MBq/g 24 h following each treatment cycle injection of $^{177}$Lu-DOTA-Bn.

6.1.3.5 Toxicity

In summary, during each of the therapy experiments, no significant average weight loss was seen in any of the treatment groups compared with controls, including those administered $^{177}$Lu-DOTA-Bn (FIG. 11 and FIG. 12). Notably, no acute toxicity was seen for the anti-HER2-DOTA-PRIT regimen with 55.5 MBq $^{177}$Lu-DOTA-Bn/cycle (FIG. 12), suggesting that more aggressive treatment regimens could be safely utilized. Table 15, Table 16, and Table 17 summarize the criteria on which animals were removed from each therapy experiment. These included: (1) euthanasia needed due to excessive weight loss, (2) the animal was discovered deceased, and (3) euthanasia needed due to excessive tumor burden. We observed in this BT-474-animal model that a few animals irrespective of treatment regimen (including non-treated controls), showed rapid deterioration, presumably related to known effects of treatment with implantable estrogen pellets (e.g., urinary retention [33] and endometrial hyperplasia [34]). Therefore, during the fractionated treatment study, three randomly selected animals that showed rapid weight loss within 12-22 d post-treatment start were submitted for full necropsy to determine cause of poor clinical condition (one each from treatment group: no-treatment, BsAb only, and Control IgG-DOTA-PRIT). It was determined that the clinical morbidity in 3/3 (100%) animals was apparently due to adverse effects of estrogen treatment (see Table 17).

TABLE 15

The number of animals taken out of the experiment based on predefined criteria of weight loss and tumor growth for single-cycle anti-HER2-DOTA-PRIT + up to 55.5 MBq of $^{177}$Lu-DOTA-Bn of groups of mice bearing medium-sized tumors. The study endpoint was ~200 d post-treatment. Survivors at ~day 85: 3/5 from no treatment, 3/5 from BsAb only, 5/5 from 55.5 MBq of $^{177}$Lu-DOTA-Bn only, and 5/5 from anti-HER2-DOTA-PRIT + 55.5 MBq of $^{177}$Lu-DOTA-Bn.

| Criteria to remove animal from experiment | No treatment | 33.3 MBq of $^{177}$Lu-DOTA-Bn only | DOTA-PRIT + 11.1 MBq of $^{177}$Lu-DOTA-Bn | DOTA-PRIT + 33.3 MBq of $^{177}$Lu-DOTA-Bn | DOTA-PRIT + 55.5 MBq of $^{177}$Lu-DOTA-Bn |
|---|---|---|---|---|---|
| Weight loss | 2/5 | 0/5 | 0/5 | 1/5 | 0/5 |
| Discovered deceased | 0/5 | 1/5 | 1/5 | 0/5 | 1/5 |
| Tumor burden | 3/5 | 4/5 | 0/5 | 3/5 | 3/5 |

TABLE 16

The number of animals taken out of the experiment based on predefined criteria of weight loss and tumor growth for single-cycle anti-HER2-DOTA-PRIT + 55.5 MBq of $^{177}$Lu-DOTA-Bn of groups of mice bearing small-sized tumors. The study endpoint was ~85 d post-treatment. Survivors at ~day 85: 3/5 from no treatment, 3/5 from BsAb only, 5/5 from 55.5 MBq of $^{177}$Lu-DOTA-Bn only, and 5/5 from anti-HER2-DOTA-PRIT + 55.5 MBq of $^{177}$Lu-DOTA-Bn.

| Criteria to remove animal from experiment | No treatment | BsAb only | 55.5 MBq of $^{177}$Lu-DOTA-Bn only | DOTA-PRIT + 55.5 MBq of $^{177}$Lu-DOTA-Bn |
|---|---|---|---|---|
| Weight loss | 2/5 | 0/5 | 0/5 | 0/5 |
| Discovered deceased | 0/5 | 2/5 | 0/5 | 0/5 |
| Tumor burden | 0/5 | 0/5 | 0/5 | 0/5 |

TABLE 17

The number of animals taken out of the experiment based on predefined criteria of weight loss and tumor growth for fractionated anti-HER2-DOTA-PRIT, study endpoint ~85 d post-treatment start. Survivors at ~day 85 included: 4/6 no treatment, 3/5 from BsAb only, 3/6 from IgG-DOTA-PRIT + $^{177}$Lu-DOTA-Bn and 8/8 from anti-HER2-DOTA-PRIT + $^{177}$Lu-DOTA-Bn. Three animals from control groups that showed rapid deterioration of health and significant weight loss within 12-22 d of treatment start were submitted for necropsy to determine the cause of toxicity. A single no-treated mouse showed rapid weight loss from pre-treatment weight at 12 d, and was submitted moribund for necropsy, while another non-treated control mouse was found dead at 18 d. The moribund animal had mild focal unilateral suppurative pyelonephritis with intralesional coccoid bacteria. A single mouse from the BsAb only group showed rapid weight loss and was submitted for necropsy moribund at 20 d. This mouse showed pyelitis (bilateral) and pyelonephritis (unilateral), neutrophilic with intralesional bacteria (large cocci). A second mouse from the BsAb only group was discovered deceased at 35 d. For treatment with Control IgG-DOTA-PRIT, three animals showed rapid weight loss from pre-treatment weight at 4, 11, and 21 d. A single mouse from this group was submitted moribund for necropsy at 22 d. This mouse was diagnosed with severe hypoplastic (aplastic) anemia and hypoplasia of growth plates in long bones with inanition, perimortem bacterial embolization and perimortem hemorrhage.

| Criteria to remove animal from experiment | No treatment | BsAb only | Control IgG-DOTA-PRIT + $^{177}$Lu-DOTA-Bn | anti-HER2-DOTA-PRIT + $^{177}$Lu-DOTA-Bn |
|---|---|---|---|---|
| Weight loss | 1/6 | 1/5 | 3/6 | 0/8 |
| Discovered deceased | 1/6 | 1/5 | 0/6 | 0/8 |
| Tumor burden | 0/6 | 0/5 | 0/6 | 0/8 |

6.1.3.6 Hematology, Clinical Chemistry, and Histopathology

At ~85 d following treatment of mice bearing small-sized s.c. tumors with single-cycle of anti-HER2-DOTA-PRIT+ 55.5 MBq $^{177}$Lu-DOTA-Bn, of the five animals with CRs submitted for necropsy (a single mouse from BsAb only and four from the anti-HER2-DOTA-PRIT treatment groups) there were four cures, one from the BsAb only group (1/3, 33.3%) and three (3/4, 75%) from the anti-HER2-DOTA-PRIT treated group. No remarkable treatment-related morphologic change was noted (Table 18). Hematology and clinical chemistry (Table 19 and Table 20) values were generally within normal ranges with the exception of the white blood cells ("WBC"), platelets ("PLT"), and neutrophils ("NEUT"), which were significantly lower (P=0.0137, 0.0195, or 0.017, respectively) in the anti-HER2-DOTA-PRIT treated group (n=4; WBC range: 2.13-2.36 K/μL; PLT range: 229-670 K/μL; NEUT range: 0.47-1.42K/μL) compared to the non-treated group (n=3; WBC range: 3.15-6.01 K/μL; PLT range: 686-946 K/μL; NEUT range: 1.51-2.47 K/μL). Also, BUN (blood urea nitrogen) was significantly elevated (P=0.0202) in the anti-HER2-DOTA-PRIT treated group (n=4; BUN range: 26.0-39.0 mg/dL) compared to the non-treated group (n=3; BUN range: 20.0-23.0 mg/dL).

TABLE 18

Histopathologic findings at ~85 d post-treatment from BT-474 tumor bearing mice (smaller tumors) that underwent single-cycle anti-HER2-DOTA-PRIT + $^{177}$Lu-DOTA-Bn. A total of 15 animals were evaluated by necropsy.

| | No treatment | | | | 55.5 MBq of $^{177}$Lu-DOTA-Bn only | | | |
|---|---|---|---|---|---|---|---|---|
| Tumor | 12 × 6 × 3 mm; AC with necrosis, and L inflammation, 3 | 7 × 6 × 2 mm; AC | Two lesions: 15 × 10 × 9 mm and 5 × 5 × 5 mm; AC, with necrosis | Two lesions: 5 × 5 × 2 mm and 2 × 2 × 2 mm AC, with L inflammation, 3 | 14 × 10 × 4 mm; AC, with L inflammation, 3 | 16 × 16 × 6 mm; AC, with necrosis, and L inflammation, 2 | 6 × 6 × 2 mm; AC | 9 × 7 × 3 mm; AC |
| Liver | Hepatitis, L, portal, MF, 1. | Hepatitis, L, portal, MF, 2. EM, 2. | Hepatitis, L, portal, MF, 1. | Hepatitis, L, portal, MF, 2. EM, 1. | Hepatitis, L, portal, MF, 1. | N | Hepatitis, L, portal, MF, 2. | Hepatitis, L, portal, MF, 1. |
| Kidney | Tubular degeneration, 2, MF, bilateral | Tubular degeneration, 2, MF, bilateral | N | N | N | Tubular degeneration, 1, focal, unilateral | Tubular degeneration, 1, focal, unilateral | (Left): MF cortical and medullary atrophy and fibrosis, chronic (consistent with multiple chronic infarcts, or chronic |

TABLE 18-continued

Histopathologic findings at ~85 d post-treatment from BT-474 tumor bearing mice (smaller tumors) that underwent single-cycle anti-HER2-DOTA-PRIT + $^{177}$Lu-DOTA-Bn. A total of 15 animals were evaluated by necropsy.

| | | | | | | | | |
|---|---|---|---|---|---|---|---|---|
| | | | | | | | | resolved pyelonephritis); (Right): pyelonephritis, 3, neutrophilic, with bacteria (cocci), subacute |
| Spleen | LH and plasmacytosis, 2 | LH, 2. EM, 3. | N | Plasmacytosis, 3. | LH and plasmacytosis, 2. | HH, 3. | N | N |
| Bones | FL | FL | FL | FL | FL | FL | FL | FL |
| Bone marrow | N | MH | MH | MH | N | MH | N | MH |

| | BsAb only | | anti-HER2-DOTA-PRIT + 55.5 MBq | | | | |
|---|---|---|---|---|---|---|---|
| Tumor | No tumor | 5 × 5 × 3 mm; AC, with lymphocytic inflammation, 2 | 13 × 9 × 4 mm; AC, with necrosis and lymphocytic inflammation, 1. | 3 × 3 × 2 mm and 2 × 2 × 2 mm; AC | 2 × 2 × 2 mm; no evidence of neoplasia | In the subcutis there is a FE area of fibrosis. There is no evidence of neoplasia. The overlying epidermis shows acanthosis and hyperkeratosis, 3. | 3 × 2 × 1 mm; no evidence of neoplasia The overlying epidermis shows acanthosis and Hyperkeratosis, 3. |
| Liver | Hepatitis, L, portal, MF, 1. | Hepatitis, L, portal, MF, 1 | N | Hepatitis, L, portal, MF, 1 | Hepatitis, L, portal, MF, 1. EM, 1. | Hepatitis, L, portal, MF, 1. | N |
| Kidney | Tubular degeneration, 1, MF, bilateral. | N | N | N | Unilateral hydronephrosis, 3. | N | N |
| Spleen | LH, 2. | EM, 3. | N | LH, 2. | N | N | LH and plasmacytosis, 2. |
| Bones | N | FL | FL | FL | FL | FL | FL |
| Bone marrow | N | N | MH | N | MH | N | N |

AC: anaplastic carcinoma,
L: lymphoplasmacytic,
N: Normal,
EM: Extramedullary hematopoiesis,
HH: Hematopoietic hyperplasia,
LH: Lymphoid hyperplasia,
FE: Focally extensive,
FL: Fibroosseous lesions,
MH: Myeloid hyperplasia,
MF: Multifocal,
MFR: Multifocal random,
1: Minimal,
2: Mild,
3: Moderate,
4: Marked

TABLE 19

Hematology values at ~85 d from s.c. BT-474-tumor bearing mice (smaller tumors) that underwent single-cycle DOTA-PRIT + 55.5 MBq $^{177}$Lu-DOTA-Bn. RBC: red blood cells, HGB: hemoglobin, PLT: platelets, WBC: white blood cells, NEUT: neutrophils, LYMPH: lymphocytes, MONO: monocytes. Notes: Two animals showed low values for PLT: a mouse treated with 55.5 MBq $^{177}$Lu-DOTA-Bn only (PLT: 57) and one treated with BsAb only (PLT: 0); since platelet clumps were noted, values were excluded from analysis and considered an artifact of blood sampling.

| | Mouse | RBC (M/μL) | HGB (g/dL) | PLT (K/μL) | WBC (K/μL) | NEUT (K/μL) | LYMPH (K/μL) | MONO (K/μL) |
|---|---|---|---|---|---|---|---|---|
| No treatment | 1 | 8.61 | 13.1 | 809 | 3.15 | 1.51 | 1.51 | 0.09 |
| | 2 | 9.90 | 14.4 | 946 | 6.01 | 3.55 | 2.10 | 0.36 |
| | 3 | 8.02 | 14.1 | 686 | 4.11 | 2.47 | 1.56 | 0.04 |
| 55.5 MBq $^{177}$Lu-DOTA-Bn only | 1 | 8.22 | 13.1 | 554 | 4.88 | 2.49 | 2.10 | 0.10 |
| | 2 | 7.74 | 12.9 | [57] | 1.84 | 1.12 | 0.70 | 0.02 |
| | 3 | 8.54 | 14.3 | 813 | 3.37 | 1.92 | 1.28 | 0.07 |
| | 4 | 8.80 | 14.9 | 502 | 2.55 | 0.92 | 1.53 | 0.08 |
| | 5 | 8.32 | 14.0 | 361 | 3.16 | 1.42 | 1.55 | 0.19 |
| BsAb only | 1 | 8.01 | 13.3 | 253 | 5.15 | 1.44 | 3.40 | 0.26 |
| | 2 | 6.03 | 11.2 | [0] | 4.60 | 2.71 | 1.79 | 0.09 |
| | 3 | 8.59 | 14.7 | 372 | 3.29 | 1.91 | 1.28 | 0.10 |
| DOTA-PRIT + 55.5 MBq $^{177}$Lu-DOTA-Bn | 1 | 7.81 | 13.4 | 229 | 2.32 | 0.90 | 1.32 | 0.05 |
| | 2 | 8.30 | 14.6 | 670 | 2.13 | 0.94 | 1.00 | 0.15 |
| | 3 | 8.54 | 13.9 | 491 | 2.36 | 0.47 | 1.79 | 0.02 |
| | 4 | 7.87 | 13.9 | 483 | 2.18 | 1.42 | 0.59 | 0.07 |

TABLE 20

Clinical chemistry values at ~85 d from s.c. BT-474 tumor bearing mice (smaller tumors) that underwent single-cycle anti-HER2-DOTA-PRIT + 55.5 MBq $^{177}$Lu-DOTA-Bn. BUN: blood urea nitrogen, CREA: creatinine, ALP: alanine phosphatase, ALT: alanine aminotransferase, and AST: aspartate aminotransferase.

| | Mouse | BUN (mg/dL) | CREA (mg/dL) | ALP (U/L) | ALT (U/L) | AST (U/L) |
|---|---|---|---|---|---|---|
| No treatment | 1 | 23 | 0.21 | 127 | 32 | 74 |
| | 2 | 20 | 0.20 | 113 | 31 | 55 |
| | 3 | 22 | 0.21 | 181 | 33 | 73 |
| 55.5 MBq $^{177}$Lu-DOTA-Bn only | 1 | 22 | 0.20 | 58 | 34 | 87 |
| | 2 | 21 | 0.18 | 115 | 40 | 94 |
| | 3 | 23 | 0.19 | 121 | 30 | 90 |
| | 4 | 33 | 0.30 | 181 | 45 | 264 |
| | 5 | 38 | 0.22 | 231 | 24 | 83 |
| BsAb only | 1 | 17 | 0.19 | 150 | 21 | 146 |
| | 2 | 20 | 0.21 | 167 | 24 | 69 |
| | 3 | 15 | 0.17 | 182 | 17 | 73 |

TABLE 20-continued

Clinical chemistry values at ~85 d from s.c. BT-474 tumor bearing mice (smaller tumors) that underwent single-cycle anti-HER2-DOTA-PRIT + 55.5 MBq $^{177}$Lu-DOTA-Bn. BUN: blood urea nitrogen, CREA: creatinine, ALP: alanine phosphatase, ALT: alanine aminotransferase, and AST: aspartate aminotransferase.

| | Mouse | BUN (mg/dL) | CREA (mg/dL) | ALP (U/L) | ALT (U/L) | AST (U/L) |
|---|---|---|---|---|---|---|
| DOTA-PRIT + 55.5 MBq $^{177}$Lu-DOTA-Bn | 1 | 28 | 0.24 | 289 | 35 | 95 |
| | 2 | 39 | 0.34 | 118 | 29 | 113 |
| | 3 | 38 | 0.36 | 169 | 417 | 1970 |
| | 4 | 26 | 0.21 | 179 | 32 | 122 |

At ~200 d following treatment of mice bearing medium-sized s.c. tumors with anti-HER2-DOTA-PRIT+11.1-55.5 MBq $^{177}$Lu-DOTA-Bn, there were a total of six survivors, including two CRs, one from each of the 11.1 MBq and 55.5 MBq groups. Both were determined to be cured. No remarkable treatment-related histopathology was noted (Table 21). Hematology and clinical chemistry values were within normal ranges (Table 22 and Table 23). Due to the absence of surviving non-treated controls and the small number of survivors of anti-HER2-DOTA-PRIT treated animals at ~200 d, statistical comparisons for hematology and clinical chemistry parameters were not conducted for this study.

TABLE 21

Histopathologic findings at ~200 d post-treatment from BT-474 tumor bearing mice (medium-sized tumors) that underwent single-cycle anti-HER2-DOTA-PRIT + $^{177}$Lu-DOTA-Bn. A total of 6 animals were evaluated by necropsy.

| | | DOTA-PRIT + 11.1 MBq | | | DOTA-PRIT + 33.3 MBq | DOTA-PRIT + 55.5 MBq |
|---|---|---|---|---|---|---|
| Tumor | FE fibrosis with minimal lymphoplasmacytic and histiocytic inflammation; no evidence of neoplasia | 15 × 10 × 6 mm; poorly demarcated and invasive neoplasm composed of epithelioid cells forming nests with an abundant fibrous stroma. There is multifocal necrosis and calcification. There is lymphocytic inflammation within the tumor, 2, MF. There is evidence of vascular invasion. The overlying epidermis shows moderate acanthosis and hyperkeratosis | 20 × 15 × 12 mm; AC, with necrosis, lymphocytic inflammation 2, and vascular invasion. The overlying epidermis shows acanthosis, 3, and hyperkeratosis. | 10 × 6 × 2 mm; poorly demarcated and invasive neoplasm. There is MF necrosis and MF lymphocytic inflammation, 3. The overlying epidermis shows moderate acanthosis and hyperkeratosis. | 10 × 5 × 5 mm; poorly demarcated and invasive neoplasm. There is MF necrosis, and MF lymphocytic inflammation, 1. The overlying epidermis shows moderate acanthosis and hyperkeratosis. | 3 × 3 × 1 mm; FE fibrosis with lymphoplasmacytic inflammation, 1; no evidence of neoplasia. The overlying epidermis shows acanthosis, 3, and hyperkeratosis. |
| Liver | Heptatitis, L and neutrophilic, 1, MFR. EM, 1. | Hepatitis, L, portal, MF, 1. | Heptatitis, L, portal, MF, 1. | Hepatitis, L, random, MF, 2. | Heptatitis, L, portal, MF, 2. | Heptatitis, L, portal, MF, 1. |
| Kidney | (Left): Pyelonephritis, neutrophilic, with bacteria (bacilli), chronic-active, 4. Membranous glomerulonephritis, multifocal, chronic, 4; (Right): Pyelonephritis, neutrophilic, with bacteria, subacute, 3. Membranous glomerulonephritis, MF, with tubular hyaline casts and degeneration, chronic, 4. | Tubular degeneration, multifocal, bilateral, 2. (Left): Pyelitis, neutrophilic, acute, 2. Metastatic AC; (Right) L, MF, with diffuse atrophy, 4, and fibrosis, chronic, 3. | Metastatic AC. Tubular degeneration, 2, necrosis, and loss, MF, bilateral | N | N | N |

TABLE 21-continued

Histopathologic findings at ~200 d post-treatment from BT-474 tumor bearing mice (medium-sized tumors) that underwent single-cycle anti-HER2-DOTA-PRIT + $^{177}$Lu-DOTA-Bn. A total of 6 animals were evaluated by necropsy.

| | DOTA-PRIT + 11.1 MBq | | | | DOTA-PRIT + 33.3 MBq | DOTA-PRIT + 55.5 MBq |
|---|---|---|---|---|---|---|
| Spleen | HH, 3. | N | LH, 2 | LH, 2 | LH, 2 | LH, 2 |
| Bones | MH | N | N | N | N | N |

AC: anaplastic carcinoma,
L: lymphoplasmacytic,
N: Normal,
EM: Extramedullary hematopoiesis,
HH: Hematopoietic hyperplasia,
LH: Lymphoid hyperplasia,
FE: Focally extensive,
FL: Fibroosseous lesions,
MH: Myeloid hyperplasia,
MF: Multifocal,
MFR: Multifocal random,
1: Minimal,
2: Mild,
3: Moderate,
4: Marked

TABLE 22

Hematology values at ~200 d from BT-474 tumor bearing mice (medium-sized tumors) that underwent single-cycle DOTA-PRIT + $^{177}$Lu-DOTA-Bn. RBC: red blood cells, HGB: hemoglobin, PLT: platelets, WBC: white blood cells, NEUT: neutrophils, LYMPH: lymphocytes, MONO: monocytes. Normal animals: Harlan, Athymic Nude, Hsd: Athymic Nude-Foxn1nu, ~3 month old females, with no estrogen or xenograft implanted.

| | Mouse | RBC (M/μL) | HGB (g/dL) | PLT (K/μL) | WBC (K/μL) | NEUT (K/μL) | LYMPH (K/μL) | MONO (K/μL) |
|---|---|---|---|---|---|---|---|---|
| Normal | 1 | 8.69 | 14.6 | 981 | 5.37 | 2.36 | 2.52 | 0.21 |
| | 2 | 9.88 | 14.5 | 939 | 4.39 | 1.71 | 2.02 | 0.22 |
| | 3 | 8.60 | 14.0 | 815 | 3.80 | 1.50 | 2.00 | 0.20 |
| DOTA-PRIT + 11.1 MBq $^{177}$Lu-DOTA-Bn | 1 | 3.52 | 5.7 | 376 | 4.87 | 2.24 | 2.53 | 0.10 |
| | 2 | 7.97 | 12.6 | 925 | 4.77 | 2.48 | 1.81 | 0.29 |
| | 3 | 9.52 | 14.6 | 727 | 5.17 | 1.65 | 3.46 | 0.00 |
| | 4 | 9.35 | 15.1 | 877 | 6.06 | 2.97 | 2.91 | 0.06 |
| DOTA-PRIT + 33.3 MBq $^{177}$Lu-DOTA-Bn | 1 | 9.86 | 15.3 | 848 | 6.62 | 2.65 | 3.64 | 0.26 |
| DOTA-PRIT + 55.5 MBq $^{177}$Lu-DOTA-Bn | 1 | 9.39 | 14.9 | 771 | 4.48 | 1.70 | 2.60 | 0.13 |

TABLE 23

Clinical chemistry values at ~200 d from BT-474 tumor bearing mice (medium-sized tumors) that underwent single-cycle anti-HER2-DOTA-PRIT + 177Lu-DOTA-Bn. BUN: blood urea nitrogen, CREA: creatinine, ALP: alanine phosphatase, ALT: alanine aminotransferase, and AST: aspartate aminotransferase. Normal animals: Harlan, Athymic Nude, Hsd: Athymic Nude-oxn1nu, ~3 month old females, with no estrogen or xenograft implanted.

| | Mouse | BUN (mg/dL) | CREA (mg/dL) | ALP (U/L) | ALT (U/L) | AST (U/L) |
|---|---|---|---|---|---|---|
| Normal | 1 | 24 | 0.21 | 126 | 29 | 64 |
| | 2 | 24 | 0.18 | 88 | 45 | 78 |
| | 3 | 26 | 0.20 | 125 | 37 | 81 |
| DOTA-PRIT + 11.1 MBq $^{177}$Lu-DOTA-Bn | 1 | 129 | 0.44 | 136 | 22 | 102 |
| | 2 | 39 | 0.25 | 128 | 25 | 94 |
| | 3 | 20 | 0.19 | 73 | 30 | 77 |
| | 4 | 25 | 0.21 | 53 | 40 | 73 |
| DOTA-PRIT + 33.3 MBq $^{177}$Lu-DOTA-Bn | 1 | 34 | 0.20 | 69 | 26 | 109 |

TABLE 23-continued

Clinical chemistry values at ~200 d from BT-474 tumor bearing mice (medium-sized tumors) that underwent single-cycle anti-HER2-DOTA-PRIT + 177Lu-DOTA-Bn. BUN: blood urea nitrogen, CREA: creatinine, ALP: alanine phosphatase, ALT: alanine aminotransferase, and AST: aspartate aminotransferase. Normal animals: Harlan, Athymic Nude, Hsd: Athymic Nude-oxn1nu, ~3 month old females, with no estrogen or xenograft implanted.

| | Mouse | BUN (mg/dL) | CREA (mg/dL) | ALP (U/L) | ALT (U/L) | AST (U/L) |
|---|---|---|---|---|---|---|
| DOTA-PRIT + 55.5 MBq $^{177}$Lu-DOTA-Bn | 1 | 27 | 0.21 | 109 | 36 | 82 |

For the fractionated treatment study, a high frequency of cures was seen with anti-HER2-DOTA-PRIT (5/8, 62.5%) at 85 d post-treatment. The other three treated animals (3/8, 37.5%) showed microscopic residual disease, primarily consisting of soft tissue sclerosis with a few scattered neoplastic cells (Table 21). Representative H&E staining of tissue sections taken from the site of tumor inoculation for all treatment groups are shown in FIG. 13 (see also Table 24).

TABLE 24

Histopathologic findings at ~85 d from BT-474 tumor bearing mice (medium-sized tumors) that underwent fractionated anti-HER2-DOTA-PRIT + $^{177}$Lu-DOTA-Bn. A total of 18 animals were evaluated by necropsy. AC: anaplastic carcinoma, L: lymphoplasmacytic, N: Normal, EM: Extramedullary hematopoises, HH: Hematopoietic hyperplasia, LH: Lymphoid hyperplasia, FE: Focally extensive, FL: Fibroosseous lesions, FM: Focal myelofibrosis, MH: Myeloid hyperplasia, MF: Multifocal, MFR: Multifocal random, 1: Minimal, 2: Mild, 3: Moderate, 4: Marked.

| | No treatment | | | | BsAb only | | |
|---|---|---|---|---|---|---|---|
| Tumor | 15 × 12 × 5 mm; AC. | 15 × 10 × 5 mm; AC. | 14 × 12 × 2 mm; AC. | 2 coalescing round nodules on the right flank. Their size was 7 mm in diameter and 5 mm thick | 10 × 15 × 3 mm; AC. | 20 × 17 × 7 mm; AC. Increased infiltration of lymphocytes and plasma cells within the subcutis immediately surrounding the mass, even forming follicular like structures. | 12 × 12 × 6 mm; AC. |
| Liver | Occasional small foci (few scattered cells) of periportal lymphocytes and plasma cells | N | Focal basophilic focus with hepatocellular hypertrophy. | Diffuse hepatocellular polyploidia and karyomegaly. | N | N | L infiltrate within portal fields, 1. |
| Kidney | N | Unilateral focal minimal hyaline casts within the medullary tubules | N | N | Within the cortex MF segmental basophilia. | N | N |
| Spleen | N | N | Slightly increased EH and hemosiderosis. | EH, 2-3. | White pulp hyperplasia (reactive) | Increase of EH, 2. | Hemosiderosis, 1. |

TABLE 24-continued

Histopathologic findings at ~85 d from BT-474 tumor bearing mice (medium-sized tumors) that underwent fractionated anti-HER2-DOTA-PRIT + $^{177}$Lu-DOTA-Bn. A total of 18 animals were evaluated by necropsy. AC: anaplastic carcinoma, L: lymphoplasmacytic, N: Normal, EM: Extramedullary hematopoises, HH: Hematopoietic hyperplasia, LH: Lymphoid hyperplasia, FE: Focally extensive, FL: Fibroosseous lesions, FM: Focal myelofibrosis, MH: Myeloid hyperplasia, MF: Multifocal, MFR: Multifocal random, 1: Minimal, 2: Mild, 3: Moderate, 4: Marked.

| | | | | | | | |
|---|---|---|---|---|---|---|---|
| Bone marrow | N | MF myelofibrosis, 2 | Slightly decreased erythroid elements. | Mild decrease of erythroid precursors density | MF myelofibrosis and slightly decreased erythroid precursors in the stifle only. | N | FM in the stifle. |

Control IgG-DOTA-PRIT + $^{177}$Lu-DOTA-Bn

| | | | |
|---|---|---|---|
| Tumor | AC, firm in texture, 0.5 × 0.5 × 0.1 cm. Tumor mass extends from subcutis into skeletal muscle | AC, 1.5 × 1.2 × 0.8 cm; texture is firm to hard | AC, 1 × 1 × 0.5 cm. Tumor extends from subcutis into fascia |
| Liver | N | N | Minimal and focal hepatocellular necrosis. Mild infiltration of lymphocytes and plasma cells within portal spaces |
| Kidney | N | N | N |
| Spleen | Increase of EH (erythroid line), 3 | Increase of EH (erythroid line), 3 to severe | N |
| Bone marrow | N | Ratio between erythroid and myeloid components is equivalent (normal 1:3). Erythroid compartment is depleted of both mature and immature forms | N |

Anti-Her2-DOTA-PRIT + $^{177}$Lu-DOTA-Bn

| | | | | | | | | |
|---|---|---|---|---|---|---|---|---|
| Tumor | No mass along flank. Subcutis is focally expanded by abundant collagen with few fibroblasts (sclerosis). Only few single neoplastic cells were found, scattered within extracellular matrix. | No mass along flank. Site consists of sclerotic stroma, with no evidence of neoplastic cells in section. | No mass along flank. Site consists of sclerotic tissue, with no evidence of neoplastic cells in section | No mass along flank. Dermis and subcutis are replaced by sclerotic collagen. No neoplastic cells were found in examined section | A single round mass, 0.3 cm diameter, 0.2 cm thick. Mass consists of sclerotic stroma in which few scattered neoplastic cells are embedded | A single round mass along right flank, 0.3 cm diameter, 0.2 cm thick. Mass consists of sclerotic stroma. No neoplastic cells | No mass along flank. Site consists of focal sclerosis with few scattered neoplastic cells | No mass along flank. No evidence of neoplastic cells in section |
| Liver | N | N | N | N | MF hepato-cellular hyper-trophy and acidophilia. L portal infiltration, 1 | N | L infiltration of the portal triads, 2 | N |
| Kidney | N | N | N | N | N | N | N | N |
| Spleen | Increase of EH (erythroid line), 2 | N | N | EH, 2-3 | EH, 3 | N | EH, 2 | EH, 2-3 |
| Bone marrow | MF myelo-fibrosis and slightly decreased erythroid precursors in stifle only | N | Decrease erythroid line elements in vertebras only | FM in stifle, 2 | FM with decreased erythroid elements | N | N | FM in stifle |

Also at 85 d post-treatment, two anti-HER2-DOTA-PRIT animals (2/8) showed notable hematology and clinical chemistry values (Table 25 and Table 26). A single mouse showed mild anemia (7.70M/μL; control range: 8.38-8.88M/μL) and hemoglobin ("HGB"; 12.7 g/dL; control range: 14.3-14.7 g/dL), and increases of aspartate aminotransferase (154 U/L; control range: 57-81 U/L) and alanine phosphatase (128 U/L; control range: 64-110 U/L). Another mouse showed mild anemia (7.89M/μL), HGB (13.1 g/dL), and thrombocytopenia (500K/μL; control range: 781-953K/μL), but normal clinical chemistry values. No change was observed in 6/8 animals. In summary, there were a few hematology parameters with significantly different ranges in the anti-HER2-DOTA-PRIT group versus no treatment group, while nothing significant was seen for clinical chemistry: with RBC and PLT were significantly lower ($P<0.05$) in the anti-HER2-DOTA-PRIT treated group (n=8; RBC range: 7.70-8.63M/μL; PLT range: 500-794K/μL) compared to the non-treated group (n=4; RBC range: 8.38-8.88M/μL; PLT range: 781-953K/μL). Notable bone marrow histopathologic changes were seen for a single anti-HER2-DOTA-PRIT treated mouse (1/8, 12.5%), which had focal myelofibrosis (severity score: 1; Table 27).

TABLE 25

Hematology values at ~85 d post-treatment start from BT-474 tumor bearing mice (medium-sized tumors) that underwent fractionated Control IgG-DOTA-PRIT or anti-HER2-DOTA-PRIT with $^{177}$Lu-DOTA-Bn (167 MBq/mouse total administered activity). RBC: red blood cells, HGB: hemoglobin, PLT: platelets, WBC: white blood cells, NEUT: neutrophils, LYMPH: lymphocytes, MONO: monocytes.

| | Mouse | RBC (M/μL) | HGB (g/dL) | PLT (K/μL) | WBC (K/μL) | NEUT (K/μL) | LYMPH (K/μL) | MONO (K/μL) |
|---|---|---|---|---|---|---|---|---|
| No treatment | 1 | 8.38 | 14.7 | 870 | 4.90 | 3.23 | 1.52 | 0.10 |
| | 2 | 8.46 | 14.6 | 781 | 3.41 | 1.81 | 1.26 | 0.20 |
| | 3 | 8.59 | 14.3 | 786 | 3.72 | 1.93 | 1.23 | 0.48 |
| | 4 | 8.88 | 14.5 | 953 | 6.16 | 2.03 | 3.63 | 0.31 |
| BsAb only | 1 | 8.22 | 13.4 | 505 | 6.67 | 0.33 | 6.20 | 0.13 |
| | 2 | 8.34 | 14.0 | 629 | 2.60 | 1.07 | 1.43 | 0.05 |
| | 3 | 8.87 | 14.2 | 739 | 4.34 | 1.61 | 2.34 | 0.35 |
| IgG-DOTA-PRIT | 1 | 8.72 | 14.3 | 767 | 4.15 | 1.55 | 2.02 | 0.53 |
| | 2 | 8.20 | 13.3 | 749 | 2.86 | 1.34 | 1.00 | 0.46 |
| | 3 | 8.55 | 14.3 | 781 | 3.84 | 1.44 | 2.04 | 0.31 |
| anti-HER2-DOTA-PRIT | 1 | 7.70 | 12.7 | 694 | 3.86 | 1.70 | 1.89 | 0.19 |
| | 2 | 8.48 | 14.0 | 767 | 4.07 | 1.67 | 1.95 | 0.24 |
| | 3 | 8.51 | 13.9 | 752 | 3.50 | 1.68 | 1.19 | 0.39 |
| | 4 | 7.91 | 14.0 | 554 | 3.17 | 1.39 | 1.55 | 0.22 |
| | 5 | 8.36 | 13.4 | 794 | 2.72 | 1.50 | 1.20 | 0.03 |
| | 6 | 8.06 | 14.0 | 788 | 5.53 | 2.60 | 2.49 | 0.33 |
| | 7 | 7.89 | 13.1 | 500 | 2.75 | 1.51 | 1.07 | 0.06 |
| | 8 | 8.63 | 15.0 | 662 | 2.66 | 1.54 | 0.80 | 0.24 |

TABLE 26

Clinical chemistry values at ~85 d post-treatment start from BT-474 tumor bearing mice (medium-sized tumors) that underwent fractionated Control IgG-DOTA-PRIT or anti-HER2-DOTA-PRIT with $^{177}$Lu-DOTA-Bn (167 MBq/mouse). BUN: blood urea nitrogen, CREA: creatinine, ALP: alanine phosphatase, ALT: alanine aminotransferase, and AST: aspartate aminotransferase.

| | Mouse | BUN (mg/dL) | CREA (mg/dL) | ALP (U/L) | ALT (U/L) | AST (U/L) |
|---|---|---|---|---|---|---|
| No treatment | 1 | 23 | 0.11 | 64 | 29 | 59 |
| | 2 | 27 | 0.11 | 87 | 22 | 57 |
| | 3 | 22 | 0.13 | 67 | 36 | 79 |
| | 4 | 27 | 0.15 | 110 | 40 | 81 |

TABLE 26-continued

Clinical chemistry values at ~85 d post-treatment start from BT-474 tumor bearing mice (medium-sized tumors) that underwent fractionated Control IgG-DOTA-PRIT or anti-HER2-DOTA-PRIT with $^{177}$Lu-DOTA-Bn (167 MBq/mouse). BUN: blood urea nitrogen, CREA: creatinine, ALP: alanine phosphatase, ALT: alanine aminotransferase, and AST: aspartate aminotransferase.

| | Mouse | BUN (mg/dL) | CREA (mg/dL) | ALP (U/L) | ALT (U/L) | AST (U/L) |
|---|---|---|---|---|---|---|
| BsAb only | 1 | 31 | 0.13 | 74 | 47 | 110 |
| | 2 | 30 | 0.13 | 102 | 29 | 74 |
| | 3 | 24 | 0.12 | 116 | 42 | 72 |
| IgG-DOTA-PRIT | 1 | 24 | 0.15 | 170 | 30 | 86 |
| | 2 | 20 | 0.13 | 63 | 39 | 87 |
| | 3 | 25 | 0.09 | 72 | 26 | 53 |
| anti-HER2-DOTA-PRIT | 1 | 29 | 0.11 | 128 | 68 | 154 |
| | 2 | 29 | 0.11 | 60 | 39 | 67 |
| | 3 | 22 | 0.14 | 59 | 40 | 88 |
| | 4 | 25 | 0.11 | 75 | 32 | 68 |
| | 5 | 24 | 0.13 | 87 | 37 | 76 |
| | 6 | 24 | 0.12 | 55 | 35 | 81 |

TABLE 26-continued

Clinical chemistry values at ~85 d post-treatment start from BT-474 tumor bearing mice (medium-sized tumors) that underwent fractionated Control IgG-DOTA-PRIT or anti-HER2-DOTA-PRIT with $^{177}$Lu-DOTA-Bn (167 MBq/mouse). BUN: blood urea nitrogen, CREA: creatinine, ALP: alanine phosphatase, ALT: alanine aminotransferase, and AST: aspartate aminotransferase.

| Mouse | BUN (mg/dL) | CREA (mg/dL) | ALP (U/L) | ALT (U/L) | AST (U/L) |
|---|---|---|---|---|---|
| 7 | 22 | 0.11 | 75 | 29 | 88 |
| 8 | 24 | 0.13 | 106 | 33 | 87 |

TABLE 27

Pathology severity scoring of remarkable morphological changes. Summary of distribution and incidence of morphologic changes in the different groups at ~85 d post-treatment start from groups that underwent fractionated DOTA-PRIT + $^{177}$Lu-DOTA-Bn. Treatment groups included: No Treatment, BsAb only (BsAb), Control IgG-DOTA-PRIT + $^{177}$Lu-DOTA-Bn (IgG-therapy), and anti-HER2-DOTA-PRIT + $^{177}$Lu-DOTA-Bn (anti-HER2-therapy). See Table 28 for scoring.

| | | % Incidence (No. mice with lesions/No. mice examined) | | | | Score* | | | |
|---|---|---|---|---|---|---|---|---|---|
| Organ | Morphologic change | No treatment | BsAb only | IgG-therapy | anti-HER2-therapy | No treatment | BsAb | IgG-therapy | anti-HER2-therapy |
| Kidney | Unilateral focal presence of hyaline casts in medullary tubules | 25 (1/4) | 0 (0/3) | 0 (0/3) | 0 (0/8) | 2 | 0 | 0 | 0 |
| | Unilateral, multifocal, cortical tubular basophilia | 0 (0/4) | 33.3 (1/3) | 0 (0/3) | 0 (0/8) | 0 | 3 | 0 | 0 |
| Total organ severity score | | | | | | 2 | 3 | 0 | 0 |
| Spleen | EMH is: 2 | 0 (0/4) | 33.3 (1/3) | 0 (0/3) | 25 (2/8) | 0 | 2 | 0 | 2 |
| | 2-3 | 25 (1/4) | 0 (0/3) | 0 (0/3) | 25 (2/8) | 2.5 | 0 | 0 | 2.5 |
| | 3 | 0 (0/4) | 0 (0/3) | 33.3 (1/3) | 12.5 (1/8) | 0 | 0 | 3 | 3 |
| | 3-4 | 0 (0/4) | 0 (0/3) | 33.3 (1/3) | 0 (0/8) | 0 | 0 | 3.5 | 0 |
| Total organ severity score | | | | | | 2.5 | 2 | 6.5 | 7.5 |
| Bone Marrow | Multifocal myelofibrosis | 25 (1/4) | 0 (0/3) | 0 (0/3) | 0 (0/8) | 2 | 0 | 0 | 0 |
| | Diffuse myelofibrosis | 0 (0/4) | 0 (0/3) | 0 (0/3) | 0 (0/8) | 0 | 0 | 0 | 0 |
| | Focal myelofibrosis | 0 (0/4) | 33.3 (1/3) | 0 (0/3) | 12.5 (1/8) | 0 | 1 | 0 | 1 |
| | Erythroid compartment is depleted of both mature and immature forms | 0 (0/4) | 0 (0/3) | 33.3 (1/3) | 0 (0/8) | 0 | 0 | 3 | 0 |
| Total organ severity score | | | | | | 2 | 1 | 3 | 1 |

EMH = extramedullary hematopoiesis;
*see Table 19 for scoring

TABLE 28

Calculation of organ severity scores described in Table 27.

| Extension | Score | Distribution (for paired genes) | Score |
|---|---|---|---|
| Focal | 1 | Single organ | 0 |
| Multifocal | 2 | Unilateral | 1 |
| Diffuse | 3 | Bilateral | 2 |

Severity scoring system of histopathologic lesions: Total scoring fomula: Extension Score + Distribution Score) Total Severity per organ: Sum of partial scores for single histopathologic legions.

6.1.4 Discussion

Safe and curative treatment for advanced human solid tumors is a major unmet need in oncology. These tumors include lung, prostate, breast, pancreas, glioma, GI malignancies; in other words, virtually all major tumors. This fact is still true despite major breakthroughs in immune checkpoint blockade and targeted drugs that are tyrosine kinase inhibitors. In particular, the heterogeneity of solid tumors in time and space, de novo or acquired, at the DNA, RNA, and protein levels, is hampering true cures with the most advanced molecular targeting drugs in clinically advanced solid tumors.

Without being bound by any particular theory, it is hypothesized that the DOTA-PRIT platform in this example (see, FIG. 14) has a good potential to improve the specificity and potency of liquid radiation and drugs/toxins in the treatment of solid tumors. The DOTA-PRIT approach has optimized RIT to permit targeting of massive amounts of radiation to tumor, while avoiding normal tissue. DOTA-PRIT targeting GD2- and GPA33-expressing human xenograft tumors in laboratory animals has been studied, and effective treatment regimens, capable of achieving 100% of CR's and a high probability of histologic cures with limited toxicity have been developed for DOTA-PRIT targeting GD2 and GPA33. TIs of 142 for blood and 23 for kidney were observed with 84.9 cGy/MBq to GD2-positive tumors, and TIs of 73 for blood and 12 for kidney were observed with 65.8 cGy/MBq to GPA33-positive tumors. These 2 target systems have clinical utility for a variety of human solid tumors, including colon cancer, pancreatic cancer, pseudomyxoma peritoneai, and subsets of pancreatic cancer for GPA33, and for neuroblastoma, glioma, sarcoma, and small cell lung cancer for GD2.

HER2 antigen is widely expressed on major human tumors, especially breast, ovary, GE junction tumors. For this reason, a DOTA-PRIT variant to target HER2 for radiotherapy was developed in this example. In contrast to GPA33 and GD2, the HER2 system is thought to be much more labile in the membrane and also more rapidly internalized once bound to its cognate antibody. Without being bound by any particular theory, it was reasoned that for pretargeted MT to succeed, the dwell time of the BsAb bound to the tumor surface could be critical, where a non-internalizing antibody-antigen complex would have a distinct advantage. In spite of this, this example sought to demonstrate proof-of-concept of anti-HER2-DOTA-PRIT, with the expectation that, without being bound by any particular theory, although the TIs for anti-HER2-DOTA-PRIT would be lower than that of anti-GPA33- or anti-GD2-DOTA-PRIT, these studies will be informative to set the kinetic limit of endocytosing antigens for PRIT.

Anti-HER2-C825 product with sufficient affinity, biochemical purity, and yields for in vivo studies was successfully prepared. The human BT-474 breast cancer cell line, a HER2-expressing tumor, was chosen as an animal model system for comparison of DOTA-PRIT treatment response. Using optimized anti-HER2-DOTA-PRIT, lower TI's were in fact observed than for the other 2 antigen systems: TIs of 28 for blood and 7 for kidney, with 39.9 cGy/MBq to tumor. Based on preliminary in vitro internalization experiments it was anticipated that the TI might be affected, yet, there was enough surface-bound BsAb at 24 h (11%) left to improve TI to a reasonable level for curative RIT.

The most direct treatment regimen for comparison with the other 2 DOTA-PRIT solid-tumor systems was triple-cycle fractionated regimen of medium sized tumors, in the range of 100-400 mg size. A triple-cycle approach, which was also used for GPA33 and GD2 targeting, was chosen because it was reasoned that a fractionated treatment approach would be ideal for safe administration of sufficient $^{177}$Lu-DOTA-Bn activities to achieve a tumoricidal absorbed radiation dose to tumor of ~70 Gy[1]. HER2(+) BT-474 tumor growth control including cures with optimized dosing was demonstrated. It was found that triple-cycle fractionated anti-HER2-DOTA-PRIT (total IA: 167 MBq/mouse) was well-tolerated and highly effective, with no animals showing acute toxicity. Total dose of radiation to tumor was ~70 Gy, and with a high frequency CRs (8/8, 100%) and complete tumor eradication to cure (5/8, 62.5%) and 37.5% microscopic residual disease (3/8) at 85 d. No CRs recurred within 85 d. It was verified using serial SPECT/CT imaging that efficient tumor targeting was achieved during each treatment cycle (FIG. 18). Survivors in control groups showed tumor progression 207±201% of pre-treatment volume at approximately 85 d, with no CRs or cures.

In terms of tumor response, a size dependent effect was observed during efficacy studies, with smaller-sized tumors requiring only a single-cycle of anti-HER2-DOTA-PRIT+ 55.5 MBq of $^{177}$Lu-DOTA-Bn to achieve a high incidence of CRs (5/5, 100%) and cures (3/4, 75%; at 85 d). Single-dose treatment of medium-sized tumors however, showed a low frequency of CRs (4/15, 26.7%) or cures (2/6 assessable animals at 200 d) irrespective of administered $^{177}$Lu-DOTA-Bn (11.1-55.5 MBq). In addition, it was observed that single dose of medium-sized tumors led to eventual recurrence of CRs (1/3 assessable, 33.3%) within 100 d post-treatment. As described above, triple-cycle treatment of 55.5 MBq was highly effective for the medium-sized tumors, leading to a high frequency of CRs and cures.

In summary, this example involves the development of a high-TI theranostic approach for PRIT of HER2(+) disease. Curative therapies for HER2-expressing tumors are a major unmet need. Treatment options for patients with HER2-overexpressing cancers, especially those resistant to trastuzumab and kinase inhibitors, are limited [35]. The success of the HER2 antibody-antigen system is a benchmark for comparison of other internalizing antigen targets, and this example serves as a guide for further adaptation of DOTA-PRIT. This example suggests that high TI targeting is feasible, with curative potential while sparing normal tissues.

6.1.5 References

1. Larson S, Carrasquillo J A, Cheung N K, Press O W. Radioimmunotherapy of human tumours. Nature reviews Cancer. 2015; 15: 347-60.
2. Kraeber-Bodere F, Rousseau C, Bodet-Milin C, Frampas E, Faivre-Chauvet A, Rauscher A, et al. A pretargeting system for tumor PET imaging and radioimmunotherapy. Front Pharmacol. 2015; 6: 54.
3. Cheal S M, Xu H, Guo H F, Zanzonico P B, Larson S M, Cheung N K. Preclinical evaluation of multistep targeting of diasialoganglioside GD2 using an IgG-scFv bispecific antibody with high affinity for GD2 and DOTA metal complex. Molecular cancer therapeutics. 2014; 13: 1803-12.0
4. Cheal S M, Xu H, Guo H F, Lee S G, Punzalan B, Chalasani S, et al. Theranostic pretargeted radioimmunotherapy of colorectal cancer xenografts in mice using picomolar affinity Y-86- or Lu-177-DOTA-Bn binding scFv C825/GPA33 IgG bispecific immunoconjugates. European journal of nuclear medicine and molecular imaging. 2016; 43: 925-37.
5. Green D J, Frayo S L, Lin Y, Hamlin D K, Fisher D R, Frost S H, et al. Comparative Analysis of Bispecific Antibody and Streptavidin-Targeted Radioimmunotherapy for B-cell Cancers. Cancer research. 2016.
6. Orcutt K D, Nasr K A, Whitehead D G, Frangioni J V, Wittrup K D. Biodistribution and clearance of small molecule hapten chelates for pretargeted radioimmunotherapy. Molecular imaging and biology: MIB: the official publication of the Academy of Molecular Imaging. 2011; 13: 215-21.
7. Austin C D, De Maziere A M, Pisacane P I, van Dijk S M, Eigenbrot C, Sliwkowski M X, et al. Endocytosis and sorting of ErbB2 and the site of action of cancer therapeutics trastuzumab and geldanamycin. Molecular biology of the cell. 2004; 15: 5268-82.
8. Menard S, Fortis S, Castiglioni F, Agresti R, Balsari A. HER2 as a prognostic factor in breast cancer. Oncology. 2001; 61 Suppl 2: 67-72.

9. Jorgensen J T, Hersom M. HER2 as a Prognostic Marker in Gastric Cancer—A Systematic Analysis of Data from the Literature. J Cancer. 2012; 3: 137-44.

10. English D P, Roque D M, Santin A D. HER2 expression beyond breast cancer: therapeutic implications for gynecologic malignancies. Mol Diagn Ther. 2013; 17: 85-99.

11. Hudis C A. Trastuzumab—mechanism of action and use in clinical practice. The New England journal of medicine. 2007; 357: 39-51.

12. Bookman M A, Darcy K M, Clarke-Pearson D, Boothby R A, Horowitz I R. Evaluation of monoclonal humanized anti-HER2 antibody, trastuzumab, in patients with recurrent or refractory ovarian or primary peritoneal carcinoma with overexpression of HER2: a phase II trial of the Gynecologic Oncology Group. Journal of clinical oncology: official journal of the American Society of Clinical Oncology. 2003; 21: 283-90.

13. Vogel C L, Cobleigh M A, Tripathy D, Gutheil J C, Harris L N, Fehrenbacher L, et al. Efficacy and safety of trastuzumab as a single agent in first-line treatment of HER2-overexpressing metastatic breast cancer. Journal of clinical oncology: official journal of the American Society of Clinical Oncology. 2002; 20: 719-26.

14. Verma S, Miles D, Gianni L, Krop I E, Welslau M, Baselga J, et al. Trastuzumab emtansine for HER2-positive advanced breast cancer. The New England journal of medicine. 2012; 367: 1783-91.

15. Brechbiel M W, Waldmann T A. Anti-HER2 radioimmunotherapy. Breast Dis. 2000; 11: 125-32.

16. Yoshida T, Jin K, Song H, Park S, Huso D L, Zhang Z, et al. Effective treatment of ductal carcinoma in situ with a HER-2-targeted alpha-particle emitting radionuclide in a preclinical model of human breast cancer. Oncotarget. 2016; 7: 33306-15.

17. Boudousq V, Bobyk L, Busson M, Garambois V, Jarlier M, Charalambatou P, et al. Comparison between internalizing anti-HER2 mAbs and non-internalizing anti-CEA mAbs in alpha-radioimmunotherapy of small volume peritoneal carcinomatosis using 212Pb. PloS one. 2013; 8: e69613.

18. Heyerdahl H, Abbas N, Sponheim K, Mollatt C, Bruland O, Dahle J. Targeted alpha therapy with 227Th-trastuzumab of intraperitoneal ovarian cancer in nude mice. Current radiopharmaceuticals. 2013; 6: 106-16.

19. Heyerdahl H, Abbas N, Brevik E M, Mollatt C, Dahle J. Fractionated therapy of HER2-expressing breast and ovarian cancer xenografts in mice with targeted alpha emitting 227Th-DOTA-p-benzyl-trastuzumab. PloS one. 2012; 7: e42345.

20. Abbas N, Heyerdahl H, Bruland O S, Borrebaek J, Nesland J, Dahle J. Experimental alpha-particle radioimmunotherapy of breast cancer using 227Th-labeled p-benzyl-DOTA-trastuzumab. EJNMMI research. 2011; 1: 18.

21. Boskovitz A, McLendon R E, Okamura T, Sampson J H, Bigner D D, Zalutsky M R. Treatment of HER2-positive breast carcinomatous meningitis with intrathecal administration of alpha-particle-emitting (211)At-labeled trastuzumab. Nuclear medicine and biology. 2009; 36: 659-69.

22. Milenic D E, Garmestani K, Brady E D, Albert P S, Ma D, Abdulla A, et al. Alpha-particle radioimmunotherapy of disseminated peritoneal disease using a (212)Pb-labeled radioimmunoconjugate targeting HER2. Cancer biotherapy & radiopharmaceuticals. 2005; 20: 557-68.

23. Borchardt P E, Yuan R R, Miederer M, McDevitt M R, Scheinberg D A. Targeted actinium-225 in vivo generators for therapy of ovarian cancer. Cancer research. 2003; 63: 5084-90.

24. Razumienko E J, Chen J C, Cai Z, Chan C, Reilly R M. Dual-Receptor-Targeted Radioimmunotherapy of Human Breast Cancer Xenografts in Athymic Mice Coexpressing HER2 and EGFR Using $^{177}$Lu- or $^{111}$In-Labeled Bispecific Radioimmunoconjugates. Journal of nuclear medicine: official publication, Society of Nuclear Medicine. 2016; 57: 444-52.

25. Abbas N, Heyerdahl H, Bruland O S, Brevik E M, Dahle J. Comparing high LET 227Th- and low LET $^{177}$Lu-trastuzumab in mice with HER-2 positive SKBR-3 xenografts. Current radiopharmaceuticals. 2013; 6: 78-86.

26. Wang H Y, Lin W Y, Chen M C, Lin T, Chao C H, Hsu F N, et al. Inhibitory effects of Rhenium-188-labeled Herceptin on prostate cancer cell growth: a possible radioimmunotherapy to prostate carcinoma. Int J Radiat Biol. 2013; 89: 346-55.

27. Ray G L, Baidoo K E, Keller L M, Albert P S, Brechbiel M W, Milenic D E. PreClinical Assessment of Lu-Labeled Trastuzumab Targeting HER2 for Treatment and Management of Cancer Patients with Disseminated Intraperitoneal Disease. Pharmaceuticals (Basel). 2011; 5: 1-15.

28. Chen K T, Lee T W, Lo J M. In vivo examination of (188)Re(I)-tricarbonyl-labeled trastuzumab to target HER2-overexpressing breast cancer. Nuclear medicine and biology. 2009; 36: 355-61.

29. O'Donoghue J A, Bardies M, Wheldon T E. Relationships between tumor size and curability for uniformly targeted therapy with beta-emitting radionuclides. Journal of nuclear medicine: official publication, Society of Nuclear Medicine. 1995; 36: 1902-9.

30. Ljungberg M, Celler A, Konijnenberg M W, Eckerman K F, Dewaraja Y K, Sjogreen-Gleisner K, et al. MIRD Pamphlet No. 26: Joint EANM/MIRD Guidelines for Quantitative $^{177}$Lu SPECT Applied for Dosimetry of Radiopharmaceutical Therapy. Journal of nuclear medicine: official publication, Society of Nuclear Medicine. 2016; 57: 151-62.

31. Delker A, Fendler W P, Kratochwil C, Brunegraf A, Gosewisch A, Gildehaus F J, et al. Dosimetry for (177) Lu-DKFZ-PSMA-617: a new radiopharmaceutical for the treatment of metastatic prostate cancer. European journal of nuclear medicine and molecular imaging. 2016; 43: 42-51.

32. Marks L B, Yorke E D, Jackson A, Ten Haken R K, Constine L S, Eisbruch A, et al. Use of normal tissue complication probability models in the clinic. International journal of radiation oncology, biology, physics. 2010; 76: S10-9.

33. Pearse G, Frith J, Randall K J, Klinowska T. Urinary retention and cystitis associated with subcutaneous estradiol pellets in female nude mice. Toxicol Pathol. 2009; 37: 227-34.

34. Yang C H, Almomen A, Wee Y S, Jarboe E A, Peterson C M, Janat-Amsbury M M. An estrogen-induced endometrial hyperplasia mouse model recapitulating human disease progression and genetic aberrations. Cancer Med. 2015; 4: 1039-50.

35. Awada G, Gombos A, Aftimos P, Awada A. Emerging drugs targeting human epidermal growth factor receptor 2 (HER2) in the treatment of breast cancer. Expert Opin E merg Drugs. 2016; 21: 91-101.

36. Orcutt K D, Ackerman M E, Cieslewicz M, Quiroz E, Slusarczyk A L, Frangioni J V, et al. A modular IgG-scFv bispecific antibody topology. Protein engineering, design & selection: PEDS. 2010; 23: 221-8.
37. Carter P, Presta L, Gorman C M, Ridgway J B, Henner D, Wong W L, et al. Humanization of an anti-p185HER2 antibody for human cancer therapy. Proceedings of the National Academy of Sciences of the United States of America. 1992; 89: 4285-9.
38. Orcutt K D, Slusarczyk A L, Cieslewicz M, Ruiz-Yi B, Bhushan K R, Frangioni J V, et al. Engineering an antibody with picomolar affinity to DOTA chelates of multiple radionuclides for pretargeted radioimmunotherapy and imaging. Nuclear medicine and biology. 2011; 38: 223-33.
39. Holliday D L, Speirs V. Choosing the right cell line for breast cancer research. Breast Cancer Res. 2011; 13: 215.
40. Green D J, Orgun N N, Jones J C, Hylarides M D, Pagel J M, Hamlin D K, et al. A preclinical model of CD38-pretargeted radioimmunotherapy for plasma cell malignancies. Cancer research. 2014; 74: 1179-89.
41. Salacinski P R, McLean C, Sykes J E, Clement-Jones V V, Lowry P J. Iodination of proteins, glycoproteins, and peptides using a solid-phase oxidizing agent, 1,3,4,6-tetrachloro-3 alpha,6 alpha-diphenyl glycoluril (Iodogen). Analytical biochemistry. 1981; 117: 136-46.
42. Orcutt K D, Rhoden J J, Ruiz-Yi B, Frangioni J V, Wittrup K D. Effect of small-molecule-binding affinity on tumor uptake in vivo: a systematic study using a pretargeted bispecific antibody. Mol Cancer Ther. 2012; 11: 1365-72.

6.2 Example 2: The Influence of the Modification of Anti-HER2-C825 Tumor-Targeting Interval on Subsequent Pretargeted $^{177}$Lu-Dota-Bn Hapten Uptake in Tumor The tumor targeting and pharmacokinetics of anti-HER2-C825 (BsAb; as described in Section 6.1 above) in mice (n=4) bearing HER2(+) BT-474 tumors was evaluated using serial PET imaging (FIG. 15). The tumor uptake was (as mean±SD) 8.87±2.50, 10.16±4.08, 7.96±2.37, and 5.62±1.44 at 4, 12, 24, and 48 hours (h) post-injection (p.i.), respectively. An approximation of the tumor half-life following peak uptake at 12 h p.i. is 36 h. The blood activity was (as mean±SD) 11.3±0.79, 6.57±0.44, 3.98±0.25, and 2.26±0.23 at 4, 12, 24, and 48 h p.i., respectively. The blood half-life was determined to be 8.1 h (non-linear fit, one phase decay; R2=0.9837).

| Tumor | | T-test P value | Blood | | T-test P value |
|---|---|---|---|---|---|
| 24 h; 7.96 ± 2.37 | 4 h; 8.87 ± 2.50 | 0.3089 | 24 h; 3.98 ± 0.25 | 4 h; 11.3 ± 0.79 | 1.05E−06 |
| 24 h; 7.96 ± 2.37 | 12 h; 10.16 ± 4.08 | 0.1941 | 24 h; 3.98 ± 0.25 | 12 h; 6.57 ± 0.44 | 2.49E−05 |
| 24 h; 7.96 ± 2.37 | 48 h; 5.62 ± 1.44 | 0.0711 | 24 h; 3.98 ± 0.25 | 48 h; 2.26 ± 0.23 | 2.76E−05 |

Initially, a 24 h interval between injection of BsAb and clearing agent was utilized. According to in vitro binding assays with $^{131}$I-anti-HER2-C825 and BT-474 cells at 37° C., the internalized fraction of $^{131}$I-anti-HER2-C825 is extensive, with 89%, 46%, 41%, 14%, and 11% remaining on the surface at t=1 min, 2 h, 4 h, 19 h, and 24 h, respectively (FIG. 2).

Two separate in vivo anti-HER2-DOTA-PRIT experiments were performed to study the impact of BsAb time interval on $^{177}$Lu-DOTA-Bn uptake (24 h p.i.) in tissue (as mean±SD). See Table 30 and Table 31.

TABLE 30

| Group | Targeting Regimen | Tumor Uptake | Blood Uptake | Kidney Uptake | Tumor:Blood | Tumor:Kidney |
|---|---|---|---|---|---|---|
| 1 | Standard; 24 h BsAb, with clearing agent ("CA") | 11.62 ± 6.48 | 0.06 ± 0.02 | 0.30 ± 0.15 | 193.7 ± 66.9 | 38.4 ± 14.3 |
| 2 | 4 h BsAb with 62.5 μg CA | 11.55 ± 6.51 | 0.19 ± 0.21 | 0.39 ± 0.16 | 61.6 ± 37.9 | 29.8 ± 10.3 |
| 3 | 4 h BsAb with 125 μg CA | 4.14 ± 3.87 | 0.03 ± 0.01 | 0.27 ± 0.05 | 165.6 ± 84.2 | 15.6 ± 7.4 |
| 4 | 4 h BsAb with 0 μg CA | 38.17 ± 11.74 | 12.07 ± 1.53 | 2.59 ± 1.06 | 3.2 ± 0.5 | 14.7 ± 3.8 |

Comparison of Group 1 vs. Group 2 (Table 30): There are no significant differences between blood, tumor, or kidney uptake when comparing group 1 and group 2 (P=0.13, 0.49, and 0.23, respectively), suggesting that the clearing agent has the equivalent effect in vivo, although the blood concentration of BsAb is estimated to be ~3× higher at 4 h (11.3±0.79 and 3.98±0.25; P=1.05E-06; for 4 h and 24 h, respectively). Also, the tumor targeting did not decrease with the shortened time interval.

Comparison of Group 1 vs. Group 3 (Table 30): There are significant differences between blood or tumor uptake when comparing group 1 and group 3 (P=0.019 and 0.047, respectively), suggesting that the increased clearing agent dose was effective at decreasing blood uptake (average 0.06 to 0.03), but at the expense of decreased tumor uptake (average 11.62 to 4.14). The tumor:blood and tumor:kidney ratios were approximately equivalent for group 1 and group 3.

Group 4 (Table 30) shows that clearing agent is clearly needed to improve the tumor:blood and tumor:kidney ratios. A dose escalation between 0-62.5 μg CA is suggested to optimize anti-HER2-DOTA-PRIT with a BsAb targeting interval of 4 h.

During a second set of experiments (Table 31), the BsAb timing interval was varied, as well as the timing interval between the clearing agent and $^{177}$Lu-DOTA-Bn. All animals were sacrificed 24 hours-post-injection of $^{177}$Lu-DOTA-Bn.

TABLE 31

| Group | Targeting Regimen | Tumor Uptake | Blood Uptake | Kidney Uptake | Tumor:Blood | Tumor:Kidney |
|---|---|---|---|---|---|---|
| 1 | Standard; 24 h BsAb, with 62.5 μg/4 h CA | 20.12 ± 6.15 | 0.08 ± 0.02 | 0.72 ± 0.20 | 243.8 ± 45.0 | 27.8 ± 5.8 |
| 2 | 4 h BsAb with 62.5 μg/4 h CA | 6.65 ± 0.67 | 0.11 ± 0.06 | 0.56 ± 0.10 | 59.0 ± 16.4 | 11.9 ± 1.2 |
| 3 | 4 h BsAb with 62.5 μg/1 h CA | 14.46 ± 4.35 | 0.18 ± 0.06 | 0.67 ± 0.10 | 80.9 ± 18.3 | 21.6 ± 3.6 |
| 4 | 2 h BsAb with 62.5 μg/4 h CA | 7.77 ± 2.50 | 0.08 ± 0.04 | 0.53 ± 0.03 | 96.8 ± 27.8 | 14.7 ± 2.4 |

Comparison of Group 1 vs Group 2 (Table 31): For blood, there was no significant difference between group 1 and group 2, but there was a significant difference for tumor (P=0.002).

Comparison of Group 1 vs Group 3 (Table 31): For blood, there was a significant difference between group 1 and group 3 (P=0.01), but not for tumor (P=0.09).

Comparison of Group 1 vs Group 4 (Table 31): For blood, there was no significant difference between group 1 and group 4, but there was a significant difference for tumor (P=0.005).

These data demonstrate that the in vivo uptake in the HER2(+) tumor cells did not vary significantly between 4 and 24 hours (see Table 30). Thus, these data, in effect, describe the equilibrium tumor-blood (plasma) kinetics of the BsAb targeting tumor, and provide a rationale for same-day PRIT (i.e., administration of a BsAb, clearing agent, and radiolabeled DOTA within a single day). Further, when comparing pretargeting with a 24-hour interval to pretargeting with a 4-hour interval with the same dose of clearing agent (62.5 μg), tumor and blood uptakes are comparable (compare Group 1 and 2 in Table 30), even though the blood concentration of $^{124}$I-bispecific antibody is estimated to be much higher at 4 hours than at 24 hours.

Moreover, effective pretargeting was even demonstrated using a 2-hour time interval (see Group 4 in Table 31). The ability to do same-day pretargeting and still get high tumor-to-tissue ratios (e.g., benchmark ratio of >50:1 for tumor: blood and >10:1 for tumor: kidney) for an internalizing target by targeting with a relatively large bispecific antibody with anticipated slow tumor uptake) in vivo pharmacokinetics is surprising.

6.3 Example 3. Extension to Human Treatment

It was previously determined that the degree of uptake of radioantibody targeting the A33 antigen (an antigen fixed in membrane and non-internalizing) of human colon cancer was proportional to the amount of A33 receptor on the tumors (see, e.g., O'Donoghue J A, et al., 124I-huA33 antibody uptake is driven by A33 antigen concentration in tissues from colorectal cancer patients imaged by immuno-PET. J Nucl Med. 2011 December; 52(12):1878-85). This observation is consistent with equilibrium kinetics of antibody uptake in vivo, meaning that the law of mass action can be used to explain the quantitative feature of the antibody-antigen (in this case, huA33 antibody-GPA33 antigen) interactions in tumor and normal tissue after administration of $^{124}$I-huA33. (see O'Donoghue J A, et al. 124I-huA33 antibody uptake is driven by A33 antigen concentration in tissues from colorectal cancer patients imaged by immuno-PET. J Nucl Med. 2011 December; 52(12):1878-85). It is not obvious that this approach can be used for an internalizing antigen antibody system. Thus, HER2-C825 BsAb was used to explore the application of the law of mass action to the case of HER2 antigen on BT474 xenografts in the laboratory.

From the equilibrium law of mass action, the antibody [L] and tumor receptor [R] concentrations can be thought of as:

$$K_a=[LR]/[L]*[R];\text{solving for }[LR]/[R],\text{which is the proportion of the tumor receptor by antibody;} \quad \text{Equation 1:}$$

$$K_a*[L]=[LR]/[R]. \quad \text{Equation 2:}$$

Since (L) can be measured in the plasma and since $K_a$ for the antibody is known, one can calculate the degree of saturation [LR]/[R].

After injection of $^{124}$I-anti-HER2-C825 into mice at a final dose of 250 micrograms (m)/mouse, it was discovered that there was initial uptake into tumor and clearance from the blood (FIG. 15). At a certain time (T), the system comes into equilibrium and the tumor and the plasma decline in parallel, and at this point after injection the concentration in the plasma was 5% of the injected dose/mL, which converts to 0.060 nM/mL or 60 nM/L.

Using a $K_a$ of $10^9$ L/M×60 nM/L and Equation 2, [LR]/[R]=60 at a dose of 250 μg/mL. 250 μg is 1.2 nM of anti-HER2-C825 at 5% dose per mL of blood, which is about 60 nM/L at equilibrium. In order to scale to man, an estimate of the total volume of blood of ~5000 mLs is used below.

Without being bound by any theory, it is desired to have sufficient antibody to come near to saturation of the binding capacity (saturation) of HER2 receptor in man, because near saturation of receptor should have the greatest amount of the hapten binding capacity at the tumor site. Without being bound by any theory, this would lead to maximum $^{177}$Lu-DOTA-Bn uptake in tumor. The clearing agents are used to remove all extraneous antibody from blood and other tissues, thus leading to high therapeutic index.

Scaling to man blood volume (~5000 mL) and considering mouse blood volume is at about 2 mL, should yield that the total dose injected should be increased by about 2500 (5000 mL of blood in man/2 mL of blood in mouse), i.e., 2500*250 microgram to get comparable concentration at equilibrium in the plasma of man. This yields about 625 mg of HER2-C825 injected to achieve a [RL]/R=60 (98.4%.) If 1/2 of this or 312.5 mg where injected [RL]/R=30 (97%); at a dose of 156.5 mg, there [RL]/R=15(94%). Without being bound by any particular theory, all of these doses are close to total binding or available antibody to receptor and so there should be little change in bifunctional antibody uptake at the tumor site. These are doses that are very close to doses usually administered e.g. dose of Herceptin that has been empirically determined as being nearly optimal for therapy. (See Herceptin package insert, e.g. 8 mg/kg IV over 90 minutes as initial infusion, or 560 mg for a 70 kg adult, in gastric Ca, for example.)

This overall finding was confirmed by the experiment below. Antibody was injected and then 24 hours later, the $^{177}$Lu-DOTA-Bn was injected. In mice, the tumor was targeted most effectively with doses>100 micrograms (FIGS. 16 and 17).

[R] is not known precisely. But, the graph in FIG. 17 can provide a crude estimate of [R], "bmax", which is about 35 pmoles/gm, using $10^8$ cells/gram, calculates out to ~210770 HER2 antigen sites per cell (assuming 1 site labeled per antibody on average).

In FIG. 2, the time course of bifunctional HER2-C825 antibody uptake onto BT474 tumor is shown. By 4 hours after injection, the uptake is nearly maximal suggesting that it may not be necessary to wait longer, to begin the process of antibody clearance with clearing agent and to inject the Lu177-DOTA-Bn to target the bifunctional antibody to tumor. Without being bound by any particular theory, this timing may be optimal for clinical application because all of the regents could be easily administered in one day, and the TI's for tumor:blood and tumor:liver, as well as the absolute uptake in tumor will be maintained at levels within 80% of maximum, which is observed at 10 hours in this experiment (see Table 32). At this uptake level, cures in mice have been seen, and the TI's are protective of the blood and kidney, the 2 critical organs. In this case the internalization of antibody-antigen is likely to be helpful because the $^{177}$Lu radiometal captured by bispecific binding agent that is bound to membrane HER2, will be taken up and the radiometal will be trapped in the tumor tissue.

TABLE 32

| Group | BsAb time (h) | CA time (h) | CA dose (μg) | n | Tumor uptake | Blood uptake | Kidney uptake | Tumor:Blood | Tumor:Kidney |
|---|---|---|---|---|---|---|---|---|---|
| 1 | 24 | 4 | 62.5 | 8 | 15.87 ± 2.62 | 0.07 ± 0.01 | 0.51 ± 0.10 | 222.7 ± 44.6 | 31.0 ± 7.8 |
| 2 | 4 | 4 | 62.5 | 8 | 9.10 ± 1.77 | 0.15 ± 0.05 | 0.47 ± 0.05 | 60.6 ± 23.9 | 19.3 ± 4.3 |
| 3 | 4 | 1 | 62.5 | 4 | 14.46 ± 2.18 | 0.18 ± 0.03 | 0.67 ± 0.05 | 80.9 ± 18.3 | 21.6 ± 3.6 |
| 4 | 2 | 4 | 62.5 | 4 | 7.77 ± 1.25 | 0.08 ± 0.02 | 0.53 ± 0.01 | 96.8 ± 27.8 | 14.7 ± 2.4 |

All uptake data is presented as average ± standard error of the mean

It should also be noted that the clearing agent is essential to achieve high TIs. When HER2-expressing tumor bearing mice were given BsAb for 4 hours, then given clearing agent ("CA") vehicle only (so total BsAb circulation time was 8 hours; see Table 33), the tumor uptake of Lu177-DOTA-Bn was exceptional at ~40% ID/g, but also with high blood uptake (12.07% ID/g), suggesting that with that Tumor: Blood ratio (~3.2) would lead to poor TI.

TABLE 33

| Group | BsAb time (h) | CA time (h) | CA dose (μg) | n | Tumor uptake | Blood uptake | Kidney uptake | Tumor:Blood | Tumor:Kidney |
|---|---|---|---|---|---|---|---|---|---|
| 5 | 4 | 4 | 0 | 4 | 38.17 ± 5.87 | 12.07 ± 0.77 | 2.59 ± 0.53 | 3.2 ± 0.5 | 14.7 ± 3.4 |

Thus, based on this data of excellent localization in vivo, with good TI's, that the DOTA-PRIT method can be applied to internalizing antibodies such as anti-HER2 antibodies and by extension, PSMA-J591 (an anti-prostate specific membrane antigen antibody) and CAIX-cG250 (an anti-carbonic anhydrase IX antibody).

7. EQUIVALENTS

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A three-step pretargeted radioimmunotherapy (PRIT) method for treating a $HER2^+$ cancer in a subject in need thereof, comprising (a) administering to the subject a therapeutically effective amount of a bispecific binding agent, wherein the bispecific binding agent comprises a first molecule covalently bound to a second molecule, wherein the first molecule (a) specifically binds to HER2 and (b) comprises the $V_H$ domain sequence of SEQ ID NO: 20 and the $V_L$ domain sequence of SEQ ID NO: 19, and wherein the second molecule (a) specifically binds to a DOTA chelator and (b) comprises the $V_H$ domain sequence of SEQ ID NO: 37 and the $V_L$ domain sequence of SEQ ID NO: 38, (b) not more than 12 hours after step (a) administering to the subject a therapeutically effective amount of a clearing agent, wherein said clearing agent binds to said second molecule and functions to reduce the bispecific binding agent circulating in the blood of the subject; and (c) after step (b), administering to the subject a therapeutically effective amount of a radiotherapeutic agent, wherein the radiotherapeutic agent comprises the DOTA chelator bound to a metal radionuclide, wherein the DOTA chelator comprises 1, 4, 7, 10-traazacyclododecane-1, 4, 7, 10-tetraacetic acid (DOTA), and the metal radionuclide comprises lutetium (Lu), actinium (Ac), yttrium (Y), bismuth (Bi), holmium (Ho), terbium (Tb), lead (Pb) or europium (Eu);

wherein HER2 is internalized into a cancer cell within 24 hours, and wherein tumors in the subject are eradicated after performing steps (a)-(c).

2. The method of claim 1, wherein step (b) is carried out not more than 10 hours, not more than 8 hours, not more than 6 hours, not more than 4 hours, not more than 2 hours, 1-12 hours, 2-12 hours, 1-2 hours, 1-3 hours, 1-4 hours, 2-6 hours, 2-8 hours, 2-10 hours, 4-6 hours, 4-8 hours, 4-10 hours, 2 hours, or 4 hours, about 2 hours, about 4 hours, about 6 hours, about 8 hours, or about 10 hours after the step (a) of administering to the subject the therapeutically effective amount of the bispecific binding agent, or wherein step (c) is carried out about 1 hour, about 2 hours, about 3 hours, about 4 hours, about 5 hours, or about 6 hours, 1-2 hours, 1-3 hours, 1-4 hours, 2-6 hours, 2-8 hours, 2-10 hours, 4-6 hours, 4-8 hours, 4-10 hours, not more than 1 hour, not more than 2 hours, not more than 3 hours, not more than 4 hours, not more than 5 hours, not more than 6 hours, 1 hour, 2 hours, 3 hours, 4 hours, 5 hours, or 6 hours after step (b).

3. The method of claim 1, wherein the clearing agent comprises a DOTA molecule bound to a molecule that is cleared predominantly by the liver, fixed phagocytic system, spleen, or bone marrow from the circulating blood, or a 500 kDa amino dextran conjugated to a DOTA molecule, or approximately 100-150 molecules of a DOTA molecule per 500 kDa of aminodextran.

4. The method of claim 1, wherein the metal radionuclide is selected from the group consisting of $^{225}Ac$, $^{227}Ac$, $^{212}Bi$, $^{213}Bi$, $^{166}Ho$, $^{177}Lu$, $^{212}Pb$, $^{166}Tb$, $^{86}Y$, $^{88}Y$ and $^{90}Y$.

5. The method of claim 1, wherein the bispecific binding agent comprises an Fc domain, or is at least 100 kDa, at least 150 kDa, at least 200 kDa, at least 250 kDa, between 100 and 300 kDa, between 150 and 300 kDa, or between 200 and 250 kDa, or is at least 100 kDa and step (b) is carried out not more than 4 hours after step (a).

6. The method of claim 1, wherein the first molecule that specifically binds to HER2 comprises an antibody or an antigen-binding fragment thereof, or wherein the second molecule that specifically binds to the DOTA chelator comprises an antibody or an antigen-binding fragment thereof, or wherein the second molecule that specifically binds to the DOTA chelator comprises a single chain variable fragment (scFv), or wherein the first molecule is covalently bound to the second molecule via a linker.

7. The method of claim 1, wherein the bispecific binding agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally, or wherein the clearing agent is administered to the subject intravenously, or wherein the radiotherapeutic agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally, or wherein the method further comprises administering to the subject an agent that increases cellular HER2 expression.

8. The method of claim 1, wherein the therapeutically effective amount of the clearing agent is an amount that yields a 10:1 molar ratio of the therapeutically effective amount of bispecific binding agent administered to the subject to the therapeutically effective amount of clearing agent administered to the subject, wherein the subject is a human, or is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after step (b), or wherein the second therapeutically effective amount of the radiotherapeutic agent is between 25 mCi and 250 mCi, between 50 mCi and 200 mCi, between 75 mCi and 175 mCi, or between 100 mCi and 150 mCi, wherein the subject is a human.

9. The method of claim 1, which comprises:

(d) not more than 1 day, not more than 2 days, not more than 3 days, not more than 4 days, not more than 5 days, not more than 6 days, or not more than 1 week after step (c), administering to the subject a second therapeutically effective amount of the bispecific binding agent;

(e) after step (d), administering to the subject a second therapeutically effective amount of the clearing agent, wherein step (e) is carried out not more than 12 hours after step (d); and (f) after step (e), administering to the subject a second therapeutically effective amount of the radiotherapeutic agent.

10. The method of claim 9, wherein the second therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg, or wherein the second therapeutically effective amount of the clearing agent is an amount that yields a 10:1 molar ratio of the therapeutically effective amount of bispecific binding agent administered to the subject to the therapeutically effective amount of clearing agent administered to the subject, or wherein the second therapeutically effective amount of the radiotherapeutic agent is between 25 mCi and 250 mCi, between 50 mCi and 200 mCi, between 75 mCi and 175 mCi, or between 100 mCi and 150 mCi, or wherein the second therapeutically effective amount of the bispecific binding agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally, or wherein the therapeutically effective amount of the clearing agent is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after the step (b) of administering to the subject the therapeutically effective amount of the clearing agent, or wherein the second therapeutically effective amount of the clearing agent is administered to the subject intravenously, or wherein the second therapeutically effective amount of the radiotherapeutic agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally.

11. The method of claim 9, which comprises:

(g) not more than 1 day, not more than 2 days, not more than 3 days, not more than 4 days, not more than 5 days, not more than 6 days, or not more than 1 week after step (f), administering to the subject a third therapeutically effective amount of the bispecific binding agent;

(h) after step (g), administering to the subject a third therapeutically effective amount of the clearing agent, wherein step (h) is carried out not more than 12 hours after step (g); and (i) after step (h), administering to the subject a third therapeutically effective amount of the radiotherapeutic agent.

12. The method of claim 11, wherein the third therapeutically effective amount of the bispecific binding agent is 100 mg to 700 mg, 200 mg to 600 mg, 200 mg to 500 mg, 300 mg to 400 mg, about 300 mg, about 450 mg, about 500 mg, about 600 mg or about 625 mg, or wherein the third therapeutically effective amount of the clearing agent is an amount that yields a 10:1 molar ratio of the therapeutically effective amount of bispecific binding agent administered to the subject to the therapeutically effective amount of clearing agent administered to the subject, or wherein the third therapeutically effective amount of the clearing agent is an amount that yields at least 90%, at least 91%, at least 92%, at least 93%, at least 94%, at least 95%, at least 96%, at least 97%, at least 98%, or at least 90% reduction in serum concentration of bispecific binding agent 1 hour, 2 hours, 3 hours, or 4 hours after administering to the subject the therapeutically effective amount of the clearing agent, or wherein the third therapeutically effective amount of the radiotherapeutic agent is between 25 mCi and 250 mCi, between 50 mCi and 200 mCi, between 75 mCi and 175 mCi, or between 100 mCi and 150 mCi, or wherein the third therapeutically effective amount of the bispecific binding agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally, or wherein the third therapeutically effective amount of the clearing agent is administered to the subject intravenously, or wherein the third therapeutically effective amount of the radiotherapeutic agent is administered to the subject intravenously, subcutaneously, intramuscularly, parenterally, transdermally, transmucosally, intraperitoneally, intra thoracic, or into any other body compartment, such as intrathecally, intraventricularly, or intraparenchymally.

* * * * *

SEQUENCE LISTING

```
<160> NUMBER OF SEQ ID NOS: 56

<210> SEQ ID NO 1
<211> LENGTH: 4664
<212> TYPE: DNA
<213> ORGANISM: Homo sapiens
<220> FEATURE:
<223> OTHER INFORMATION: Human HER2, NM_004448.3

<400> SEQUENCE: 1

gcttgctccc aatcacagga gaaggaggag gtggaggagg agggctgctt gaggaagtat      60

aagaatgaag ttgtgaagct gagattcccc tccattggga ccggagaaac caggggagcc     120

ccccgggcag ccgcgcgccc cttcccacgg ggccctttac tgcgccgcgc gcccggcccc     180

cacccctcgc agcaccccgc gccccgcgcc ctcccagccg ggtccagccg gagccatggg     240

gccggagccg cagtgagcac catggagctg gcggccttgt gccgctgggg gctcctcctc     300

gccctcttgc cccccggagc cgcgagcacc caagtgtgca ccggcacaga catgaagctg     360

cggctccctg ccagtcccga gacccacctg gacatgctcc gccacctcta ccagggctgc     420

caggtggtgc agggaaacct ggaactcacc tacctgccca ccaatgccag cctgtccttc     480

ctgcaggata tccaggaggt gcagggctac gtgctcatcg ctcacaacca agtgaggcag     540

gtcccactgc agaggctgcg gattgtgcga ggcacccagc tctttgagga caactatgcc     600

ctggccgtgc tagacaatgg agacccgctg aacaatacca cccctgtcac aggggcctcc     660

ccaggaggcc tgcgggagct gcagcttcga agcctcacag agatcttgaa aggaggggtc     720

ttgatccagc ggaaccccca gctctgctac caggacacga ttttgtggaa ggacatcttc     780

cacaagaaca accagctggc tctcacactg atagacacca accgctctcg ggcctgccac     840

ccctgttctc cgatgtgtaa gggctcccgc tgctggggag agagttctga ggattgtcag     900

agcctgacgc gcactgtctg tgccggtggc tgtgcccgct gcaaggggcc actgcccact     960

gactgctgcc atgagcagtg tgctgccggc tgcacgggcc ccaagcactc tgactgcctg    1020

gcctgcctcc acttcaacca cagtggcatc tgtgagctgc actgcccagc cctggtcacc    1080

tacaacacag acacgtttga gtccatgccc aatcccgagg gccggtatac attcggcgcc    1140

agctgtgtga ctgcctgtcc ctacaactac ctttctacgg acgtgggatc ctgcaccctc    1200

gtctgccccc tgcacaacca agaggtgaca gcagaggatg gaacacagcg gtgtgagaag    1260

tgcagcaagc cctgtgcccg agtgtgctat ggtctgggca tggagcactt gcgagaggtg    1320

agggcagtta ccagtgccaa tatccaggag tttgctggct gcaagaagat ctttgggagc    1380

ctggcatttc tgccggagag ctttgatggg gacccagcct ccaacactgc cccgctccag    1440

ccagagcagc tccaagtgtt tgagactctg gaagagatca caggttacct atacatctca    1500

gcatggccgg acagcctgcc tgacctcagc gtcttccaga acctgcaagt aatccgggga    1560

cgaattctgc acaatggcgc ctactcgctg accctgcaag ggctgggcat cagctggctg    1620

gggctgcgct cactgaggga actgggcagt ggactggccc tcatccacca taacacccac    1680
```

-continued

```
ctctgcttcg tgcacacggt gccctgggac cagctctttc ggaacccgca ccaagctctg   1740
ctccacactg ccaaccggcc agaggacgag tgtgtgggcg agggcctggc ctgccaccag   1800
ctgtgcgccc gagggcactg ctggggtcca gggcccaccc agtgtgtcaa ctgcagccag   1860
ttccttcggg gccaggagtg cgtggaggaa tgccgagtac tgcaggggct ccccagggag   1920
tatgtgaatg ccaggcactg tttgccgtgc caccctgagt gtcagcccca gaatggctca   1980
gtgacctgtt ttggaccgga ggctgaccag tgtgtggcct gtgcccacta taaggaccct   2040
cccttctgcg tggcccgctg ccccagcggt gtgaaacctg acctctccta catgcccatc   2100
tggaagtttc cagatgagga gggcgcatgc cagccttgcc ccatcaactg cacccactcc   2160
tgtgtggacc tggatgacaa gggctgcccc gccgagcaga gagccagccc tctgacgtcc   2220
atcatctctg cggtggttgg cattctgctg gtcgtggtct tgggggtggt ctttgggatc   2280
ctcatcaagc gacggcagca gaagatccgg aagtacacga tgcggagact gctgcaggaa   2340
acggagctgg tggagccgct gacacctagc ggagcgatgc ccaaccaggc gcagatgcgg   2400
atcctgaaag agacggagct gaggaaggtg aaggtgcttg gatctggcgc ttttggcaca   2460
gtctacaagg gcatctggat ccctgatggg gagaatgtga aaattccagt ggccatcaaa   2520
gtgttgaggg aaaacacatc ccccaaagcc aacaaagaaa tcttagacga agcatacgtg   2580
atggctggtg tgggctcccc atatgtctcc cgccttctgg gcatctgcct gacatccacg   2640
gtgcagctgg tgacacagct tatgccctat ggctgcctct tagaccatgt ccgggaaaac   2700
cgcggacgcc tgggctccca ggacctgctg aactggtgta tgcagattgc caaggggatg   2760
agctacctgg aggatgtgcg gctcgtacac agggacttgg ccgctcggaa cgtgctggtc   2820
aagagtccca accatgtcaa aattacagac ttcgggctgg ctcggctgct ggacattgac   2880
gagacagagt accatgcaga tggggggcaag gtgcccatca agtggatggc gctggagtcc   2940
attctccgcc ggcggttcac ccaccagagt gatgtgtgga gttatggtgt gactgtgtgg   3000
gagctgatga cttttggggc caaaccttac gatgggatcc cagcccggga gatccctgac   3060
ctgctggaaa agggggagcg gctgccccag cccccccatct gcaccattga tgtctacatg   3120
atcatggtca aatgttggat gattgactct gaatgtcggc caagattccg ggagttggtg   3180
tctgaattct cccgcatggc cagggacccc cagcgctttg tggtcatcca gaatgaggac   3240
ttgggcccag ccagtccctt ggacagcacc ttctaccgct cactgctgga ggacgatgac   3300
atgggggacc tggtggatgc tgaggagtat ctggtacccc agcagggctt cttctgtcca   3360
gaccctgccc cgggcgctgg gggcatggtc caccacaggc accgcagctc atctaccagg   3420
agtggcggtg gggacctgac actagggctg gagccctctg aagaggaggc ccccaggtct   3480
ccactggcac cctccgaagg ggctggctcc gatgtatttg atggtgacct gggaatgggg   3540
gcagccaagg ggctgcaaag cctcccccaca catgacccca gccctctaca gcggtacagt   3600
gaggacccca cagtacccct gccctctgag actgatggct acgttgcccc cctgacctgc   3660
agcccccagc ctgaatatgt gaaccagcca gatgttcggc cccagccccc ttcgccccga   3720
gagggccctc tgcctgctgc ccgacctgct ggtgccactc tggaaaggcc caagactctc   3780
tccccaggga agaatggggt cgtcaaagac gtttttgcct ttgggggtgc cgtggagaac   3840
cccgagtact tgacacccca gggaggagct gcccctcagc cccaccctcc tcctgccttc   3900
agcccagcct tcgacaacct ctattactgg gaccaggacc caccagagcg gggggctcca   3960
cccagcacct tcaaagggac acctacggca gagaacccag agtacctggg tctggacgtg   4020
```

-continued ccagtgtgaa ccagaaggcc aagtccgcag aagccctgat gtgtcctcag ggagcaggga 4080
aggcctgact tctgctggca tcaagaggtg ggagggccct ccgaccactt ccaggggaac 4140
ctgccatgcc aggaacctgt cctaaggaac cttccttcct gcttgagttc ccagatggct 4200
ggaaggggtc cagcctcgtt ggaagaggaa cagcactggg gagtctttgt ggattctgag 4260
gccctgccca atgagactct agggtccagt ggatgccaca gcccagcttg gccctttcct 4320
tccagatcct gggtactgaa agccttaggg aagctggcct gagaggggaa gcggccctaa 4380
gggagtgtct aagaacaaaa gcgacccatt cagagactgt ccctgaaacc tagtactgcc 4440
ccccatgagg aaggaacagc aatggtgtca gtatccaggc tttgtacaga gtgcttttct 4500
gtttagtttt tactttttttt gttttgtttt tttaaagatg aaataaagac ccagggggag 4560
aatgggtgtt gtatggggag gcaagtgtgg ggggtccttc tccacaccca ctttgtccat 4620
ttgcaaatat attttggaaa acagctaaaa aaaaaaaaaa aaaa 4664

<210> SEQ ID NO 2
<211> LENGTH: 1255
<212> TYPE: PRT
<213> ORGANISM: Homo sapiens
<220> FEATURE:
<223> OTHER INFORMATION: Human HER2, NP_004439.2

<400> SEQUENCE: 2

Met Glu Leu Ala Ala Leu Cys Arg Trp Gly Leu Leu Leu Ala Leu Leu
1 5 10 15

Pro Pro Gly Ala Ala Ser Thr Gln Val Cys Thr Gly Thr Asp Met Lys
20 25 30

Leu Arg Leu Pro Ala Ser Pro Glu Thr His Leu Asp Met Leu Arg His
35 40 45

Leu Tyr Gln Gly Cys Gln Val Val Gln Gly Asn Leu Glu Leu Thr Tyr
50 55 60

Leu Pro Thr Asn Ala Ser Leu Ser Phe Leu Gln Asp Ile Gln Glu Val
65 70 75 80

Gln Gly Tyr Val Leu Ile Ala His Asn Gln Val Arg Gln Val Pro Leu
85 90 95

Gln Arg Leu Arg Ile Val Arg Gly Thr Gln Leu Phe Glu Asp Asn Tyr
100 105 110

Ala Leu Ala Val Leu Asp Asn Gly Asp Pro Leu Asn Asn Thr Thr Pro
115 120 125

Val Thr Gly Ala Ser Pro Gly Gly Leu Arg Glu Leu Gln Leu Arg Ser
130 135 140

Leu Thr Glu Ile Leu Lys Gly Gly Val Leu Ile Gln Arg Asn Pro Gln
145 150 155 160

Leu Cys Tyr Gln Asp Thr Ile Leu Trp Lys Asp Ile Phe His Lys Asn
165 170 175

Asn Gln Leu Ala Leu Thr Leu Ile Asp Thr Asn Arg Ser Arg Ala Cys
180 185 190

His Pro Cys Ser Pro Met Cys Lys Gly Ser Arg Cys Trp Gly Glu Ser
195 200 205

Ser Glu Asp Cys Gln Ser Leu Thr Arg Thr Val Cys Ala Gly Gly Cys
210 215 220

Ala Arg Cys Lys Gly Pro Leu Pro Thr Asp Cys Cys His Glu Gln Cys
225 230 235 240

Ala Ala Gly Cys Thr Gly Pro Lys His Ser Asp Cys Leu Ala Cys Leu
245 250 255

-continued

```
His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670
```

```
Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Ser Gly  Gly Gly Asp Leu Thr  Leu Gly Leu Glu Pro  Ser Glu Glu
    1055                1060                1065

Glu Ala  Pro Arg Ser Pro Leu  Ala Pro Ser Glu Gly  Ala Gly Ser
    1070                1075                1080

Asp Val  Phe Asp Gly Asp Leu  Gly Met Gly Ala Ala  Lys Gly Leu
```

```
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185

Gly Ala  Val Glu Asn Pro Glu  Tyr Leu Thr Pro Gln  Gly Gly Ala
    1190                1195                1200

Ala Pro  Gln Pro His Pro Pro  Pro Ala Phe Ser Pro  Ala Phe Asp
    1205                1210                1215

Asn Leu  Tyr Tyr Trp Asp Gln  Asp Pro Pro Glu Arg  Gly Ala Pro
    1220                1225                1230

Pro Ser  Thr Phe Lys Gly Thr  Pro Thr Ala Glu Asn  Pro Glu Tyr
    1235                1240                1245

Leu Gly  Leu Asp Val Pro Val
    1250                1255
```

<210> SEQ ID NO 3
<211> LENGTH: 3780
<212> TYPE: DNA
<213> ORGANISM: Canis familiaris
<220> FEATURE:
<223> OTHER INFORMATION: Canine HER2, NM_001003217.1

<400> SEQUENCE: 3

```
atggagctgg cggcctggtg ccgctggggg ctccttctcg ccctcctgcc ctccggagcc     60

gcgggcaccc aagtgtgcac cggcacagac atgaagctcc ggctcccggc cagtcccgag    120

acccacctgg atatgctccg ccacctgtac cagggctgtc aagtggtaca ggggaacctg    180

gagctcactt acctgcctgc caatgccagc ctgtccttcc tgcaggatat ccaggaggtg    240

cagggctatg tgctcattgc tcacagccaa gtgaggcaga tcccactgca gaggctacga    300

attgtgcgag gcacccagct ctttgaggac aactacgccc tggccgtgct ggacaatgga    360

gacccgctgg agggtggcat ccctgcacca ggggcggccc aaggagggct gcgggagctg    420

cagcttcgaa gcctcacaga gatcctgaag ggaggggtct tgattcagcg gagcccgcag    480

ctctgccacc aggacacgat tttatggaag gacgtcttcc ataagaacaa ccagctggcc    540

ctcacgctga tagacaccaa ccgcttttcg gcctgcccgc cctgttctcc agcttgtaaa    600

gacgcccact gctgggggc cagctccggg gactgtcaga gcttgacgcg gactgtctgt    660

gccgggggct gtgcccgctg caagggccca caacccaccg actgctgcca cgagcagtgt    720

gctgctggct gcacgggccc caagcactct gactgcctgg cctgccttca cttcaaccac    780

agtggcatct gtgagctgca ctgcccagcc ctggtcacct acaacacgga caccttcgaa    840

tccatgccca accctgaggg ccgatatacc ttcggggcca gctgtgtgac ctcctgtccc    900

tacaactacc tgtctacgga tgtgggatcc tgcaccctgg tctgtcccct gaacaaccaa    960

gaggtgacgg ctgaggatgg gacacagcgg tgcgagaaat gcagcaagcc ctgtgcccga   1020
```

-continued

```
gtgtgctacg gtctgggcat ggagcacctg cgagaggtga gagcggtcac cagtgcgaac   1080
atccaggagt ttgccggctg caagaagatc tttggaagcc tggcattttt gccagagagc   1140
tttgatgggg acccagcctc caacactgcc cccctacagc ctgagcagct cagagtgttt   1200
gaggctctgg aggagatcac aggttacctg tacatctcag cgtggccaga cagcctgcct   1260
aacctcagtg tcttccagaa cctgcgagta atccggggac gagttctgca tgatggtgcc   1320
tactcgctga ccctgcaagg gctgggcatc agctggctgg ggctgcgctc gctgcgggaa   1380
ctgggcagtg ggctggccct catccaccgc aacgcccgcc tttgcttcgt gcacacggtg   1440
ccctgggacc agctcttccg gaacccccac caggccctgc tccatagtgc caaccggcca   1500
gaggaggagt gcgtgggcga gggcctggcc tgctacccct gtgcccatgg gcactgctgg   1560
ggtccagggc ccacccagtg cgtcaactgc agccaattcc tccggggcca ggagtgcgtg   1620
gaggaatgcc gagtactgca ggggctgccc cgagagtatg tgaaggacag gtactgtcta   1680
ccgtgccact cagagtgtca gccccagaat ggctcagtga cctgtttcgg atcggaggct   1740
gaccagtgtg tggcctgcgc ccactacaag gaccctccct tctgtgtggc tcgctgcccc   1800
agtggtgtga aacctgacct gtccttcatg cccatctgga agttcgcaga tgaggagggc   1860
acttgccagc cgtgccccat caactgcacc cactcctgtg cggacctgga cgagaagggc   1920
tgtcccgccg agcagagagc cagccctgtg acatccatca ttgccgctgt ggtgggcatt   1980
ctgctggctg tggtcgtggg gctggtcctc ggcatcctga tcaagcgaag gcggcagaag   2040
atccggaagt acactatgcg gaggctgctg caggaaaccg agctggtgga gccgctgacg   2100
cctagtggag cgatgcccaa ccaggctcag atgcggatcc tgaaagagac agagctgagg   2160
aaggtgaagg tgcttggatc cggagctttt ggcacagtct acaagggcat ctggatccct   2220
gatggggaaa atgtgaaaat cccagtggcc atcaaagtgt tgagggaaaa cacatctccc   2280
aaagccaaca aagaaatctt ggacgaagca tatgtgatgg ctggagtggg ctccccgtat   2340
gtgtcccgcc tcctgggcat ctgcctgaca tccacggtgc agctggtgac acagcttatg   2400
ccctacggct gcctcttaga ccatgtccga gaacaccgtg ggcgcctggg ctcccaggac   2460
ttgctgaact ggtgtgtgca gattgccaag ggatgagct acttggagga tgtccggctg   2520
gtgcacaggg acctggctgc ccggaatgtg ctggtcaaga gtcccaacca tgtcaagatt   2580
acagatttcg ggctggctcg gttgctggac atcgacgaga cagagtacca tgcggatggg   2640
ggcaaggtgc ccatcaagtg gatggcgctg gagtccattc ctccgcggcg gttcacccac   2700
cagagtgatg tgtggagcta tggtgtgact gtgtgggaac tgatgacttt tggggccaaa   2760
ccttatgatg ggatcccagc ccgggagatc cctgacctgc tggagaaggg ggaacggctg   2820
ccccagcccc ccatctgcac cattgatgtc tacatgatca tggtcaagtg ctggatgata   2880
gactctgaat gccgaccccg gttccgggag ttggtggccg aattctcacg tatggccagg   2940
gacccccagc gctttgtggt cattcagaat gaagacttgg gccccgccag cccccttggac   3000
agcaccttct accgttcact actggaagat gatgacatgg gggacctggt ggatgctgag   3060
gagtacctgg taccccagca gggtttcttc tgcccagaac ctaccccagg ggctgggggc   3120
actgcccacc gacggcaccg cagctcatcc accaggaatg gcggtggtga gctgactcta   3180
ggactggagc cctccgagga ggagcccccc aagtctccac tggcaccctc agagggcgct   3240
ggctctgacg tgtttgatgg tgacttggga atgggggcag ccaaggggct gcagagcctt   3300
ccctcacagg accccagccc tctccagcgg tacagtgagg accctacggt acccttgccc   3360
cctgagactg atggtaaggt tgcccccctg acctgcagcc cccagcctga atatgtgaac   3420
```

-continued

```
cagccagaag tttggccgca gccccccctt gccctagaag gccctttgcc tccttcccga   3480

ccggctggtg ccactctgga aaggcccaag actctgtccc ccaagactct ctcccctggc   3540

aagaatgggg ttgtcaaaga cgtttttgcc tttgggagtg ctgtggagaa tccggagtac   3600

ctggcacccc ggggcagagc tgcccctcag ccccaccctc ctccagcctt cagcccagcc   3660

tttgacaacc tgtattactg ggaccaggat ccatcagagc ggggctctcc acccagcacc   3720

tttgaaggga cccctacagc agagaacccg gagtacctgg ggctggacgt gccagtgtga   3780


<210> SEQ ID NO 4
<211> LENGTH: 1259
<212> TYPE: PRT
<213> ORGANISM: Canis familiaris
<220> FEATURE:
<223> OTHER INFORMATION: Canine HER2, NP_001003217.1

<400> SEQUENCE: 4

Met Glu Leu Ala Ala Trp Cys Arg Trp Gly Leu Leu Leu Ala Leu Leu
1               5                   10                  15

Pro Ser Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Ala Asn Ala Ser Leu Ser Phe Leu Gln Asp Ile Gln Glu Val
65                  70                  75                  80

Gln Gly Tyr Val Leu Ile Ala His Ser Gln Val Arg Gln Ile Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Glu Gly Gly Ile Pro
        115                 120                 125

Ala Pro Gly Ala Ala Gln Gly Gly Leu Arg Glu Leu Gln Leu Arg Ser
    130                 135                 140

Leu Thr Glu Ile Leu Lys Gly Gly Val Leu Ile Gln Arg Ser Pro Gln
145                 150                 155                 160

Leu Cys His Gln Asp Thr Ile Leu Trp Lys Asp Val Phe His Lys Asn
                165                 170                 175

Asn Gln Leu Ala Leu Thr Leu Ile Asp Thr Asn Arg Phe Ser Ala Cys
            180                 185                 190

Pro Pro Cys Ser Pro Ala Cys Lys Asp Ala His Cys Trp Gly Ala Ser
        195                 200                 205

Ser Gly Asp Cys Gln Ser Leu Thr Arg Thr Val Cys Ala Gly Gly Cys
    210                 215                 220

Ala Arg Cys Lys Gly Pro Gln Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ser Cys Pro Tyr Asn Tyr Leu
    290                 295                 300
```

-continued

```
Ser Thr Asp Val Gly Ser Cys Thr Leu Val Cys Pro Leu Asn Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Arg Val Phe
385                 390                 395                 400

Glu Ala Leu Glu Glu Ile Thr Gly Tyr Leu Tyr Ile Ser Ala Trp Pro
                405                 410                 415

Asp Ser Leu Pro Asn Leu Ser Val Phe Gln Asn Leu Arg Val Ile Arg
            420                 425                 430

Gly Arg Val Leu His Asp Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His Arg Asn Ala Arg Leu Cys Phe Val His Thr Val
465                 470                 475                 480

Pro Trp Asp Gln Leu Phe Arg Asn Pro His Gln Ala Leu Leu His Ser
                485                 490                 495

Ala Asn Arg Pro Glu Glu Glu Cys Val Gly Glu Gly Leu Ala Cys Tyr
            500                 505                 510

Pro Cys Ala His Gly His Cys Trp Gly Pro Gly Pro Thr Gln Cys Val
        515                 520                 525

Asn Cys Ser Gln Phe Leu Arg Gly Gln Glu Cys Val Glu Glu Cys Arg
    530                 535                 540

Val Leu Gln Gly Leu Pro Arg Glu Tyr Val Lys Asp Arg Tyr Cys Leu
545                 550                 555                 560

Pro Cys His Ser Glu Cys Gln Pro Gln Asn Gly Ser Val Thr Cys Phe
                565                 570                 575

Gly Ser Glu Ala Asp Gln Cys Val Ala Cys Ala His Tyr Lys Asp Pro
            580                 585                 590

Pro Phe Cys Val Ala Arg Cys Pro Ser Gly Val Lys Pro Asp Leu Ser
        595                 600                 605

Phe Met Pro Ile Trp Lys Phe Ala Asp Glu Glu Gly Thr Cys Gln Pro
    610                 615                 620

Cys Pro Ile Asn Cys Thr His Ser Cys Ala Asp Leu Asp Glu Lys Gly
625                 630                 635                 640

Cys Pro Ala Glu Gln Arg Ala Ser Pro Val Thr Ser Ile Ile Ala Ala
                645                 650                 655

Val Val Gly Ile Leu Leu Ala Val Val Val Gly Leu Val Leu Gly Ile
            660                 665                 670

Leu Ile Lys Arg Arg Arg Gln Lys Ile Arg Lys Tyr Thr Met Arg Arg
        675                 680                 685

Leu Leu Gln Glu Thr Glu Leu Val Glu Pro Leu Thr Pro Ser Gly Ala
    690                 695                 700

Met Pro Asn Gln Ala Gln Met Arg Ile Leu Lys Glu Thr Glu Leu Arg
705                 710                 715                 720
```

-continued

```
Lys Val Lys Val Leu Gly Ser Gly Ala Phe Gly Thr Val Tyr Lys Gly
                725                 730                 735

Ile Trp Ile Pro Asp Gly Glu Asn Val Lys Ile Pro Val Ala Ile Lys
            740                 745                 750

Val Leu Arg Glu Asn Thr Ser Pro Lys Ala Asn Lys Glu Ile Leu Asp
        755                 760                 765

Glu Ala Tyr Val Met Ala Gly Val Gly Ser Pro Tyr Val Ser Arg Leu
    770                 775                 780

Leu Gly Ile Cys Leu Thr Ser Thr Val Gln Leu Val Thr Gln Leu Met
785                 790                 795                 800

Pro Tyr Gly Cys Leu Leu Asp His Val Arg Glu His Arg Gly Arg Leu
                805                 810                 815

Gly Ser Gln Asp Leu Leu Asn Trp Cys Val Gln Ile Ala Lys Gly Met
            820                 825                 830

Ser Tyr Leu Glu Asp Val Arg Leu Val His Arg Asp Leu Ala Ala Arg
        835                 840                 845

Asn Val Leu Val Lys Ser Pro Asn His Val Lys Ile Thr Asp Phe Gly
    850                 855                 860

Leu Ala Arg Leu Leu Asp Ile Asp Glu Thr Glu Tyr His Ala Asp Gly
865                 870                 875                 880

Gly Lys Val Pro Ile Lys Trp Met Ala Leu Glu Ser Ile Pro Pro Arg
                885                 890                 895

Arg Phe Thr His Gln Ser Asp Val Trp Ser Tyr Gly Val Thr Val Trp
            900                 905                 910

Glu Leu Met Thr Phe Gly Ala Lys Pro Tyr Asp Gly Ile Pro Ala Arg
        915                 920                 925

Glu Ile Pro Asp Leu Leu Glu Lys Gly Glu Arg Leu Pro Gln Pro Pro
    930                 935                 940

Ile Cys Thr Ile Asp Val Tyr Met Ile Met Val Lys Cys Trp Met Ile
945                 950                 955                 960

Asp Ser Glu Cys Arg Pro Arg Phe Arg Glu Leu Val Ala Glu Phe Ser
                965                 970                 975

Arg Met Ala Arg Asp Pro Gln Arg Phe Val Val Ile Gln Asn Glu Asp
            980                 985                 990

Leu Gly Pro Ala Ser Pro Leu Asp  Ser Thr Phe Tyr Arg  Ser Leu Leu
        995                 1000                1005

Glu Asp  Asp Asp Met Gly Asp  Leu Val Asp Ala Glu  Glu Tyr Leu
    1010                1015                1020

Val Pro  Gln Gln Gly Phe Phe  Cys Pro Glu Pro Thr  Pro Gly Ala
    1025                1030                1035

Gly Gly  Thr Ala His Arg Arg  His Arg Ser Ser Ser  Thr Arg Asn
    1040                1045                1050

Gly Gly  Gly Glu Leu Thr Leu  Gly Leu Glu Pro Ser  Glu Glu Glu
    1055                1060                1065

Pro Pro  Lys Ser Pro Leu Ala  Pro Ser Glu Gly Ala  Gly Ser Asp
    1070                1075                1080

Val Phe  Asp Gly Asp Leu Gly  Met Gly Ala Ala Lys  Gly Leu Gln
    1085                1090                1095

Ser Leu  Pro Ser Gln Asp Pro  Ser Pro Leu Gln Arg  Tyr Ser Glu
    1100                1105                1110

Asp Pro  Thr Val Pro Leu Pro  Pro Glu Thr Asp Gly  Lys Val Ala
    1115                1120                1125

Pro Leu  Thr Cys Ser Pro Gln  Pro Glu Tyr Val Asn  Gln Pro Glu
```

```
    1130                1135                1140

Val Trp  Pro Gln Pro Pro Leu  Ala Leu Glu Gly Pro  Leu Pro Pro
    1145                1150                1155

Ser Arg  Pro Ala Gly Ala Thr  Leu Glu Arg Pro Lys  Thr Leu Ser
    1160                1165                1170

Pro Lys  Thr Leu Ser Pro Gly  Lys Asn Gly Val Val  Lys Asp Val
    1175                1180                1185

Phe Ala  Phe Gly Ser Ala Val  Glu Asn Pro Glu Tyr  Leu Ala Pro
    1190                1195                1200

Arg Gly  Arg Ala Ala Pro Gln  Pro His Pro Pro Pro  Ala Phe Ser
    1205                1210                1215

Pro Ala  Phe Asp Asn Leu Tyr  Tyr Trp Asp Gln Asp  Pro Ser Glu
    1220                1225                1230

Arg Gly  Ser Pro Pro Ser Thr  Phe Glu Gly Thr Pro  Thr Ala Glu
    1235                1240                1245

Asn Pro  Glu Tyr Leu Gly Leu  Asp Val Pro Val
    1250                1255


<210> SEQ ID NO 5
<211> LENGTH: 460
<212> TYPE: PRT
<213> ORGANISM: Artificial Sequence
<220> FEATURE:
<223> OTHER INFORMATION: Trastuzumab LC-(G4S)2AS linker- C825 VH-G4S
      linker-C825 VL

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220
```

```
Ala Ser His Val Lys Leu Gln Glu Ser Gly Pro Gly Leu Val Gln Pro
225                 230                 235                 240

Ser Gln Ser Leu Ser Leu Thr Cys Thr Val Ser Gly Phe Ser Leu Thr
                245                 250                 255

Asp Tyr Gly Val His Trp Val Arg Gln Ser Pro Gly Lys Gly Leu Glu
            260                 265                 270

Trp Leu Gly Val Ile Trp Ser Gly Gly Gly Thr Ala Tyr Asn Thr Ala
        275                 280                 285

Leu Ile Ser Arg Leu Asn Ile Tyr Arg Asp Asn Ser Lys Asn Gln Val
    290                 295                 300

Phe Leu Glu Met Asn Ser Leu Gln Ala Glu Asp Thr Ala Met Tyr Tyr
305                 310                 315                 320

Cys Ala Arg Arg Gly Ser Tyr Pro Tyr Asn Tyr Phe Asp Ala Trp Gly
                325                 330                 335

Cys Gly Thr Thr Val Thr Val Ser Ser Gly Gly Gly Gly Ser Gln Ala
            340                 345                 350

Val Val Ile Gln Glu Ser Ala Leu Thr Thr Pro Pro Gly Glu Thr Val
        355                 360                 365

Thr Leu Thr Cys Gly Ser Ser Thr Gly Ala Val Thr Ala Ser Asn Tyr
    370                 375                 380

Ala Asn Trp Val Gln Glu Lys Pro Asp His Cys Phe Thr Gly Leu Ile
385                 390                 395                 400

Gly Gly His Asn Asn Arg Pro Pro Gly Val Pro Ala Arg Phe Ser Gly
                405                 410                 415

Ser Leu Ile Gly Asp Lys Ala Ala Leu Thr Ile Ala Gly Thr Gln Thr
            420                 425                 430

Glu Asp Glu Ala Ile Tyr Phe Cys Ala Leu Trp Tyr Ser Asp His Trp
        435                 440                 445

Val Ile Gly Gly Gly Thr Arg Leu Thr Val Leu Gly
    450                 455                 460


<210> SEQ ID NO 6
<211> LENGTH: 465
<212> TYPE: PRT
<213> ORGANISM: Artificial Sequence
<220> FEATURE:
<223> OTHER INFORMATION: Trastuzumab LC-(G4S)2AS linker- C825 VH-(G4S)2
      linker-C825 VL

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Ala Ser His Val Lys Leu Gln Glu Ser Gly Pro Gly Leu Val Gln Pro
225                 230                 235                 240

Ser Gln Ser Leu Ser Leu Thr Cys Thr Val Ser Gly Phe Ser Leu Thr
                245                 250                 255

Asp Tyr Gly Val His Trp Val Arg Gln Ser Pro Gly Lys Gly Leu Glu
            260                 265                 270

Trp Leu Gly Val Ile Trp Ser Gly Gly Gly Thr Ala Tyr Asn Thr Ala
        275                 280                 285

Leu Ile Ser Arg Leu Asn Ile Tyr Arg Asp Asn Ser Lys Asn Gln Val
    290                 295                 300

Phe Leu Glu Met Asn Ser Leu Gln Ala Glu Asp Thr Ala Met Tyr Tyr
305                 310                 315                 320

Cys Ala Arg Arg Gly Ser Tyr Pro Tyr Asn Tyr Phe Asp Ala Trp Gly
                325                 330                 335

Cys Gly Thr Thr Val Thr Val Ser Ser Gly Gly Gly Gly Ser Gly Gly
            340                 345                 350

Gly Gly Ser Gln Ala Val Val Ile Gln Glu Ser Ala Leu Thr Thr Pro
        355                 360                 365

Pro Gly Glu Thr Val Thr Leu Thr Cys Gly Ser Ser Thr Gly Ala Val
    370                 375                 380

Thr Ala Ser Asn Tyr Ala Asn Trp Val Gln Glu Lys Pro Asp His Cys
385                 390                 395                 400

Phe Thr Gly Leu Ile Gly Gly His Asn Asn Arg Pro Pro Gly Val Pro
                405                 410                 415

Ala Arg Phe Ser Gly Ser Leu Ile Gly Asp Lys Ala Ala Leu Thr Ile
            420                 425                 430

Ala Gly Thr Gln Thr Glu Asp Glu Ala Ile Tyr Phe Cys Ala Leu Trp
        435                 440                 445

Tyr Ser Asp His Trp Val Ile Gly Gly Gly Thr Arg Leu Thr Val Leu
    450                 455                 460

Gly
465


<210> SEQ ID NO 7
<211> LENGTH: 470
<212> TYPE: PRT
<213> ORGANISM: Artificial Sequence
<220> FEATURE:
<223> OTHER INFORMATION: Trastuzumab LC-(G4S)2AS linker- C825 VH-(G4S)3
      linker-C825 VL

<400> SEQUENCE: 7

Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Ala Ser His Val Lys Leu Gln Glu Ser Gly Pro Gly Leu Val Gln Pro
225                 230                 235                 240

Ser Gln Ser Leu Ser Leu Thr Cys Thr Val Ser Gly Phe Ser Leu Thr
                245                 250                 255

Asp Tyr Gly Val His Trp Val Arg Gln Ser Pro Gly Lys Gly Leu Glu
            260                 265                 270

Trp Leu Gly Val Ile Trp Ser Gly Gly Gly Thr Ala Tyr Asn Thr Ala
        275                 280                 285

Leu Ile Ser Arg Leu Asn Ile Tyr Arg Asp Asn Ser Lys Asn Gln Val
    290                 295                 300

Phe Leu Glu Met Asn Ser Leu Gln Ala Glu Asp Thr Ala Met Tyr Tyr
305                 310                 315                 320

Cys Ala Arg Arg Gly Ser Tyr Pro Tyr Asn Tyr Phe Asp Ala Trp Gly
                325                 330                 335

Cys Gly Thr Thr Val Thr Val Ser Ser Gly Gly Gly Gly Ser Gly Gly
            340                 345                 350

Gly Gly Ser Gly Gly Gly Gly Ser Gln Ala Val Val Ile Gln Glu Ser
        355                 360                 365

Ala Leu Thr Thr Pro Pro Gly Glu Thr Val Thr Leu Thr Cys Gly Ser
    370                 375                 380

Ser Thr Gly Ala Val Thr Ala Ser Asn Tyr Ala Asn Trp Val Gln Glu
385                 390                 395                 400

Lys Pro Asp His Cys Phe Thr Gly Leu Ile Gly Gly His Asn Asn Arg
                405                 410                 415

Pro Pro Gly Val Pro Ala Arg Phe Ser Gly Ser Leu Ile Gly Asp Lys
            420                 425                 430
```

```
Ala Ala Leu Thr Ile Ala Gly Thr Gln Thr Glu Asp Glu Ala Ile Tyr
        435                 440                 445

Phe Cys Ala Leu Trp Tyr Ser Asp His Trp Val Ile Gly Gly Gly Thr
    450                 455                 460

Arg Leu Thr Val Leu Gly
465                 470


<210> SEQ ID NO 8
<211> LENGTH: 475
<212> TYPE: PRT
<213> ORGANISM: Artificial Sequence
<220> FEATURE:
<223> OTHER INFORMATION: Trastuzumab LC-(G4S)2AS linker- C825 VH-(G4S)4
      linker-C825 VL

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Ala Ser His Val Lys Leu Gln Glu Ser Gly Pro Gly Leu Val Gln Pro
225                 230                 235                 240

Ser Gln Ser Leu Ser Leu Thr Cys Thr Val Ser Gly Phe Ser Leu Thr
                245                 250                 255

Asp Tyr Gly Val His Trp Val Arg Gln Ser Pro Gly Lys Gly Leu Glu
            260                 265                 270

Trp Leu Gly Val Ile Trp Ser Gly Gly Gly Thr Ala Tyr Asn Thr Ala
        275                 280                 285

Leu Ile Ser Arg Leu Asn Ile Tyr Arg Asp Asn Ser Lys Asn Gln Val
    290                 295                 300

Phe Leu Glu Met Asn Ser Leu Gln Ala Glu Asp Thr Ala Met Tyr Tyr
```

```
305                 310                 315                 320

Cys Ala Arg Arg Gly Ser Tyr Pro Tyr Asn Tyr Phe Asp Ala Trp Gly
                325                 330                 335

Cys Gly Thr Thr Val Thr Val Ser Ser Gly Gly Gly Gly Ser Gly Gly
            340                 345                 350

Gly Gly Ser Gly Gly Gly Gly Ser Gly Gly Gly Gly Ser Gln Ala Val
        355                 360                 365

Val Ile Gln Glu Ser Ala Leu Thr Thr Pro Pro Gly Glu Thr Val Thr
    370                 375                 380

Leu Thr Cys Gly Ser Ser Thr Gly Ala Val Thr Ala Ser Asn Tyr Ala
385                 390                 395                 400

Asn Trp Val Gln Glu Lys Pro Asp His Cys Phe Thr Gly Leu Ile Gly
                405                 410                 415

Gly His Asn Asn Arg Pro Pro Gly Val Pro Ala Arg Phe Ser Gly Ser
            420                 425                 430

Leu Ile Gly Asp Lys Ala Ala Leu Thr Ile Ala Gly Thr Gln Thr Glu
        435                 440                 445

Asp Glu Ala Ile Tyr Phe Cys Ala Leu Trp Tyr Ser Asp His Trp Val
    450                 455                 460

Ile Gly Gly Gly Thr Arg Leu Thr Val Leu Gly
465                 470                 475
```

<210> SEQ ID NO 9
<211> LENGTH: 480
<212> TYPE: PRT
<213> ORGANISM: Artificial Sequence
<220> FEATURE:
<223> OTHER INFORMATION: Trastuzumab LC-(G4S)2AS linker- C825 VH-(G4S)5 linker-C825 VL

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Ala Ser His Val Lys Leu Gln Glu Ser Gly Pro Gly Leu Val Gln Pro
225                 230                 235                 240

Ser Gln Ser Leu Ser Leu Thr Cys Thr Val Ser Gly Phe Ser Leu Thr
                245                 250                 255

Asp Tyr Gly Val His Trp Val Arg Gln Ser Pro Gly Lys Gly Leu Glu
            260                 265                 270

Trp Leu Gly Val Ile Trp Ser Gly Gly Gly Thr Ala Tyr Asn Thr Ala
        275                 280                 285

Leu Ile Ser Arg Leu Asn Ile Tyr Arg Asp Asn Ser Lys Asn Gln Val
    290                 295                 300

Phe Leu Glu Met Asn Ser Leu Gln Ala Glu Asp Thr Ala Met Tyr Tyr
305                 310                 315                 320

Cys Ala Arg Arg Gly Ser Tyr Pro Tyr Asn Tyr Phe Asp Ala Trp Gly
                325                 330                 335

Cys Gly Thr Thr Val Thr Val Ser Ser Gly Gly Gly Gly Ser Gly Gly
            340                 345                 350

Gly Gly Ser Gly Gly Gly Gly Ser Gly Gly Gly Gly Ser Gly Gly Gly
        355                 360                 365

Gly Ser Gln Ala Val Val Ile Gln Glu Ser Ala Leu Thr Thr Pro Pro
    370                 375                 380

Gly Glu Thr Val Thr Leu Thr Cys Gly Ser Ser Thr Gly Ala Val Thr
385                 390                 395                 400

Ala Ser Asn Tyr Ala Asn Trp Val Gln Glu Lys Pro Asp His Cys Phe
                405                 410                 415

Thr Gly Leu Ile Gly Gly His Asn Asn Arg Pro Pro Gly Val Pro Ala
            420                 425                 430

Arg Phe Ser Gly Ser Leu Ile Gly Asp Lys Ala Ala Leu Thr Ile Ala
        435                 440                 445

Gly Thr Gln Thr Glu Asp Glu Ala Ile Tyr Phe Cys Ala Leu Trp Tyr
    450                 455                 460

Ser Asp His Trp Val Ile Gly Gly Gly Thr Arg Leu Thr Val Leu Gly
465                 470                 475                 480
```

<210> SEQ ID NO 10
<211> LENGTH: 485
<212> TYPE: PRT
<213> ORGANISM: Artificial Sequence
<220> FEATURE:
<223> OTHER INFORMATION: Trastuzumab LC-(G4S)2AS linker- C825 VH-(G4S)6 linker-C825 VL

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Ala Ser His Val Lys Leu Gln Glu Ser Gly Pro Gly Leu Val Gln Pro
225                 230                 235                 240

Ser Gln Ser Leu Ser Leu Thr Cys Thr Val Ser Gly Phe Ser Leu Thr
                245                 250                 255

Asp Tyr Gly Val His Trp Val Arg Gln Ser Pro Gly Lys Gly Leu Glu
            260                 265                 270

Trp Leu Gly Val Ile Trp Ser Gly Gly Gly Thr Ala Tyr Asn Thr Ala
        275                 280                 285

Leu Ile Ser Arg Leu Asn Ile Tyr Arg Asp Asn Ser Lys Asn Gln Val
    290                 295                 300

Phe Leu Glu Met Asn Ser Leu Gln Ala Glu Asp Thr Ala Met Tyr Tyr
305                 310                 315                 320

Cys Ala Arg Arg Gly Ser Tyr Pro Tyr Asn Tyr Phe Asp Ala Trp Gly
                325                 330                 335

Cys Gly Thr Thr Val Thr Val Ser Ser Gly Gly Gly Gly Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gln Ala Val Val Ile Gln Glu Ser Ala
    370                 375                 380

Leu Thr Thr Pro Pro Gly Glu Thr Val Thr Leu Thr Cys Gly Ser Ser
385                 390                 395                 400

Thr Gly Ala Val Thr Ala Ser Asn Tyr Ala Asn Trp Val Gln Glu Lys
                405                 410                 415

Pro Asp His Cys Phe Thr Gly Leu Ile Gly Gly His Asn Asn Arg Pro
            420                 425                 430

Pro Gly Val Pro Ala Arg Phe Ser Gly Ser Leu Ile Gly Asp Lys Ala
        435                 440                 445

Ala Leu Thr Ile Ala Gly Thr Gln Thr Glu Asp Glu Ala Ile Tyr Phe
    450                 455                 460

Cys Ala Leu Trp Tyr Ser Asp His Trp Val Ile Gly Gly Gly Thr Arg
465                 470                 475                 480

Leu Thr Val Leu Gly
                485
```

<210> SEQ ID NO 11
<211> LENGTH: 214
<212> TYPE: PRT
<213> ORGANISM: Artificial Sequence
<220> FEATURE:
<223> OTHER INFORMATION: Trastuzumab light chain

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 12
<211> LENGTH: 1350
<212> TYPE: DNA
<213> ORGANISM: Artificial Sequence
<220> FEATURE:
<223> OTHER INFORMATION: Nucleic acid encoding Trastuzumab VH with human IgG1 constant region and N297A

<400> SEQUENCE: 12

```
gaagtgcagc tggtcgagag cggaggaggt ctggtgcagc ccggaggttc cctgagactg      60

tcctgtgccg catctgggtt taatatcaag gacacataca tccactgggt gagacaggca     120

cccggcaaag gactggagtg ggtcgccagg atctacccta ccaacgggta cacaagatat     180

gctgactctg tgaagggccg gttcaccatc tccgccgata ctagcaaaaa caccgcttac     240

ctgcagatga attccctgag ggcagaagat accgctgtct actactgttc aagatggggg     300

ggggatggtt tttacgctat ggattattgg ggccagggca ccctggtgac cgtgtcctcc     360

gcctccacca agggcccatc ggtcttcccc ctggcaccct cctccaagag cacctctggg     420

ggcacagcgg ccctgggctg cctggtcaag gactacttcc ccgaaccggt gacggtgtcg     480
```

-continued tggaactcag gcgccctgac cagcggcgtg cacaccttcc cggccgtcct acagtcctca 540
ggactctact ccctcagcag cgtggtgacc gtgccctcca gcagcttggg cacccagacc 600
tacatctgca acgtgaatca caagcccagc aacaccaagg tggacaagag agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacgcc 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggatgag 1080
ctgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa 1350

<210> SEQ ID NO 13
<211> LENGTH: 642
<212> TYPE: DNA
<213> ORGANISM: Artificial Sequence
<220> FEATURE:
<223> OTHER INFORMATION: Nucleic acid encoding Trastuzumab light chain

<400> SEQUENCE: 13
gatattcaga tgactcagtc tccctcttcc ctgtccgctt cagtcggcga tcgggtcact 60
attacttgtc gggcttcaca ggatgtcaac acagccgtgg cttggtacca gcagaagccc 120
gggaaagcac ctaagctgct gatctactct gccagtttcc tgtattctgg cgtcccaagt 180
aggttttcag gctcccggag cggaactgac ttcaccctga caatttccag cctgcagccc 240
gaggattttg ctacctacta ttgccagcag cattatacta ccccccccaac attcggccag 300 ggcacaaaag tcgaaatcaa gcggaccgtg gccgccccct ccgtgttcat cttccccccc 360
tccgacgagc agctgaagtc cggcaccgcc tccgtggtgt gcctgctgaa caacttctac 420
ccccgggagg ccaaggtgca gtggaaggtg gacaacgccc tgcagtccgg caactcccag 480
gagtccgtga ccgagcagga ctccaaggac tccacctact ccctgtcctc caccctgacc 540
ctgtccaagg ccgactacga gaagcacaag gtgtacgcct gcgaggtgac ccaccagggc 600
ctgtcctccc ccgtgaccaa gtccttcaac cggggcgagt gc 642

<210> SEQ ID NO 14
<211> LENGTH: 450
<212> TYPE: PRT
<213> ORGANISM: Artificial Sequence
<220> FEATURE:
<223> OTHER INFORMATION: Trastuzumab VH domain with human IgG1 constant region

<400> SEQUENCE: 14

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

-continued

```
Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
```

```
    450


<210> SEQ ID NO 15
<211> LENGTH: 450
<212> TYPE: PRT
<213> ORGANISM: Artificial Sequence
<220> FEATURE:
<223> OTHER INFORMATION: Trastuzumab VH with human IgG1 constant region
      and N297A

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 16
<211> LENGTH: 450
<212> TYPE: PRT
<213> ORGANISM: Artificial Sequence
<220> FEATURE:
<223> OTHER INFORMATION: Trastuzumab VH with human IgG1 constant region,
      N297A, and K322A

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 17
<211> LENGTH: 450
<212> TYPE: PRT
<213> ORGANISM: Artificial Sequence
<220> FEATURE:
<223> OTHER INFORMATION: Trastuzumab VH domain with human IgG1 constant
      region; K322A

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

-continued

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 18
<211> LENGTH: 1410
<212> TYPE: DNA
<213> ORGANISM: Artificial Sequence
<220> FEATURE:
<223> OTHER INFORMATION: Nucleic acid encoding Trastuzumab LC-(G4S)2AS
      linker- C825 VH-(G4S)3 linker-C825 VL

<400> SEQUENCE: 18

gatattcaga tgactcagtc tccctcttcc ctgtccgctt cagtcggcga tcgggtcact      60

attacttgtc gggcttcaca ggatgtcaac acagccgtgg cttggtacca gcagaagccc     120

gggaaagcac ctaagctgct gatctactct gccagtttcc tgtattctgg cgtcccaagt     180

aggttttcag gctcccggag cggaactgac ttcaccctga caatttccag cctgcagccc     240

gaggattttg ctacctacta ttgccagcag cattatacta cccccccaac attcggccag     300
```

```
ggcacaaaag tcgaaatcaa gcggaccgtg gccgcccct ccgtgttcat cttcccccc     360

tccgacgagc agctgaagtc cggcaccgcc tccgtggtgt gcctgctgaa caacttctac    420

ccccgggagg ccaaggtgca gtggaaggtg gacaacgccc tgcagtccgg caactcccag    480

gagtccgtga ccgagcagga ctccaaggac tccacctact ccctgtcctc caccctgacc    540

ctgtccaagg ccgactacga gaagcacaag gtgtacgcct gcgaggtgac ccaccagggc    600

ctgtcctccc ccgtgaccaa gtccttcaac cggggcgagt gcggtggtgg tggtagcggc    660

ggcggtggaa gcgcatccca tgtgaaactg caggaaagcg gcccaggtct ggtccagcca    720

tcccagtctc tgagcctgac atgcactgtg agcggattct ctctgacaga ctatggggtg    780

cactgggtca gacagagtcc aggaaagggg ctggagtggc tgggcgtcat ctggtcaggc    840

ggagggactg cttataacac cgcactgatc agcagactga atatctaccg cgacaactct    900

aaaaatcagg tgttcctgga gatgaacagt ctgcaggccg aagataccgc tatgtactat    960

tgcgccaggc ggggcagcta cccttataat tactttgacg cttggggttg tggcaccaca   1020

gtgacagtct ccagcggtgg aggagggagt ggtggaggag ggtcaggtgg aggagggtcc   1080

caggcagtgg tcattcagga gtctgccctg actacccccc ctggagaaac cgtgacactg   1140

acttgcggat ctagtacagg ggcagtgact gcctccaact atgcaaattg ggtccaggaa   1200

aagcctgatc actgtttcac tggcctgatc ggtggccata acaatcgacc acccggagtg   1260

ccagctaggt tttcaggttc cctgatcggc gacaaagccg ctctgaccat tgctggcacc   1320

cagacagagg atgaagcaat ctacttttgt gccctgtggt attccgatca ctgggtcatt   1380

ggggggggga cacgtctgac tgtgctgggg                                     1410
```

<210> SEQ ID NO 19
<211> LENGTH: 108
<212> TYPE: PRT
<213> ORGANISM: Artificial Sequence
<220> FEATURE:
<223> OTHER INFORMATION: Trastuzumab VL

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105
```

<210> SEQ ID NO 20
<211> LENGTH: 120
<212> TYPE: PRT
<213> ORGANISM: Artificial Sequence
<220> FEATURE:
<223> OTHER INFORMATION: Trastuzumab VH

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 21
<211> LENGTH: 119
<212> TYPE: PRT
<213> ORGANISM: Artificial Sequence
<220> FEATURE:
<223> OTHER INFORMATION: C825 VH

<400> SEQUENCE: 21

His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser
        115


<210> SEQ ID NO 22
<211> LENGTH: 110
<212> TYPE: PRT
<213> ORGANISM: Artificial Sequence
<220> FEATURE:
<223> OTHER INFORMATION: C825 VL

<400> SEQUENCE: 22

Gln Ala Val Val Ile Gln Glu Ser Ala Leu Thr Thr Pro Pro Gly Glu
1               5                   10                  15

Thr Val Thr Leu Thr Cys Gly Ser Ser Thr Gly Ala Val Thr Ala Ser
            20                  25                  30

Asn Tyr Ala Asn Trp Val Gln Glu Lys Pro Asp His Cys Phe Thr Gly
        35                  40                  45

Leu Ile Gly Gly His Asn Asn Arg Pro Pro Gly Val Pro Ala Arg Phe
```

-continued

```
    50                  55                  60

Ser Gly Ser Leu Ile Gly Asp Lys Ala Ala Leu Thr Ile Ala Gly Thr
65                  70                  75                  80

Gln Thr Glu Asp Glu Ala Ile Tyr Phe Cys Ala Leu Trp Tyr Ser Asp
                85                  90                  95

His Trp Val Ile Gly Gly Gly Thr Arg Leu Thr Val Leu Gly
            100                 105                 110


<210> SEQ ID NO 23
<211> LENGTH: 12
<212> TYPE: PRT
<213> ORGANISM: Artificial Sequence
<220> FEATURE:
<223> OTHER INFORMATION: (G4S)2AS Linker

<400> SEQUENCE: 23

Gly Gly Gly Gly Ser Gly Gly Gly Gly Ser Ala Ser
1               5                   10


<210> SEQ ID NO 24
<211> LENGTH: 732
<212> TYPE: DNA
<213> ORGANISM: Artificial Sequence
<220> FEATURE:
<223> OTHER INFORMATION: Nucleic acid encoding C825 VH-(G4S)3 intra-scFv
      linker-C825 VL

<400> SEQUENCE: 24

catgtgaaac tgcaggaaag cggcccaggt ctggtccagc catcccagtc tctgagcctg     60

acatgcactg tgagcggatt ctctctgaca gactatgggg tgcactgggt cagacagagt    120

ccaggaaagg ggctggagtg gctgggcgtc atctggtcag gcggagggac tgcttataac    180

accgcactga tcagcagact gaatatctac cgcgacaact ctaaaaatca ggtgttcctg    240

gagatgaaca gtctgcaggc cgaagatacc gctatgtact attgcgccag gcggggcagc    300

taccctata attactttga cgcttggggt tgtggcacca cagtgacagt ctccagcggt    360

ggaggaggga gtggtggagg agggtcaggt ggaggagggt cccaggcagt ggtcattcag    420

gagtctgccc tgactacccc ccctggagaa accgtgacac tgacttgcgg atctagtaca    480

ggggcagtga ctgcctccaa ctatgcaaat tgggtccagg aaaagcctga tcactgtttc    540

actggcctga tcggtggcca taacaatcga ccacccggag tgccagctag gttttcaggt    600

tccctgatcg gcgacaaagc cgctctgacc attgctggca cccagacaga ggatgaagca    660

atctactttt gtgccctgtg gtattccgat cactgggtca ttgggggggg gacacgtctg    720

actgtgctgg gg                                                        732


<210> SEQ ID NO 25
<211> LENGTH: 5
<212> TYPE: PRT
<213> ORGANISM: Artificial Sequence
<220> FEATURE:
<223> OTHER INFORMATION: G4S Linker

<400> SEQUENCE: 25

Gly Gly Gly Gly Ser
1               5


<210> SEQ ID NO 26
<211> LENGTH: 10
<212> TYPE: PRT
<213> ORGANISM: Artificial Sequence
```

<220> FEATURE:
<223> OTHER INFORMATION: (G4S)2 Linker

<400> SEQUENCE: 26

```
Gly Gly Gly Gly Ser Gly Gly Gly Gly Ser
1               5                   10
```

<210> SEQ ID NO 27
<211> LENGTH: 15
<212> TYPE: PRT
<213> ORGANISM: Artificial Sequence
<220> FEATURE:
<223> OTHER INFORMATION: (G4S)3 Linker

<400> SEQUENCE: 27

```
Gly Gly Gly Gly Ser Gly Gly Gly Gly Ser Gly Gly Gly Gly Ser
1               5                   10                  15
```

<210> SEQ ID NO 28
<211> LENGTH: 20
<212> TYPE: PRT
<213> ORGANISM: Artificial Sequence
<220> FEATURE:
<223> OTHER INFORMATION: (G4S)4 Linker

<400> SEQUENCE: 28

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 29
<211> LENGTH: 25
<212> TYPE: PRT
<213> ORGANISM: Artificial Sequence
<220> FEATURE:
<223> OTHER INFORMATION: (G4S)5 Linker

<400> SEQUENCE: 29

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 30
<211> LENGTH: 30
<212> TYPE: PRT
<213> ORGANISM: Artificial Sequence
<220> FEATURE:
<223> OTHER INFORMATION: (G4S)6 Linker

<400> SEQUENCE: 30

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 31
<211> LENGTH: 234
<212> TYPE: PRT
<213> ORGANISM: Artificial Sequence
<220> FEATURE:
<223> OTHER INFORMATION: C825 VH-(G4S) intra-scFv linker-C825 VL

<400> SEQUENCE: 31

-continued

```
His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gln Ala Val Val
        115                 120                 125

Ile Gln Glu Ser Ala Leu Thr Thr Pro Pro Gly Glu Thr Val Thr Leu
    130                 135                 140

Thr Cys Gly Ser Ser Thr Gly Ala Val Thr Ala Ser Asn Tyr Ala Asn
145                 150                 155                 160

Trp Val Gln Glu Lys Pro Asp His Cys Phe Thr Gly Leu Ile Gly Gly
                165                 170                 175

His Asn Asn Arg Pro Pro Gly Val Pro Ala Arg Phe Ser Gly Ser Leu
            180                 185                 190

Ile Gly Asp Lys Ala Ala Leu Thr Ile Ala Gly Thr Gln Thr Glu Asp
        195                 200                 205

Glu Ala Ile Tyr Phe Cys Ala Leu Trp Tyr Ser Asp His Trp Val Ile
    210                 215                 220

Gly Gly Gly Thr Arg Leu Thr Val Leu Gly
225                 230


<210> SEQ ID NO 32
<211> LENGTH: 239
<212> TYPE: PRT
<213> ORGANISM: Artificial Sequence
<220> FEATURE:
<223> OTHER INFORMATION: C825 VH-(G4S)2 intra-scFv linker-C825 VL

<400> SEQUENCE: 32

His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125
```

```
Ser Gln Ala Val Val Ile Gln Glu Ser Ala Leu Thr Thr Pro Pro Gly
    130                 135                 140

Glu Thr Val Thr Leu Thr Cys Gly Ser Ser Thr Gly Ala Val Thr Ala
145                 150                 155                 160

Ser Asn Tyr Ala Asn Trp Val Gln Glu Lys Pro Asp His Cys Phe Thr
                165                 170                 175

Gly Leu Ile Gly Gly His Asn Asn Arg Pro Pro Gly Val Pro Ala Arg
            180                 185                 190

Phe Ser Gly Ser Leu Ile Gly Asp Lys Ala Ala Leu Thr Ile Ala Gly
        195                 200                 205

Thr Gln Thr Glu Asp Glu Ala Ile Tyr Phe Cys Ala Leu Trp Tyr Ser
    210                 215                 220

Asp His Trp Val Ile Gly Gly Gly Thr Arg Leu Thr Val Leu Gly
225                 230                 235


<210> SEQ ID NO 33
<211> LENGTH: 244
<212> TYPE: PRT
<213> ORGANISM: Artificial Sequence
<220> FEATURE:
<223> OTHER INFORMATION: C825 VH-(G4S)3 intra-scFv linker-C825 VL

<400> SEQUENCE: 33

His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Pro Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly
```

```
<210> SEQ ID NO 34
<211> LENGTH: 249
<212> TYPE: PRT
<213> ORGANISM: Artificial Sequence
<220> FEATURE:
<223> OTHER INFORMATION: C825 VH-(G4S)4 intra-scFv linker-C825 VL

<400> SEQUENCE: 34

His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gln Ala Val Val Ile
    130                 135                 140

Gln Glu Ser Ala Leu Thr Thr Pro Pro Gly Glu Thr Val Thr Leu Thr
145                 150                 155                 160

Cys Gly Ser Ser Thr Gly Ala Val Thr Ala Ser Asn Tyr Ala Asn Trp
                165                 170                 175

Val Gln Glu Lys Pro Asp His Cys Phe Thr Gly Leu Ile Gly Gly His
            180                 185                 190

Asn Asn Arg Pro Pro Gly Val Pro Ala Arg Phe Ser Gly Ser Leu Ile
        195                 200                 205

Gly Asp Lys Ala Ala Leu Thr Ile Ala Gly Thr Gln Thr Glu Asp Glu
    210                 215                 220

Ala Ile Tyr Phe Cys Ala Leu Trp Tyr Ser Asp His Trp Val Ile Gly
225                 230                 235                 240

Gly Gly Thr Arg Leu Thr Val Leu Gly
                245


<210> SEQ ID NO 35
<211> LENGTH: 254
<212> TYPE: PRT
<213> ORGANISM: Artificial Sequence
<220> FEATURE:
<223> OTHER INFORMATION: C825 VH-(G4S)5 intra-scFv linker-C825 VL

<400> SEQUENCE: 35

His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60
```

```
Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gln Ala Val Val Ile Gln Glu Ser Ala Leu Thr Thr Pro Pro Gly Glu
145                 150                 155                 160

Thr Val Thr Leu Thr Cys Gly Ser Ser Thr Gly Ala Val Thr Ala Ser
                165                 170                 175

Asn Tyr Ala Asn Trp Val Gln Glu Lys Pro Asp His Cys Phe Thr Gly
            180                 185                 190

Leu Ile Gly Gly His Asn Asn Arg Pro Pro Gly Val Pro Ala Arg Phe
        195                 200                 205

Ser Gly Ser Leu Ile Gly Asp Lys Ala Ala Leu Thr Ile Ala Gly Thr
    210                 215                 220

Gln Thr Glu Asp Glu Ala Ile Tyr Phe Cys Ala Leu Trp Tyr Ser Asp
225                 230                 235                 240

His Trp Val Ile Gly Gly Gly Thr Arg Leu Thr Val Leu Gly
                245                 250


<210> SEQ ID NO 36
<211> LENGTH: 259
<212> TYPE: PRT
<213> ORGANISM: Artificial Sequence
<220> FEATURE:
<223> OTHER INFORMATION: C825 VH-(G4S)6 intra-scFv linker-C825 VL

<400> SEQUENCE: 36

His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gln Ala Val Val Ile Gln Glu Ser Ala Leu Thr
145                 150                 155                 160

Thr Pro Pro Gly Glu Thr Val Thr Leu Thr Cys Gly Ser Ser Thr Gly
                165                 170                 175
```

```
Ala Val Thr Ala Ser Asn Tyr Ala Asn Trp Val Gln Glu Lys Pro Asp
            180                 185                 190

His Cys Phe Thr Gly Leu Ile Gly Gly His Asn Asn Arg Pro Pro Gly
        195                 200                 205

Val Pro Ala Arg Phe Ser Gly Ser Leu Ile Gly Asp Lys Ala Ala Leu
    210                 215                 220

Thr Ile Ala Gly Thr Gln Thr Glu Asp Glu Ala Ile Tyr Phe Cys Ala
225                 230                 235                 240

Leu Trp Tyr Ser Asp His Trp Val Ile Gly Gly Gly Thr Arg Leu Thr
                245                 250                 255

Val Leu Gly


<210> SEQ ID NO 37
<211> LENGTH: 119
<212> TYPE: PRT
<213> ORGANISM: Artificial Sequence
<220> FEATURE:
<223> OTHER INFORMATION: Humanized C825 VH domain

<400> SEQUENCE: 37

His Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Gly Ser Tyr Pro Tyr Asn Tyr Phe Asp Ala Trp Gly Cys Gly
            100                 105                 110

Thr Leu Val Thr Val Ser Ser
        115


<210> SEQ ID NO 38
<211> LENGTH: 110
<212> TYPE: PRT
<213> ORGANISM: Artificial Sequence
<220> FEATURE:
<223> OTHER INFORMATION: Humanized C825 VL domain

<400> SEQUENCE: 38

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ala Ser
            20                  25                  30

Asn Tyr Ala Asn Trp Val Gln Gln Lys Pro Gly Gln Cys Pro Arg Gly
        35                  40                  45

Leu Ile Gly Gly His Asn Asn Arg Pro Pro Gly Val Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asp
                85                  90                  95
```

```
His Trp Val Ile Gly Gly Gly Thr Lys Leu Thr Val Leu Gly
            100                 105                 110


<210> SEQ ID NO 39
<211> LENGTH: 234
<212> TYPE: PRT
<213> ORGANISM: Artificial Sequence
<220> FEATURE:
<223> OTHER INFORMATION: Humanized C825 VH-(G4S) intra-scFv
      linker-humanized C825 VL

<400> SEQUENCE: 39

His Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Gly Ser Tyr Pro Tyr Asn Tyr Phe Asp Ala Trp Gly Cys Gly
            100                 105                 110

Thr Leu Val Thr Val Ser Ser Gly Gly Gly Gly Ser Gln Ala Val Val
        115                 120                 125

Thr Gln Glu Pro Ser Leu Thr Val Ser Pro Gly Gly Thr Val Thr Leu
    130                 135                 140

Thr Cys Gly Ser Ser Thr Gly Ala Val Thr Ala Ser Asn Tyr Ala Asn
145                 150                 155                 160

Trp Val Gln Gln Lys Pro Gly Gln Cys Pro Arg Gly Leu Ile Gly Gly
                165                 170                 175

His Asn Asn Arg Pro Pro Gly Val Pro Ala Arg Phe Ser Gly Ser Leu
            180                 185                 190

Leu Gly Gly Lys Ala Ala Leu Thr Leu Leu Gly Ala Gln Pro Glu Asp
        195                 200                 205

Glu Ala Glu Tyr Tyr Cys Ala Leu Trp Tyr Ser Asp His Trp Val Ile
    210                 215                 220

Gly Gly Gly Thr Lys Leu Thr Val Leu Gly
225                 230


<210> SEQ ID NO 40
<211> LENGTH: 239
<212> TYPE: PRT
<213> ORGANISM: Artificial Sequence
<220> FEATURE:
<223> OTHER INFORMATION: Humanized C825 VH-(G4S)2 intra-scFv
      linker-humanized C825 VL

<400> SEQUENCE: 40

His Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Leu
        35                  40                  45
```

Gly Val Ile Trp Ser Gly Gly Gly Thr Ala Tyr Asn Thr Ala Leu Ile
50 55 60

Ser Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Arg Gly Ser Tyr Pro Tyr Asn Tyr Phe Asp Ala Trp Gly Cys Gly
100 105 110

Thr Leu Val Thr Val Ser Ser Gly Gly Gly Gly Ser Gly Gly Gly Gly
115 120 125

Ser Gln Ala Val Val Thr Gln Glu Pro Ser Leu Thr Val Ser Pro Gly
130 135 140

Gly Thr Val Thr Leu Thr Cys Gly Ser Ser Thr Gly Ala Val Thr Ala
145 150 155 160

Ser Asn Tyr Ala Asn Trp Val Gln Gln Lys Pro Gly Gln Cys Pro Arg
165 170 175

Gly Leu Ile Gly Gly His Asn Asn Arg Pro Pro Gly Val Pro Ala Arg
180 185 190

Phe Ser Gly Ser Leu Leu Gly Gly Lys Ala Ala Leu Thr Leu Leu Gly
195 200 205

Ala Gln Pro Glu Asp Glu Ala Glu Tyr Tyr Cys Ala Leu Trp Tyr Ser
210 215 220

Asp His Trp Val Ile Gly Gly Gly Thr Lys Leu Thr Val Leu Gly
225 230 235

<210> SEQ ID NO 41
<211> LENGTH: 244
<212> TYPE: PRT
<213> ORGANISM: Artificial Sequence
<220> FEATURE:
<223> OTHER INFORMATION: Humanized C825 VH-(G4S)3 intra-scFv linker-humanized C825 VL

<400> SEQUENCE: 41

His Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Thr Asp Tyr
20 25 30

Gly Val His Trp Val Arg Gln Ala Pro Gly Lys Gly Leu Glu Trp Leu
35 40 45

Gly Val Ile Trp Ser Gly Gly Gly Thr Ala Tyr Asn Thr Ala Leu Ile
50 55 60

Ser Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Arg Gly Ser Tyr Pro Tyr Asn Tyr Phe Asp Ala Trp Gly Cys Gly
100 105 110

Thr Leu Val Thr Val Ser Ser Gly Gly Gly Gly Ser Gly Gly Gly Gly
115 120 125

Ser Gly Gly Gly Gly Ser Gln Ala Val Val Thr Gln Glu Pro Ser Leu
130 135 140

Thr Val Ser Pro Gly Gly Thr Val Thr Leu Thr Cys Gly Ser Ser Thr
145 150 155 160

Gly Ala Val Thr Ala Ser Asn Tyr Ala Asn Trp Val Gln Gln Lys Pro
165 170 175

```
Gly Gln Cys Pro Arg Gly Leu Ile Gly Gly His Asn Asn Arg Pro Pro
            180                 185                 190

Gly Val Pro Ala Arg Phe Ser Gly Ser Leu Leu Gly Gly Lys Ala Ala
        195                 200                 205

Leu Thr Leu Leu Gly Ala Gln Pro Glu Asp Glu Ala Glu Tyr Tyr Cys
    210                 215                 220

Ala Leu Trp Tyr Ser Asp His Trp Val Ile Gly Gly Gly Thr Lys Leu
225                 230                 235                 240

Thr Val Leu Gly


<210> SEQ ID NO 42
<211> LENGTH: 249
<212> TYPE: PRT
<213> ORGANISM: Artificial Sequence
<220> FEATURE:
<223> OTHER INFORMATION: Humanized C825 VH-(G4S)4 intra-scFv
      linker-humanized C825 VL

<400> SEQUENCE: 42

His Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Gly Ser Tyr Pro Tyr Asn Tyr Phe Asp Ala Trp Gly Cys Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gln Ala Val Val Thr
    130                 135                 140

Gln Glu Pro Ser Leu Thr Val Ser Pro Gly Gly Thr Val Thr Leu Thr
145                 150                 155                 160

Cys Gly Ser Ser Thr Gly Ala Val Thr Ala Ser Asn Tyr Ala Asn Trp
                165                 170                 175

Val Gln Gln Lys Pro Gly Gln Cys Pro Arg Gly Leu Ile Gly Gly His
            180                 185                 190

Asn Asn Arg Pro Pro Gly Val Pro Ala Arg Phe Ser Gly Ser Leu Leu
        195                 200                 205

Gly Gly Lys Ala Ala Leu Thr Leu Leu Gly Ala Gln Pro Glu Asp Glu
    210                 215                 220

Ala Glu Tyr Tyr Cys Ala Leu Trp Tyr Ser Asp His Trp Val Ile Gly
225                 230                 235                 240

Gly Gly Thr Lys Leu Thr Val Leu Gly
                245


<210> SEQ ID NO 43
<211> LENGTH: 254
<212> TYPE: PRT
<213> ORGANISM: Artificial Sequence
```

```
<220> FEATURE:
<223> OTHER INFORMATION: Humanized C825 VH-(G4S)5 intra-scFv
      linker-humanized C825 VL

<400> SEQUENCE: 43

His Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Gly Ser Tyr Pro Tyr Asn Tyr Phe Asp Ala Trp Gly Cys Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gln Ala Val Val Thr Gln Glu Pro Ser Leu Thr Val Ser Pro Gly Gly
145                 150                 155                 160

Thr Val Thr Leu Thr Cys Gly Ser Ser Thr Gly Ala Val Thr Ala Ser
                165                 170                 175

Asn Tyr Ala Asn Trp Val Gln Gln Lys Pro Gly Gln Cys Pro Arg Gly
            180                 185                 190

Leu Ile Gly Gly His Asn Asn Arg Pro Pro Gly Val Pro Ala Arg Phe
        195                 200                 205

Ser Gly Ser Leu Leu Gly Gly Lys Ala Ala Leu Thr Leu Leu Gly Ala
    210                 215                 220

Gln Pro Glu Asp Glu Ala Glu Tyr Tyr Cys Ala Leu Trp Tyr Ser Asp
225                 230                 235                 240

His Trp Val Ile Gly Gly Gly Thr Lys Leu Thr Val Leu Gly
                245                 250


<210> SEQ ID NO 44
<211> LENGTH: 259
<212> TYPE: PRT
<213> ORGANISM: Artificial Sequence
<220> FEATURE:
<223> OTHER INFORMATION: Humanized C825 VH-(G4S)6 intra-scFv
      linker-humanized C825 VL

<400> SEQUENCE: 44

His Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95

Arg Arg Gly Ser Tyr Pro Tyr Asn Tyr Phe Asp Ala Trp Gly Cys Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gln Ala Val Val Thr Gln Glu Pro Ser Leu Thr
145                 150                 155                 160

Val Ser Pro Gly Gly Thr Val Thr Leu Thr Cys Gly Ser Ser Thr Gly
                165                 170                 175

Ala Val Thr Ala Ser Asn Tyr Ala Asn Trp Val Gln Gln Lys Pro Gly
            180                 185                 190

Gln Cys Pro Arg Gly Leu Ile Gly Gly His Asn Asn Arg Pro Pro Gly
        195                 200                 205

Val Pro Ala Arg Phe Ser Gly Ser Leu Leu Gly Gly Lys Ala Ala Leu
    210                 215                 220

Thr Leu Leu Gly Ala Gln Pro Glu Asp Glu Ala Glu Tyr Tyr Cys Ala
225                 230                 235                 240

Leu Trp Tyr Ser Asp His Trp Val Ile Gly Gly Gly Thr Lys Leu Thr
                245                 250                 255

Val Leu Gly


<210> SEQ ID NO 45
<211> LENGTH: 465
<212> TYPE: PRT
<213> ORGANISM: Artificial Sequence
<220> FEATURE:
<223> OTHER INFORMATION: Trastuzumab LC-TS(G4S)3 linker- humanized C825
      VH-G4S linker- humanized C825 VL

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Thr Ser Gly Gly Gly Gly Ser Gly Gly Gly
210 215 220

Gly Ser Gly Gly Gly Gly Ser His Val Gln Leu Val Glu Ser Gly Gly
225 230 235 240

Gly Leu Val Gln Pro Gly Gly Ser Leu Arg Leu Ser Cys Ala Ala Ser
245 250 255

Gly Phe Ser Leu Thr Asp Tyr Gly Val His Trp Val Arg Gln Ala Pro
260 265 270

Gly Lys Gly Leu Glu Trp Leu Gly Val Ile Trp Ser Gly Gly Gly Thr
275 280 285

Ala Tyr Asn Thr Ala Leu Ile Ser Arg Phe Thr Ile Ser Arg Asp Asn
290 295 300

Ser Lys Asn Thr Leu Tyr Leu Gln Met Asn Ser Leu Arg Ala Glu Asp
305 310 315 320

Thr Ala Val Tyr Tyr Cys Ala Arg Arg Gly Ser Tyr Pro Tyr Asn Tyr
325 330 335

Phe Asp Ala Trp Gly Cys Gly Thr Leu Val Thr Val Ser Ser Gly Gly
340 345 350

Gly Gly Ser Gln Ala Val Val Thr Gln Glu Pro Ser Leu Thr Val Ser
355 360 365

Pro Gly Gly Thr Val Thr Leu Thr Cys Gly Ser Ser Thr Gly Ala Val
370 375 380

Thr Ala Ser Asn Tyr Ala Asn Trp Val Gln Gln Lys Pro Gly Gln Cys
385 390 395 400

Pro Arg Gly Leu Ile Gly Gly His Asn Asn Arg Pro Pro Gly Val Pro
405 410 415

Ala Arg Phe Ser Gly Ser Leu Leu Gly Gly Lys Ala Ala Leu Thr Leu
420 425 430

Leu Gly Ala Gln Pro Glu Asp Glu Ala Glu Tyr Tyr Cys Ala Leu Trp
435 440 445

Tyr Ser Asp His Trp Val Ile Gly Gly Gly Thr Lys Leu Thr Val Leu
450 455 460

Gly
465

<210> SEQ ID NO 46
<211> LENGTH: 470
<212> TYPE: PRT
<213> ORGANISM: Artificial Sequence
<220> FEATURE:
<223> OTHER INFORMATION: Trastuzumab LC-TS(G4S)3 linker- humanized C825
VH-(G4S)2 linker- humanized C825 VL

<400> SEQUENCE: 46

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly

```
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser His Val Gln Leu Val Glu Ser Gly Gly
225                 230                 235                 240

Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Gly Ser Gln Ala Val Val Thr Gln Glu Pro
        355                 360                 365

Ser Leu Thr Val Ser Pro Gly Gly Thr Val Thr Leu Thr Cys Gly Ser
    370                 375                 380

Ser Thr Gly Ala Val Thr Ala Ser Asn Tyr Ala Asn Trp Val Gln Gln
385                 390                 395                 400

Lys Pro Gly Gln Cys Pro Arg Gly Leu Ile Gly Gly His Asn Asn Arg
                405                 410                 415

Pro Pro Gly Val Pro Ala Arg Phe Ser Gly Ser Leu Leu Gly Gly Lys
            420                 425                 430

Ala Ala Leu Thr Leu Leu Gly Ala Gln Pro Glu Asp Glu Ala Glu Tyr
        435                 440                 445

Tyr Cys Ala Leu Trp Tyr Ser Asp His Trp Val Ile Gly Gly Gly Thr
    450                 455                 460

Lys Leu Thr Val Leu Gly
465                 470
```

<210> SEQ ID NO 47
<211> LENGTH: 475
<212> TYPE: PRT
<213> ORGANISM: Artificial Sequence
<220> FEATURE:
<223> OTHER INFORMATION: Trastuzumab LC-TS(G4S)3 linker- humanized C825
      VH-(G4S)3 linker-humanized C825 VL

<400> SEQUENCE: 47

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser His Val Gln Leu Val Glu Ser Gly Gly
225                 230                 235                 240

Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Gly Ser Gly Gly Gly Gly Ser Gln Ala Val
```

-continued

```
        355                 360                 365

Val Thr Gln Glu Pro Ser Leu Thr Val Ser Pro Gly Gly Thr Val Thr
    370                 375                 380

Leu Thr Cys Gly Ser Ser Thr Gly Ala Val Thr Ala Ser Asn Tyr Ala
385                 390                 395                 400

Asn Trp Val Gln Gln Lys Pro Gly Gln Cys Pro Arg Gly Leu Ile Gly
                405                 410                 415

Gly His Asn Asn Arg Pro Pro Gly Val Pro Ala Arg Phe Ser Gly Ser
            420                 425                 430

Leu Leu Gly Gly Lys Ala Ala Leu Thr Leu Leu Gly Ala Gln Pro Glu
        435                 440                 445

Asp Glu Ala Glu Tyr Tyr Cys Ala Leu Trp Tyr Ser Asp His Trp Val
    450                 455                 460

Ile Gly Gly Gly Thr Lys Leu Thr Val Leu Gly
465                 470                 475


<210> SEQ ID NO 48
<211> LENGTH: 480
<212> TYPE: PRT
<213> ORGANISM: Artificial Sequence
<220> FEATURE:
<223> OTHER INFORMATION: Trastuzumab LC-TS(G4S)3 linker- humanized C825
      VH-(G4S)4 linker- humanized C825 VL

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser His Val Gln Leu Val Glu Ser Gly Gly
225                 230                 235                 240
```

```
Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gln Ala Val Val Thr Gln Glu Pro Ser Leu Thr Val Ser Pro
    370                 375                 380

Gly Gly Thr Val Thr Leu Thr Cys Gly Ser Ser Thr Gly Ala Val Thr
385                 390                 395                 400

Ala Ser Asn Tyr Ala Asn Trp Val Gln Gln Lys Pro Gly Gln Cys Pro
                405                 410                 415

Arg Gly Leu Ile Gly Gly His Asn Asn Arg Pro Pro Gly Val Pro Ala
            420                 425                 430

Arg Phe Ser Gly Ser Leu Leu Gly Gly Lys Ala Ala Leu Thr Leu Leu
        435                 440                 445

Gly Ala Gln Pro Glu Asp Glu Ala Glu Tyr Tyr Cys Ala Leu Trp Tyr
    450                 455                 460

Ser Asp His Trp Val Ile Gly Gly Gly Thr Lys Leu Thr Val Leu Gly
465                 470                 475                 480


<210> SEQ ID NO 49
<211> LENGTH: 485
<212> TYPE: PRT
<213> ORGANISM: Artificial Sequence
<220> FEATURE:
<223> OTHER INFORMATION: Trastuzumab LC-TS(G4S)3 linker- humanized C825
      VH-(G4S)5 linker- humanized C825 VL

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser His Val Gln Leu Val Glu Ser Gly Gly
225                 230                 235                 240

Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gln Ala Val Val Thr Gln Glu Pro Ser
    370                 375                 380

Leu Thr Val Ser Pro Gly Gly Thr Val Thr Leu Thr Cys Gly Ser Ser
385                 390                 395                 400

Thr Gly Ala Val Thr Ala Ser Asn Tyr Ala Asn Trp Val Gln Gln Lys
                405                 410                 415

Pro Gly Gln Cys Pro Arg Gly Leu Ile Gly Gly His Asn Asn Arg Pro
            420                 425                 430

Pro Gly Val Pro Ala Arg Phe Ser Gly Ser Leu Leu Gly Gly Lys Ala
        435                 440                 445

Ala Leu Thr Leu Leu Gly Ala Gln Pro Glu Asp Glu Ala Glu Tyr Tyr
    450                 455                 460

Cys Ala Leu Trp Tyr Ser Asp His Trp Val Ile Gly Gly Gly Thr Lys
465                 470                 475                 480

Leu Thr Val Leu Gly
                485
```

<210> SEQ ID NO 50
<211> LENGTH: 490
<212> TYPE: PRT
<213> ORGANISM: Artificial Sequence
<220> FEATURE:
<223> OTHER INFORMATION: Trastuzumab LC-TS(G4S)3 linker- humanized C825
VH-(G4S)6 linker- humanized C825 VL

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser His Val Gln Leu Val Glu Ser Gly Gly
225                 230                 235                 240

Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Gln Ala Val Val
    370                 375                 380

Thr Gln Glu Pro Ser Leu Thr Val Ser Pro Gly Gly Thr Val Thr Leu
385                 390                 395                 400

Thr Cys Gly Ser Ser Thr Gly Ala Val Thr Ala Ser Asn Tyr Ala Asn
                405                 410                 415
```

```
Trp Val Gln Gln Lys Pro Gly Gln Cys Pro Arg Gly Leu Ile Gly Gly
            420                 425                 430

His Asn Asn Arg Pro Pro Gly Val Pro Ala Arg Phe Ser Gly Ser Leu
        435                 440                 445

Leu Gly Gly Lys Ala Ala Leu Thr Leu Leu Gly Ala Gln Pro Glu Asp
    450                 455                 460

Glu Ala Glu Tyr Tyr Cys Ala Leu Trp Tyr Ser Asp His Trp Val Ile
465                 470                 475                 480

Gly Gly Gly Thr Lys Leu Thr Val Leu Gly
                485                 490


<210> SEQ ID NO 51
<211> LENGTH: 7
<212> TYPE: PRT
<213> ORGANISM: Artificial Sequence
<220> FEATURE:
<223> OTHER INFORMATION: TSG4S Linker

<400> SEQUENCE: 51

Thr Ser Gly Gly Gly Gly Ser
1               5


<210> SEQ ID NO 52
<211> LENGTH: 12
<212> TYPE: PRT
<213> ORGANISM: Artificial Sequence
<220> FEATURE:
<223> OTHER INFORMATION: TS(G4S)2 Linker

<400> SEQUENCE: 52

Thr Ser Gly Gly Gly Gly Ser Gly Gly Gly Gly Ser
1               5                   10


<210> SEQ ID NO 53
<211> LENGTH: 17
<212> TYPE: PRT
<213> ORGANISM: Artificial Sequence
<220> FEATURE:
<223> OTHER INFORMATION: TS(G4S)3 Linker

<400> SEQUENCE: 53

Thr Ser Gly Gly Gly Gly Ser Gly Gly Gly Gly Ser Gly Gly Gly Gly
1               5                   10                  15

Ser


<210> SEQ ID NO 54
<211> LENGTH: 22
<212> TYPE: PRT
<213> ORGANISM: Artificial Sequence
<220> FEATURE:
<223> OTHER INFORMATION: TS(G4S)4 Linker

<400> SEQUENCE: 54

Thr Ser Gly Gly Gly Gly Ser Gly Gly Gly Gly Ser Gly Gly Gly Gly
1               5                   10                  15

Ser Gly Gly Gly Gly Ser
            20


<210> SEQ ID NO 55
<211> LENGTH: 27
<212> TYPE: PRT
<213> ORGANISM: Artificial Sequence
<220> FEATURE:
```

-continued

```
<223> OTHER INFORMATION: TS(G4S)5 Linker

<400> SEQUENCE: 55

Thr Ser Gly Gly Gly Gly Ser Gly Gly Gly Gly Ser Gly Gly Gly Gly
1               5                   10                  15

Ser Gly Gly Gly Gly Ser Gly Gly Gly Gly Ser
            20                  25


<210> SEQ ID NO 56
<211> LENGTH: 32
<212> TYPE: PRT
<213> ORGANISM: Artificial Sequence
<220> FEATURE:
<223> OTHER INFORMATION: TS(G4S)6 Linker

<400> SEQUENCE: 56

Thr Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30
```